(12) United States Patent
Sakurai et al.

(10) Patent No.: US 9,975,871 B2
(45) Date of Patent: May 22, 2018

(54) CONTINUOUS ARYCYCLIC COMPOUND

(71) Applicant: MITSUBISHI TANABE PHARMA CORPORATION, Osaka-shi, Osaka (JP)

(72) Inventors: Osamu Sakurai, Osaka (JP); Kunio Saruta, Osaka (JP); Norimitsu Hayashi, Osaka (JP); Takashi Goi, Osaka (JP); Kenji Morokuma, Osaka (JP); Hidekazu Tsujishima, Osaka (JP); Hiroaki Sawamoto, Osaka (JP); Hiroaki Shitama, Osaka (JP); Ritsuo Imashiro, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 0 days. days.

(21) Appl. No.: 15/050,154

(22) Filed: Feb. 22, 2016

(65) Prior Publication Data

US 2016/0272614 A1  Sep. 22, 2016

Related U.S. Application Data

(62) Division of application No. 13/994,543, filed as application No. PCT/JP2011/079958 on Dec. 16, 2011, now Pat. No. 9,302,996.

(60) Provisional application No. 61/424,365, filed on Dec. 17, 2010.

(51) Int. Cl.
| | |
|---|---|
| C07D 401/04 | (2006.01) |
| C07D 233/64 | (2006.01) |
| C07D 401/10 | (2006.01) |
| C07D 401/14 | (2006.01) |
| C07D 403/04 | (2006.01) |
| C07D 403/10 | (2006.01) |
| C07D 405/14 | (2006.01) |

(52) U.S. Cl.
CPC ......... *C07D 401/04* (2013.01); *C07D 233/64* (2013.01); *C07D 401/10* (2013.01); *C07D 401/14* (2013.01); *C07D 403/04* (2013.01); *C07D 403/10* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,340,810 | A | 8/1994 | Clitherow et al. |
| 5,459,148 | A | 10/1995 | Yanagisawa et al. |
| 2003/0114457 | A1 | 6/2003 | Hu et al. |
| 2005/0004175 | A1 | 1/2005 | Nakamura et al. |
| 2008/0096895 | A1 | 4/2008 | Kamboj et al. |
| 2008/0182861 | A1 | 7/2008 | Souers et al. |
| 2011/0034506 | A1 | 2/2011 | Sun |
| 2011/0319403 | A1 | 12/2011 | Zhou et al. |

FOREIGN PATENT DOCUMENTS

| | | |
|---|---|---|
| JP | 6-116251 A | 4/1994 |
| JP | 2008-513514 A | 5/2008 |
| JP | 2008-255024 A | 10/2008 |
| JP | 2010-511058 A | 4/2010 |
| RU | 2109736 | 4/1998 |
| WO | WO 95/15594 A1 | 6/1995 |
| WO | WO 99/58518 A2 | 11/1999 |
| WO | WO 00/59506 A1 | 10/2000 |
| WO | WO 00/66578 A1 | 11/2000 |
| WO | WO 00/78726 A1 | 12/2000 |
| WO | WO 03/006011 A1 | 1/2003 |
| WO | WO 03/006670 A2 | 1/2003 |
| WO | WO 03/064410 A1 | 8/2003 |
| WO | WO 03/093248 A1 | 11/2003 |
| WO | WO 2004/099168 A2 | 11/2004 |
| WO | WO 2004/100881 A2 | 11/2004 |
| WO | WO 2006/034440 A3 | 3/2006 |
| WO | WO 2007/016538 A2 | 2/2007 |
| WO | WO 2008/067257 A2 | 6/2008 |
| WO | WO 2009/011285 A1 | 1/2009 |
| WO | WO 2009/079593 A1 | 6/2009 |
| WO | WO 2009/126861 A2 | 10/2009 |
| WO | WO 2010/107765 A1 | 9/2010 |
| WO | WO 2011/002067 A1 | 1/2011 |
| WO | WO 2012/009217 A1 | 1/2012 |
| WO | WO 2012/015693 A1 | 2/2012 |
| WO | WO 2012/044567 A2 | 4/2012 |
| WO | WO 2012/044567 A3 | 4/2012 |
| WO | WO 2012/047772 A2 | 4/2012 |

OTHER PUBLICATIONS

"Medi 315," Division of Medicinal Chemistry Scientific Abstracts for the 239th National Meeting and Exposition, Mar. 21-25, 2010.

(Continued)

*Primary Examiner* — Heidi Reese
(74) *Attorney, Agent, or Firm* — Birch, Stewart, Kolasch & Birch, LLP

(57) ABSTRACT

This is to provide a continuous arycyclic compound having a DGAT1 inhibitory activity, and useful for prophylaxis and/or treatment of obesity or hyperlipidemia caused by obesity, hypertriglyceridemia, lipid metabolism disorder, fatty liver, hypertension, arteriosclerosis, diabetes, etc., as well as to provide a DGAT1 inhibitor comprising the continuous arycyclic compound or a pharmaceutically acceptable salt thereof as an effective ingredient. Disclosed is the continuous arycyclic compound is represented by the formula: wherein the substituents in the formula are the same as defined in the specification, or a pharmaceutically acceptable salt thereof.

(I)

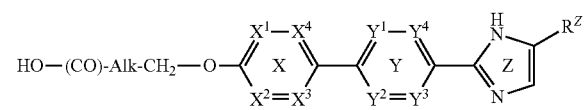

12 Claims, No Drawings

(56) References Cited

OTHER PUBLICATIONS

Cases et al., "Identification of a gene encoding an acyl CoA:diacylglycerol acyltransferase, a key enzyme in triacylglycerol synthesis," Proc. Natl. Acad. Sci., vol. 95, Oct. 1998, pp. 13018-13023.

Chen et al., "Increased insulin and leptin sensitivity in mice lacking acyl CoA: diacylglycerol acyltransferase 1," The Journal of Clinical Investigation, vol. 109, No. 8, Apr. 2002, pp. 1049-1055.

Chen et al., "Inhibition of Triglyceride Synthesis as a Treatment Strategy for Obesity," Arterioscler Thromb Vasc Biol., Mar. 2005, pp. 482-486.

International Preliminary Report on Patentability and Written Opinion dated Jun. 27, 2013, in PCT International Application No. PCT/JP2011/079958.

International Search Report issued in PCT/JP2011/079958, dated Feb. 14, 2012.

International Search Report issued in PCT/JP2013/066431, dated Sep. 17, 2013.

Liu et al., Discovery of Potent, Selective, Orally Bioavailable Stearoyl-CoA Desaturase 1 Inhibitors, J. Med. Chem., 50(13), pp. 3086-3100 (2007).

Nanzando's Medical Dictionary 19th Edition, Nanzando Company, Limited, 2006, pp. 2112-2113.

Partial English translation of Nanzando's Medical Dictionary 19th Edition, Nanzando Company, Limited, 2006, pp. 2112-2113.

Sulsky et al., "Potent and selective biphenyl azole inhibitors of adipocyte fatty acid binding protein (aFABP)," Bioorganic & Medicinal Chemistry Letters 17, 2007, pp. 3511-3515.

Written Opinion of the International Searching Authority issued in PCT/JP2011/079958, dated Feb. 14, 2012.

Yen et al., "MGAT2, a Monoacylglycerol Acyltransferase Expressed in the Small Intestine," The Journal of Biological Chemistry, vol. 278, No. 20, May 16, 2003, pp. 18532-18537.

Gilchrist, "Heterocyclic Chemistry," Third Edition, Addison Wesley Longman, 1997, p. 257.

CONTINUOUS ARYCYCLIC COMPOUND

CROSS REFERENCE TO RELATED APPLICATIONS

This application is a Divisional of copending application Ser. No. 13/994,543, filed on Jun. 14, 2013, which was filed as the National Phase of PCT/JP2011/079958 filed on Dec. 16, 2011, which claims priority under 35 U.S.C. § 119(e) to U.S. Provisional Application No. 61/424,365 filed on Dec. 17, 2010, all of which are hereby expressly incorporated by reference into the present application.

TECHNICAL FIELD

The present invention relates to a continuous arycyclic compound or a pharmaceutically acceptable salt thereof having acyl coenzyme A: diacylglycerol acyltransferase (DGAT) 1 inhibitory activity.

BACKGROUND ART

Obesity is a state in which fat is excessively accumulated in a body (Non-Patent Literature 1), hyperlipidemia, hypertriglyceridemia (TG), and causes lifestyle diseases such as lipid metabolism disorder, fatty liver, diabetes, hypertension, arteriosclerosis, etc.; cerebrovascular disease, coronary heart disease, dyspnoea, lumbago, knee osteoarthritis, etc., and among obesity, those involving these diseases, or having a possibility of causing these diseases in the future are defined to be obesity and handled as one disease.

DGAT is an enzyme catalyzing a reaction from diacylglycerol to TG which is the final stage of TG synthesis, and it has been known that two kinds of subtypes of DGAT1 and DGAT2 exist in DGAT. Of these, DGAT1 has been known to exist in liver, skeletal muscle, adipocytes, etc., and to participate in TG synthesis in the respective tissues (Non-Patent Literature 2).

Also, at the time of TG absorption at the small intestine, TG is decomposed to fatty acid and monoacyl glycerol by pancreatic lipase in lumen of the small intestine, then, took into small intestinal epithelial cells, and absorbed after resynthesis to TG in the epithelial cells. It has also been known that DGAT1 is participated in TG resynthesis at the final stage in the small intestinal epithelial cells (Non-Patent Literature 3).

Thus, a drug which inhibits an action of DGAT1 can inhibit the final stage of TG synthesis so that it can not only inhibit TG synthesis in adipocyte, liver, etc., but also inhibit TG resynthesis in the small intestine, whereby it is expected to inhibit TG absorption in the small intestine and the diseased state of obesity can be improved (Non-Patent Literature 4).

Further, a thesis that accumulation of TG in liver, skeletal muscle, etc. (ectopic adiposity) is a cause of insulin resistance of type 2 diabetes accompanied by obesity has widely been accepted, so that it has been said that a drug which inhibits an action of DGAT1 is expected to improve insulin sensitivity and to have a treatment effect on type 2 diabetes by reducing ectopic adiposity (Non-Patent Literature 4). Also, it has been reported that improvement in insulin sensitivity can be admitted in a mouse in which DGAT1 is knocked out by gene manipulation (DGAT1 knockout mouse) as compared with that of a wild type mouse (Non-Patent Literature 5). Recently, it has also been reported that the compound which inhibits the action of DGAT1 stimulates actions of glucagon-like peptide-1 (GLP-1) and a protein which causes loss of appetite (anorexia) (Non-Patent Literature 6).

As a compound having a continuous arycyclic structure, the following have been known. For example, Patent Literature 1 discloses (2S)-2-[4'-(1-benzyl-1H-benzimidazol-2-yl)-biphenyl-4-yloxy]-3-phenyl-propionic acid (Example 70), etc., as a compound which inhibits Protein-tyrosine phosphatases (PTPases), and useful for the treatment of obesity, glucose intolerance, diabetes, hypertension, and insulin tolerance accompanied by ischemic disease.

Patent Literature 2 discloses, as a compound having Protein-tyrosine phosphatase-1B (PTP-1B) inhibitory activity useful for the treatment of type 2 diabetes, 2-benzyl-4-[4'-(2-benzyl-benzofuran-3-yl)-biphenyl-4-yl]-4-oxo-butyric acid (Example 1), ({4'-(3-benzylamino)imidazo[1,2-a]pyridin-2-yl)biphenyl-4-yl}oxy)(phenyl)acetic acid, {[4'-(5-methyl-1H-indol-1-yl)biphenyl-4-yl]oxy}(phenyl)acetic acid (Example 3), etc.

Patent Literature 3, Patent Literature 4 and Patent Literature 5 disclose compounds having structures in which biphenyl having an inhibitory activity against factor VIIa, factor IXa, factor Xa and factor XIa, and a nitrogen-containing fused hetero ring are bonded. However, their chemical structures are limited to the structures in which the nitrogen-containing fused hetero ring is bonded to 3-position of the biphenyl.

Patent Literature 6 discloses 2-[[2'-(5-phenyl-1H-imidazol-2-yl)[1,1'-biphenyl]-3-yl]oxy]acetic acid (Example 46), etc. as a compound having a treatment effect on obesity and diabetes by inhibiting adipocyte-type fatty acid binding protein (aP2).

Non-Patent Literature 7 reports 2-[[2'-(1-ethyl-4,5-diphenyl-1H-imidazol-2-yl)[1,1'-biphenyl]-3-yl]oxy]acetic acid, 2-[[2'-(4,5-diphenyl-1H-imidazol-2-yl)[1,1'-biphenyl]-3-yl]oxy]acetic acid, etc. as a compound binding to adipocyte-type fatty acid binding protein (aFABP).

PRIOR ART LITERATURES

Patent Literatures

[Patent Literature 1] WO99/58518A
[Patent Literature 2] WO2004/99168A
[Patent Literature 3] WO2003/6670A
[Patent Literature 4] WO2003/6011A
[Patent Literature 5] US 2003/0114457A
[Patent Literature 6] WO00/59506A

Non-Patent Literatures

[Non-Patent Literature 1] Nanzando Co., Ltd., Medical Dictionary (19th Edition) p. 2113, 2006
[Non-Patent Literature 2] Proc. Natl. Acad. Sci. USA vol. 95, p. 13018, 1998
[Non-Patent Literature 3] J. Biol. Chem. Vol. 278, p. 18532, 2003
[Non-Patent Literature 4] Arterioscler. Thromb. Vasc. Biol. Vol. 25, p. 482, 2005
[Non-Patent Literature 5] The Journal of Clinical Investigation, 109(8) 1049-1055, 2002
[Non-Patent Literature 6] American Chemical Society National Meeting Abst. MEDI 315, 2010
[Non-Patent Literature 7] Bioorganic & Medicinal Chemistry Letters 17(12) 3511-3515, 2007

DISCLOSURE OF THE INVENTION

Problems to be Solved by the Invention

An object of the present invention is to provide a continuous arycyclic compound or a pharmaceutically acceptable salt thereof having a DGAT1 inhibitory activity, and a DGAT1 inhibitor useful for prophylaxis and/or treatment of obesity or hyperlipidemia caused by obesity, hypertriglyceridemia, lipid metabolism disorder, fatty liver, hypertension, arteriosclerosis, diabetes, etc. Also, another object of the same is to provide a DGAT1 inhibitor comprising a continuous arycyclic compound or a pharmaceutically acceptable salt thereof as an effective ingredient.

Means to Solve the Problems

The present inventors have carried out intensive studies to solve the above-mentioned problems, and as a result, they have found that the continuous arycyclic compound or a pharmaceutically acceptable salt thereof of the present invention has excellent DGAT1 inhibitory activity whereby the present invention has accomplished. That is, the present invention is as follows.

1. A continuous arycyclic compound represented by the formula:

[Formula 1]

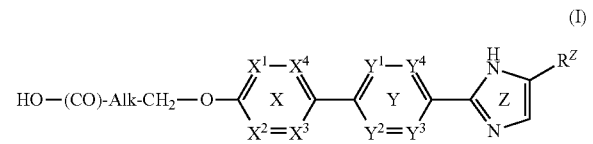

(I)

{wherein Alk represents a linear $C_{1-6}$ alkylene group, branched $C_{1-6}$ alkylene group, or $C_{1-6}$ alkylene group having a ring structure (a part of the carbon atoms constituting the ring structure may be optionally substituted by an oxygen atom, a nitrogen atom or a sulfur atom),
in Ring X,
$X^1$ represents N or $CR^{X1}$,
$X^2$ represents N or $CR^{X2}$,
$X^3$ represents N or $CR^{X3}$,
$X^4$ represents N or $CR^{X4}$,
$R^{X1}$, $R^{X2}$, $R^{X3}$, and $R^{X4}$ each independently represent a hydrogen atom; a linear or branched $C_{1-6}$ alkyl group which may be substituted by a halogen atom(s); a $C_{3-7}$ alkyl group having a ring structure which may be substituted by a halogen atom(s); a linear or branched $C_{1-6}$ alkoxy group; a halogen atom or cyano group,
in Ring Y,
$Y^1$ represents N or $CR^{Y1}$,
$Y^2$ represents N or $CR^{Y2}$,
$Y^3$ represents N or $CR^{Y3}$,
$Y^4$ represents N or $CR^{Y4}$,
$R^{Y1}$, $R^{Y2}$, $R^{Y3}$ and $R^{Y4}$ each independently represent a hydrogen atom; a linear or branched $C_{1-6}$ alkyl group which may be substituted by a halogen atom(s); a $C_{3-7}$ alkyl group having a ring structure which may be substituted by a halogen atom(s); a linear or branched $C_{1-6}$ alkoxy group; a halogen atom or cyano group,
in Ring Z,
$R^Z$ represents a linear or branched $C_{1-6}$ alkyl group which may be substituted by a halogen atom(s) or $C_{3-7}$ alkyl group having a ring structure which may be substituted by a halogen atom(s).}
or a pharmaceutically acceptable salt thereof.

2. The continuous arycyclic compound or a pharmaceutically acceptable salt thereof described in the above item 1, wherein Ring X has a structure represented by any one of the following formulae:

[Formula 2]

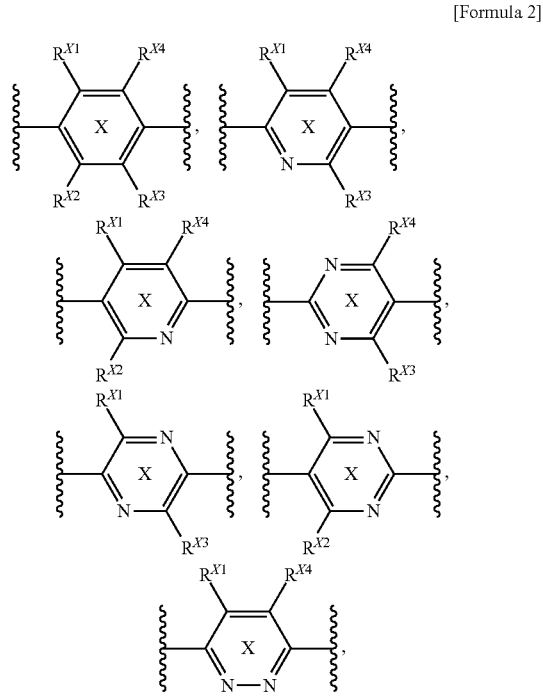

wherein $R^{X1}$ to $R^{X4}$ have the same meanings as defined above,
Ring Y has a structure represented by any one of the following formulae:

[Formula 3]

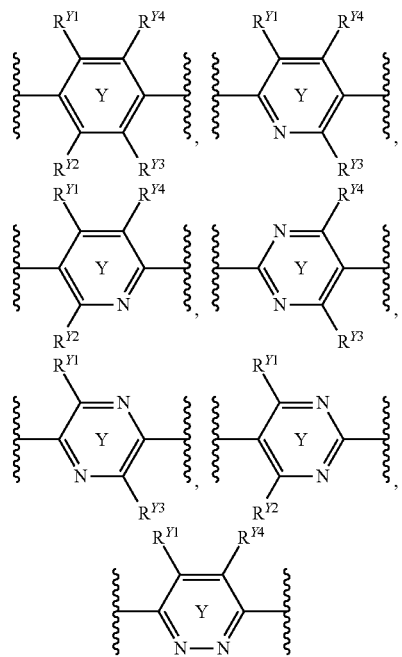

wherein $R^{Y1}$ to $R^{Y4}$ have the same meanings as defined above.

3. The continuous arycyclic compound or a pharmaceutically acceptable salt thereof described in the above item 2, wherein Ring X has a structure represented by any one of the following formulae:

[Formula 4]

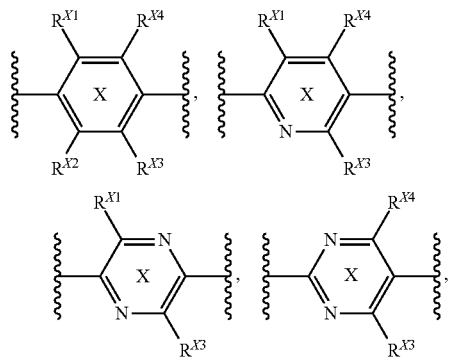

wherein $R^{X1}$ to $R^{X4}$ have the same meanings as defined above,

Ring Y has a structure represented by any one of the following formulae:

[Formula 5]

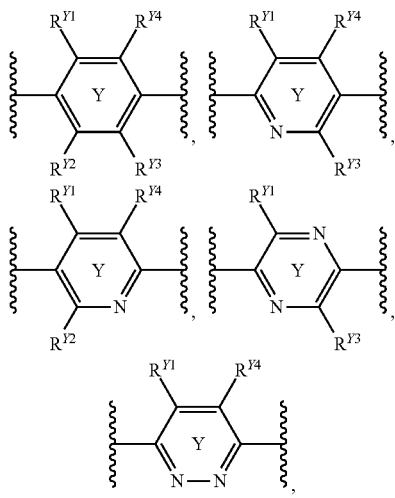

wherein $R^{Y1}$ to $R^{Y4}$ have the same meanings as defined above.

It is preferred that Ring X has a structure represented by any one of the following formulae:

[Formula 6]

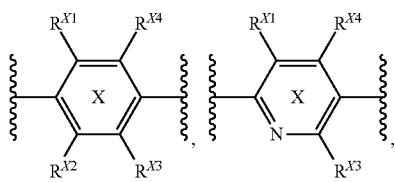

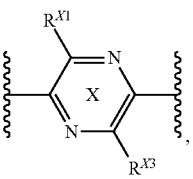

wherein $R^{X1}$ to $R^{X4}$ have the same meanings as defined above,

Ring Y has a structure represented by any one of the following formulae:

[Formula 7]

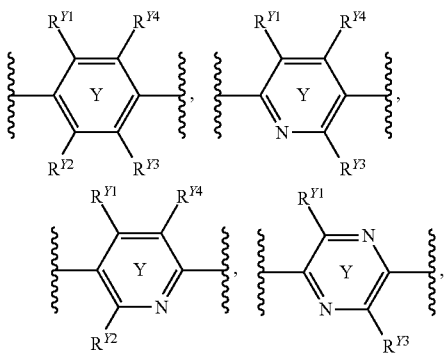

wherein $R^{Y1}$ to $R^{Y4}$ have the same meanings as defined above.

It is more preferred that Ring X and Ring Y have structures represented by any one of the following formulae:

[Formula 8]

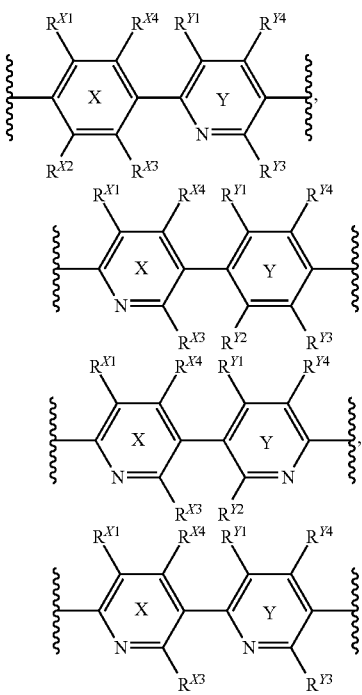

-continued

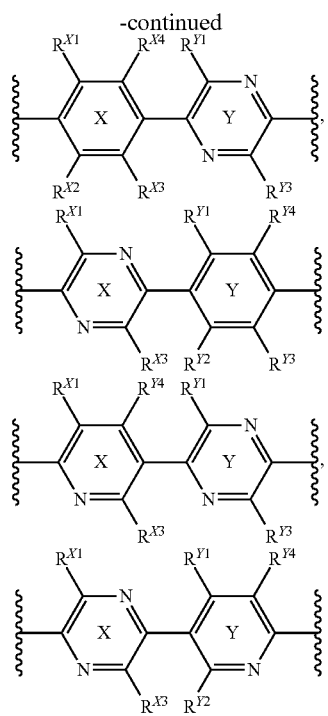

wherein $R^{X1}$ to $R^{X4}$ and $R^{Y1}$ to $R^{Y4}$ have the same meanings as defined above.

4. The continuous arycyclic compound or a pharmaceutically acceptable salt thereof described in the above item 3, wherein $R^Z$ is a linear or branched $C_{1-6}$ alkyl group which is substituted by a halogen atom(s), or a $C_{3-7}$ alkyl group having a ring structure which may be substituted by a halogen atom(s).

5. The continuous arycyclic compound or a pharmaceutically acceptable salt thereof described in the above item 4, wherein Alk is a branched $C_{2-4}$ alkylene group.

6. A continuous arycyclic compound which is any one of the following compounds:
2,2-dimethyl-3-(4-{5-[5-(trifluoromethyl)-1H-imidazol-2-yl]pyridin-2-yl}phenoxy)-propanoic acid;
2,2-dimethyl-3-(4-{5-[5-(2,2,2-trifluoro-1,1-dimethylethyl)-1H-imidazol-2-yl]pyridin-2-yl}phenoxy)propanoic acid;
2,2-dimethyl-3-(4-{4-methyl-5-[5-(trifluoromethyl)-1H-imidazol-2-yl]pyridin-2-yl}-phenoxy)propanoic acid;
2,2-dimethyl-3-[4-(5-{5-[1-(trifluoromethyl)cyclopropyl]-1H-imidazol-2-yl}pyridin-2-yl)phenoxy)propanoic acid;
2,2-dimethyl-3-(4-{5-[5-(trifluoromethyl)-1H-imidazol-2-yl]pyrazin-2-yl}phenoxy)-propanoic acid;
1-[(3-methyl-4-{5-[5-(trifluoromethyl)-1H-imidazol-2-yl]pyridin-2-yl}phenoxy)-methyl]cyclobutanecarboxylic acid;
3-(4-{5-[5-(3,3-difluorocyclobutyl)-1H-imidazol-2-yl]pyridin-2-yl}phenoxy)-2,2-dimethylpropanoic acid;
2,2-dimethyl-3-({4-methyl-6'-[5-(trifluoromethyl)-1H-imidazol-2-yl]-3,3'-bipyridin-6-yl}oxy)propanoic acid;
2,2-dimethyl-3-({4'-methyl-6-[5-(trifluoromethyl)-1H-imidazol-2-yl]-2,3'-bipyridin-6'-yl}oxy)propanoic acid;
2,2-dimethyl-3-[(4-methyl-5-{4-[5-(trifluoromethyl)-1H-imidazol-2-yl]phenyl}pyridin-2-yl)oxy]propanoic acid;
2,2-dimethyl-3-[(6-methyl-5-{4-[5-(trifluoromethyl)-1H-imidazol-2-yl]phenyl}pyridin-2-yl)oxy]propanoic acid;
3-[(5-{3-fluoro-4-[5-(trifluoromethyl)-1H-imidazol-2-yl]phenyl}pyridin-2-yl)oxy]-2,2-dimethylpropanoic acid;
2,2-dimethyl-3-[(5-{4-[4-(trifluoromethyl)-1H-imidazol-2-yl]phenyl}pyrazin-2-yl)oxy]-propanoic acid;
2,2-dimethyl-3-[(4-methyl-5-{3-methyl-4-[5-(trifluoromethyl)-1H-imidazol-2-yl]-phenyl}pyridin-2-yl)oxy]propanoic acid;
3-[(5-{3-fluoro-4-[5-(trifluoromethyl)-1H-imidazol-2-yl]phenyl}-4-methylpyridin-2-yl)oxy]-2,2-dimethylpropanoic acid;
2,2-dimethyl-3-[4-[5-[4-(trifluoromethyl)-1H-imidazol-2-yl]-2-pyridyl]phenoxy]-propanoic acid;
3-[(5-{3-chloro-4-[4-(trifluoromethyl)-1H-imidazol-2-yl]phenyl}-4-methylpyridin-2-yl)oxy]-2,2-dimethylpropanoic acid;
3-{[5-(3-fluoro-4-{5-[1-(trifluoromethyl)cyclopropyl]-1H-imidazol-2-yl}phenyl)-4-methylpyridin-2-yl]oxy}-2,2-dimethylpropanoic acid;
2,2-dimethyl-3-[(4-methyl-5-{5-[5-(trifluoromethyl)-1H-imidazol-2-yl]pyrazin-2-yl}pyridin-2-yl)oxy]propanoic acid;
3-[(5-{4-[5-(cyclopropylmethyl)-1H-imidazol-2-yl]-3-fluorophenyl}-4-methylpyridin-2-yl)oxy]-2,2-dimethylpropanoic acid;
1-[({4-methyl-6'-[5-(trifluoromethyl)-1H-imidazol-2-yl]-3,3'-bipyridin-6-yl}oxy)methyl]cyclobutanecarboxylic acid;
1-{[(5-{3-fluoro-4-[5-(trifluoromethyl)-1H-imidazol-2-yl]phenyl}-4-methylpyridin-2-yl)oxy]methyl}cyclobutanecarboxylic acid;
1-[({5'-chloro-4-methyl-6'-[5-(trifluoromethyl)-1H-imidazol-2-yl]-3,3'-bipyridin-6-yl}oxy)methyl]cyclobutanecarboxylic acid;
1-{[(5-{3-chloro-4-[5-(trifluoromethyl)-1H-imidazol-2-yl]phenyl}-4-methylpyridin-2-yl)oxy]methyl}cyclopropanecarboxylic acid;
1-{[(5-{3-chloro-4-[5-(trifluoromethyl)-1H-imidazol-2-yl]phenyl}-4-methylpyridin-2-yl)oxy]methyl}cyclobutanecarboxylic acid,
or a pharmaceutically acceptable salt thereof.

7. An acyl coenzyme A: diacylglycerol acyltransferase (DGAT) 1 inhibitor comprising the continuous arycyclic compound or a pharmaceutically acceptable salt thereof described in any one of the above items 1 to 6 as an effective ingredient.

8. The DGAT1 inhibitor described in the above item 7 which is a prophylactic or treatment agent of obesity.

9. The DGAT1 inhibitor described in the above item 8 which is a prophylactic or treatment agent of hyperlipidemia, hypertriglyceridemia, lipid metabolism disorder or fatty liver.

10. The DGAT1 inhibitor described in the above item 7 which is a prophylactic or treatment agent of type 2 diabetes, diabetic complication (including diabetic peripheral neuropathy, diabetic nephropathy, diabetic retinopathy and diabetic macrovascular disease), arteriosclerosis, hypertension, cerebrovascular disease, coronary heart disease, dyspnoea, lumbago or knee osteoarthritis.

11. The DGAT1 inhibitor described in the above item 10 which is a prophylactic or treatment agent of type 2 diabetes or diabetic complication.

12. Use of the continuous arycyclic compound or a pharmaceutically acceptable salt thereof described in any one of the above items 1 to 6 for the prophylaxis or treatment of hyperlipidemia, hypertriglyceridemia, lipid metabolism disorder, fatty liver; type 2 diabetes, diabetic complication (including diabetic peripheral neuropathy, diabetic nephropathy, diabetic retinopathy and diabetic macrovascular disease), arteriosclerosis, hypertension, cerebrovascular disease, coronary heart disease, dyspnoea, lumbago or knee osteoarthritis.

13. A prophylaxis or treatment method of hyperlipidemia, hypertriglyceridemia, lipid metabolism disorder, fatty liver; type 2 diabetes, diabetic complication (including diabetic peripheral neuropathy, diabetic nephropathy, diabetic retinopathy and diabetic macrovascular disease), arteriosclerosis, hypertension, cerebrovascular disease, coronary heart disease, dyspnoea, lumbago or knee osteoarthritis which comprises administering therapeutically effective amount of the continuous arycyclic compound or a pharmaceutically acceptable salt thereof described in any one of the above items 1 to 6 to a patient.

In the above descriptions, the linear or branched $C_{1-6}$ alkylene group includes a linear $C_{1-6}$ alkylene group and a branched $C_{2-6}$ alkylene group, and specifically mentioned the following alkylene group.

1) —$CH_2$—;
2) —$CH_2CH_2$—, —$CH(CH_3)$—;
3) —$CH_2CH_2CH_2$—, —$CH(CH_3)CH_2$—, —$CH_2CH(CH_3)$—, —$C(CH_3)_2$—, —$CH(C_2H_5)$—;
4) —$CH_2CH_2CH_2CH_2$—, —$CH(CH_3)CH_2CH_2$—, —$CH_2CH(CH_3)CH_2$—, —$CH_2CH_2CH(CH_3)$—, —$C(CH_3)_2CH_2$—, —$CH_2C(CH_3)_2$—, —$CH(C_2H_5)CH_2$—, —$CH_2CH(C_2H_5)$—, —$CH(n-C_3H_7)$—, —$CH(i-C_3H_7)$—;
5) —$CH_2CH_2CH_2CH_2CH_2$—, —$CH(CH_3)CH_2CH_2CH_2$—, —$CH_2CH(CH_3)CH_2CH_2$—, —$CH_2CH_2CH(CH_3)CH_2$—, —$CH_2CH_2CH_2CH(CH_3)$—, —$C(CH_3)_2CH_2CH_2$—, —$CH_2C(CH_3)_2CH_2$—, —$CH_2CH_2C(CH_3)_2$—, —$CH(CH_3)CH(CH_3)CH_2$—, —$CH(CH_3)CH_2CH(CH_3)$—, —$CH(CH_3)CH_2CH(CH_3)$—, —$CH_2CH(CH_3)CH(CH_3)$—, —$CH(C_2H_5)CH_2CH_2$—, —$CH_2CH(C_2H_5)CH_2$—, —$CH_2CH_2CH(C_2H_5)$—, —$C(CH_3)_2CH(CH_3)$—, —$CH(CH_3)C(CH_3)_2$—, —$CH(C_2H_5)CH(CH_3)$—, —$CH(CH_3)CH(C_2H_5)$—, —$CH(n-C_3H_7)CH_2$—, —$CH(i-C_3H_7)CH_2$—, —$CH_2CH(n-C_3H_7)$—, —$CH_2CH(i-C_3H_7)$—, —$CH(n-C_4H_9)$—, —$CH(i-C_4H_9)$—, —$CH(sec-C_4H_9)$— or —$CH(t-C_4H_9)$—;
6) —$CH_2CH_2CH_2CH_2CH_2CH_2$—, —$CH(CH_3)CH_2CH_2CH_2CH_2$—, —$CH_2CH(CH_3)CH_2CH_2CH_2$—, —$CH_2CH_2CH(CH_3)CH_2CH_2$—, —$CH_2CH_2CH_2CH(CH_3)CH_2$—, —$CH_2CH_2CH_2CH_2CH(CH_3)$—, —$C(CH_3)_2CH_2CH_2CH_2$—, —$CH_2C(CH_3)_2CH_2CH_2$—, —$CH_2CH_2C(CH_3)_2CH_2$—, —$CH_2CH_2CH_2C(CH_3)_2$—, —$CH(CH_3)CH(CH_3)CH_2CH_2$—, —$CH(CH_3)CH_2CH(CH_3)CH_2$—, —$CH(CH_3)CH_2CH_2CH(CH_3)$—, —$CH_2CH(CH_3)CH(CH_3)CH_2$—, —$CH_2CH(CH_3)CH_2CH(CH_3)$—, —$CH_2CH_2CH(CH_3)CH(CH_3)$—, —$CH(C_2H_5)CH_2CH_2CH_2$—, —$CH_2CH(C_2H_5)CH_2CH_2$—, —$CH_2CH_2CH(C_2H_5)CH_2$—, —$CH_2CH_2CH_2CH(C_2H_5)$—, —$CH(CH_3)CH(CH_3)CH(CH_3)$—, —$CH(C_2H_5)CH(CH_3)CH_2$—, —$CH(C_2H_5)CH_2CH(CH_3)$—, —$CH(C_2H_5)CH_2CH(CH_3)$—, —$CH(CH_3)CH(C_2H_5)CH_2$—, —$CH_2CH(C_2H_5)CH(CH_3)$—, —$CH(CH_3)CH_2CH(C_2H_5)$—, —$CH_2CH(CH_3)CH(C_2H_5)$—.

Of these alkylene groups, a branched $C_{2-6}$ alkylene group is preferred, a branched $C_{2-4}$ alkylene group is more preferred, and —$C(CH_3)_2$— is particularly preferred.

In the above-mentioned descriptions, the "$C_{1-6}$ alkylene group having a ring structure" includes the structure represented by the following formula:

[Formula 9]

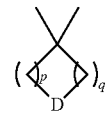

(wherein D represents $CH_2$, NH, O, or S, p is an integer of 1 to 2, and q is an integer of 0 to 2.)

more specifically, the following structures are mentioned.

[Formula 10]

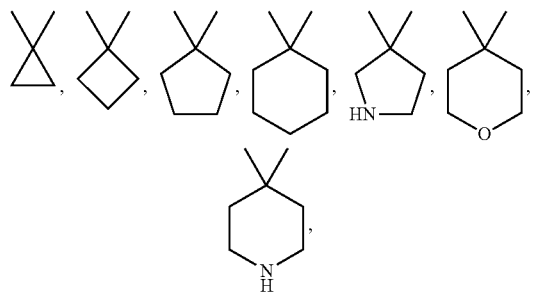

The linear and branched $C_{1-6}$ alkyl group and the linear and branched $C_{1-6}$ alkoxy group may be mentioned an alkyl group and an alkoxy group corresponding to the above-mentioned linear and branched alkylene groups. The alkyl group is preferably a linear $C_{1-6}$ alkyl group, more preferably a linear $C_{1-4}$ alkyl group, particularly preferably methyl group and ethyl group. Also, the alkoxy group is preferably a linear $C_{1-6}$ alkoxy group, more preferably a linear $C_{1-4}$ alkoxy group, particularly preferably methoxy group and ethoxy group.

The $C_{3-7}$ alkyl group having a ring structure includes those comprising a cycloalkyl ring alone, and those comprising a cycloalkyl ring and a linear alkyl group in combination, and specifically mentioned the following.

3)

[Formula 11]

4)

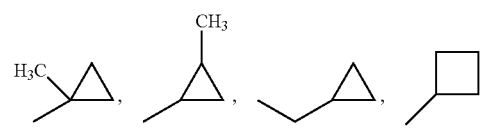

[Formula 12]

5)

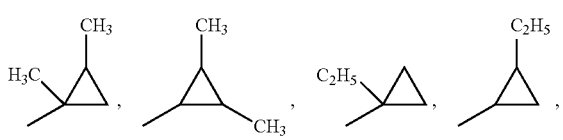

[Formula 13]

-continued

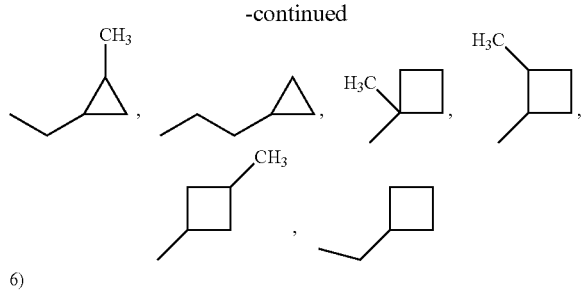

6)

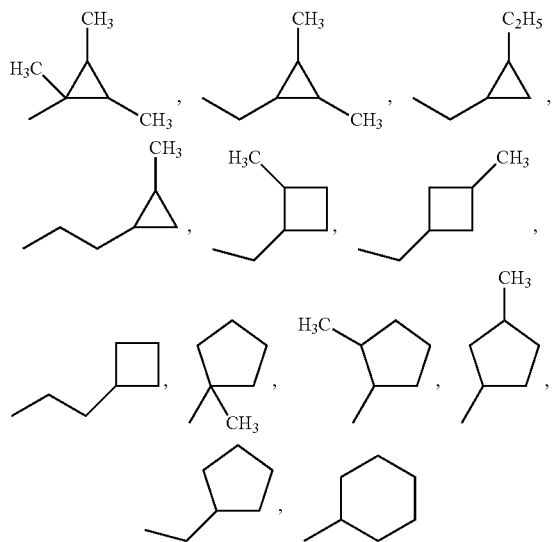

7)

[Formula 15]

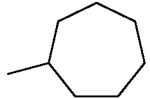

Among the $C_{3-6}$ alkyl group having a ring structure of $R^{X1}$, $R^{X2}$, $R^{X3}$, $R^{X4}$, $R^{Y1}$, $R^{Y2}$, $R^{Y3}$, and $R^{Y4}$, a $C_{3-5}$ alkyl group having a ring structure is more preferred, and particularly preferably the following cyclopropylmethyl group.

[Formula 16]

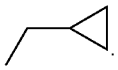

Among the $C_{3-6}$ alkyl group having a ring structure of $R^Z$, a $C_{3-5}$ alkyl group having a ring structure is preferred, and particularly preferably the following:

[Formula 17]

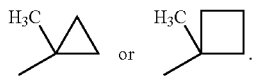

The halogen atom which may be substituted to the linear or branched $C_{1-6}$ alkyl group or the $C_{3-7}$ alkyl group having a ring structure may be mentioned a fluorine atom, a chlorine atom, a bromine atom or an iodine atom, and a fluorine atom is preferred.

The linear or branched $C_{1-6}$ alkyl group or the $C_{3-7}$ alkyl group having a ring structure may be substituted by 1 to 5 halogen atom(s), and more preferably may be substituted by 2 or 3 halogen atoms.

The continuous arycyclic compound (I) of the present invention has a structure in which Ring X and Ring Y are both 6-membered aromatic rings, and they are bonded at the 1,4-positions, so that it has a linear structure as a whole molecule, and has a novel structure in which it has an acidic carboxyl group at one end of the molecule, and has a basic imidazole ring at the other end of the same.

In the continuous arycyclic compound (I) of the present invention, a tautomerism shown by the following formula is caused by transfer of a hydrogen ion on Ring Z, and even when the continuous arycyclic compound (I) of the present invention is shown by either one of the chemical structures, it includes either of the tautomers and a mixture thereof.

[Formula 18]

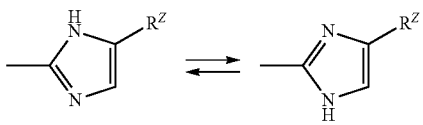

The continuous arycyclic compound (I) of the present invention has a basic group and a acidic group in the molecule, and the pharmaceutically acceptable salt thereof may be mentioned an acid addition salt (for example, an inorganic acid salt such as a hydrochloride, a sulfate, a phosphate, a hydrobromide, etc., an organic acid salt such as an acetate, a fumarate, a maleate, an oxalate, a citrate, a methanesulfonate, a benzenesulfonate, toluenesulfonate, etc.) and a salt with a base (for example, an alkali metal salt such as a sodium salt, potassium salt, etc., an alkaline earth metal salt such as a calcium salt, etc., an organic base salt such as a triethylamine salt, etc., an amino acid salt such as a lysine salt, etc.).

Effects of the Invention

The continuous arycyclic compound (I) or a pharmaceutically acceptable salt thereof of the present invention has excellent DGAT1 inhibitory activity, and useful as a medicine for prophylaxis and/or treatment of the following mentioned diseases of a warm blooded animals (preferably mammals including human).

(1) Diseases relating to fat accumulation (adiposity): hyperlipidemia, hypertriglyceridemia, lipid metabolism disorder, fatty liver, etc.

(2) Diseases considered to be caused by fat accumulation (adiposity): type 2 diabetes, diabetic complication (including diabetic peripheral neuropathy, diabetic nephropathy, diabetic retinopathy and diabetic macrovascular disease); arteriosclerosis, hypertension, cerebrovascular disease, coronary heart disease; dyspnoea, lumbago, knee osteoarthritis, etc.

Also, the continuous arycyclic compound (I) or a pharmaceutically acceptable salt thereof of the present invention has a GLP-1 secretagogue action based on the DGAT1 inhibitory activity, so that it can be expected to have an insulin secretomotory action and pancreas protecting action.

BEST MODE TO CARRY OUT THE INVENTION
The continuous arycyclic compound (I) of the present invention can be prepared according to the methods mentioned below.
(Method A)
[Formula 19]
Step 1A
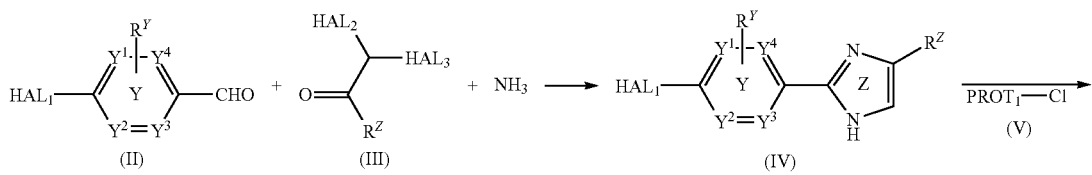
Step 2A
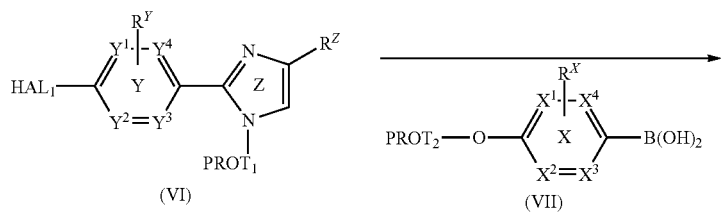
Step 3A
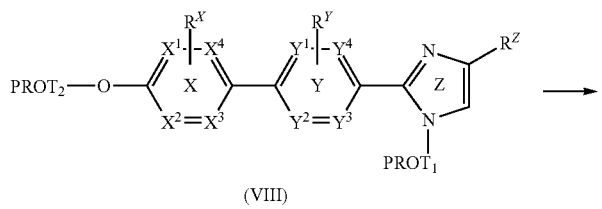
Step 4A
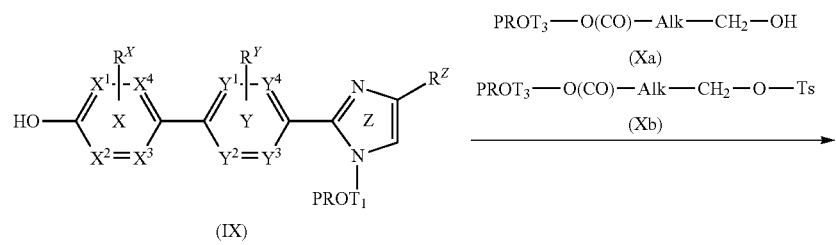
Step 5A
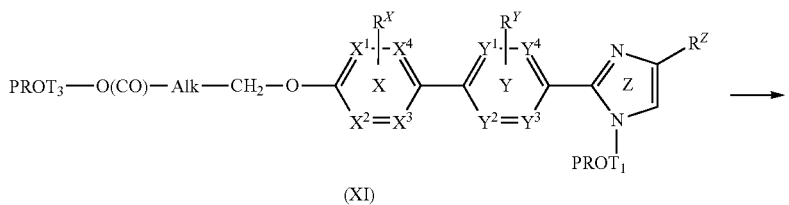
Step 6A
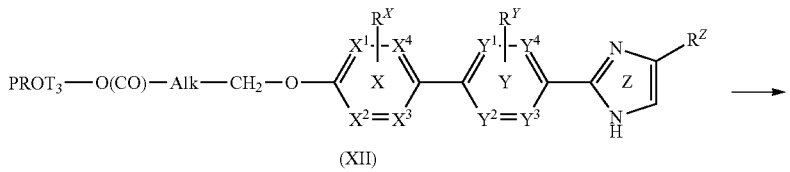

Step 7A

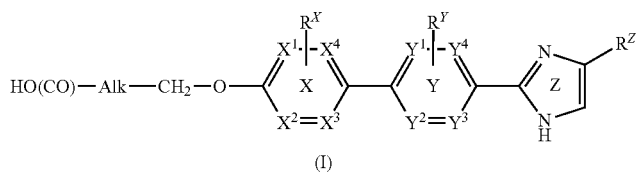

(I)

(in the above-mentioned formulae, $HAL_1$, $HAL_2$ and $HAL_3$ each represent a halogen atom, $PROT_1$ represents a protective group for a polar functional group, $PROT_2$ represents a protective group for a hydroxyl group, $PROT_3$ represents a protective group for a carboxyl group, and the other symbols have the same meanings as defined above.)

(Method B)

[Formula 20]

Step 1B

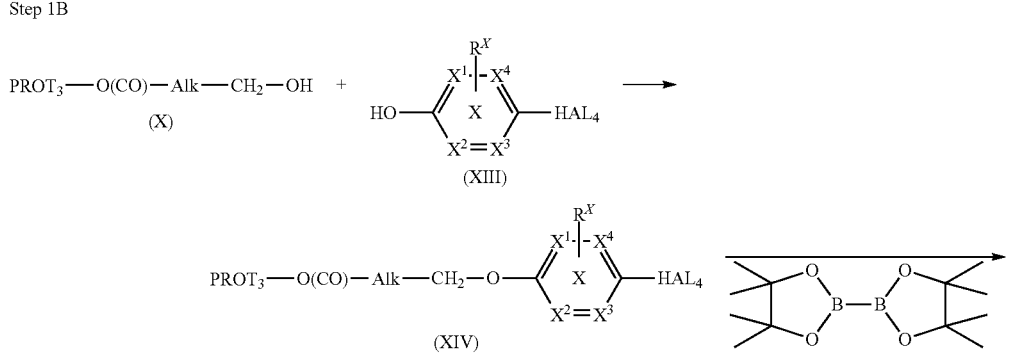

Step 2B

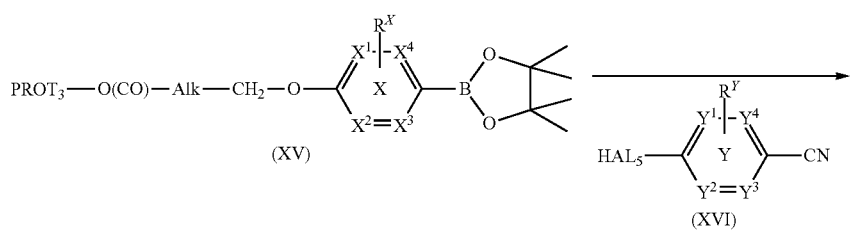

Step 3B

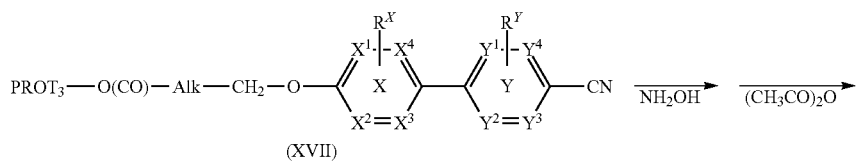

Step 4B

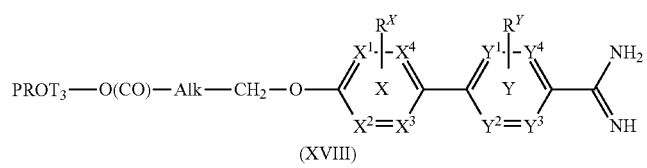

Step 5B

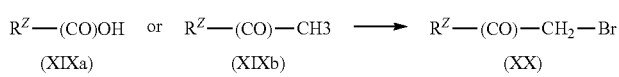

Step 6B
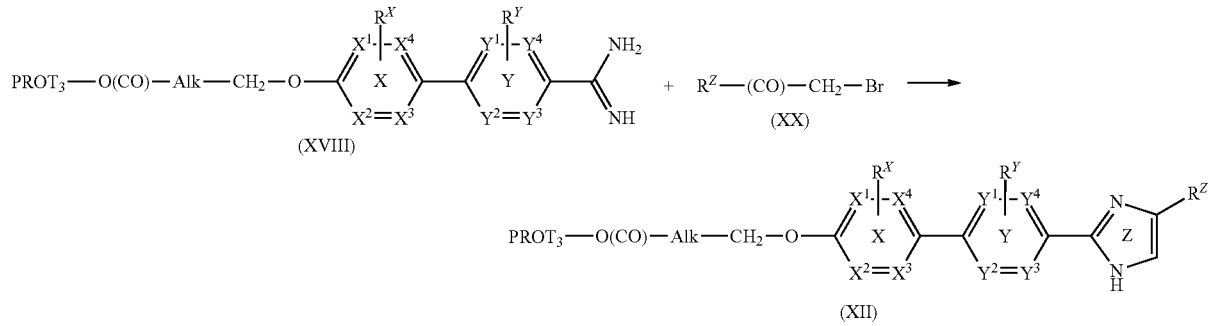
(in the above-mentioned reaction formula, HAL$_4$ and HAL$_5$ each represent a halogen atom, and the other symbols have the same meanings as defined above.)
(Method C)
[Formula 21]
Step 1C
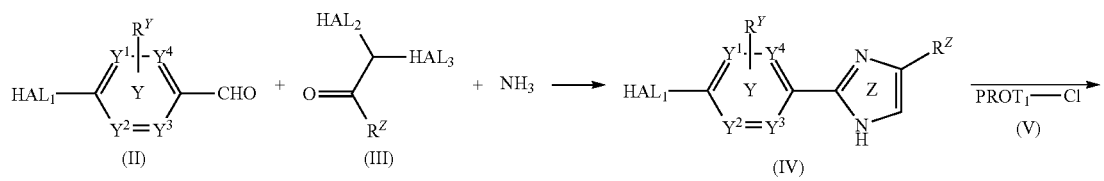
Step 2C
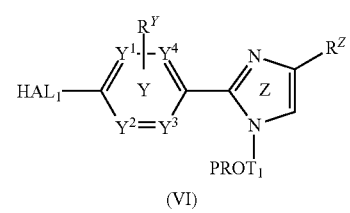
Step 3C
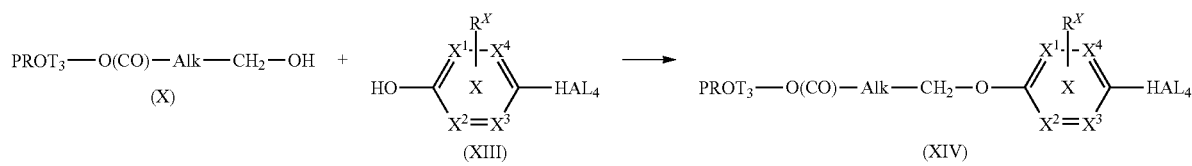
Step 4C
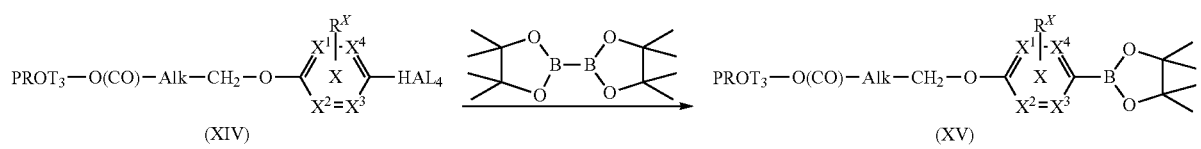
Step 5C
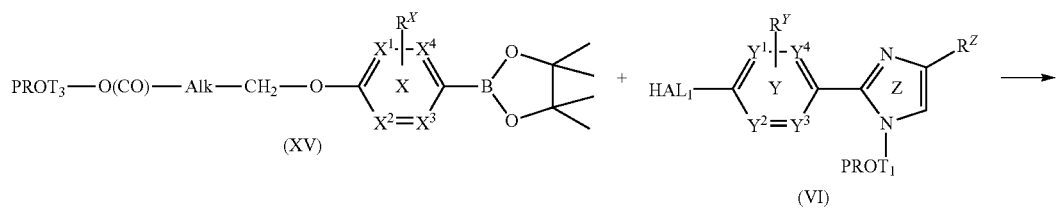

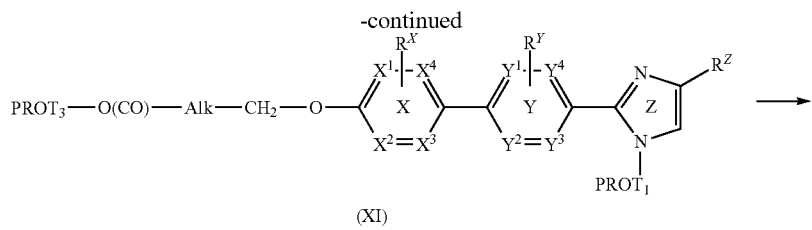
(XI)
Step 6C
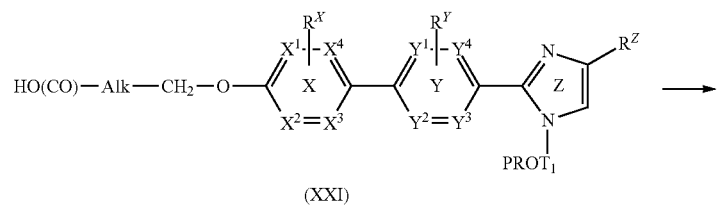
(XXI)
Step 7C
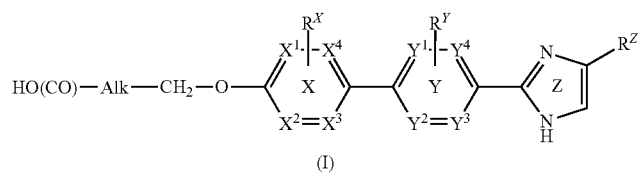
(I)
(in the above-mentioned reaction formula, the symbols have the same meanings as defined above.)
(Method D)
[Formula 22]
Step 1D
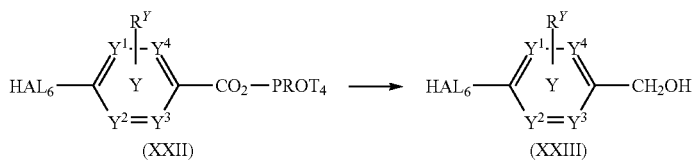
Step 2D
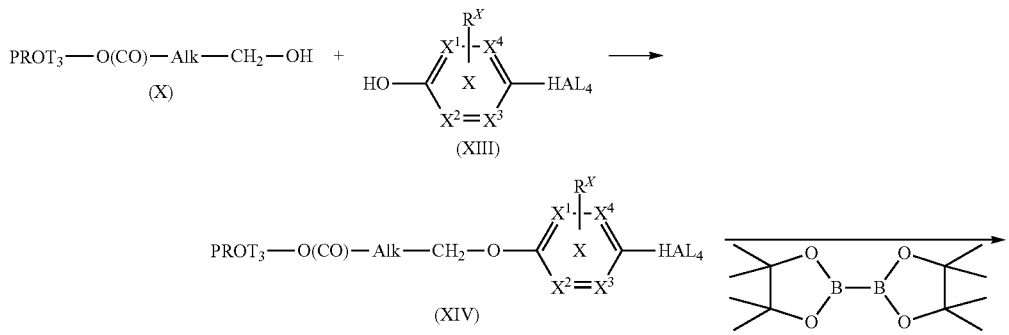
Step 3D
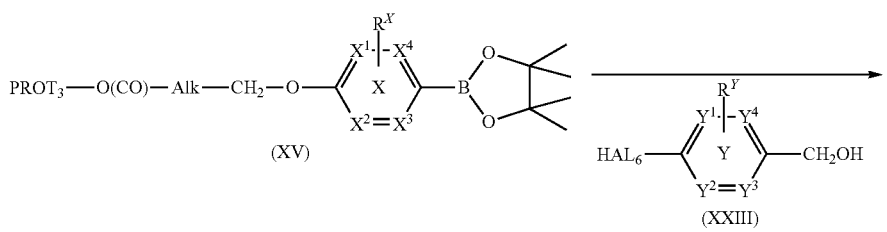

Step 4D

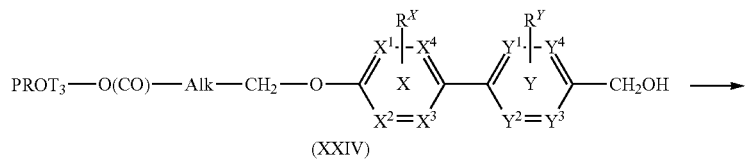

(XXIV)

Step 5D

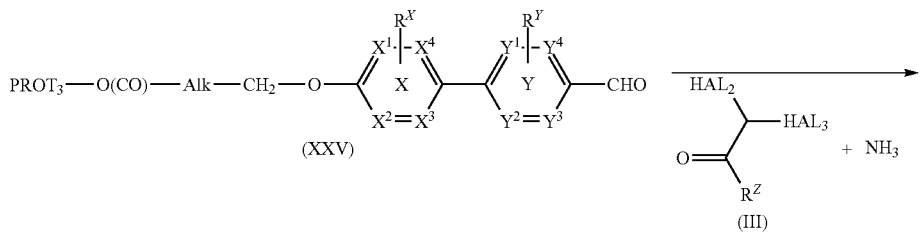

(XXV)                                                (III)

Step 6D

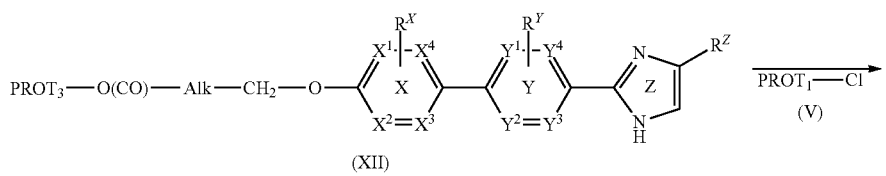

(XII)

Step 7D

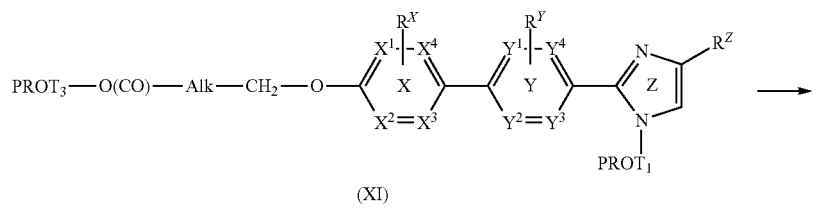

(XI)

Step 8D

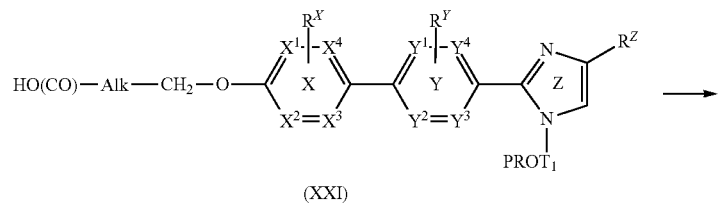

(XXI)

Step 9d

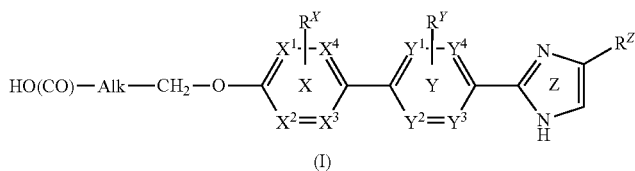

(I)

(in the above-mentioned reaction formula, $HAL_6$ represents a halogen atom, $PROT_4$ represents a protective group for a carboxyl group, and the other symbols have the same meanings as defined above.)

(Method A)

Step 1A

As Compound (II) and Compound (III), those in which $HAL_1$, $HAL_2$ and $HAL_3$ are a chlorine atom, bromine atom or iodine atom can be used.

A ring-forming reaction of Compound (II) or a salt thereof and Compound (III) or a salt thereof and ammonia can be carried out, for example, according to the description of J. J. Baldwin et al., Journal of Medicinal Chemistry, 29(6), 1065-1080, 1986, etc., in a suitable solvent, in the presence of a base. As the solvent, water, and an alcoholic solvent such as methanol, ethanol, etc. can be used alone or in admixture. The base can be optionally used an organic base such as an alkali metal acetate (for example, sodium acetate), etc. The reaction can be carried out firstly heating Compound (III) or a salt thereof at 90 to 100° C. in the presence of a base, and after cooling, adding Compound (II) or a salt thereof and ammonia to the mixture, under ice-cooling to 50° C., preferably room temperature to 40° C.

Step 2A

Compound (V) may be mentioned that in which $PROT_1$ is, for example, a protective group for the polar functional group which is generally used in the organic synthetic chemistry as described in "Protective Groups in Organic Synthesis" T. W. Greene, P. M. G. Wuts, John Wiley and Sons 1991, and such a protective group may be mentioned, for example, 2-(trimethylsilyl)ethoxymethyl group, t-butoxycarbonyl group, benzyloxycarbonyl group, benzyl group, 9-fluorenylmethoxycarbonyl group, 2,2,2-trichloroethoxycarbonyl group, etc.

The reaction of Compound (IV) formed in Step 1A with Compound (V) can be carried out depending on the kind of a protective group according to the conventional method of introducing the protective group to the polar functional group. For example, when $PROT_1$ is 2-(trimethylsilyl)ethoxymethyl group or benzyl group, it can be carried out in the presence of a strong base in an aprotic polar solvent. The aprotic polar solvent may be suitably used, for example, N,N-dimethylformamide, N,N-dimethylacetamide, N-methylpyrrolidone, etc., and the strong base may be suitably used, for example, an alkali metal hydride (sodium hydride, lithium hydride) or an alkali metal carbonate (potassium carbonate). The reaction can be carried out at −20 to 50° C., preferably under ice-cooling to room temperature.

Step 3A

Compound (VII) may be mentioned that in which $PROT_2$ is, for example, a protective group for the hydroxyl group which is generally used in the organic synthetic chemistry as described in "Protective Groups in Organic Synthesis" T. W. Greene, P. M. G. Wuts, John Wiley and Sons 1991, and such a protective group may be mentioned, for example, benzyl group, trimethylsilyl group, t-butyldimethylsilyl group, etc.

The coupling reaction of Compound (VI) or a salt thereof formed in Step 2A and Compound (VII) or a salt thereof can be carried out, for example, according to the method described in Advanced Organic Chemistry Part B (F. A. Carey & R. J. Sundberg, Springer), etc., in the presence of a palladium catalyst and a base in a suitable solvent. The —B(OH)$_2$ portion of Compound (VII) may be protected, if necessary, and, for example, the —B(OH)$_2$ portion may form 4,4,5,5-tetramethyl-1, 3-dioxaboran-2-yl group with the protective group. The solvent may be used water, an amide solvent such as N,N-dimethylformamide, etc., an ether solvent such as tetrahydrofuran, 1,4-dioxane, dimethoxyethane, etc, and toluene, etc., singly or in combination of admixture thereof. The palladium catalyst may be used palladium chloride, palladium acetate, tetrakis(triphenylphosphine) palladium, etc., and the base may be used an alkali metal base such as sodium carbonate, potassium carbonate, potassium phosphate, sodium hydroxide, etc., and cesium carbonate, etc. If necessary, a ligand such as 1,1'-bis(diphenylphosphino)ferrocene and 2-dicyclohexylphosphino-2',6'-dimethoxybiphenyl, etc., may be used. The reaction can be carried out at room temperature to 150° C., preferably at 60 to 120° C.

Step 4A

The reaction of removing the protective group ($PROT_2$) from Compound (VIII) formed in Step 3A can be carried out by the deprotecting method of the protective group for the hydroxyl group which is generally used in the organic synthetic chemistry as described in "Protective Groups in Organic Synthesis" T. W. Greene, P. M. G. Wuts, John Wiley and Sons 1991, and optimum method can be optionally selected depending on the kind of the protective group. For example, when $PROT_2$ is benzyl group, removal of the protective group can be carried out in the presence of a palladium catalyst such as palladium hydroxide, palladium carbon, etc., in an alcohol solvent such as methanol, ethanol, etc., or an ether solvent such as tetrahydrofuran, 1,4-dioxane, etc., under hydrogen atmosphere.

Step 5A

Compound (Xa) and (Xb) may be mentioned those in which $PROT_3$ is, for example, a protective group for the carboxyl group which is generally used in the organic synthetic chemistry as described in "Protective Groups in Organic Synthesis" T. W. Greene, P. M. G. Wuts, John Wiley and Sons 1991, and such a protective group may be mentioned, for example, an alkyl group such as methyl group, ethyl group, etc., benzyl group, t-butyl group, allyl group, etc.

The dehydration reaction of Compound (IX) or a salt thereof formed in Step 4A and Compound (Xa) or a salt thereof can be carried out, for example, according to the method described in Advanced Organic Chemistry Part B (F. A. Carey & R. J. Sundberg, Springer), Okuda, M.; Tomioka, K.; Tetrahedron Lett [TELEAY] 1994, 35 (26), 4585-4586, etc., in the presence of a dehydrating agent in a suitable solvent. The solvent may be used an ether solvent such as tetrahydrofuran, 1,4-dioxane, etc., a halogenated aliphatic hydrocarbon solvent such as methylene chloride, etc., and toluene singly or in combination of admixture thereof. The dehydrating agent may be used an azodicarboxylic acid derivative such as tetramethylazodicarboxamide, diethylazodicarboxylate, etc., a trialkylphosphine such as tri-n-butylphosphine, etc.; and a triarylphosphine such as triphenylphosphine, etc. The reaction can be carried out at 0 to 80° C. The reaction can be also carried out by using a corresponding p-toluenesulfonate (Xb) led from Compound (Xa), and reacting it with Compound (IX) under the similar reaction conditions as in Step 2A.

Step 6A

The reaction of removing the protective group ($PROT_1$) from Compound (XI) formed in Step 5A can be carried out, for example, by the deprotecting method of the protective group which is generally used in the organic synthetic chemistry as described in "Protective Groups in Organic Synthesis" T. W. Greene, P. M. G. Wuts, John Wiley and Sons 1991, and optimum method can be optionally selected depending on the kind of the protective group. For example, when $PROT_1$ is 2-(trimethylsilyl)ethoxymethyl group, it can be carried out by treating with an acid such as hydrochloric acid, trifluoroacetic acid, methanesulfonic acid, etc., in water, a water-miscible ether solvent such as 1,4-dioxane, tetrahydrofuran, etc., or an alcohol solvent such as methanol, ethanol, etc., or in the absence of a solvent. The reaction can be practiced suitably at room temperature. Also, when $PROT_1$ is benzyl group, it can be carried out by treating with a palladium catalyst such as palladium hydroxide-carbon, etc., under hydrogen atmosphere in a water-miscible ether solvent such as tetrahydrofuran, etc., or an alcohol solvent such as methanol, ethanol, etc.

Step 7A

The reaction of removing the protective group ($PROT_3$) from Compound (XII) formed in Step 6A can be carried out, for example, by the deprotecting method of the protective group for the carboxyl group which is generally used in the organic synthetic chemistry as described in "Protective Groups in Organic Synthesis" T. W. Greene, P. M. G. Wuts, John Wiley and Sons 1991, and optimum method can be optionally selected depending on the kind of the protective group. For example, when $PROT_3$ is an alkyl group such as methyl group, ethyl group, etc., it can be carried out according to the conventional manner in the ester hydrolysis, and, for example, it can be carried out by treating with an alkali metal hydroxide such as potassium hydroxide, sodium hydroxide, etc., in water, an alcohol solvent such as methanol, ethanol, etc., or an ether solvent such as tetrahydrofuran, 1,4-dioxane, etc. Also, when $PROT_3$ is benzyl group, removal of the protective group can be carried out in the presence of a palladium catalyst such as palladium hydroxide, palladium carbon, etc., under hydrogen atmosphere in an alcohol solvent such as methanol, ethanol, etc., or an ether solvent such as tetrahydrofuran, 1,4-dioxane, etc. Also, when $PROT_3$ is tert-butyl group, it can be carried out by treating with an acid such as hydrochloric acid, trifluoroacetic acid, methanesulfonic acid, etc., in water, a water-miscible ether solvent such as 1,4-dioxane, tetrahydrofuran, etc., or an alcohol solvent such as methanol, ethanol, etc. or in the absence of a solvent. The reaction can be carried out suitably at room temperature.

(Method B)

Step 1B

Compound (XIII) may be used that in which $HAL_4$ is chlorine atom, bromine atom or iodine atom, and preferred is that in which it is bromine atom. The dehydration reaction of Compound (X) or a salt thereof and Compound (XIII) or a salt thereof can be carried out in the same manner as in the dehydration reaction of the above-mentioned Step 5A.

Step 2B

The reaction of Compound (XIV) or a salt thereof formed in Step 1B and bis(pinacolato)diboron can be carried out in the presence of a palladium catalyst and a base in a suitable solvent. The solvent may be used an amide solvent such as N,N-dimethylformamide, etc., an ether solvent such as dimethylsulfoxide, tetrahydrofuran, 1,4-dioxane, dimethoxyethane, etc., and toluene, etc., singly or in admixture thereof. The palladium catalyst may be used palladium chloride, palladium acetate, tetrakis(triphenylphosphine) palladium, etc., and if necessary, a ligand such as 1,1'-bis(diphenylphosphino)ferrocene, etc., may be used. The base may be used an alkali metal base such as sodium carbonate, potassium carbonate, potassium acetate, potassium phosphate, sodium hydroxide, etc., and cesium carbonate, etc. The reaction can be carried out at room temperature to 150° C., preferably at 80 to 120° C.

Step 3B

Compound (XVI) may be used that in which $HAL_5$ is chlorine atom, bromine atom or iodine atom. The coupling reaction of Compound (XV) or a salt thereof formed in Step 2B and Compound (XVI) or a salt thereof can be carried out in the same manner as in the coupling reaction of the above-mentioned Step 3A.

Step 4B

The reaction of Compound (XVII) or a salt thereof formed in Step 3B and hydroxylamine can be carried out, for example, according to the conventional manner of the reaction of the cyano group and hydroxylamine described in U.S. Pat. No. 5,576,447, etc., in a suitable solvent. The solvent may be used water, an alcohol solvent such as methanol, ethanol, etc., and an ether solvent such as tetrahydrofuran, 1,4-dioxane, etc., singly or in admixture thereof. The reaction can be carried out at room temperature to 100° C., preferably at 50 to 80° C.

The product is treated with acetic acid-acetic anhydride according to the conventional method, then, and stirred in a solvent such as an alcohol solvent including methanol, ethanol, etc., or an ether solvent such as tetrahydrofuran, etc., in the presence of a palladium catalyst such as palladium carbon, etc., under hydrogen atmosphere to obtain Compound (XVIII). The reaction can be carried out under ice-cooling to 50° C., preferably at room temperature.

Step 5B

Conversion from Compound (XIXa) to Compound (XX) can be carried out by reacting oxalyl chloride to Compound (XIXa) or a salt thereof in a suitable solvent, the solvent is distilled off from the reaction mixture, (trimethylsilyl)diazomethane is reacted with a product in a suitable solvent, and hydrobromic acid is acted on the product.

The solvent to be used in the reaction of Compound (XIXa) and oxalyl chloride may be mentioned methylene chloride and tetrahydrofuran, etc., and the reaction can be carried out by adding a catalytic amount of N,N-dimethylformamide at −20 to 40° C., preferably under ice-cooling to room temperature.

As the solvent to be used in the subsequent reaction with trimethylsilyldiazomethane, there may be mentioned acetonitrile, tetrahydrofuran, methylene chloride, etc. The reaction can be carried out at −20 to 40° C., preferably under ice-cooling to room temperature.

The hydrobromic acid treatment can be carried out by gradually adding hydrobromic acid to the product of the previous reaction. The reaction can be carried out at −20 to 40° C., preferably under ice-cooling to room temperature.

Also, conversion from Compound (XIXb) to Compound (XX) can be carried out by reacting Compound (XIXb) or a salt thereof with a brominating reagent such as dioxane dibromide, etc., in a suitable solvent such as methanol, etc.

Step 6B

The reaction of Compound (XVIII) formed in Step 4B and Compound (XX) or a salt thereof formed in Step 5B can be carried out, for example, according to the method described in I. M. Mallick et al., Journal of the American Chemical Society, 106(23), 7252-7254, 1984, etc., in the presence of a base in a suitable solvent. The solvent may be used water, an alcohol solvent such as methanol, ethanol, etc., an aprotic polar solvent such as N,N-dimethylformamide, N-methylpyrrolidone, etc., a halogenated hydrocarbon solvent such as methylene chloride, etc., and tetrahydrofuran, acetonitrile, etc., singly or in admixture thereof, and the base may be used an alkali metal base such as potassium hydrogen carbonate, potassium carbonate, sodium ethylate, etc. The reaction can be carried out at room temperature to 100° C., preferably at 50 to 80° C.

Subsequent Step 7B is the same as the reaction (Step 7A) corresponding to the above-mentioned Method A, and can be carried out in the same manner as mentioned above.

Step 8B

The coupling reaction of Compound (XIV) or a salt thereof formed in Step 1B and Compound (XXVI) or a salt thereof can be carried out in the same manner as in the coupling reaction of the above-mentioned Step 3A.

(Method C)

Step 1C, Step 2C, Step 3C and Step 4C are each the same with Step 1A, Step 2A, Step 1B and Step 2B, respectively, and can be carried out in the same manner as mentioned above.

Step 5C

The reaction of Compound (VI) or a salt thereof formed in Step 2C and Compound (XV) or a salt thereof formed in Step 4C can be carried out in the same manner as in the coupling reaction of the above-mentioned Step 3A.

Step 6C

The reaction of removing the protective group ($PROT_3$) from Compound (XI) formed in Step 5C can be carried out in the same manner as in the removal reaction of the protective group of the above-mentioned Step 7A.

Step 7C

The reaction of removing the protective group (PROT$_1$) from Compound (XXI) formed in Step 6C can be carried out in the same manner as in the removal reaction of the protective group of the above-mentioned Step 6A.

Step 8C

The reaction of forming Compound (XXVII) from Compound (VI) formed in Step 2C is the same as Step 2B, and can be carried out in the same manner as in the same.

Step 9C

The reaction of Compound (XIV) or a salt thereof formed in Step 3C and Compound (XXVII) or a salt thereof formed in Step 8C can be carried out in the same manner as in the coupling reaction of the above-mentioned Step 3A.

(Method D)

Step 1D

Compound (XXII) may be mentioned that in which HAL$_6$ is chlorine atom, bromine atom or iodine atom, PROT$_4$ is, for example, by the deprotecting method of the protective group for the carboxyl group which is generally used in the organic synthetic chemistry as described in "Protective Groups in Organic Synthesis" T. W. Greene, P. M. G. Wuts, John Wiley and Sons 1991, and such a protective group may be mentioned an ester residue, for example, an alkyl group such as methyl group, ethyl group, etc., benzyl group, etc.

Reduction of Compound (XXII) can be carried out according to the conventional manner of reducing a carboxylic acid ester to an alcohol, by treating with a reducing agent in a suitable solvent. The solvent may be used an ether solvent such as tetrahydrofuran, ether, etc., and the reducing agent may be used isobutyl aluminum hydride, lithium aluminum hydride, lithium borohydride, etc. The reaction can be carried out at −30° C. to room temperature.

Step 2D, Step 3D

The reactions of Step 2D and Step 3D are the same as the above-mentioned Step 3C and the above-mentioned Step 4C, and can be carried out in the same manner as mentioned above.

Step 4D

The reaction of Step 4D can be carried out in the same manner as the reaction of the above-mentioned Step 3B.

Step 5D

Oxidation of Compound (XXIV) or a salt thereof formed in Step 4D can be carried out according to the conventional manner of oxidation of an alcohol, and for example, can be carried out by Swern oxidation. It can be carried out by using an oxidizing agent such as dimethylsulfoxide in a suitable solvent. The solvent may be used a halogenated hydrocarbon solvent such as methylene chloride, etc., and an activating agent may be preferably used oxalyl chloride, etc. The reaction can be carried out at −78° C. to room temperature.

Step 6D

Compound (XXV) formed in Step 5D is subjected to the same reaction as in the above-mentioned Step 1A to prepare Compound (XII).

Step 7D

The reaction of Compound (XII) formed in Step 6D and Compound (V) can be carried out in the same manner as in the above-mentioned Step 2A.

Step 8D

The reaction of removing the protective group (PROT$_3$) from Compound (XI) formed in Step 7D can be carried out in the same manner as in the removal reaction of the protective group of the above-mentioned Step 7A.

Step 9D

The reaction of removing the protective group (PROT$_1$) from Compound (XXI) formed in Step 8D can be carried out in the same manner as in the removal reaction of the protective group of the above-mentioned Step 7C.

In the above-mentioned (Method A), (Method B), (Method C) and (Method D), isolation and/or purification of the product is/are carried out, these can be carried out by the usual separation and/or purification methods such as extraction, fractional crystallization, various kinds of chromatographies, etc.

The thus obtained Compound (I) can be converted into a pharmaceutically acceptable salt depending on necessity by treating with an acid or a base corresponding to the pharmaceutically acceptable salt in a suitable solvent. Also, the compound or a pharmaceutically acceptable salt thereof of the present invention include both of their solvent and hydrate, etc. For example, an alkali metal salt of Compound (I) can be obtained by treating Compound (I) with an alkali metal hydroxide such as sodium hydroxide, potassium hydroxide, etc., or an alkali metal carbonate such as sodium carbonate, potassium carbonate, etc., in water, a water-soluble ether solvent such as tetrahydrofuran, 1,4-dioxane, etc., a nitrile solvent such as acetonitrile, etc., an alcohol solvent such as methanol, ethanol, etc., or a mixed solvent thereof, to prepare a corresponding metal salt. Moreover, a hydrate or a solvate thereof can be obtained by treating the same with water, a water-containing solvent or a hydrated solvent or other solvents according to the conventional manner.

When Compound (I) or a pharmaceutically acceptable salt thereof of the present invention is a racemic mixture or contains optical isomers, each optical isomer can be separated according to the usual optically resolving means. For example, it can be optically resolved to a desired optical isomer by a fractional crystallization method due to a salt with an optically active acid or base, or by passing through a column filled with an optically active carrier. Or else, an optically active isomer of the compound of the formula (I) or a pharmaceutically acceptable salt thereof may be synthesized by using an optically pure starting material or a compound configuration of which has already been known.

The thus obtained continuous arycyclic compound (I) or a pharmaceutically acceptable salt thereof of the present invention can be formulated as a medical composition containing a pharmaceutically effective amount of the compound and a pharmaceutically acceptable carrier. The pharmaceutically acceptable carrier may be mentioned a binder (for example, hydroxypropylcellulose, polyvinyl alcohol, polyvinylpyrrolidone, polyethylene glycol), an excipient (for example, lactose, sucrose, mannitol, sorbitol, corn starch, potato starch, crystalline cellulose, calcium carbonate), a lubricant (for example, magnesium stearate, calcium stearate, talc), a disintegrator (for example, low-substitution degree hydroxypropylcellulose, cross-linked carboxymethylcellulose) and a wetting agent (for example, sodium laurylsulfate), etc.

The continuous arycyclic compound (I) or a pharmaceutically acceptable salt thereof of the present invention can be administered orally or parenterally, and can be used as a suitable medical preparation. As a suitable medical preparation for oral administration, there may be mentioned, for example, a solid preparation such as a tablet, granule, capsule, powder, etc., or a solution preparation, suspension preparation or emulsion preparation, etc. As a suitable medical preparation for parenteral administration, there may be mentioned a suppository, an injection using distilled water for injection, physiological saline or aqueous glucose solution, etc., or infusion preparation, or inhalations, etc.

An administration dose of the continuous arycyclic compound (I) or a pharmaceutically acceptable salt thereof of the present invention may vary depending on an administration method, an age, body weight and conditions of a patient, and in the case of oral administration, it is generally administered 0.001 to 100 mg/kg/day, preferably 0.1 to 30 mg/kg/day, more preferably 0.1 to 10 mg/kg/day, once a day or dividing into 2 to 4 times. In the case of parenteral administration, it is preferably administered 0.0001 to 10 mg/kg/day, and once a day or dividing into several times. Also, when it is transmucosally administered, it is preferably administered 0.001 to 100 mg/kg/day, once a day or dividing into several times.

In the following, the present invention will be explained in detail by referring to Examples and Experimental examples, but the present invention is not limited by these. Also, in the chemical formulae in Examples, a hydrogen atom on a saturated ring, a hydrogen atom on an alkyl chain, and a hydrogen atom on a nitrogen atom are sometimes omitted.

EXAMPLES

Example 1

[Formula 23]

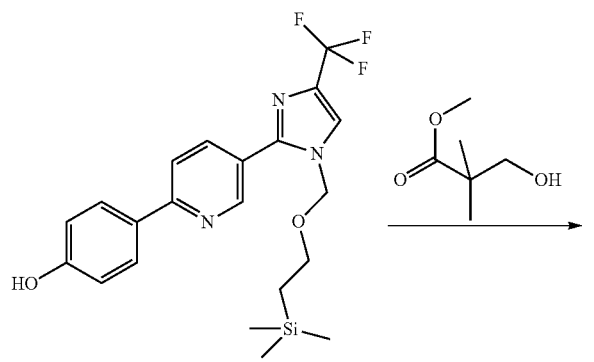

1) After 40% diethyl azodicarboxylate-toluene solution (313.1 μL) was added dropwise to a tetrahydrofuran (3 mL) solution containing 4-{5-[4-(trifluoromethyl)-1-{[2-(trimethylsilyl)ethoxy]methyl}-1H-imidazol-2-yl]pyridin-2-yl}phenol (150 mg), methyl hydroxylpivalate (65.9 μL) and triphenylphosphine (180.7 mg) under ice-cooling, the mixture was stirred at room temperature for one hour, and at 70° C. overnight. To the mixture were further added methyl hydroxypivalate (22 μL), triphenylphosphine (63 mg) and 40% diethyl azodicarboxylate-toluene solution (109 μL), and the mixture was stirred at 70° C. for one hour. After cooling a temperature of the reaction mixture to room temperature, the mixture was concentrated under reduced pressure and the resulting residue was purified by silica gel column chromatography (n-hexane:ethyl acetate=88:12 to 76:24) to obtain methyl 2,2-dimethyl-3-(4-{5-[4-(trifluoromethyl)-1-{[2-(trimethylsilyl)ethoxy]methyl}-1H-imidazol-2-yl]pyridin-2-yl}phenoxy)propanoate (144.2 mg).

MS (m/z): 550 [M+H]$^+$

[Formula 24]

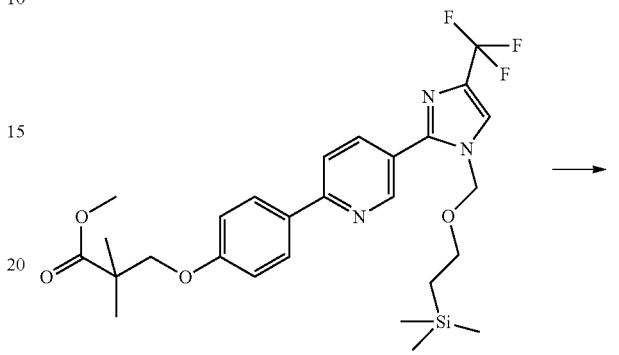

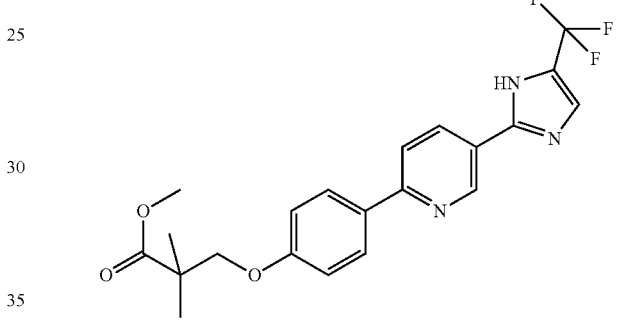

2) In trifluoroacetic acid (2.9 mL) and water (0.3 mL) was dissolved methyl 2,2-dimethyl-3-(4-{5-[4-(trifluoromethyl)-1-{[2-(trimethylsilyl)ethoxy]methyl}-1H-imidazol-2-yl]pyridin-2-yl}phenoxy)propanoate (144 mg) under ice-cooling, and the mixture was stirred at room temperature overnight. To the residue obtained by concentrating the reaction mixture under reduced pressure were added chloroform and a saturated aqueous sodium bicarbonate solution. The formed insoluble material was dissolved in methanol and combined with the organic layer. The organic layer was washed with water, and concentrated under reduced pressure. The obtained residue was pulverized by cooled ether, collected by filtration and dried to obtain methyl 2,2-dimethyl-3-(4-{5-[5-(trifluoromethyl)-1H-imidazol-2-yl]pyridin-2-yl}phenoxy)propanoate (85.9 mg).

MS (m/z): 420 [M+H]$^+$

[Formula 25]

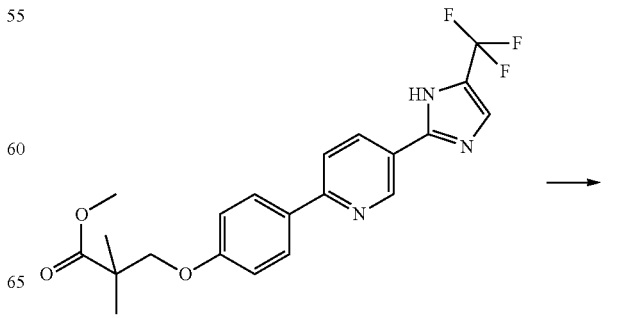

-continued

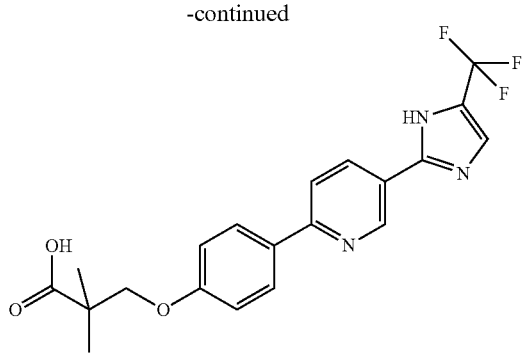

3) In tetrahydrofuran (0.85 mL) and methanol (0.85 mL) was dissolved methyl 2,2-dimethyl-3-(4-{5-[5-(trifluoromethyl)-1H-imidazol-2-yl]pyridin-2-yl}phenoxy)propanoate (85 mg), 2N aqueous sodium hydroxide solution (1013.35 µL) was added to the solution, and the mixture was stirred at room temperature overnight. Acetic acid was added to the reaction mixture, and the mixture was concentrated under reduced pressure. To the residue were added acetic acid, water, and a phosphate buffer (pH 6.8), and after stirring the mixture, the organic layer was separated and concentrated under reduced pressure. After purification of the residue by LC-MS, it was dissolved in water and ethyl acetate, and the liquids were separated by adding 0.1 N phosphate buffer (pH 7.0). The organic layer was separated and concentrated under reduced pressure, and the obtained residue was pulverized by cooled ethyl acetate and collected by filtration to obtain 2,2-dimethyl-3-(4-{5-[5-(trifluoromethyl)-1H-imidazol-2-yl]-pyridin-2-yl}phenoxy)propanoic acid (29.3 mg).

MS (m/z): 406 [M+H]$^+$

[Formula 26]

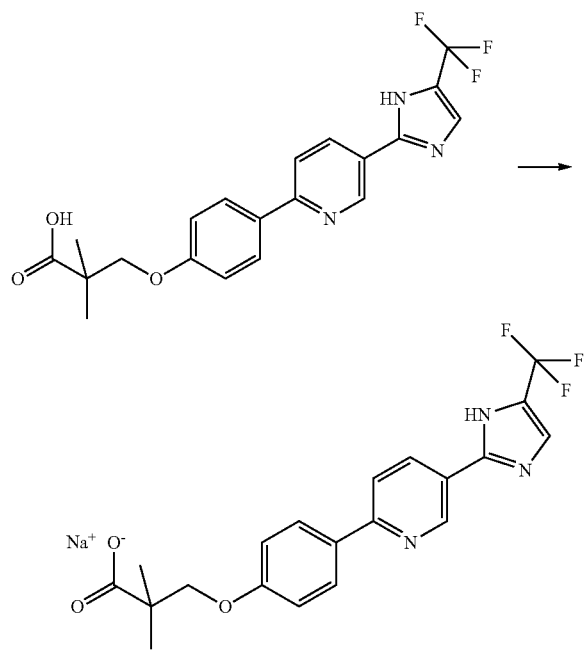

4) In tetrahydrofuran (2.5 mL) was dissolved 2,2-dimethyl-3-(4-{5-[5-(trifluoromethyl)-1H-imidazol-2-yl]pyridin-2-yl}phenoxy)propanoic acid (250 mg), 10M aqueous sodium hydroxide solution (65 µL) was added to the solution dividing into several times, and the mixture was stirred at room temperature overnight. The precipitate was collected by filtration, washed with tetrahydrofuran (1 mL), and dried at 40° C. under reduced pressure to obtain sodium 2,2-dimethyl-3-(4-{5-[5-(trifluoromethyl)-1H-imidazol-2-yl]pyridin-2-yl}phenoxy)propanoate (216 mg).

MS (m/z): 404 [M−Na]$^-$

Example 2

[Formula 27]

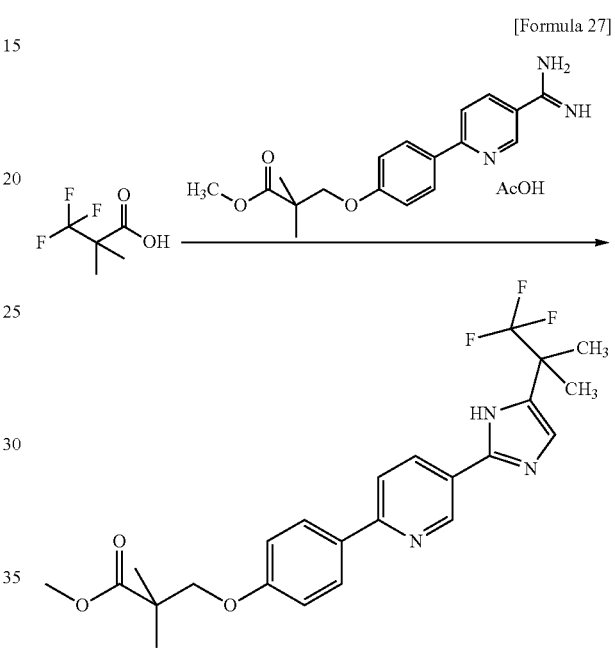

1) In methylene chloride (5 mL) was dissolved 3,3,3-trifluoro-2,2-dimethylpropanoic acid (250 mg), and oxalyl chloride (279 µL) was added dropwise to the mixture. After adding N,N-dimethylformamide (one drop), the mixture was stirred at room temperature for one hour. After concentrating the reaction mixture under reduced pressure, acetonitrile (2 mL) was added to the residue. 2M (trimethylsilyl)diazomethane-n-hexane solution (1682 µL) was added dropwise to the mixture under ice-cooling, and the resulting mixture was stirred at room temperature for one hour. The reaction mixture was ice-cooled, 48% hydrobromic acid (272 µL) was added dropwise, and the mixture was stirred for 15 minutes. To the reaction mixture were added ether and water, and the liquids were separated. The organic layer was separated, washed with a saturated aqueous sodium bicarbonate solution, dried over anhydrous sodium sulfate and concentrated under reduced pressure. The obtained oily substance was dissolved in methylene chloride (5 mL), methyl 3-(4-{5-[amino(imino)methyl]pyridin-2-yl}-phenoxy)-2,2-dimethylpropanoate acetate (558 mg), potassium carbonate (885 mg) and saturated brine (5 mL) were added to the solution, and the mixture was stirred at 45° C. overnight. To the reaction mixture were added ethyl acetate and water, and the liquids were separated. The organic layer was separated, washed with water, dried over anhydrous sodium sulfate, and the residue obtained by concentrating the reaction mixture under reduced pressure was purified by silica gel column chromatography (chloroform:methanol=100:0 to 95:5) to obtain methyl 2,2-dimethyl-3-(4-{5-[5-(2,2,2-trifluoro-1,1-dimethylethyl)-1H-imidazol-2-yl]pyridin-2-yl}phenoxy)propanoate (178 mg).

MS (m/z): 462 [M+H]+

[Formula 28]

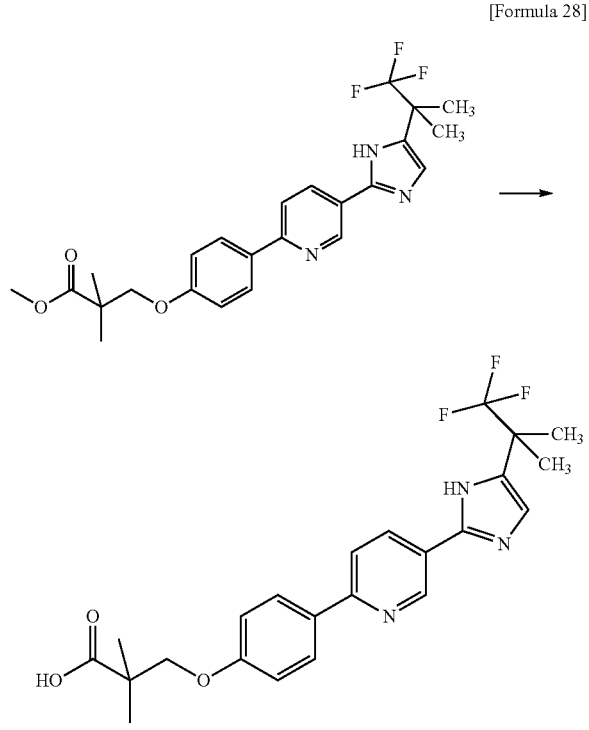

2) In methanol (2 mL) and tetrahydrofuran (2 mL) was dissolved methyl 2,2-dimethyl-3-(4-{5-[5-(2,2,2-trifluoro-1,1-dimethylethyl)-1H-imidazol-2-yl]pyridin-2-yl}-phenoxy)propanoate (176 mg), 2N aqueous sodium hydroxide solution (900 μL) was added to the solution, and the mixture was stirred at room temperature overnight.

Acetic acid (3 mL) was added to the mixture, and the resulting mixture was concentrated under reduced pressure. Water was added to the residue and the formed solid was collected by filtration and dried to obtain 2,2-dimethyl-3-(4-{5-[5-(2,2,2-trifluoro-1,1-dimethylethyl)-1H-imidazol-2-yl]pyridin-2-yl}phenoxy)propanoic acid (167 mg).

MS (m/z): 448 [M+H]+

[Formula 29]

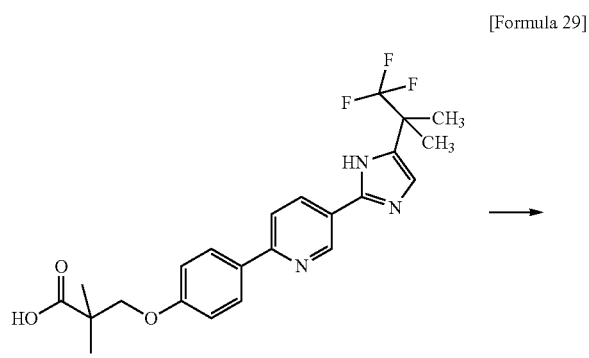

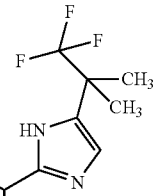

3) In acetonitrile (4 mL) was suspended 2,2-dimethyl-3-(4-{5-[5-(2,2,2-trifluoro-1,1-dimethylethyl)-1H-imidazol-2-yl]pyridin-2-yl}phenoxy)propanoic acid (175 mg), and 2N aqueous sodium hydroxide solution (391 μL) was added dropwise to the suspension. After adding acetonitrile (1 mL), the reaction mixture was stirred at room temperature overnight. Methanol was added until the reaction mixture became uniform solution, and tar-state insoluble material was separated by filtration. The filtrate was concentrated under reduced pressure, and the obtained solid residue was pulverized by ether, collected by filtration, washed with ether, and dried at room temperature in vacuum to obtain sodium 2,2-dimethyl-3-(4-{5-[5-(2,2,2-trifluoro-1,1-dimethylethyl)-1H-imidazol-2-yl]pyridin-2-yl}phenoxy)propanoate (174 mg).

MS (m/z): 446 [M−Na]−

Example 3

[Formula 30]

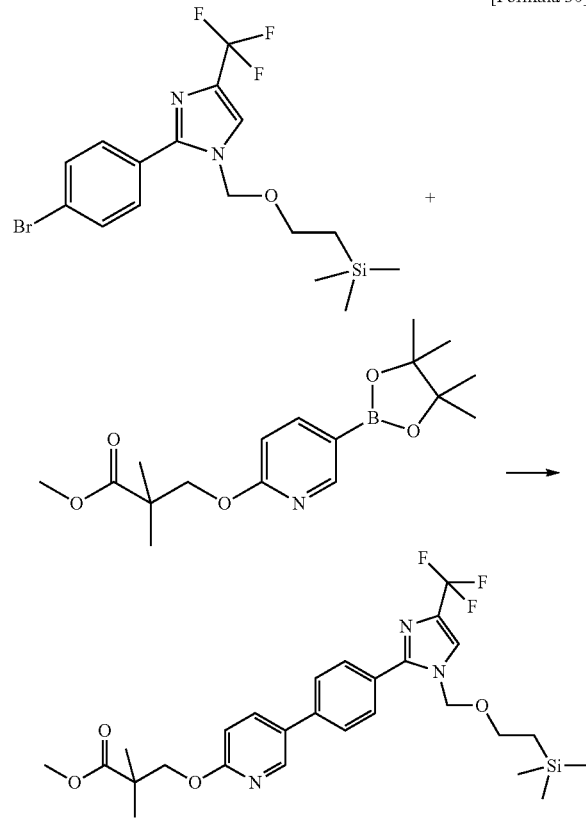

1) By using 2-(4-bromophenyl)-4-(trifluoromethyl)-1-{[2-(trimethylsilyl)ethoxy]-methyl}-1H-imidazole (400 mg) and methyl 2,2-dimethyl-3-{[5-(4,4,5,5-tetramethyl-1,3,2-dioxaboloran-2-yl)pyridin-2-yl]oxy}propanoate (537 mg), the procedure was carried out in the same manner as in Reference example 1-3) to obtain methyl 2,2-dimethyl-3-[(5-{4-[4-(trifluoromethyl)-1-{[2-(trimethylsilyl)ethoxy]methyl}-1H-imidazol-2-yl]phenyl}pyridin-2-yl)oxy]propanoate (490 mg).

MS (m/z): 550 [M+H]+

[Formula 32]

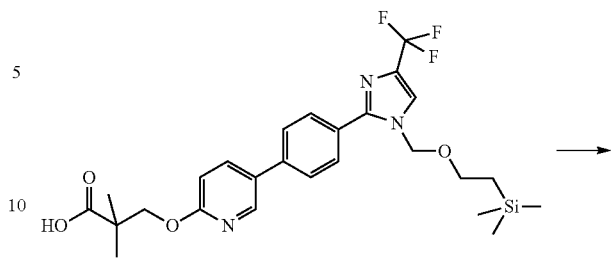

[Formula 31]

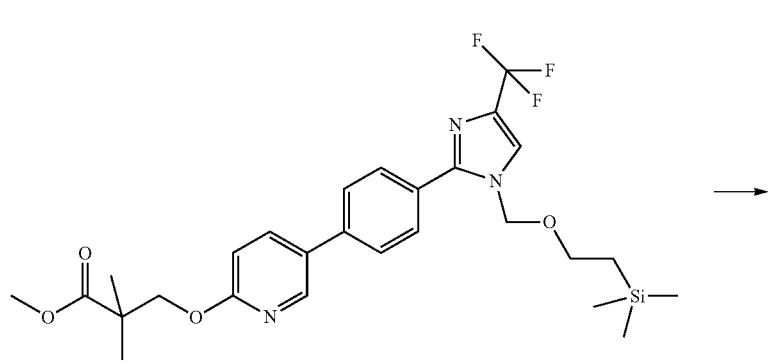

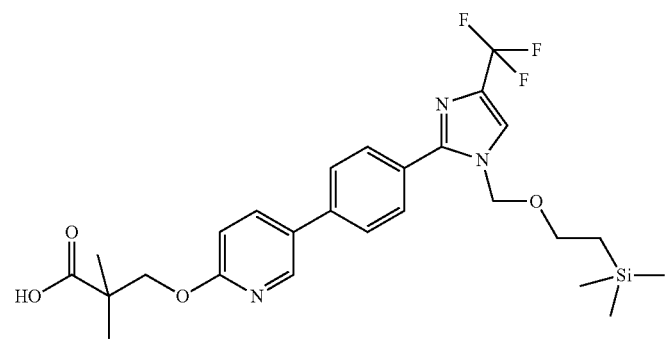

2) In ethanol (10 mL) was dissolved methyl 2,2-dimethyl-3-[(5-{4-[4-(trifluoromethyl)-1-{[2-(trimethylsilyl)ethoxy]methyl}-1H-imidazol-2-yl]phenyl}pyridin-2-yl)oxy]-propanoate (490 mg), 2N aqueous sodium hydroxide solution (2.2 mL) was added to the solution, and the mixture was stirred at room temperature overnight. The reaction mixture was ice-cooled and neutralized with 2N hydrochloric acid (2.2 mL), then, ethyl acetate and saturated brine were added to the mixture, and the liquids were separated. The organic layer was separated, dried over anhydrous sodium sulfate, and concentrated under reduced pressure. The residue was purified by silica gel column chromatography (chloroform: methanol=100:0 to 97:3) to obtain 2,2-dimethyl-3-[(5-{4-[4-(trifluoromethyl)-1-{[2-(trimethylsilyl)ethoxy]methyl}-1H-imidazol-2-yl]phenyl}-pyridin-2-yl)oxy]propanoic acid (287 mg).

MS (m/z): 536 [M+H]+

-continued

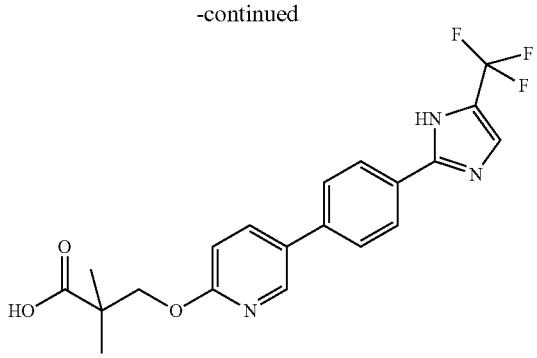

3) In trifluoroacetic acid (10 mL) and water (1 mL) was dissolved 2,2-dimethyl-3-[(5-{4-[4-(trifluoromethyl)-1-{[2-(trimethylsilyl)ethoxy]methyl}-1H-imidazol-2-yl]-phenyl}pyridin-2-yl)oxy]propanoic acid (287 mg), and the mixture was stirred at room temperature overnight. The residue obtained by concentrating the reaction mixture under reduced pressure was dissolved in acetic acid, and the mixture was concentrated under reduced pressure. The obtained solid residue was pulverized by adding ether, collected by filtration, washed with ether and dried to obtain 2,2-dimethyl-3-[(5-{4-[5-(trifluoromethyl)-1H-imidazol-2-yl]phenyl}pyridin-2-yl)oxy]propanoic acid (175 mg).

MS (m/z): 406 [M+H]$^+$

Example 4

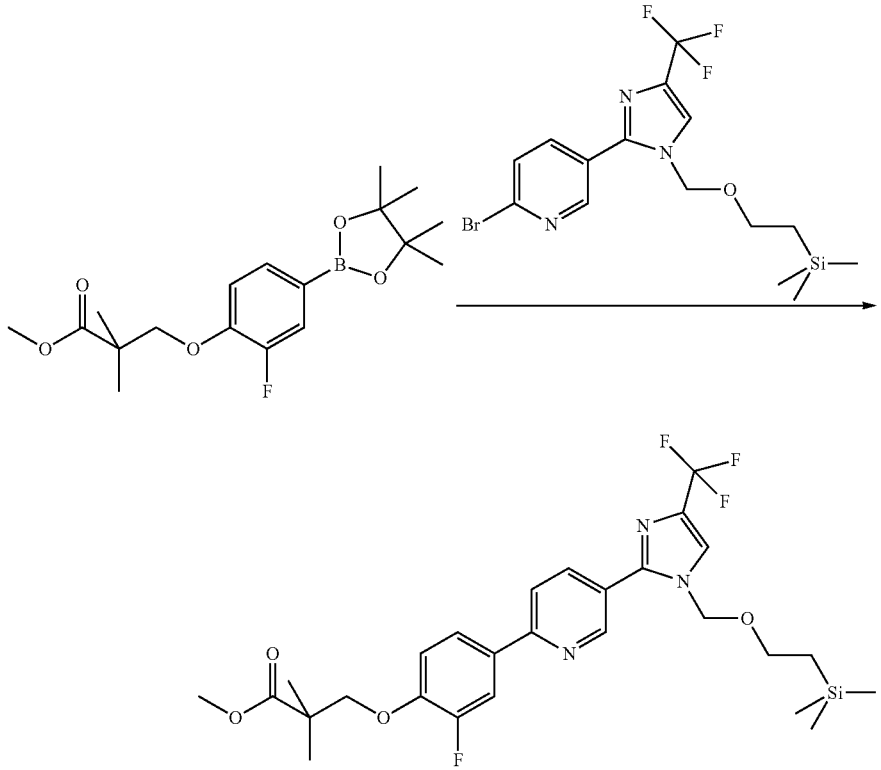

[Formula 33]

1) By using methyl 3-[2-fluoro-4-(4,4,5,5-tetramethyl-1,3,2-dioxaboloran-2-yl)-phenoxy]-2,2-dimethylpropanoate (375 mg) and 2-bromo-5-[4-(trifluoromethyl)-1-{[2-(trimethylsilyl)ethoxy]methyl}-1H-imidazol-2-yl]pyridine (300 mg), the procedure was carried out in the same manner as in Reference example 1-3) to obtain methyl 3-(2-fluoro-4-{5-[4-(trifluoromethyl)-1-{[2-(trimethylsilyl)ethoxy]methyl}-1H-imidazol-2-yl]pyridin-2-yl}phenoxy)-2,2-dimethylpropanoate.

MS (m/z): 568 [M+H]$^+$

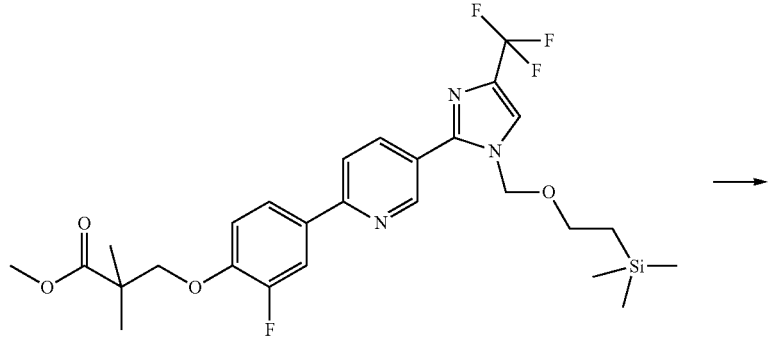

[Formula 34]

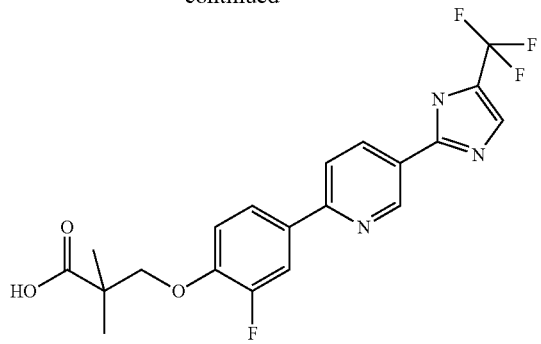

1) In tetrahydrofuran (5.0 mL) were mixed 2-chloro-4-methyl-5-[4-(trifluoromethyl)-1-{[2-(trimethylsilyl)ethoxy]methyl}-1H-imidazol-2-yl]pyridine (400 mg), methyl 2,2-dimethyl-3-[4-(4,4,5,5-tetramethyl-1,3,2-dioxaboloran-2-yl)phenoxy]propanoate (409.4 mg), palladium acetate (22.9 mg), potassium phosphate (433.3 mg), 2-dicyclohexylphosphino-2',6'-dimethoxybiphenyl (83.8 mg), and the mixture was stirred at 70° C. in nitrogen atmosphere overnight. A saturated aqueous sodium bicarbonate solution was added to the mixture and after stirring the mixture, ethyl acetate was added to the same and the liquids were separated. The organic layer was separated, washed with saturated brine, and the residue obtained by concentrating the organic layer under reduced pressure was purified by silica gel column chromatography (n-hexane:ethyl acetate=90:10 to 65:35) to obtain methyl 2,2-dimethyl-3-(4-{4-methyl-5-[4-(trifluoromethyl)-1-{[2-(trimethylsilyl)ethoxy]methyl}-1H-imidazol-2-yl]pyridin-2-yl}phenoxy)-propanoate (152 mg).
MS (m/z): 564 [M+H]+

2) In methanol (6 mL) and tetrahydrofuran (3 mL) was dissolved methyl 3-(2-fluoro-4-{5-[4-(trifluoromethyl)-1-{[2-(trimethylsilyl)ethoxy]methyl}-1H-imidazol-2-yl]pyridin-2-yl}phenoxy)-2,2-dimethylpropanoate obtained in the above-mentioned 1), 10N aqueous sodium hydroxide solution (0.3 mL) was added to the solution, and the mixture was stirred at room temperature overnight, and then refluxed for 4 hours. The residue obtained by concentrating the reaction mixture under reduced pressure was dissolved in trifluoroacetic acid (10 mL) and water (1 mL), and the mixture was stirred at room temperature overnight. The residue obtained by concentrating the reaction mixture under reduced pressure was dissolved in acetic acid (2 mL), and the solution was concentrated under reduced pressure. To the obtained residue were added ethyl acetate (0.5 mL) and water (10 mL), and the mixture was stirred room temperature for 2 hours. Powdery solid was collected by filtration, washed with water, dried, washed with ether and dried to obtain 3-(2-fluoro-4-{5-[5-(trifluoromethyl)-1H-imidazol-2-yl]pyridin-2-yl}phenoxy)-2,2-dimethylpropanoic acid (281 mg).
MS (m/z): 424 [M+H]+

Example 5

[Formula 35]

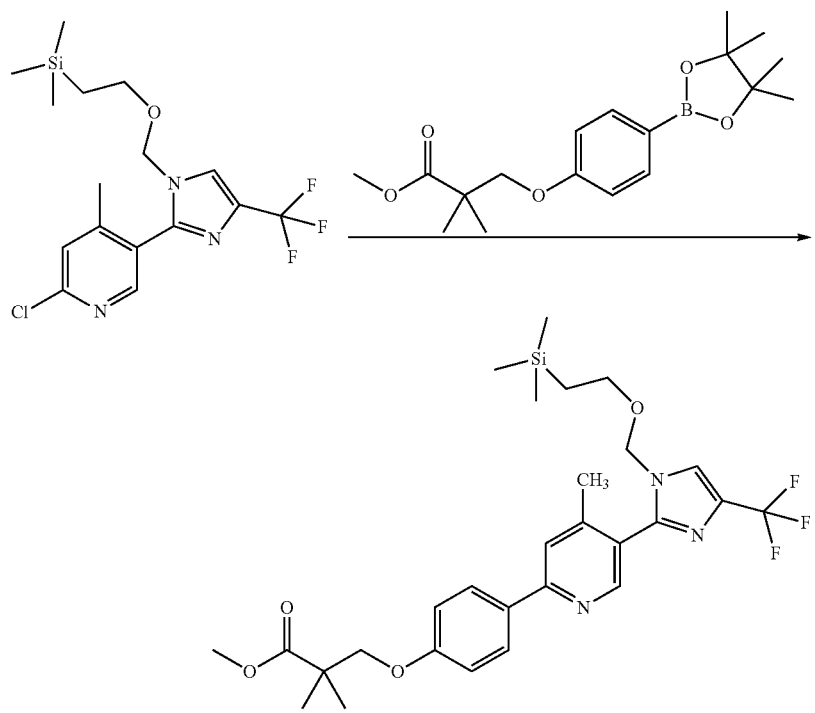

[Formula 36]

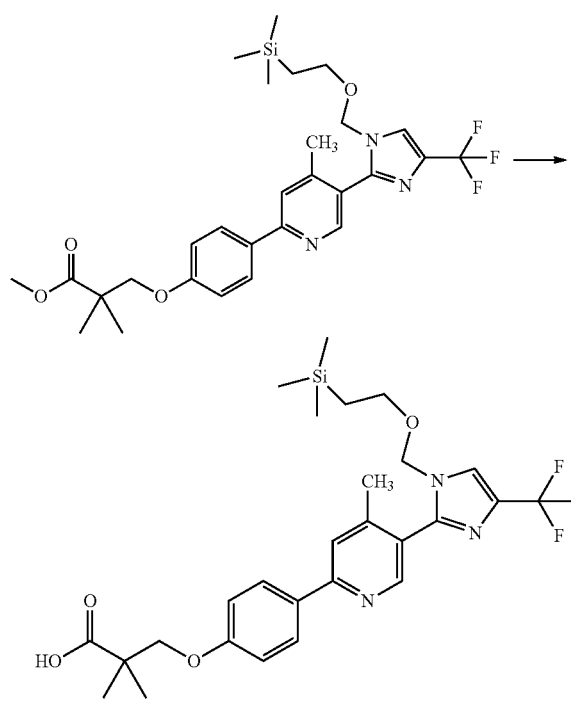

2) By using methyl 2,2-dimethyl-3-(4-{4-methyl-5-[4-(trifluoromethyl)-1-{[2-(trimethylsilyl)ethoxy]methyl}-1H-imidazol-2-yl]pyridin-2-yl}phenoxy)propanoate (150 mg), the procedure was carried out in the same manner as in Example 3-2) to obtain 2,2-dimethyl-3-(4-{4-methyl-5-[4-(trifluoromethyl)-1-{[2-(trimethylsilyl)-ethoxy]methyl}-1H-imidazol-2-yl]pyridin-2-yl}phenoxy)propanoic acid (141 mg).

MS (m/z): 550 [M+H]$^+$

[Formula 37]

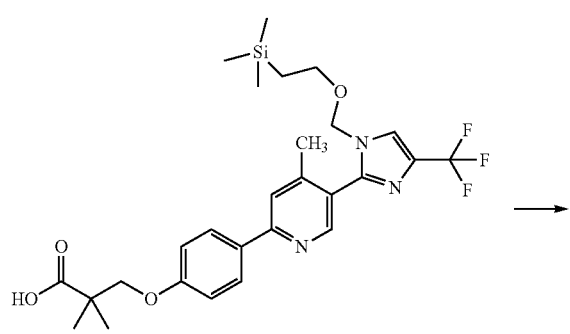

3) By using 2,2-dimethyl-3-(4-{4-methyl-5-[4-(trifluoromethyl)-1-{[2-(trimethylsilyl)-ethoxy]methyl}-1H-imidazol-2-yl]pyridin-2-yl}phenoxy)propanoic acid (140 mg), the procedure was carried out in the same manner as in Example 3-3) to obtain 2,2-dimethyl-3-(4-{4-methyl-5-[5-(trifluoromethyl)-1H-imidazol-2-yl]pyridin-2-yl}-phenoxy)propanoic acid (35.9 mg).

MS (m/z): 420 [M+H]$^+$

Example 6

[Formula 38]

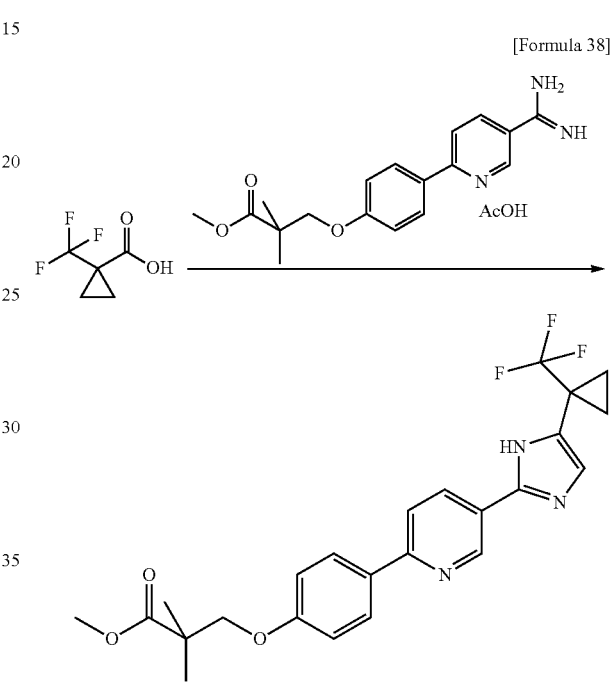

1) By using 1-(trifluoromethyl)-1-cyclopropanecarboxylic acid (300 mg), and methyl 3-(4-{5-[amino(imino)methyl]pyridin-2-yl}phenoxy)-2,2-dimethylpropanoate acetate (453 mg), the procedure was carried out in the same manner as in Example 2-1) to obtain methyl 2,2-dimethyl-3-[4-(5-{5-[1-(trifluoromethyl)cyclopropyl]-1H-imidazol-2-yl}pyridin-2-yl)phenoxy)propanoate (439 mg).

MS (m/z): 460 [M+H]$^+$

[Formula 39]

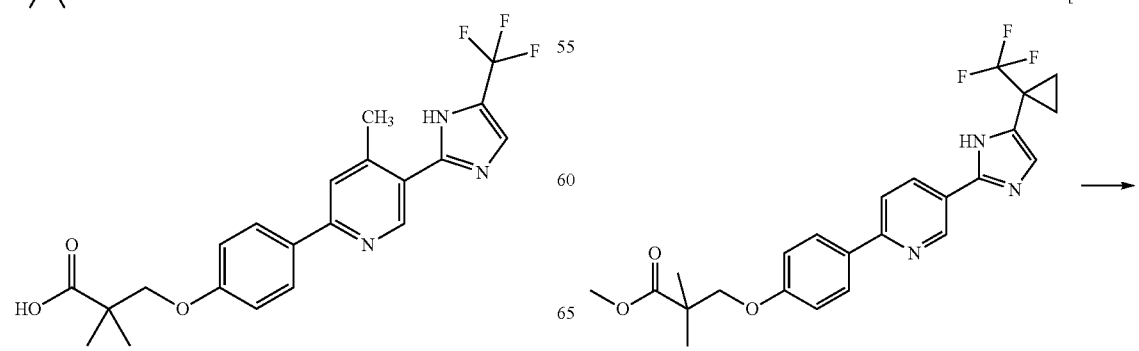

43
-continued

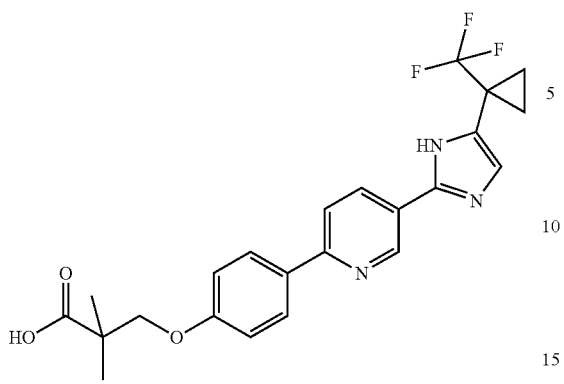

2) By using methyl 2,2-dimethyl-3-[4-(5-{5-[1-(trifluoromethyl)cyclopropyl]-1H-imidazol-2-yl}pyridin-2-yl)phenoxy)propanoate (369 mg), the procedure was carried out in the same manner as in Example 2-2) to obtain 2,2-dimethyl-3-[4-(5-{5-[1-(trifluoromethyl)cyclopropyl]-1H-imidazol-2-yl}pyridin-2-yl)phenoxy)propanoic acid (320 mg).

MS (m/z):446[M+H]$^+$

[Formula 40]

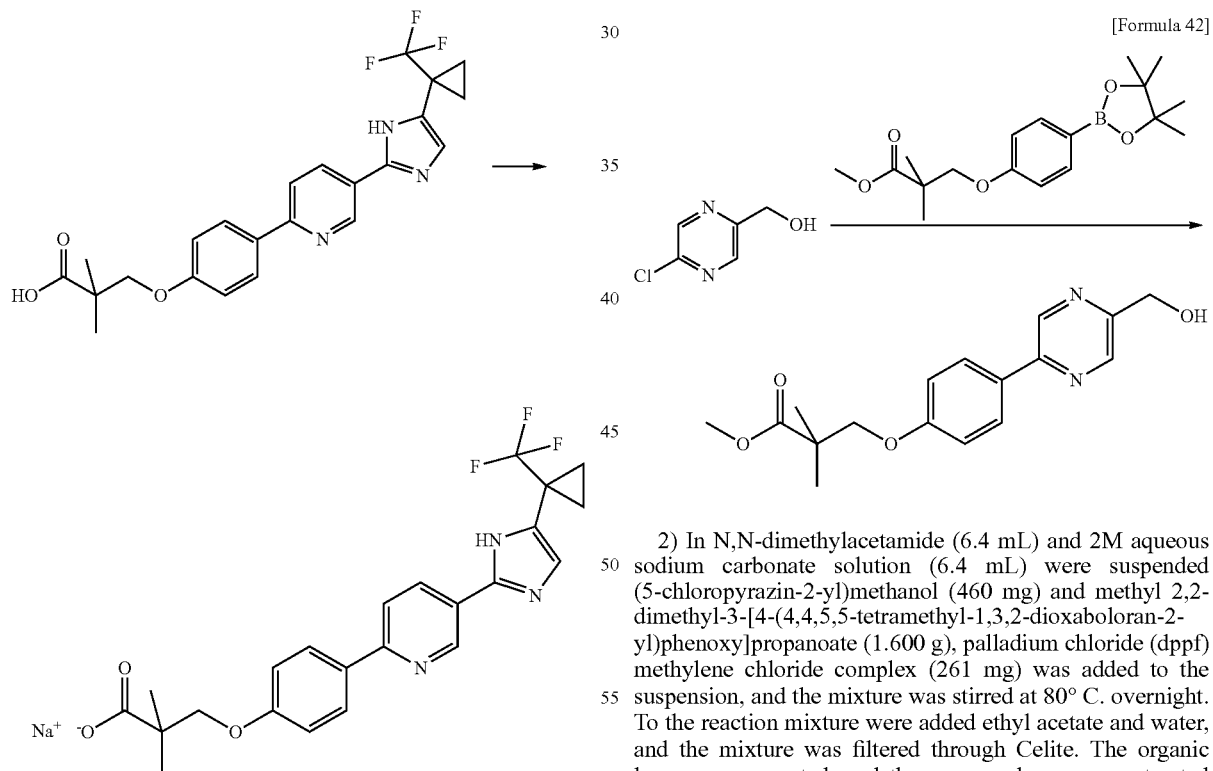

3) By using 2,2-dimethyl-3-[4-(5-{5-[1-(trifluoromethyl)cyclopropyl]-1H-imidazol-2-yl}pyridin-2-yl)phenoxy)propanoic acid (320 mg), the procedure was carried out in the same manner as in Example 2-3) to obtain sodium 2,2-dimethyl-3-[4-(5-{5-[1-(trifluoromethyl)cyclopropyl]-1H-imidazol-2-yl}pyridin-2-yl)phenoxy)propanoate (313 mg).

MS (m/z):444 [M–Na]$^-$

44
Example 7

[Formula 41]

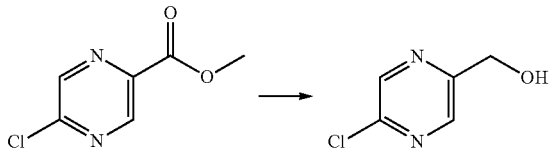

1) In tetrahydrofuran (75 mL) was dissolved methyl 5-chloropyrazin-2-carboxylate (2.589 g), 1M diisobutyl aluminum hydride-tetrahydrofuran solution (30 mL) was added dropwise to the solution at 0° C., and the mixture was stirred at the same temperature for 15 minutes. To the mixture were added water and 1N hydrochloric acid, then, a saturated aqueous sodium bicarbonate solution was added to the same to make the pH to 7. The mixture was filtered through Celite, and then, extracted with chloroform 3 times. The organic layer was separated, dried over anhydrous sodium sulfate, and the residue obtained by concentrating the same under reduced pressure was purified by silica gel column chromatography (n-hexane:ethyl acetate=90:10 to 65:35 to 50:50) to obtain (5-chloropyrazin-2-yl)methanol (465 mg).

MS (m/z): 147/145 [M+H]$^+$

[Formula 42]

2) In N,N-dimethylacetamide (6.4 mL) and 2M aqueous sodium carbonate solution (6.4 mL) were suspended (5-chloropyrazin-2-yl)methanol (460 mg) and methyl 2,2-dimethyl-3-[4-(4,4,5,5-tetramethyl-1,3,2-dioxaboloran-2-yl)phenoxy]propanoate (1.600 g), palladium chloride (dppf) methylene chloride complex (261 mg) was added to the suspension, and the mixture was stirred at 80° C. overnight. To the reaction mixture were added ethyl acetate and water, and the mixture was filtered through Celite. The organic layer was separated, and the aqueous layer was extracted twice with ethyl acetate. The organic layers were combined, washed twice with water, washed with saturated brine, dried over anhydrous sodium sulfate, and concentrated under reduced pressure. The obtained residue was purified by silica gel column chromatography (n-hexane:ethyl acetate=70:30 to 40:60 to 0:100) to obtain methyl 3-{4-[5-(hydroxylmethyl)pyrazin-2-yl]phenoxy}-2,2-dimethylpropanoate (660 mg).

MS (m/z): 317 [M+H]$^+$

[Formula 43]

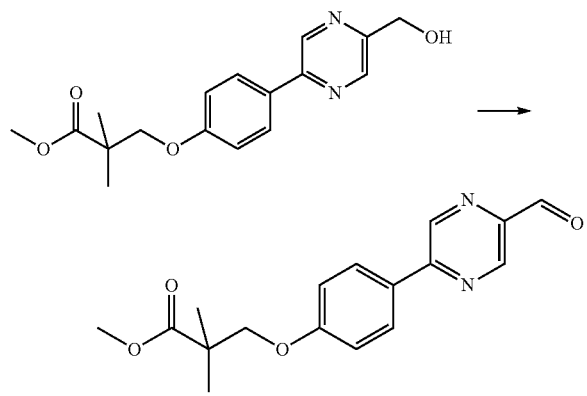

3) To a methylene chloride (11 mL) solution of oxalyl chloride (355 μL) was added dropwise a methylene chloride (2 mL) solution of dimethylsulfoxide (450 μL) at −78° C., and the mixture was stirred for 15 minutes. To the mixture was added dropwise a methylene chloride (6 mL) solution of methyl 3-{4-[5-(hydroxymethyl)pyrazin-2-yl]-phenoxy}-2,2-dimethylpropanoate (655 mg) at −78° C., and the mixture was stirred for 10 minutes, and the mixture was stirred for 1 hour and 30 minutes. Triethylamine (2.05 mL) was added to the mixture, the temperature of the mixture was raised to 0° C., and the mixture was stirred for 30 minutes. To the reaction mixture were added a saturated aqueous ammonium chloride solution and ethyl acetate, and the organic layer was separated. The aqueous layer was extracted twice with ethyl acetate. The organic layers were combined, washed twice with water, and with saturated brine, dried over anhydrous sodium sulfate, and concentrated under reduced pressure. The obtained residue was purified by silica gel column chromatography (n-hexane:ethyl acetate=95:5 to 75:25) to obtain methyl 3-{4-[5-formylpyrazin-2-yl]phenoxy}-2,2-dimethylpropanoate (585 mg).

MS (m/z): 315 [M+H]$^+$

[Formula 44]

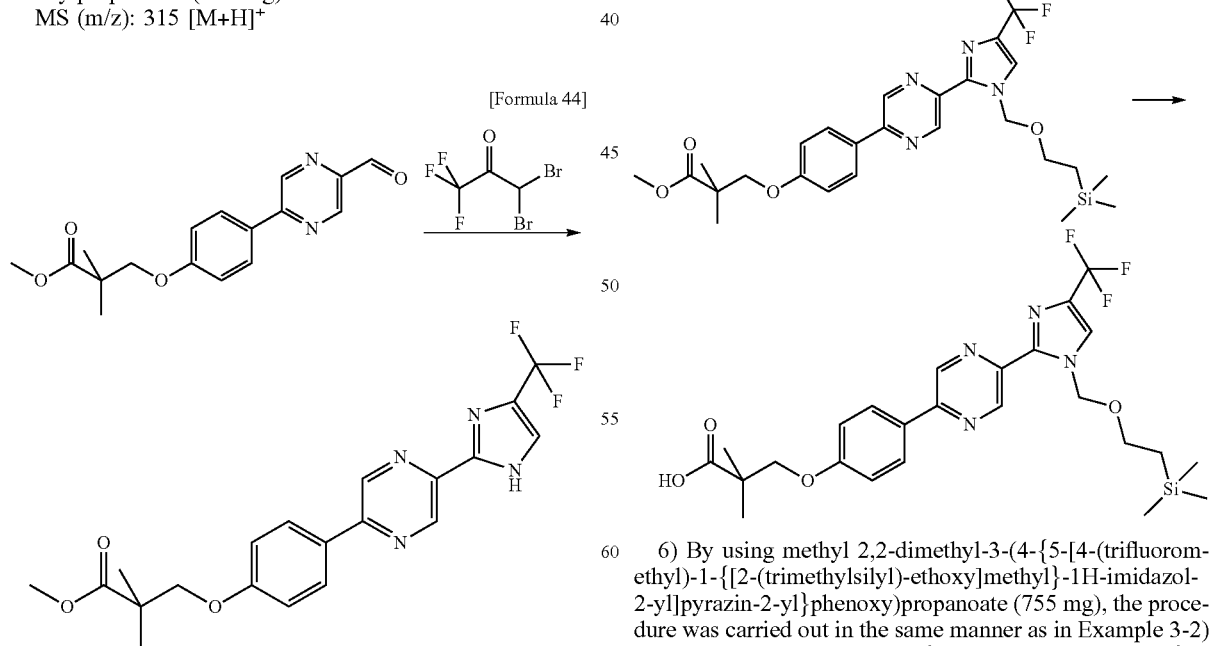

4) By using methyl 3-{4-[5-formylpyrazin-2-yl]phenoxy}-2,2-dimethylpropanoate (580 mg), the procedure was carried out in the same manner as in Reference example 1-1) to obtain methyl 2,2-dimethyl-3-(4-{5-[5-(trifluoromethyl)-1H-imidazol-2-yl]pyrazin-2-yl}phenoxy)propanoate (640 mg).

MS (m/z): 421 [M+H]$^+$

[Formula 45]

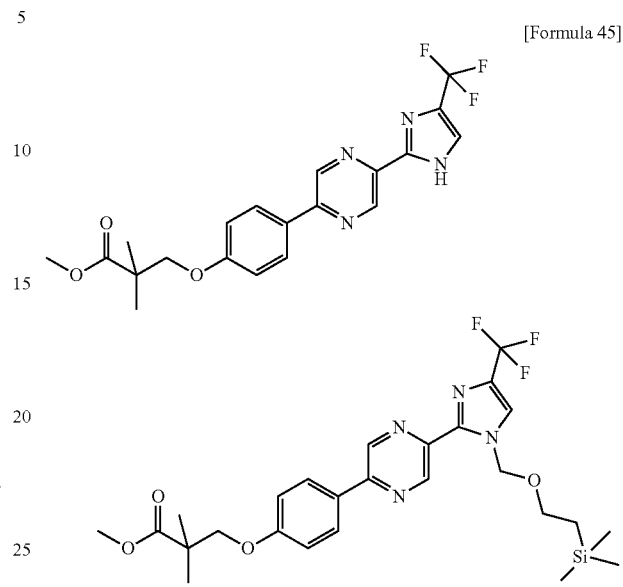

5) By using methyl 2,2-dimethyl-3-(4-{5-[5-(trifluoromethyl)-1H-imidazol-2-yl]-pyrazin-2-yl}phenoxy)propanoate (640 mg), the procedure was carried out in the same manner as in Reference example 1-2) to obtain methyl 2,2-dimethyl-3-(4-{5-[4-(trifluoromethyl)-1-{[2-(trimethylsilyl)ethoxy]methyl}-1H-imidazol-2-yl]pyrazin-2-yl}phenoxy)propanoate (759 mg).

MS (m/z): 551 [M+H]$^+$

[Formula 46]

6) By using methyl 2,2-dimethyl-3-(4-{5-[4-(trifluoromethyl)-1-{[2-(trimethylsilyl)-ethoxy]methyl}-1H-imidazol-2-yl]pyrazin-2-yl}phenoxy)propanoate (755 mg), the procedure was carried out in the same manner as in Example 3-2) to obtain 2,2-dimethyl-3-(4-{5-[4-(trifluoromethyl)-1-{[2-(trimethylsilyl)ethoxy]methyl}-1H-imidazol-2-yl]pyrazin-2-yl}phenoxy)propanoic acid (545 mg).

MS (m/z): 537 [M+H]$^+$

47

[Formula 47]

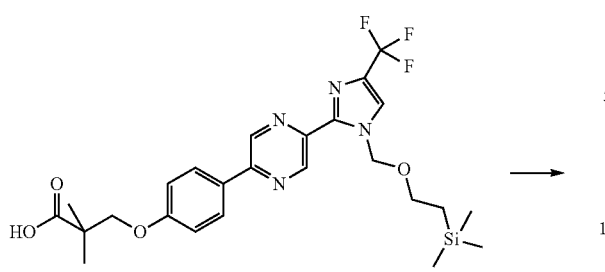

7) By using 2,2-dimethyl-3-(4-{5-[4-(trifluoromethyl)-1-{[2-(trimethylsilyl)ethoxy]-methyl}-1H-imidazol-2-yl]pyrazin-2-yl}phenoxy)propanoic acid (540 mg), the procedure was carried out in the same manner as in Example 3-3) to obtain 2,2-dimethyl-3-(4-{5-[5-(trifluoromethyl)-1H-imidazol-2-yl]pyrazin-2-yl}phenoxy)propanoic acid (335 mg).

MS (m/z): 407 [M+H]$^+$

Example 8

[Formula 48]

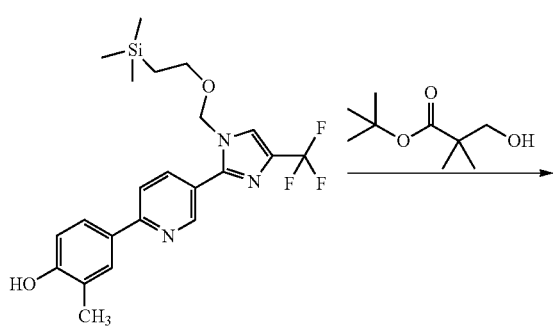

48

1) By using 2-methyl-4-[5-[4-(trifluoromethyl)-1-(2-trimethylsilylethoxymethyl)-imidazol-2-yl]-2-pyridyl]phenol (224 mg) and tert-butyl 3-hydroxy-2,2-dimethylpropanoate (284 mg), the procedure was carried out in the same manner as in Example 1-1) to obtain tert-butyl 2,2-dimethyl-3-[2-methyl-4-[5-[4-(trifluoromethyl)-1-(2-trimethylsilylethoxymethyl)imidazol-2-yl]-2-pyridyl]phenoxy]propanoate (104 mg).

MS (m/z): 606 [M+H]$^+$

[Formula 49]

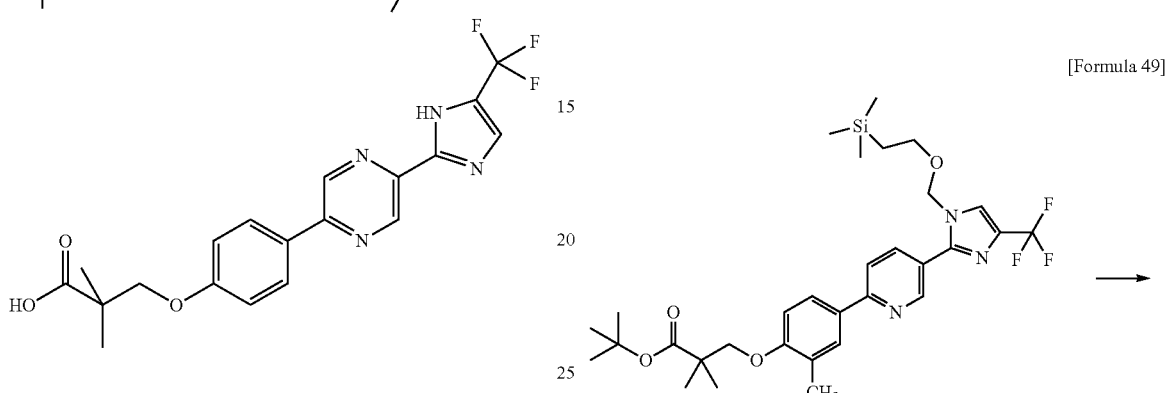

2) In trifluoroacetic acid (5 mL) and water (0.5 mL) was dissolved tert-butyl 2,2-dimethyl-3-[2-methyl-4-[5-[4-(trifluoromethyl)-1-(2-trimethylsilylethoxymethyl)-imidazol-2-yl]-2-pyridyl]phenoxy]propanoate (103 mg), and the mixture was stirred at room temperature overnight. The residue obtained by concentrating the reaction mixture under reduced pressure was dissolved in tetrahydrofuran, and 1N aqueous sodium hydroxide solution was added to the mixture to adjust a pH thereof to 7. To the mixture were added 0.1N phosphate buffer, ethyl acetate and water, and the liquids were separated. The organic layer was separated, dried over anhydrous sodium sulfate, and ether was added to the residue obtained by concentrating the solution under reduced pressure to pulverize the precipitates to obtain 2,2-dimethyl-3-[2-methyl-4-[5-[5-(trifluoromethyl)-1H-imidazol-2-yl]-2-pyridyl]phenoxy]propanoic acid (59.1 mg).

MS (m/z): 420 [M+H]$^+$

By using the corresponding starting materials, the following mentioned compounds were synthesized in the same manner as in Example 8.

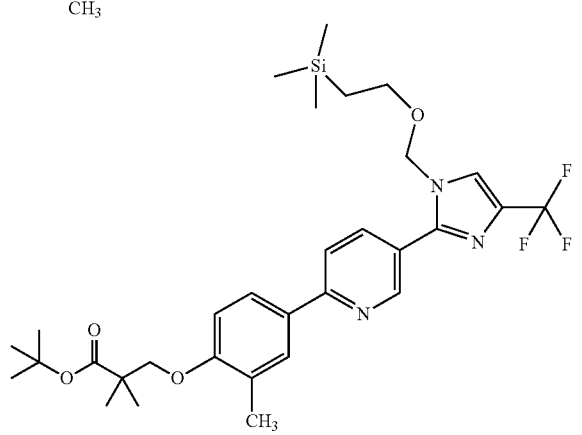

TABLE 1

| Example | Starting substance | Product | MS (m/z) |
|---------|-------------------|---------|----------|
| 9 | | | 420 [M + H]+ |
| 10 | | | 421 [M + H]+ |
| 11 | | | 392 [M + H]+ |
| 12 | | | 402 [M + H]+ |

Example 13

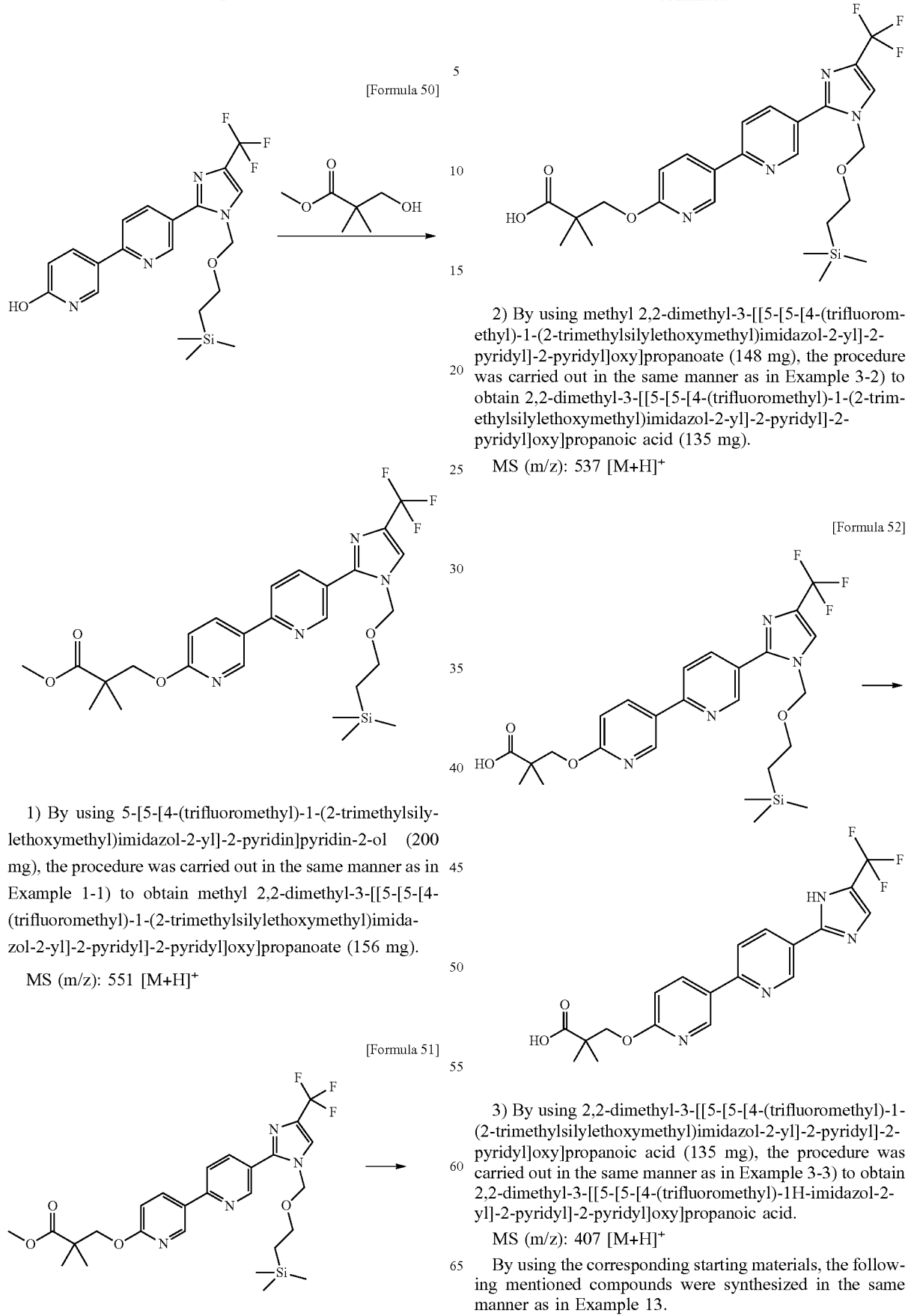

1) By using 5-[5-[4-(trifluoromethyl)-1-(2-trimethylsilylethoxymethyl)imidazol-2-yl]-2-pyridin]pyridin-2-ol (200 mg), the procedure was carried out in the same manner as in Example 1-1) to obtain methyl 2,2-dimethyl-3-[[5-[5-[4-(trifluoromethyl)-1-(2-trimethylsilylethoxymethyl)imidazol-2-yl]-2-pyridyl]-2-pyridyl]oxy]propanoate (156 mg).

MS (m/z): 551 [M+H]+

2) By using methyl 2,2-dimethyl-3-[[5-[5-[4-(trifluoromethyl)-1-(2-trimethylsilylethoxymethyl)imidazol-2-yl]-2-pyridyl]-2-pyridyl]oxy]propanoate (148 mg), the procedure was carried out in the same manner as in Example 3-2) to obtain 2,2-dimethyl-3-[[5-[5-[4-(trifluoromethyl)-1-(2-trimethylsilylethoxymethyl)imidazol-2-yl]-2-pyridyl]-2-pyridyl]oxy]propanoic acid (135 mg).

MS (m/z): 537 [M+H]+

3) By using 2,2-dimethyl-3-[[5-[5-[4-(trifluoromethyl)-1-(2-trimethylsilylethoxymethyl)imidazol-2-yl]-2-pyridyl]-2-pyridyl]oxy]propanoic acid (135 mg), the procedure was carried out in the same manner as in Example 3-3) to obtain 2,2-dimethyl-3-[[5-[5-[4-(trifluoromethyl)-1H-imidazol-2-yl]-2-pyridyl]-2-pyridyl]oxy]propanoic acid.

MS (m/z): 407 [M+H]+

By using the corresponding starting materials, the following mentioned compounds were synthesized in the same manner as in Example 13.

TABLE 2
| Example | Starting substance | Product | MS (m/z) |
|---------|-------------------|---------|----------|
| 14 | 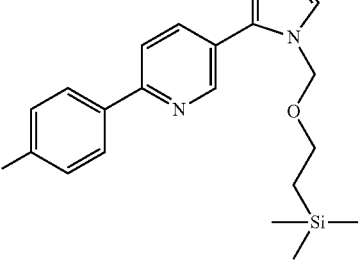 | 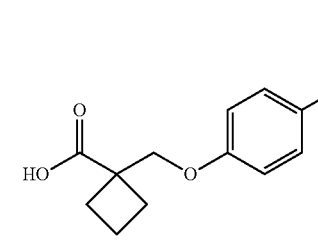 | 418 [M + H]+ |
| 15 | 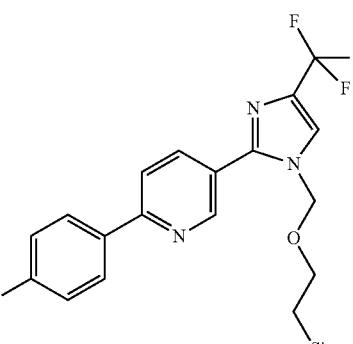 | 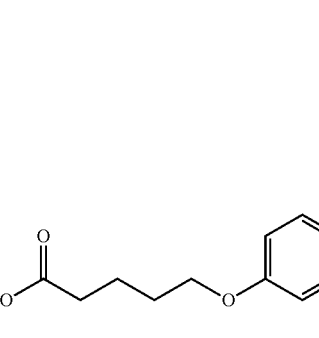 | 406 [M + H]+ |
| 16 | 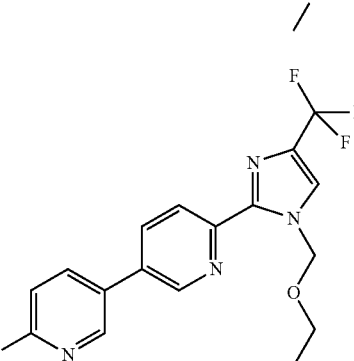 | 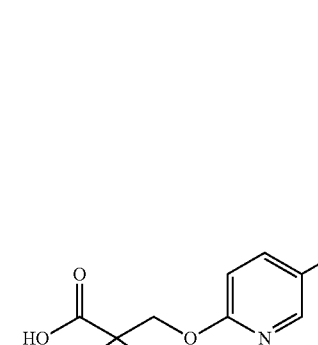 | 433 [M + H]+ |
| 17 | 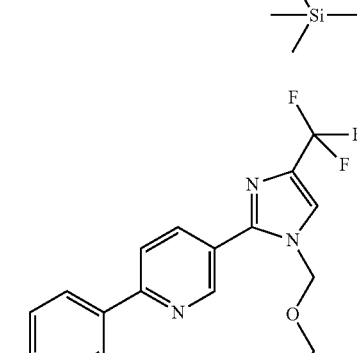 | 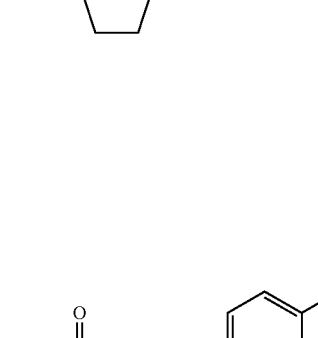 | 433 [M + H]+ |

Example 18
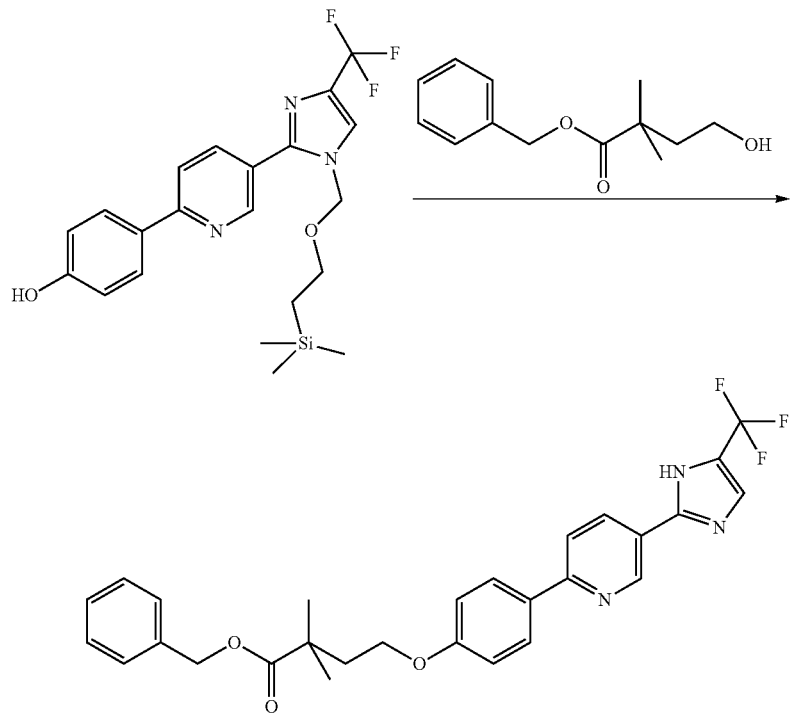
[Formula 53]
1) By using 4-{5-[4-(trifluoromethyl)-1-{[2-(trimethylsilyl)ethoxy]methyl}-1H-imidazol-2-yl]pyridin-2-yl}phenol (400 mg) and benzyl 4-hydroxy-2,2-dimethylbutanoate (306 mg), the procedures were carried out in the same manner as in Example 1-1) and 1-2) to obtain benzyl 2,2-dimethyl-4-[4-[5-[5-(trifluoromethyl)-1H-imidazol-2-yl]-2-pyridin]phenoxy]butanoate (366 mg).
MS (m/z): 510 [M+H]⁺
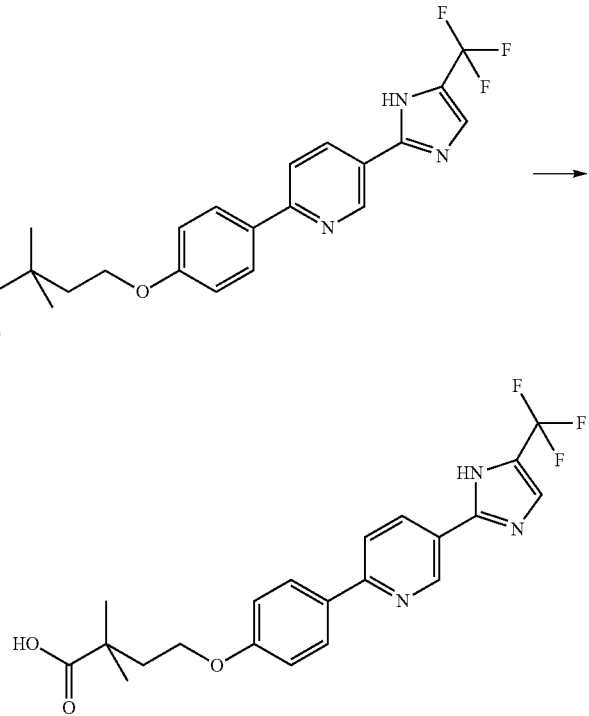
[Formula 54]

2) In tetrahydrofuran (20 mL) was dissolved benzyl 2,2-dimethyl-4-[4-[5-[5-(trifluoromethyl)-1H-imidazol-2-yl]-2-pyridin]phenoxy]butanoate (365 mg), 10% palladium-carbon (400 mg) was added to the solution, and the mixture was stirred under hydrogen atmosphere at room temperature for 6 hours. The palladium-carbon was filtered off, and washed with tetrahydrofuran and chloroform. The filtrate was concentrated under reduced pressure, isopropanol and isopropyl ether were added to the obtained solid residue to suspend therein, and the solid was collected by filtration to obtain 2,2-dimethyl-4-[4-[5-[5-(trifluoromethyl)-1H-imidazol-2-yl]-2-pyridin]phenoxy]butanoic acid (200 mg).

MS (m/z): 420 [M+H]$^+$

Example 19 aqueous ammonium chloride solution and ethyl acetate, and the liquids were separated. The aqueous layer was separated, and extracted with ethyl acetate. The organic layers were combined, washed with water and saturated brine in this order, dried over anhydrous sodium sulfate, and concentrated under reduced pressure. The obtained residue was purified by silica gel column chromatography (n-hexane:ethyl acetate=95:5 to 50:50) to obtain methyl 2-ethyl-2-[[4-[5-[4-(trifluoromethyl)-1-(2-trimethylsilylethoxymethyl)imidazol-2-yl]-2-pyridyl]phenoxy]methyl]butanoate (248 mg).

MS (m/z): 578 [M+H]$^+$

[Formula 55]

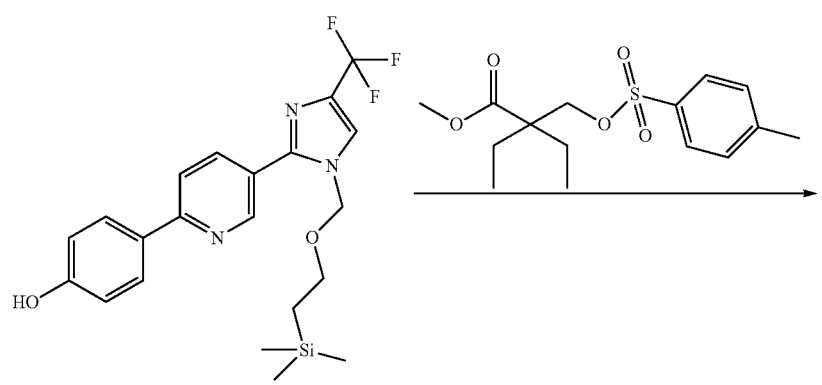

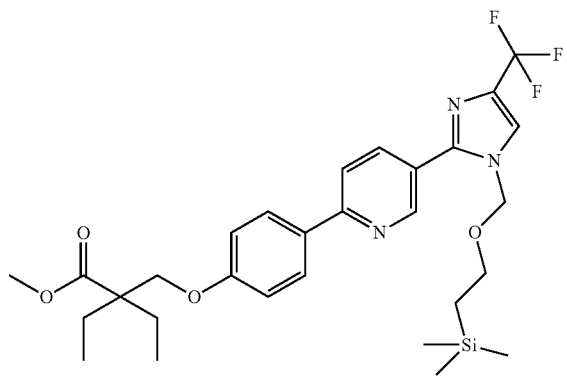

1) In N,N-dimethylformamide (1.4 mL) was dissolved 4-{5-[4-(trifluoromethyl)-1-{[2-(trimethylsilyl)ethoxy]methyl}-1H-imidazol-2-yl]pyridin-2-yl}phenol (305 mg), 60% sodium hydride (34 mg) was added to the solution at room temperature and the mixture was stirred for one hour. To the reaction mixture was added an N,N-dimethylformamide (1 mL) solution containing methyl 2-ethyl-2-(p-tolylsulfonyloxymethyl)butanoate (264 mg) under ice-cooling. The reaction mixture was stirred at 100° C. overnight. To the reaction mixture was added 60% sodium hydride (9 mg) under ice-cooling, and the mixture was stirred at 100° C. overnight. To the reaction mixture were added a saturated

[Formula 56]

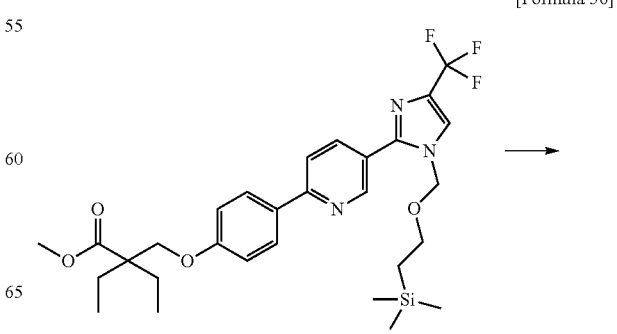

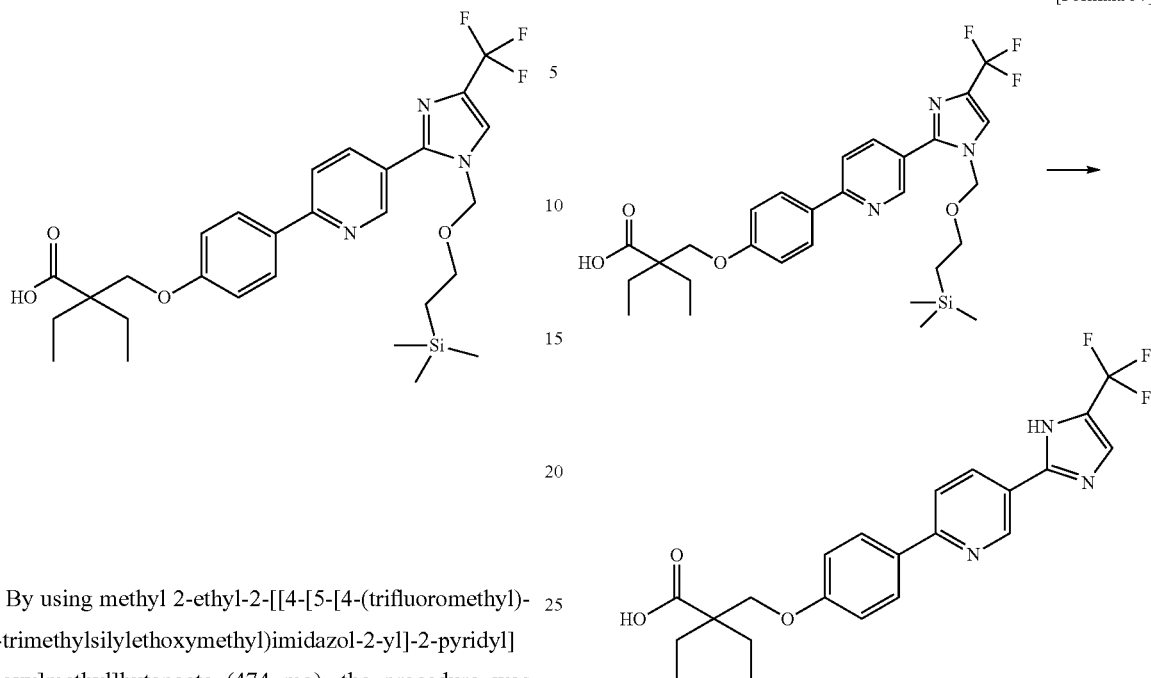

2) By using methyl 2-ethyl-2-[[4-[5-[4-(trifluoromethyl)-1-(2-trimethylsilylethoxymethyl)imidazol-2-yl]-2-pyridyl]phenoxy]methyl]butanoate (474 mg), the procedure was carried out in the same manner as in Example 3-2) to obtain 2-ethyl-2-[[4-[5-[4-(trifluoromethyl)-1-(2-trimethylsilylethoxymethyl)imidazol-2-yl]-2-pyridyl]phenoxy]-methyl]butanoic acid (414 mg).

MS (m/z):564 [M+H]$^+$

3) By using 2-ethyl-2-[[4-[5-[4-(trifluoromethyl)-1-(2-trimethylsilylethoxymethyl)imidazol-2-yl]-2-pyridyl]phenoxy]methyl]butanoic acid (465 mg), the procedure was carried out in the same manner as in Example 3-3) to obtain 2-ethyl-2-[[4-[5-[4-(trifluoromethyl)-1H-imidazol-2-yl]-2-pyridyl]phenoxy]methyl]butanoic acid (249 mg).

MS (m/z): 434 [M+H]$^+$

By using the corresponding starting materials, the following mentioned compounds were synthesized in the same manner as in Example 19.

TABLE 3

| Example | Starting substance | Product | MS (m/z) |
|---------|---------|---------|---------|
| 20 | | | 432 [M + H]$^+$ |

TABLE 3-continued
| Example | Starting substance | Product | MS (m/z) |
|---|---|---|---|
| 21 | 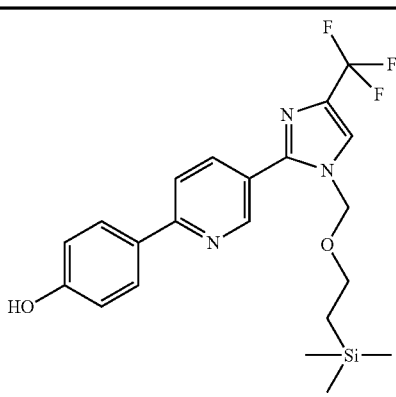 | 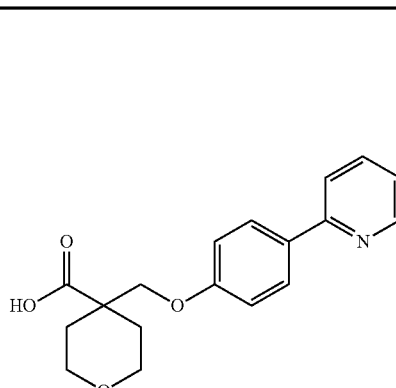 | 448 [M + H]+ |
| 22 | 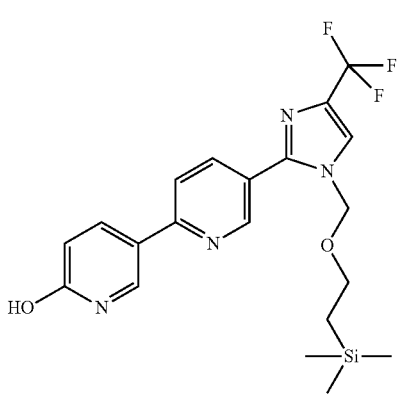 [SMILES: C[Si](C)(C)CCOCn1cc(C(F)(F)F)nc1-c1ccc(-c2ccc(O)nc2)nc1] | 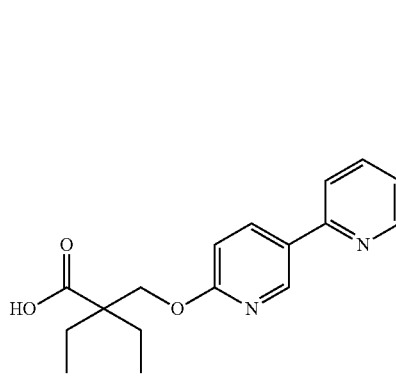 | 435 [M + H]+ |
| 23 | 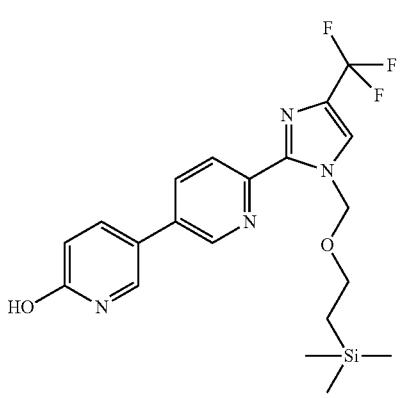 [SMILES: C[Si](C)(C)CCOCn1cc(C(F)(F)F)nc1-c1ccc(-c2ccc(O)nc2)cn1] | 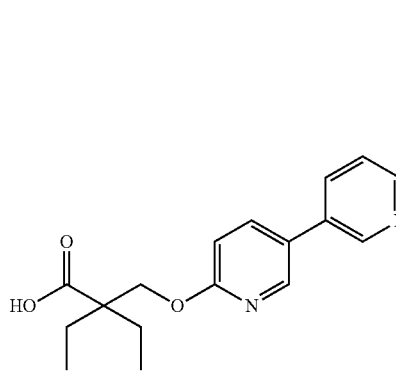 | 435 [M + H]+ |
By using the corresponding carboxylic acid, the following compounds were synthesized in the same manner as in Example 2.

TABLE 4

| Example | Starting substance | Product | MS (m/z) |
|---|---|---|---|
| 24 | 4,4,4-trifluorobutanoic acid | (structure) | 434 [M + H]+ |
| 25 | 4-methylpentanoic acid | (structure) | 408 [M + H]+ |
| 26 | 3-methylbutanoic acid | (structure) | 394 [M + H]+ |
| 27 | 2-cyclopropylacetic acid | (structure) | 392 [M + H]+ |

TABLE 4-continued
| Example | Starting substance | Product | MS (m/z) |
|---|---|---|---|
| 28 | 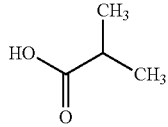 | 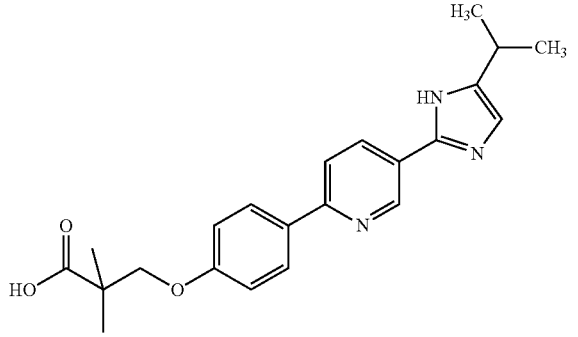 [SMILES: CC(C)c1cnc(-c2ccc(-c3ccc(OCC(C)(C)C(=O)O)cc3)nc2)[nH]1] | 380 [M + H]+ |
| 29 | 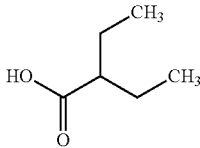 | 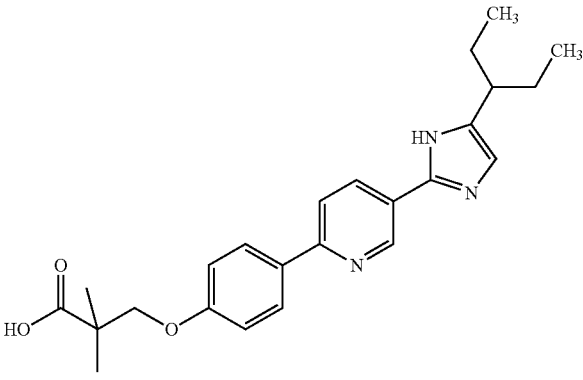 [SMILES: CCC(CC)c1cnc(-c2ccc(-c3ccc(OCC(C)(C)C(=O)O)cc3)nc2)[nH]1] | 408 [M + H]+ |
| 30 | 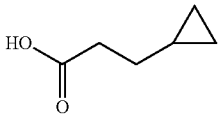 | 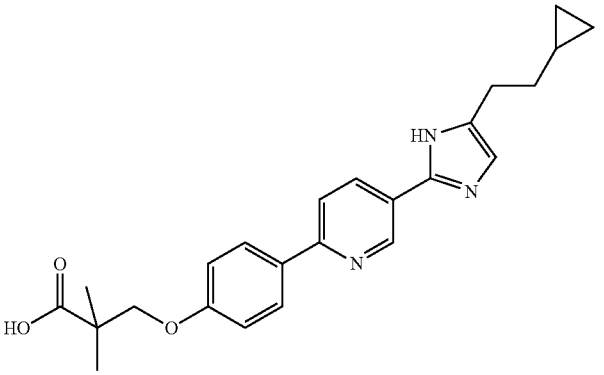 [SMILES: CC(C)(COc1ccc(-c2ccc(-c3ncc(CCC4CC4)[nH]3)cn2)cc1)C(=O)O] | 406 [M + H]+ |
| 31 | 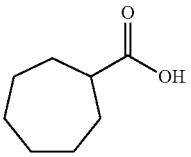 | 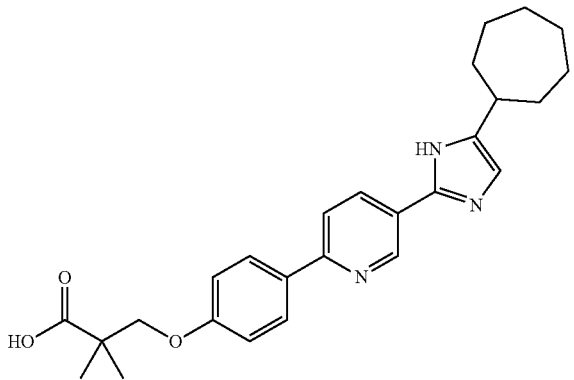 [SMILES: CC(C)(COc1ccc(-c2ccc(-c3ncc(C4CCCCCC4)[nH]3)cn2)cc1)C(=O)O] | 434 [M + H]+ |

TABLE 4-continued

| Example | Starting substance | Product | MS (m/z) |
|---|---|---|---|
| 32 | HO-C(=O)-CH2-CH2-CH3 | (structure) | 380 [M + H]+ |
| 33 | 3,3-difluorocyclobutanecarboxylic acid | (structure) | 428 [M + H]+ |
| 34 | 4,4-difluorocyclohexanecarboxylic acid | (structure) | 456 [M + H]+ |

Example 35

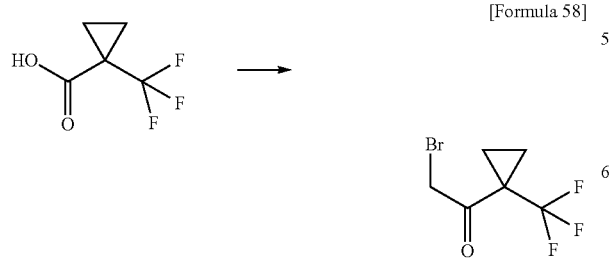

1) To methylene chloride (10 mL) was added 3,3,3-trifluoro-2,2-dimethylpropanoic acid (1000 mg), and oxalyl chloride (1132 μL) was added dropwise to the mixture. N,N-dimethylformamide (5 drops) was added to the mixture, and the resulting mixture was stirred at room temperature for one hour. After concentrating the reaction mixture under reduced pressure, acetonitrile (7 mL) was added to the residue. 2M trimethylsilyldiazomethane-n-hexane solution (6814 μL) was added dropwise to the mixture at 0° C., and the mixture was stirred at room temperature for 1.5 hours. After cooling the mixture to 0° C., 48% hydrobromic acid (1.1 mL) was added dropwise to the mixture, and the mixture was stirred for 30 minutes. To the reaction mixture were added ethyl acetate and saturated aqueous sodium bicarbonate solution, and the liquids were separated. The organic layer was separated, washed with saturated brine, dried over anhydrous sodium sulfate, and concentrated under reduced pressure to obtain 2-bromo-1-[1-(trifluoromethyl)cyclopropyl]ethanone (1413 mg).

NMR (400 MHz, CDCl$_3$) σ: 1.47-1.75 (m, 4H), 4.38 (s, 3H)

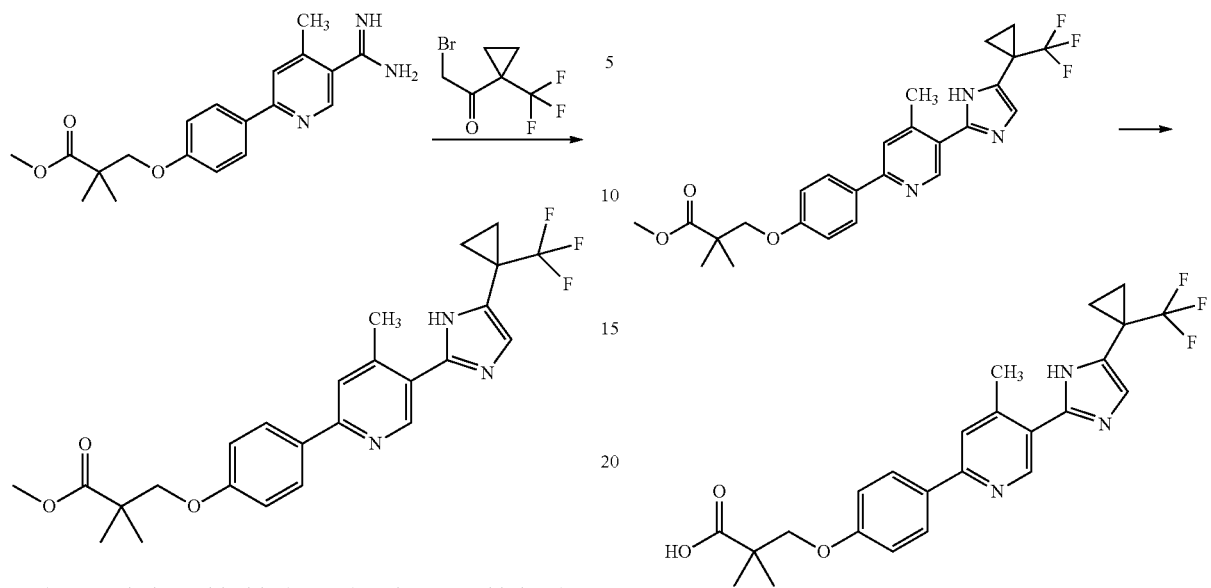

2) To methylene chloride (10 mL) and saturated brine (10 mL) were added methyl 3-[4-(5-carbamimidoyl-4-methyl-pyridin-2-yl)phenoxy]-2,2-dimethylpropanoate (500 mg) and potassium carbonate (430.3 mg), then, 2-bromo-1-[1-(trifluoromethyl)cyclopropyl]-ethanone (431.6 mg) was added to the mixture, and the resulting mixture was stirred at 50° C. overnight. The organic layer was separated and the residue obtained by concentrating the same under reduced pressure was purified by silica gel column chromatography (n-hexane:ethyl acetate=75:25 to 25:75) to obtain methyl 2,2-dimethyl-3-[4-(4-methyl-5-{5-[1-(trifluoromethyl)cyclopropyl]-1H-imidazol-2-yl}pyridin-2-yl)phenoxy]propanoate (423 mg).

MS (m/z): 474 [M+H]$^+$

3) By using methyl 2,2-dimethyl-3-[4-(4-methyl-5-{5-[1-(trifluoromethyl)cyclopropyl]-1H-imidazol-2-yl}pyridin-2-yl)phenoxy]propanoate (422 mg), the procedure was carried out in the same manner as in Example 2-2) to obtain 2,2-dimethyl-3-[4-(4-methyl-5-{5-[1-(trifluoromethyl)cyclopropyl]-1H-imidazol-2-yl}pyridin-2-yl)phenoxy]-propanoic acid (378 mg).

MS (m/z): 460 [M+H]$^+$

By using the corresponding starting materials, the following compounds were synthesized in the same manner as in Example 35.

TABLE 5

| Example | Starting substance 1 | Starting substance 2 | Product | MS (m/z) |
|---|---|---|---|---|
| 36 | (bromoacetyl 1-(trifluoromethyl)cyclopropane) | 5-(6-((3-methoxy-2,2-dimethyl-3-oxopropoxy))-4-methylpyridin-3-yl)picolinimidamide · 2AcOH | corresponding imidazole product | 461 [M + H]⁺ |
| 37 | (bromoacetyl 1-(trifluoromethyl)cyclopropane) | 4-(6-((3-methoxy-2,2-dimethyl-3-oxopropoxy))-4-methylpyridin-3-yl)-2-methylbenzimidamide · AcOH | corresponding imidazole product | 474 [M + H]⁺ |

TABLE 5-continued

| Example | Starting substance 1 | Starting substance 2 | Product | MS (m/z) |
|---|---|---|---|---|
| 38 | (bromoacetyl 1-(trifluoromethyl)cyclopropane) | methyl 3-[(5-{3-methyl-4-carbamimidoylphenyl}pyridin-2-yl)oxy]-2,2-dimethylpropanoate | 3-[(5-{3-methyl-4-[5-(1-(trifluoromethyl)cyclopropyl)-1H-imidazol-2-yl]phenyl}pyridin-2-yl)oxy]-2,2-dimethylpropanoic acid | 460 [M + H]$^+$ |
| 39 | (bromoacetyl 1-(trifluoromethyl)cyclopropane) | methyl 3-[(4-methyl-5-{4-carbamimidoylphenyl}pyridin-2-yl)oxy]-2,2-dimethylpropanoate · AcOH | 3-[(4-methyl-5-{4-[5-(1-(trifluoromethyl)cyclopropyl)-1H-imidazol-2-yl]phenyl}pyridin-2-yl)oxy]-2,2-dimethylpropanoic acid | 460 [M + H]$^+$ |
| 40 | (1-bromo-3,3-dimethyl-4,4,4-trifluorobutan-2-one) | methyl 3-[(4-methyl-5-{4-carbamimidoylphenyl}pyridin-2-yl)oxy]-2,2-dimethylpropanoate · AcOH | 3-[(4-methyl-5-{4-[5-(1,1,1-trifluoro-2-methylpropan-2-yl)-1H-imidazol-2-yl]phenyl}pyridin-2-yl)oxy]-2,2-dimethylpropanoic acid | 461 [M + H]$^+$ |

TABLE 5-continued
| Example | Starting substance 1 | Starting substance 2 | Product | MS (m/z) |
|---|---|---|---|---|
| 41 | 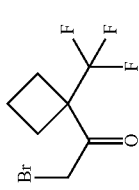 | 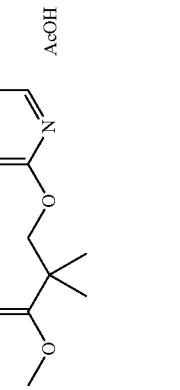 AcOH | 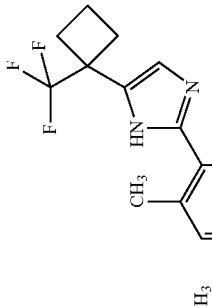 | 474 [M + H]+ |
| 42 | 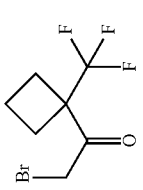 | 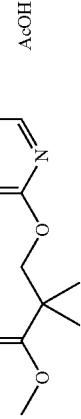 AcOH | 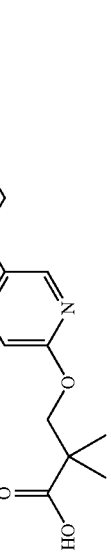 | 488 [M + H]+ |

TABLE 5-continued

| Example | Starting substance 1 | Starting substance 2 | Product | MS (m/z) |
|---------|---------------------|---------------------|---------|----------|
| 43 | | | | 474 [M + H]⁺ |
| 44 | | | | 476 [M + H]⁺ |

TABLE 5-continued
| Example | Starting substance 1 | Starting substance 2 | Product | MS (m/z) |
|---|---|---|---|---|
| 45 | 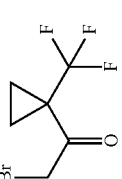 | 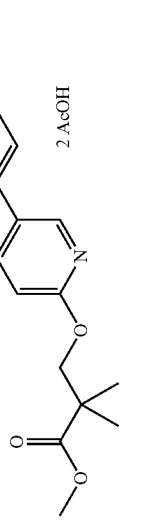 | 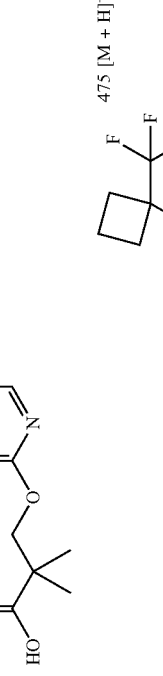 | 464 [M + H]⁺ |
| 46 | 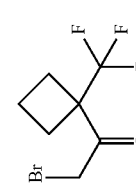 | 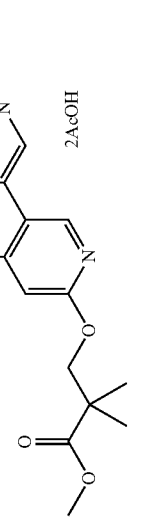 |  | 475 [M + H]⁺ |
| 47 | 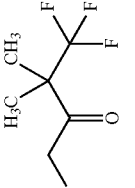 | 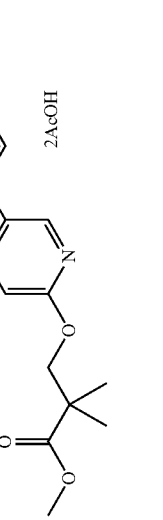 |  | 463 [M + H]⁺ |

TABLE 5-continued
| Example | Starting substance 1 | Starting substance 2 | Product | MS (m/z) |
|---|---|---|---|---|
| 48 | 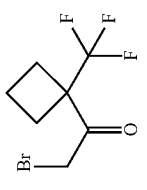 | 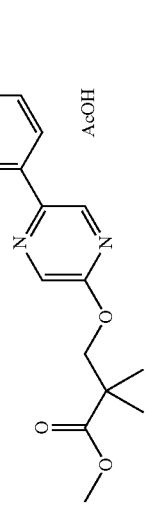 AcOH | 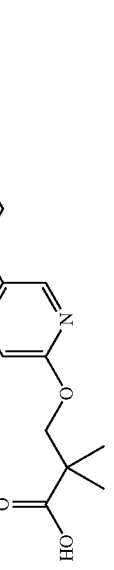 | 461 [M + H]+ |
| 49 | 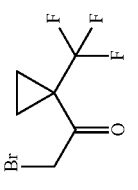 | 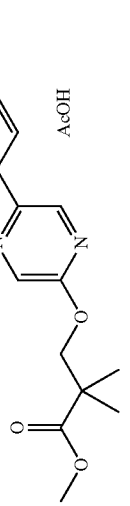 AcOH | 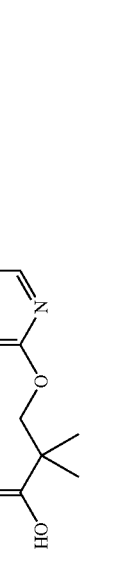 | 447 [M + H]+ |

TABLE 5-continued

| Example | Starting substance 1 | Starting substance 2 | Product | MS (m/z) |
|---|---|---|---|---|
| 50 | | | | 449 [M + H]+ |
| 51 | | | | 465 [M + H]+ |

TABLE 5-continued
| Example | Starting substance 1 | Starting substance 2 | Product | MS (m/z) |
|---|---|---|---|---|
| 52 | 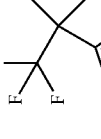 | 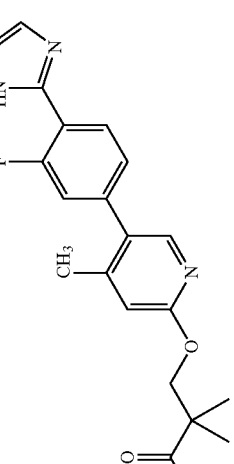 AcOH |  | 492 [M + H]+ |
| 53 |  | 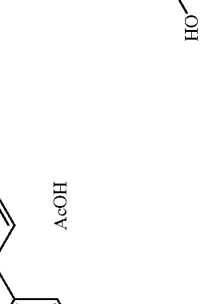 2 AcOH |  | 466 [M + H]+ |

Example 54

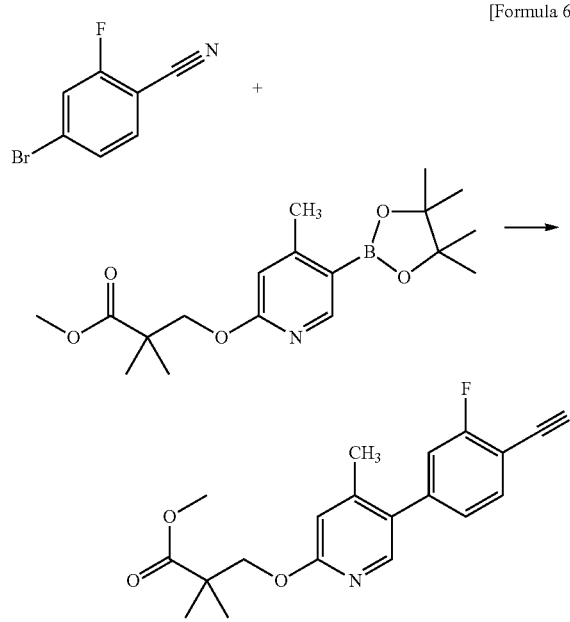

[Formula 61]

1) N,N-dimethylformamide (30 mL) was added to 4-bromo-2-fluorobenzonitrile (2000 mg), methyl 2,2-dimethyl-3-{[4-methyl-5-(4,4,5,5-tetramethyl-1,3,2-dioxaborolan-2-yl)pyridin-2-yl]oxy}propanoate (4191 mg) and palladium chloride (dppf) methylene chloride complex (408 mg), and after adding 2N aqueous sodium carbonate solution (15 mL) to the mixture, the atmosphere was replaced with nitrogen and the resulting mixture was stirred at 60° C. for 7 hours. Ethyl acetate and water were added to the reaction mixture, and the liquids were separated. The organic layer was separated, washed with a saturated brine, and the residue obtained by concentrating the mixture under reduced pressure was purified by silica gel column chromatography (n-hexane:ethyl acetate=90:10 to 80:20) to obtain methyl 3-{[5-(4-cyano-3-fluorophenyl)-4-methylpyridin-2-yl]oxy}-2,2-dimethylpropanoate (3587 mg).

MS (m/z): 343 [M+H]$^+$

[Formula 62]

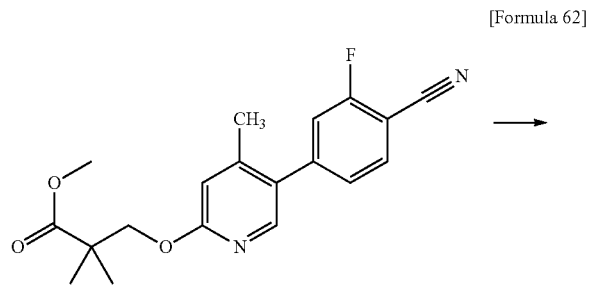

2) A mixture in which methanol (20 mL) and tetrahydrofuran (20 mL) were added to methyl 3-{[5-(4-cyano-3-fluorophenyl)-4-methylpyridin-2-yl]oxy}-2,2-dimethylpropanoate (3.55 g) and hydroxylamine (50% aqueous solution, 13.7 g) was stirred at 80° C. for 5 hours. After concentrating the mixture under reduced pressure, chloroform and water were added to the residue, and the liquids were separated. The organic layer was separated, washed with a saturated brine, concentrated under reduced pressure and dried to obtain methyl 3-({5-[3-fluoro-4-(N-hydroxycarbamimidoyl)phenyl]-4-methylpyridin-2-yl}oxy)-2,2-dimethylpropanoate (3.66 g).

MS (m/z): 376 [M+H]$^+$

[Formula 63]

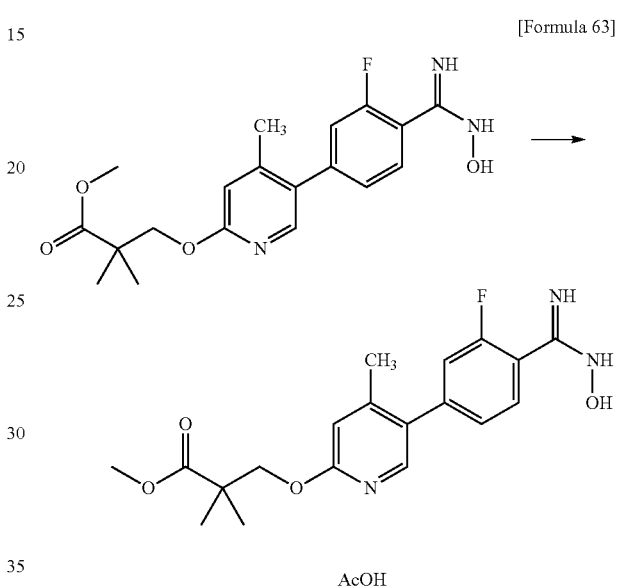

3) Acetic anhydride (1.62 mL) was added to an acetic acid (10 mL) solution containing methyl 3-({5-[3-fluoro-4-(N-hydroxycarbamimidoyl)phenyl]-4-methylpyridin-2-yl}-oxy)-2,2-dimethylpropanoate (3.65 g), and the mixture was stirred at room temperature for 5 hours. The reaction mixture was concentrated under reduced pressure. The residue was dissolved in methanol (30 mL), 10% palladium carbon (50%, 365 mg) was added to the resulting solution, and the mixture was stirred under hydrogen atmosphere at room temperature for 13 hours. The catalyst was filtered off by using a membrane filter, and the filtrate was concentrated under reduced pressure. Ether was added to the obtained residue, and the precipitated solid was collected by filtration, washed with ether and dried to obtain methyl 3-{[5-(4-carbamimidoyl-3-fluorophenyl)-4-methylpyridin-2-yl]oxy}-2,2-dimethylpropanoate acetic acid salt (2.45 g).

MS (m/z): 360 [M+H]$^+$

[Formula 64]

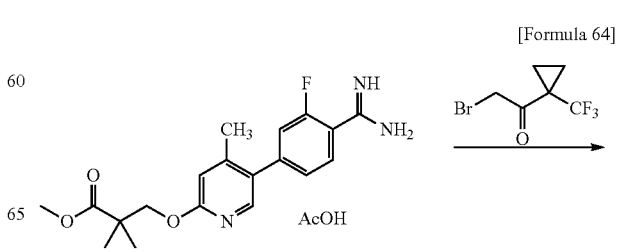

-continued

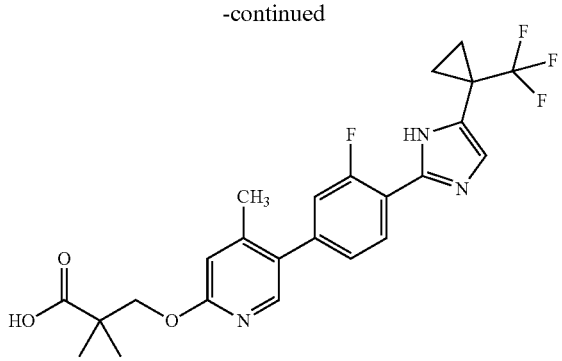

4) A mixture in which methylene chloride (8 mL) and a saturated brine (8 mL) were added to methyl 3-{[5-(4-carbamimidoyl-3-fluorophenyl)-4-methylpyridin-2-yl]oxy}-2,2-dimethylpropanoate acetic acid salt (400 mg), 2-bromo-1-[1-(trifluoromethyl)cyclopropyl]ethanone (289 mg) and potassium carbonate (404 mg) was stirred at 50° C. for 8 hours. The organic layer was separated, and concentrated under reduced pressure. The obtained residue was dissolved in tetrahydrofuran (2.0 mL) and methanol (2.0 mL), and after adding 2N aqueous sodium hydroxide solution (3.0 mL) to the solution, the resulting mixture was stirred at 50° C. for 3 hours. The mixture was diluted by ethyl acetate, and then, neutralized by adding 1N hydrochloric acid. The organic layer was separated, ether was added to the residue obtained by concentrating the mixture under reduced pressure and the resulting mixture was stirred. The precipitated solid was collected by filtration and dried to obtain 3-{[5-(3-fluoro-4-{5-[1-(trifluoromethyl)cyclopropyl]-1H-imidazol-2-yl}phenyl)-4-methylpyridin-2-yl]oxy}-2,2-dimethylpropanoic acid (339 mg).

MS (m/z): 478 [M+H]$^+$

Example 55

[Formula 65]

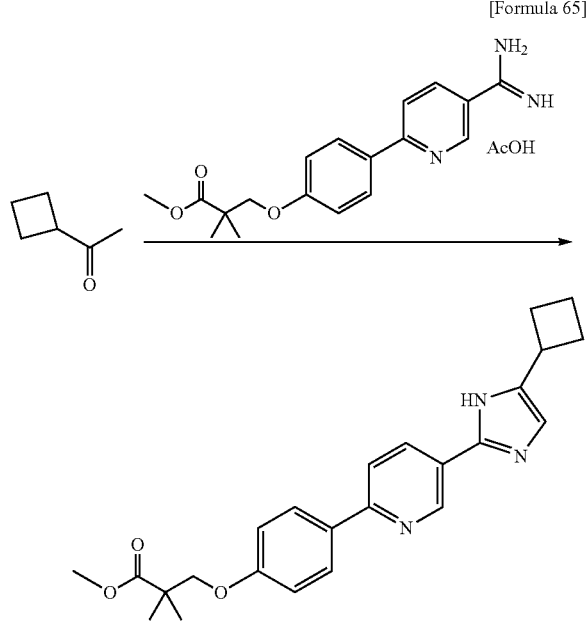

1) In methanol (30 mL) was dissolved 1-cyclobutylethanone (1.05 g), dioxane dibromide (2.68 g) was added to the solution, and the mixture was stirred at room temperature for 1 hour and 40 minutes. To the reaction mixture was added a saturated aqueous sodium bicarbonate solution, then, water was added to the same and the mixture was extracted with ether. The organic layer was separated, washed with saturated brine, and dried over anhydrous sodium sulfate. The residue obtained by concentrating the mixture under reduced pressure was dissolved in methylene chloride (20 mL), then, methyl 3-(4-{5-[amino(imino)methyl]pyridin-2-yl}phenoxy)-2,2-dimethylpropanoate acetate (700 mg), potassium carbonate (1.25 g) and saturated brine (20 mL) were added to the solution, and the resulting mixture was stirred at 50° C. overnight. The reaction mixture was separated, and the aqueous layer was extracted with methylene chloride. The organic layers were combined, and dried over anhydrous sodium sulfate. The residue obtained by concentrating the reaction mixture under reduced pressure was purified by NH-silica gel column chromatography (n-hexane:ethyl acetate=65:35 to 15:85) and then by silica gel column chromatography (n-hexane:ethyl acetate=65:35 to 20:80) to obtain methyl 3-[4-[5-(5-cyclobutyl-1H-imidazol-2-yl)-2-pyridyl]phenoxy]-2,2-dimethylpropanoate (266 mg).

MS (m/z): 406 [M+H]$^+$

[Formula 66]

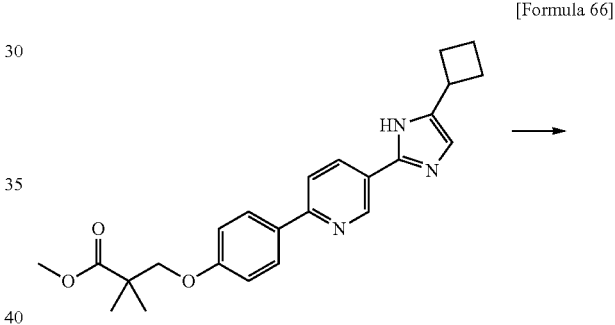

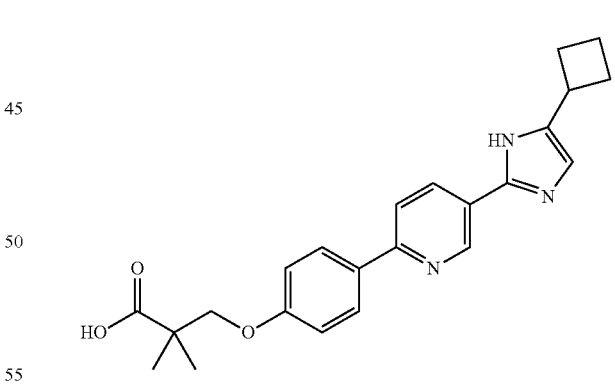

2) By using methyl 3-[4-[5-(5-cyclobutyl-1H-imidazol-2-yl)-2-pyridyl]phenoxy]-2,2-dimethylpropanoate (260 mg), the procedure was carried out in the same manner as in Example 2-2) to obtain 3-[4-[5-(5-cyclobutyl-1H-imidazol-2-yl)-2-pyridyl]phenoxy]-2,2-dimethylpropanoic acid (230 mg).

MS (m/z): 392 [M+H]$^+$

By using the corresponding ketone, the following compounds were synthesized in the same manner as in Example 55.

TABLE 6

| Example | Ketone | Product | MS (m/z) |
|---|---|---|---|
| 56 | | | 420 [M + H]+ |
| 57 | | | 394 [M + H]+ |

Example 58

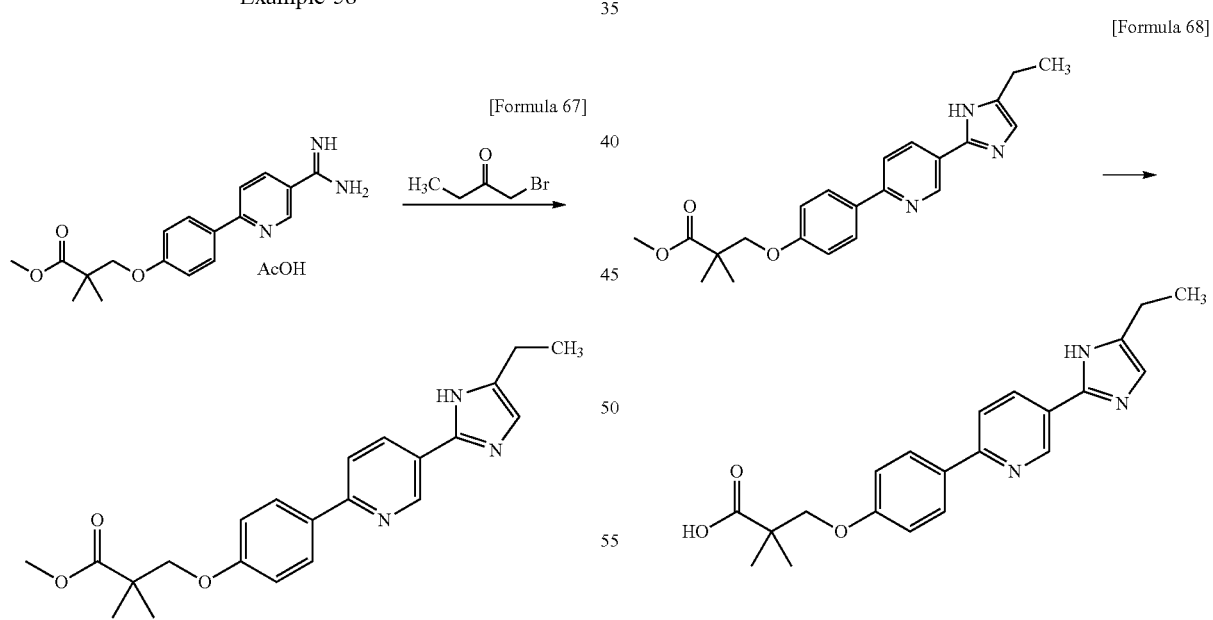

[Formula 67]

[Formula 68]

1) By using methyl 3-(4-{5-[amino(imino)methyl]pyridin-2-yl}phenoxy)-2,2-dimethylpropanoate acetate (400 mg), and 1-bromobutan-2-one (234 mg), the procedure was carried out in the same manner as in Example 35(2) to obtain methyl 3-[4-[5-(5-ethyl-1H-imidazol-2-yl)-2-pyridyl]phenoxy]-2,2-dimethylpropanoate (397 mg).

MS (m/z): 380 [M+H]+

2) By using methyl 3-[4-[5-(5-ethyl-1H-imidazol-2-yl)-2-pyridyl]phenoxy]-2,2-dimethylpropanoate (270 mg), the procedure was carried out in the same manner as in Example 2-2) to obtain 3-[4-[5-(5-ethyl-1H-imidazol-2-yl)-2-pyridyl]phenoxy]-2,2-dimethylpropanoic acid (218 mg).

MS (m/z): 366 [M+H]+

By using the corresponding starting materials, the following compounds were synthesized in the same manner as in Example 58.

TABLE 7

| Example | Starting substance 1 | Starting substance 2 | Product | MS (m/z) |
|---|---|---|---|---|
| 59 | 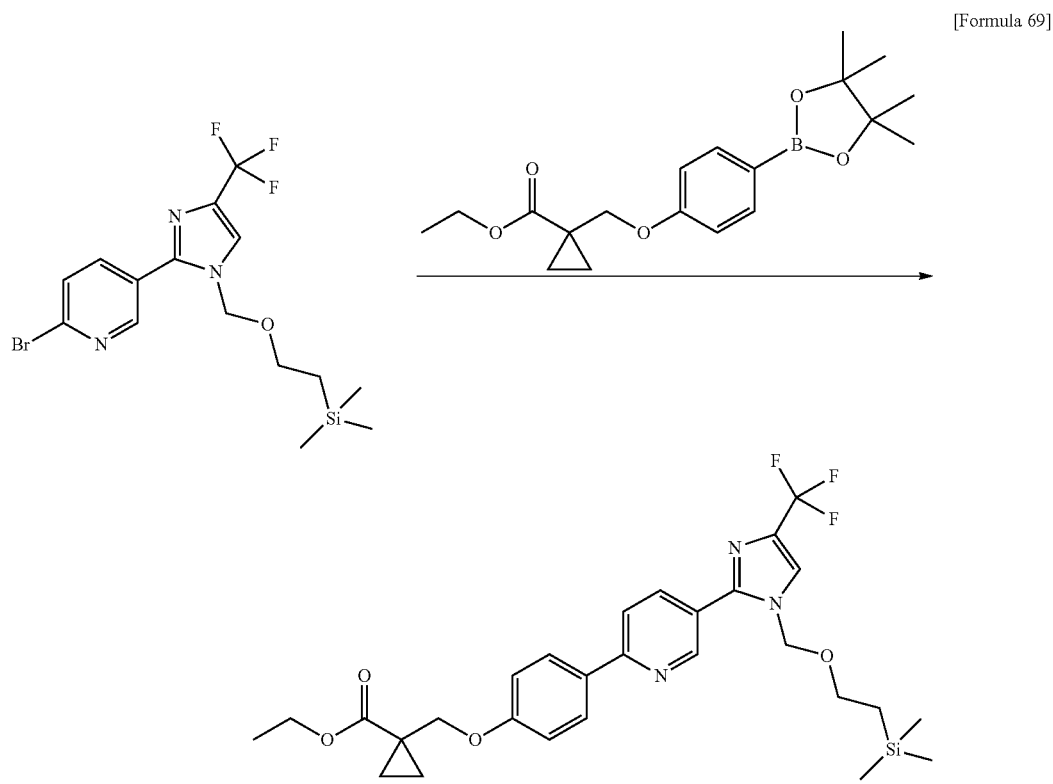 | | | 395 [M + H]+ |

Example 60

[Formula 69]

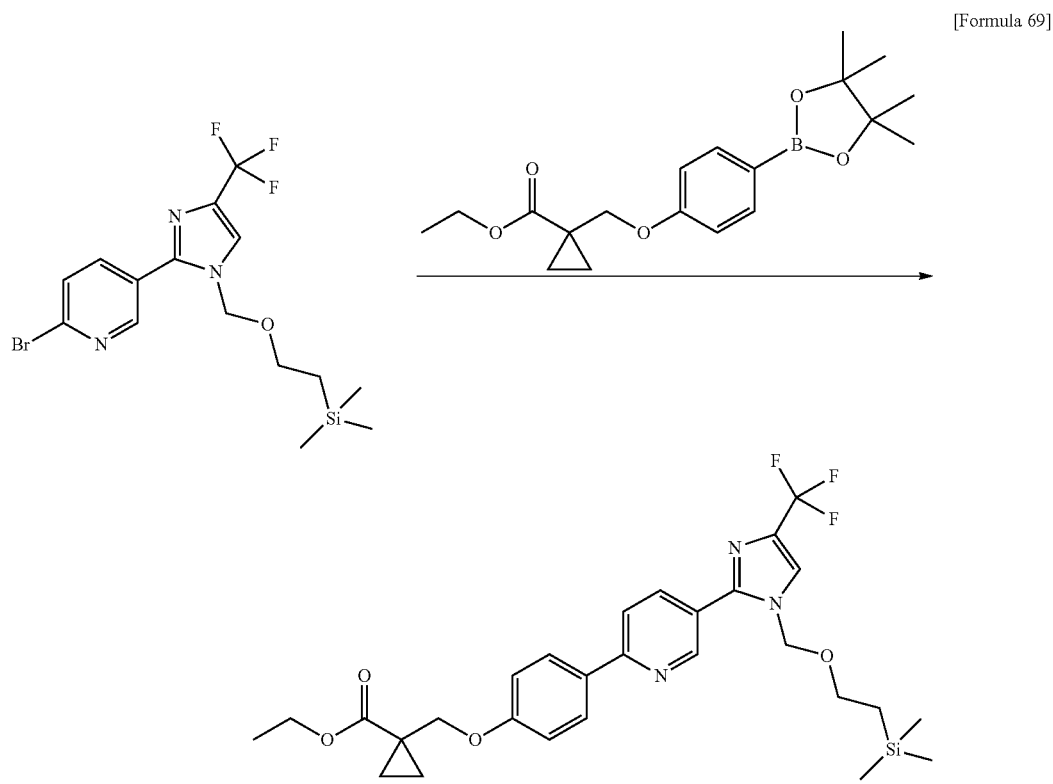

1) To dimethoxyethane (12 mL) were added 2-bromo-5-[4-(trifluoromethyl)-1-{[2-(trimethylsilyl)ethoxy]methyl}-1H-imidazol-2-yl]pyridine (489 mg), methyl 1-[[4-(4,4,5,5-tetramethyl-1,3,2-dioxaboloran-2-yl)phenoxy]methyl] cyclopropane carboxylate (500 mg), tetrakis(triphenylphosphine)palladium (134 mg) and 2M aqueous sodium carbonate solution (2.32 mL), and the mixture was stirred at 80° C. under nitrogen atmosphere overnight. The reaction mixture was passed through NH-silica gel short column and washed with ethyl acetate. The filtrate was concentrated under reduced pressure, and the obtained residue was purified by NH-silica gel column chromatography (n-hexane:ethyl acetate=88:12 to 71:29) to obtain methyl 1-[[4-[5-[4-(trifluoromethyl)-1-(2-trimethylsilylethoxym- ethyl)imidazol-2-yl]-2-pyridyl]phenoxy]methyl]-cyclopropane carboxylate (491 mg).

MS (m/z): 548 [M+H]+

[Formula 70]

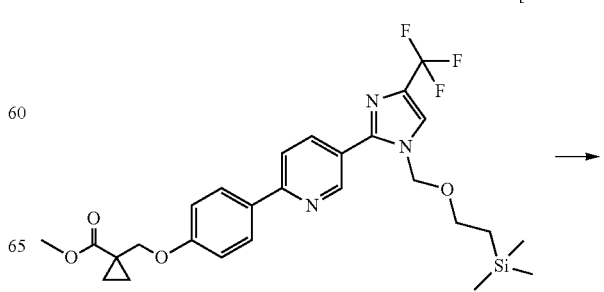

-continued

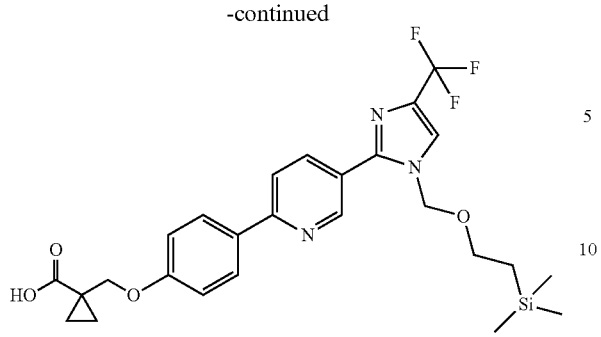

2) By using methyl 1-[[4-[5-[4-(trifluoromethyl)-1-(2-trimethylsilylethoxymethyl)imidazol-2-yl]-2-pyridyl]phenoxy]methyl]cyclopropane carboxylate (484 mg), the procedure was carried out in the same manner as in Example 3-2) to obtain 1-[[4-[5-[4-(trifluoromethyl)-1-(2-trimethylsilylethoxymethyl)imidazol-2-yl]-2-pyridyl]phenoxy]methyl]cyclopropanecarboxylic acid (439 mg).
MS (m/z): 534 [M+H]$^+$

[Formula 71]

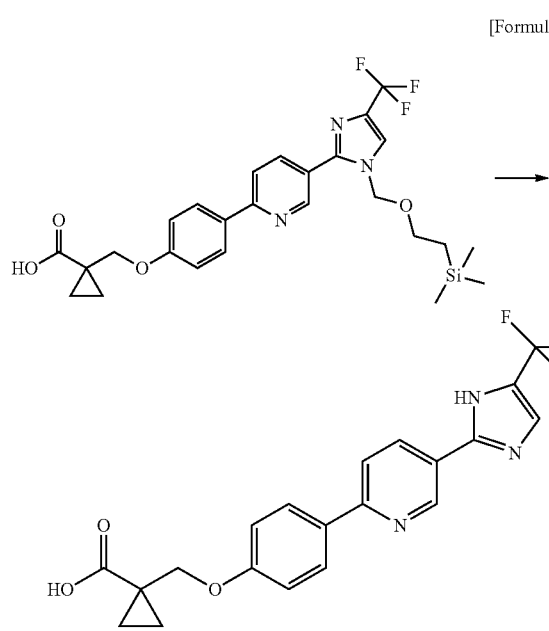

3) By using 1-[[4-[5-[4-(trifluoromethyl)-1-(2-trimethylsilylethoxymethyl)imidazol-2-yl]-2-pyridyl]phenoxy]methyl]cyclopropanecarboxylic acid (431 mg), the procedure was carried out in the same manner as in Example 3-3) to obtain 1-[[4-[5-[5-(trifluoromethyl)-1H-imidazol-2-yl]-2-pyridyl]phenoxy]methyl]cyclopropanecarboxylic acid (235.7 mg).
MS (m/z): 404 [M+H]$^+$ Example 61

[Formula 72]

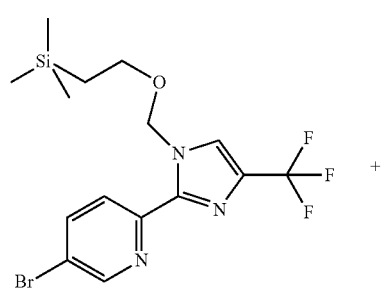

+

-continued

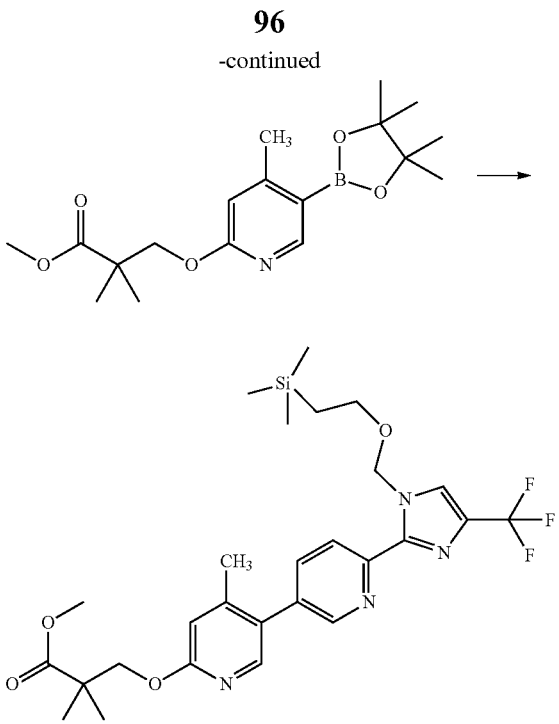

1) A mixture in which tetrahydrofuran (6 mL) was added to 5-bromo-2-[4-(trifluoromethyl)-1-{[2-(trimethylsilyl)ethoxy]methyl}-1H-imidazol-2-yl]pyridine (542 mg), methyl 2,2-dimethyl-3-{[4-methyl-5-(4,4,5,5-tetramethyl-1,3,2-dioxaborolan-2-yl)pyridin-2-yl]oxy}propanoate (372 mg), potassium phosphate (302 mg), palladium acetate (8 mg) and 2-dicyclohexylphosphino-2',6'-dimethoxybiphenyl (29 mg) was stirred under nitrogen atmosphere at 50° C. for 6 hours. After cooling the mixture to room temperature, a saturated aqueous sodium bicarbonate solution, water and ethyl acetate were added to the mixture and the resulting mixture was stirred. The organic layer was separated, washed with a saturated brine, and the residue obtained by concentrating under reduced pressure was purified by silica gel column chromatography (n-hexane:ethyl acetate=90:10 to 60:40) to obtain methyl 2,2-dimethyl-3-({4-methyl-6'-[4-(trifluoromethyl)-1-{[2-(trimethylsilyl)ethoxy]methyl}-1H-imidazol-2-yl]-3,3'-bipyridin-6-yl}oxy)propanoate (100 mg).
MS (m/z): 565 [M+H]$^+$

[Formula 73]

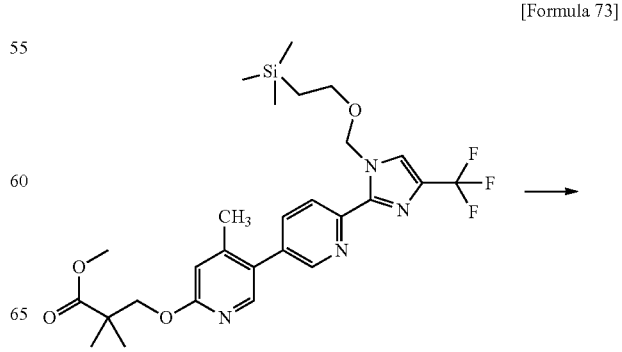

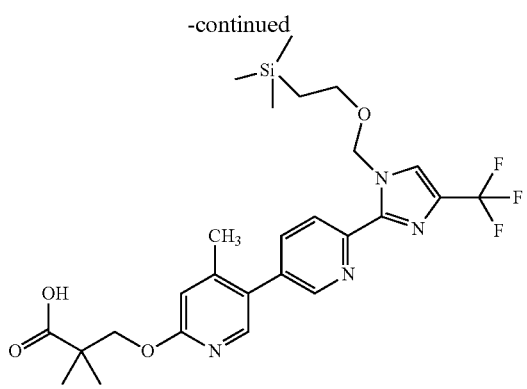

2) Methanol (0.7 mL) and tetrahydrofuran (0.7 mL) were added to methyl 2,2-dimethyl-3-({4-methyl-6'-[4-(trifluoromethyl)-1-{[2-(trimethylsilyl)ethoxy]methyl}-1H-imidazol-2-yl]-3,3'-bipyridin-6-yl}oxy)propanoate (99 mg), and after adding 2N aqueous sodium hydroxide solution (0.7 mL) to the mixture, the resulting mixture was stirred at 50° C. for 2 hours. To the reaction mixture was added ethyl acetate, and the mixture was neutralized by 2N hydrochloric acid. The organic layer was separated, washed with a saturated brine, and the residue obtained by concentrating the mixture under reduced pressure was purified by silica gel column chromatography (n-hexane:ethyl acetate=76:24 to 0:100) to obtain 2,2-dimethyl-3-({4-methyl-6'-[4-(trifluoromethyl)-1-{[2-(trimethylsilyl)ethoxy]methyl}-1H-imidazol-2-yl]-3,3'-bipyridin-6-yl}oxy)propanoic acid (81 mg).

MS (m/z): 551 [M+H]+

[Formula 74]

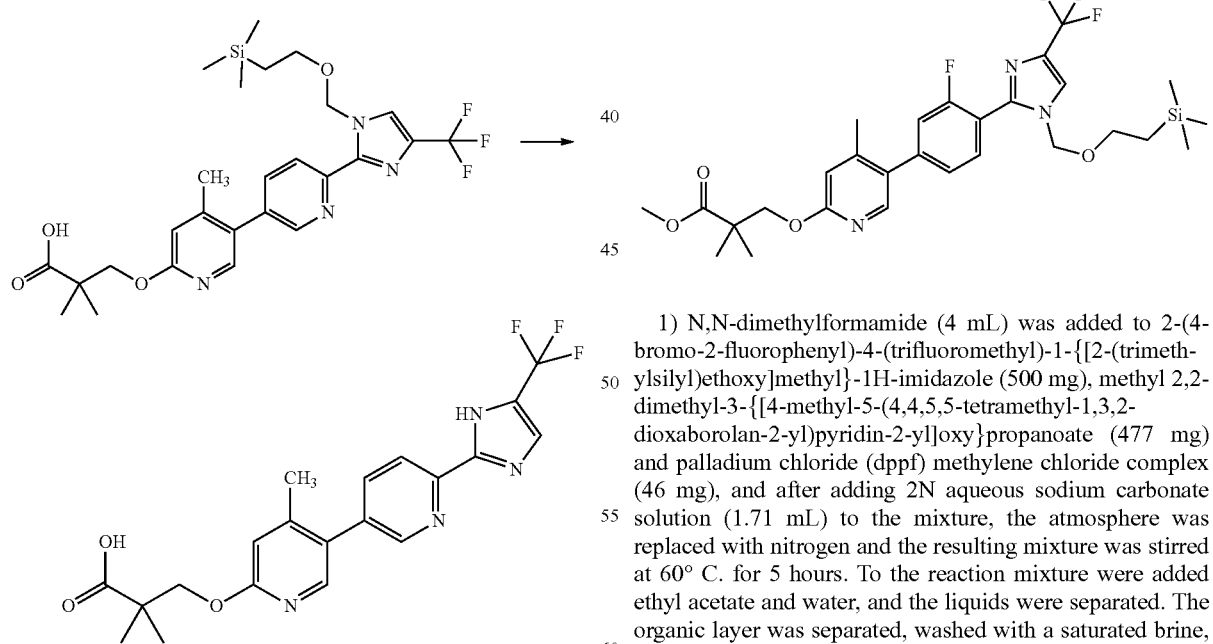

3) In trifluoroacetic acid (2.0 mL) and water (0.1 mL) was dissolved 2,2-dimethyl-3-({4-methyl-6'-[4-(trifluoromethyl)-1-{[2-(trimethylsilyl)ethoxy]methyl}-1H-imidazol-2-yl]-3,3'-bipyridin-6-yl}oxy)propanoic acid (80 mg), and the solution was stirred at room temperature for 7 hours. To the solution was added 2N aqueous sodium hydroxide solution to make a pH of the same 2 to 3, and the resulting mixture was extracted with ethyl acetate. The extract was washed with a saturated brine, the organic layer was separated and concentrated under reduced pressure. Isopropyl ether was added to the obtained residue, and the precipitated solid was collected by filtration and dried under reduced pressure to obtain 2,2-dimethyl-3-({4-methyl-6'-[5-(trifluoromethyl)-1H-imidazol-2-yl]-3,3'-bipyridin-6-yl}oxy)propanoic acid (30 mg).

MS (m/z): 421 [M+H]+

Example 62

[Formula 75]

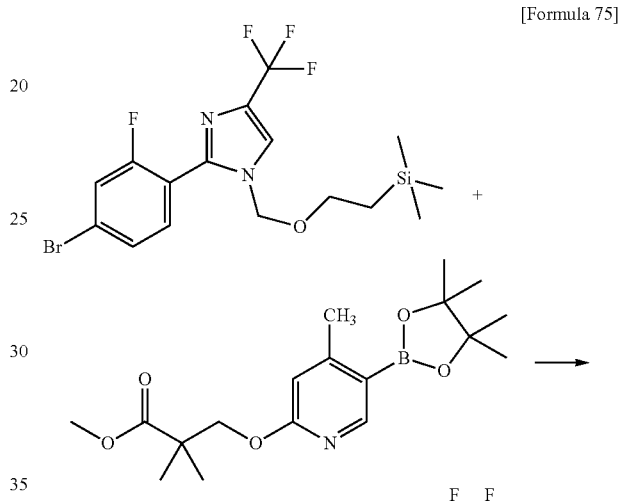

1) N,N-dimethylformamide (4 mL) was added to 2-(4-bromo-2-fluorophenyl)-4-(trifluoromethyl)-1-{[2-(trimethylsilyl)ethoxy]methyl}-1H-imidazole (500 mg), methyl 2,2-dimethyl-3-{[4-methyl-5-(4,4,5,5-tetramethyl-1,3,2-dioxaborolan-2-yl)pyridin-2-yl]oxy}propanoate (477 mg) and palladium chloride (dppf) methylene chloride complex (46 mg), and after adding 2N aqueous sodium carbonate solution (1.71 mL) to the mixture, the atmosphere was replaced with nitrogen and the resulting mixture was stirred at 60° C. for 5 hours. To the reaction mixture were added ethyl acetate and water, and the liquids were separated. The organic layer was separated, washed with a saturated brine, and the residue obtained by concentrating the mixture under reduced pressure was purified by silica gel column chromatography (n-hexane:ethyl acetate=95:5 to 82:18) to obtain methyl 3-[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoate (677 mg).

MS (m/z): 582 [M+H]+

[Formula 76]

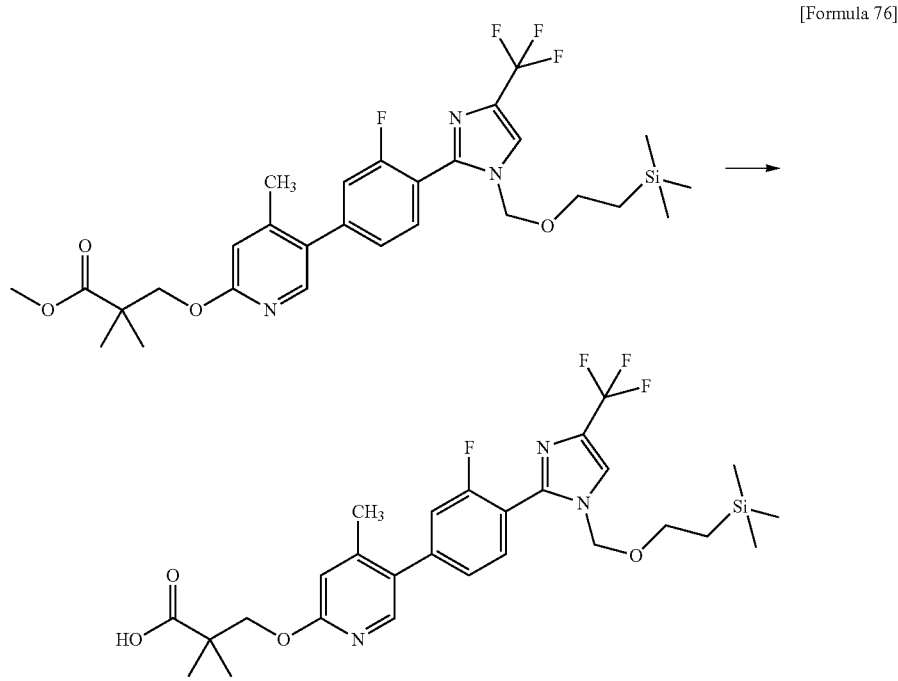

2) Methanol (3.0 mL) and tetrahydrofuran (3.0 mL) were added to methyl 3-[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoate (660 mg), and after adding 2N aqueous sodium hydroxide solution (4.0 mL) to the mixture, the resulting mixture was stirred at 50° C. for 2 hours. Ethyl acetate was added to the reaction mixture, and the mixture was neutralized by 2N hydrochloric acid. The organic layer was separated, washed with a saturated brine, and concentrated under reduced pressure to obtain 3-[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoic acid (721 mg).

MS (m/z): 568 [M+H]$^+$

3) In trifluoroacetic acid (2.0 mL) and water (0.1 mL) was dissolved 3-[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoic acid (640 mg), and the solution was stirred at room temperature for 10 hours. The solution was neutralized by adding 2N aqueous sodium hydroxide solution, and the resulting mixture was extracted with ethyl acetate. The extract was washed with a saturated brine, the organic layer was separated and concentrated under reduced pressure. Ether was added to the obtained residue, and the precipitated solid was collected by filtration and dried under reduced pressure to obtain 3-[(5-{3-fluoro-4-[5-(trifluoromethyl)-1H-imidazol-2-yl]phenyl}-4-methylpyridin-2-yl)oxy]-2,2-dimethylpropanoic acid (432 mg).

MS (m/z): 438 [M+H]$^+$

Example 63

[Formula 77]

[Formula 78]

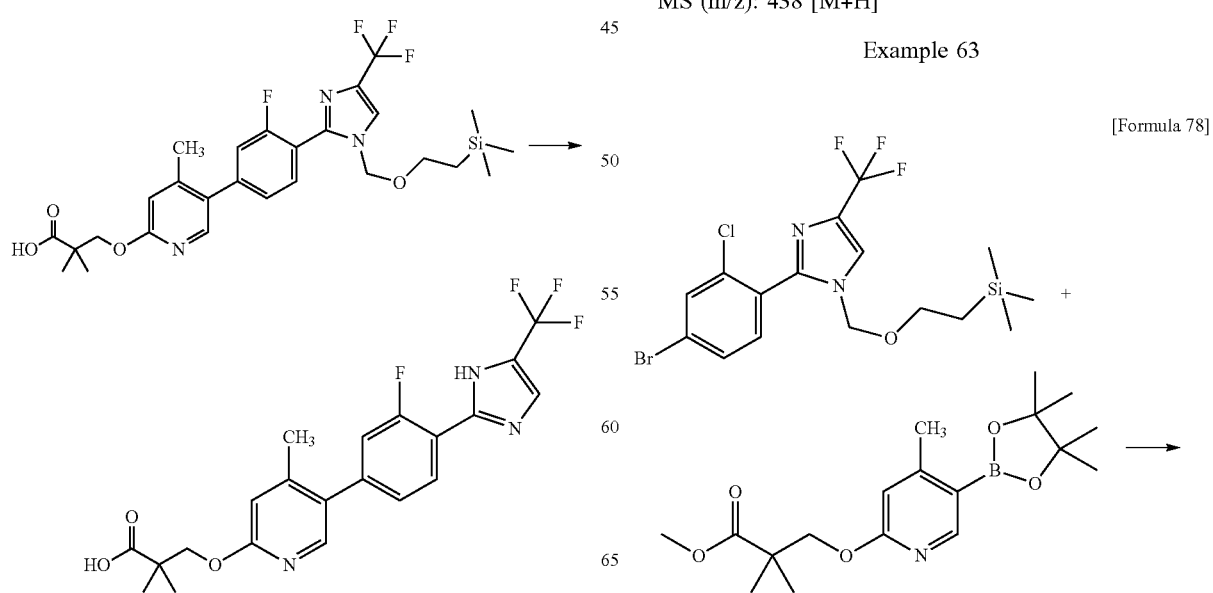

-continued

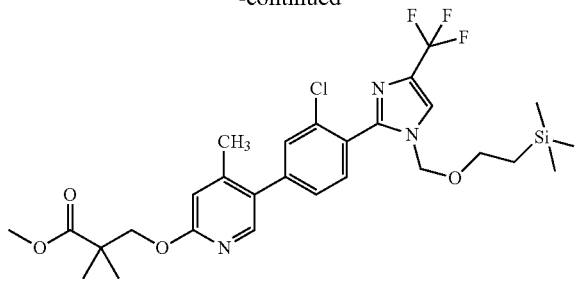

1) N,N-dimethylformamide (2 mL) was added to 2-(4-bromo-2-chlorophenyl)-4-(trifluoromethyl)-1-{[2-(trimethylsilyl)ethoxy]methyl}-1H-imidazole (297 mg), methyl 2,2-dimethyl-3-{[4-methyl-5-(4,4,5,5-tetramethyl-1,3,2-dioxaborolan-2-yl)pyridin-2-yl]oxy}propanoate (228 mg) and palladium chloride (dppf) methylene chloride complex (27 mg), and after adding 2N aqueous sodium carbonate solution (0.98 mL) to the mixture, the atmosphere was replaced with nitrogen and the resulting mixture was stirred at 60° C. for 5 hours. To the reaction mixture were added ethyl acetate and water, and the liquids were separated. The organic layer was separated, washed with a saturated brine, and the residue obtained by concentrating the mixture under reduced pressure was purified by silica gel column chromatography (n-hexane:ethyl acetate=94:6 to 82:18) to obtain methyl 3-[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoate (278 mg).

MS (m/z): 598/600 [M+H]$^+$

[Formula 79]

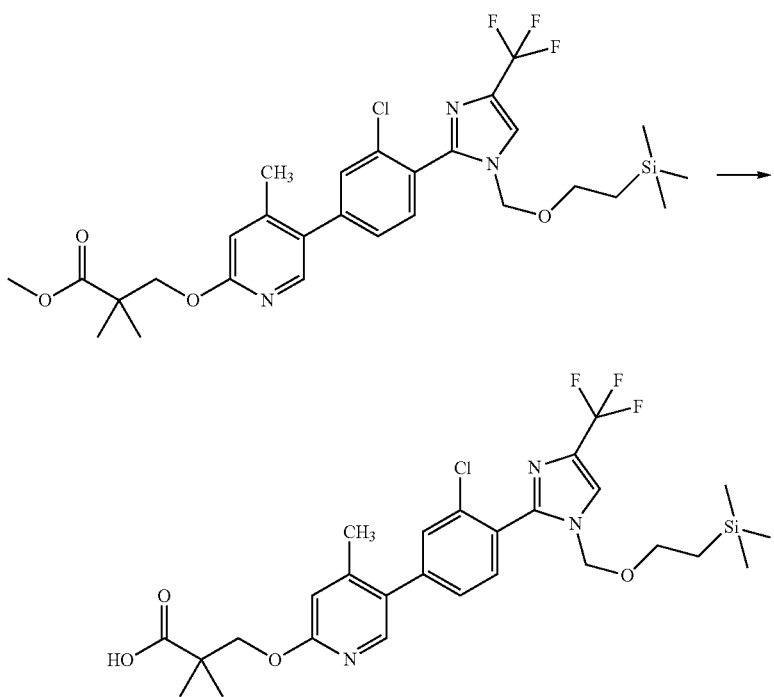

2) Methanol (1.5 mL) and tetrahydrofuran (1.5 mL) were added to methyl 3-[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoate (274 mg), and after adding 2N aqueous sodium hydroxide solution (1.5 mL) to the mixture, the resulting mixture was stirred 50° C. for 2 hours. Ethyl acetate was added to the reaction mixture, and the resulting mixture was neutralized by 1N hydrochloric acid. The organic layer was separated, washed with a saturated brine, and concentrated under reduced pressure to obtain 3-[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoic acid (279 mg).

MS (m/z): 584/586 [M+H]$^+$

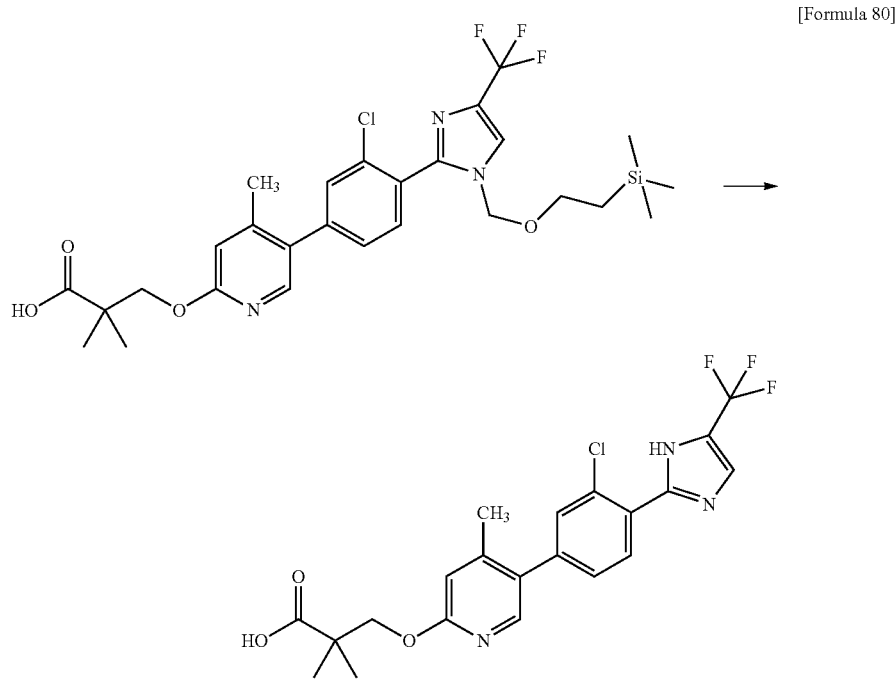

[Formula 80]

3) In trifluoroacetic acid (1.0 mL) and water (0.05 mL) was dissolved 3-[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]-2,2-dimethylpropanoic acid (268 mg), and the solution was stirred at room temperature for 10 hours. The solution was neutralized by adding 2N aqueous sodium hydroxide solution, and extracted with ethyl acetate. The extract was washed with a saturated brine, and the organic layer was separated and concentrated under reduced pressure. Ether was added to the obtained residue, and the precipitated solid was collected by filtration and dried under reduced pressure to obtain 3-[(5-{3-chloro-4-[5-(trifluoromethyl)-1H-imidazol-2-yl]phenyl}-4-methylpyridin-2-yl)oxy]-2,2-dimethylpropanoic acid (133 mg).

MS (m/z): 454/456 [M+H]+

By using the corresponding starting materials, the following compounds were synthesized in the same manner as in Example 60.

TABLE 8

| Example | Starting substance 1 | Starting substance 2 |
|---|---|---|
| 64 | | |
| 65 | | |

TABLE 8-continued
66 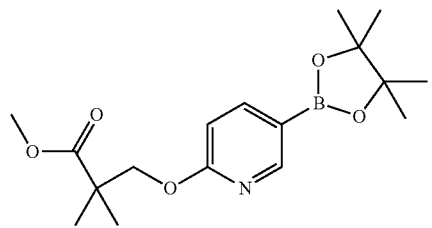 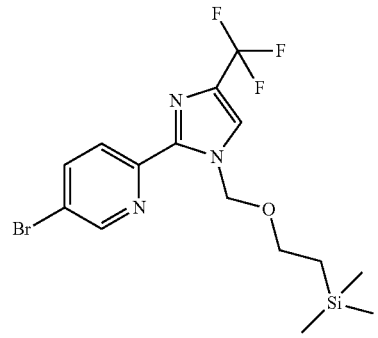 [SMILES: C[Si](C)(C)CCOCn1cc(C(F)(F)F)nc1-c1ccc(Br)cn1]
67 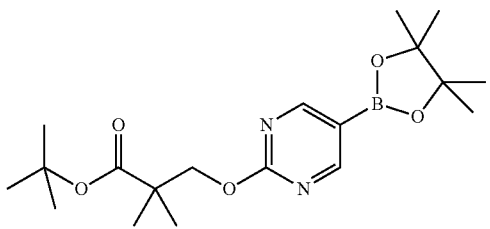 [SMILES: CC(C)(C)OC(=O)C(C)(C)COc1ncc(B2OC(C)(C)C(C)(C)O2)cn1] 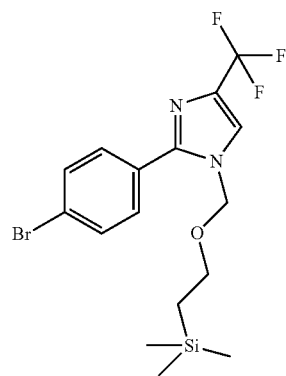 [SMILES: C[Si](C)(C)CCOCn1cc(C(F)(F)F)nc1-c1ccc(Br)cc1]
68 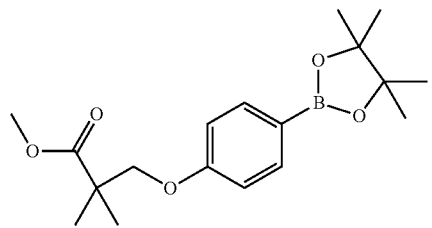 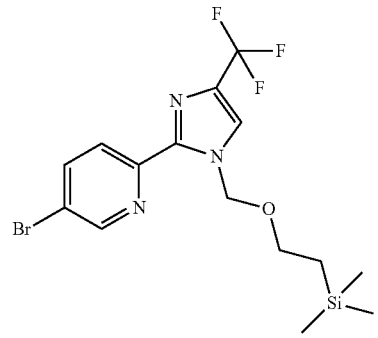 [SMILES: C[Si](C)(C)CCOCn1cc(C(F)(F)F)nc1-c1ccc(Br)cn1]
69 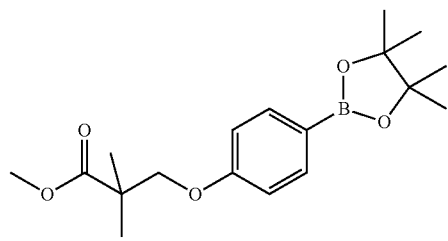 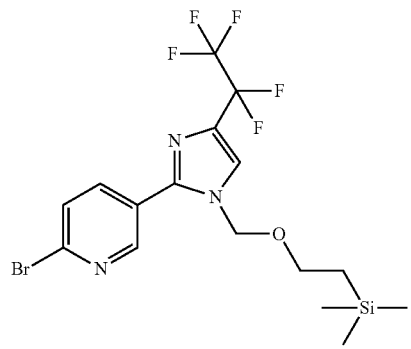 [SMILES: C[Si](C)(C)CCOCn1cc(C(F)(F)C(F)(F)F)nc1-c1ccc(Br)nc1]

TABLE 8-continued
| 70 | 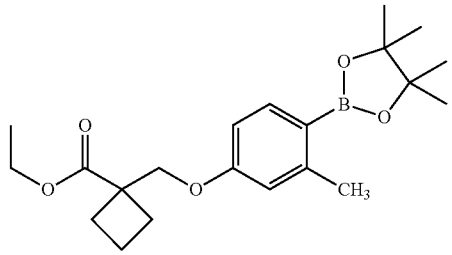 [SMILES: CCOC(=O)C1(COc2ccc(B3OC(C)(C)C(C)(C)O3)c(C)c2)CCC1] | 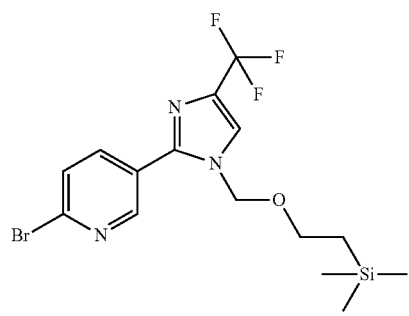 [SMILES: C[Si](C)(C)CCOCn1cc(C(F)(F)F)nc1-c1ccc(Br)nc1] |
| --- | --- | --- |
| 71 | 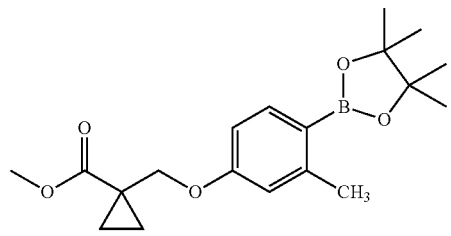 | 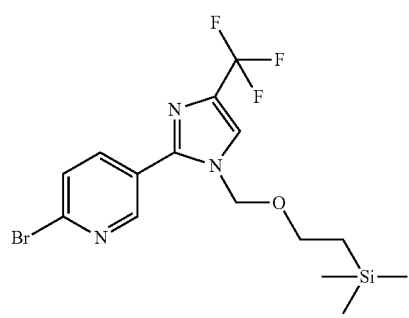 [SMILES: C[Si](C)(C)CCOCn1cc(C(F)(F)F)nc1-c1ccc(Br)nc1] |
| 72 | 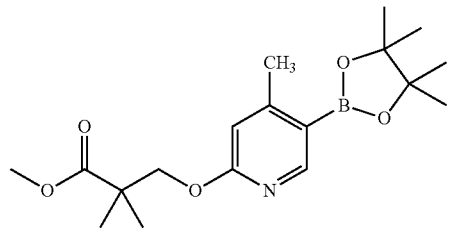 | 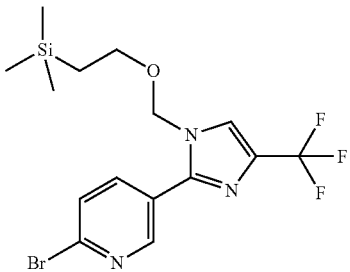 [SMILES: C[Si](C)(C)CCOCn1cc(C(F)(F)F)nc1-c1ccc(Br)nc1] |
| 73 | 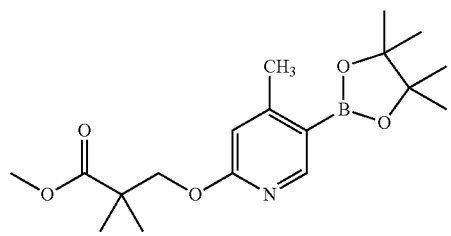 | 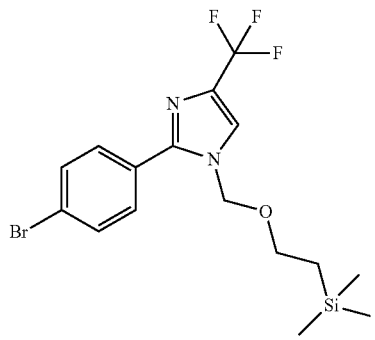 [SMILES: C[Si](C)(C)CCOCn1cc(C(F)(F)F)nc1-c1ccc(Br)cc1] |
| 74 | 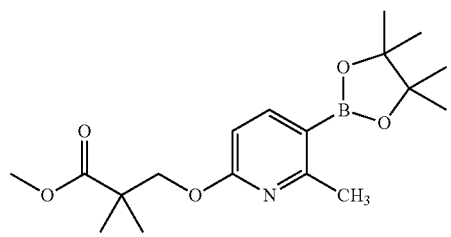 | 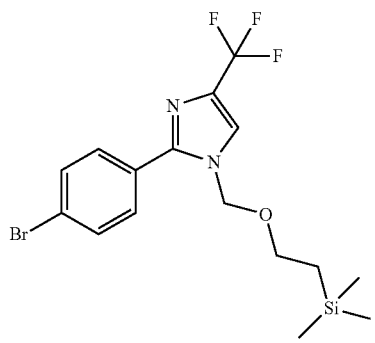 [SMILES: C[Si](C)(C)CCOCn1cc(C(F)(F)F)nc1-c1ccc(Br)cc1] |

TABLE 8-continued
| | | |
|---|---|---|
| 75 | 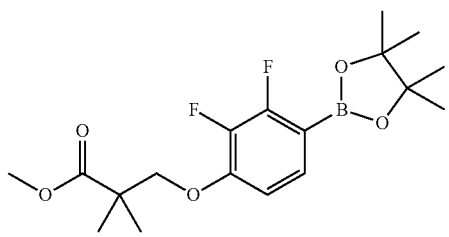 | 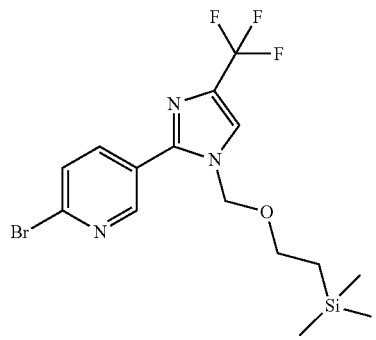 [SMILES: C[Si](C)(C)CCOCn1cc(C(F)(F)F)nc1-c1ccc(Br)nc1] |
| 76 | 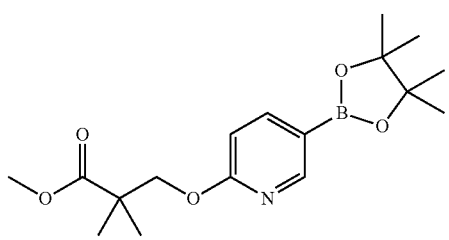 | 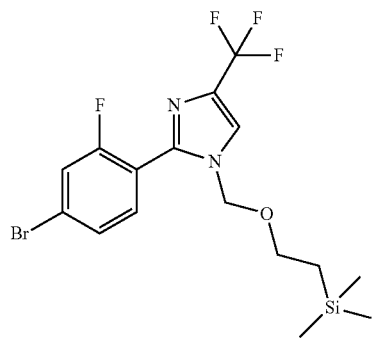 [SMILES: C[Si](C)(C)CCOCn1cc(C(F)(F)F)nc1-c1ccc(Br)cc1F] |
| 77 | 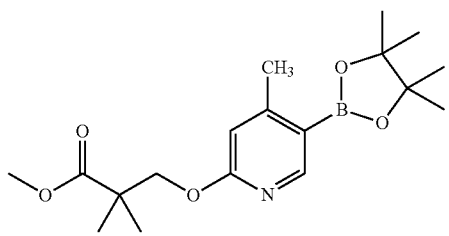 | 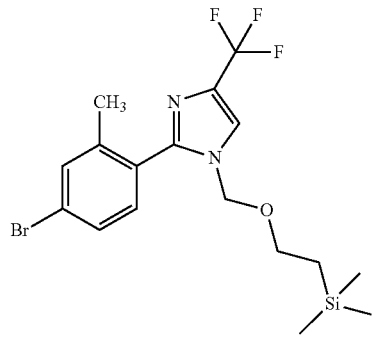 [SMILES: Cc1cc(Br)ccc1-c1nc(C(F)(F)F)cn1COCC[Si](C)(C)C] |
| 78 | 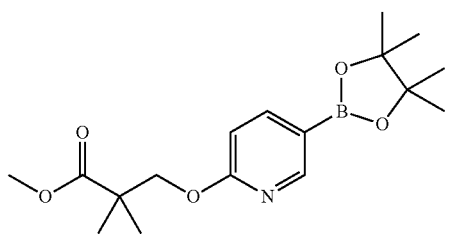 | 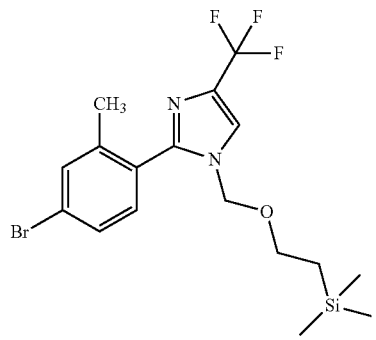 [SMILES: Cc1cc(Br)ccc1-c1nc(C(F)(F)F)cn1COCC[Si](C)(C)C] |
| 79 | 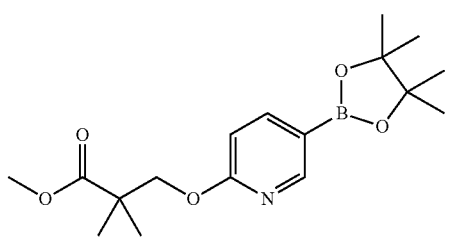 | 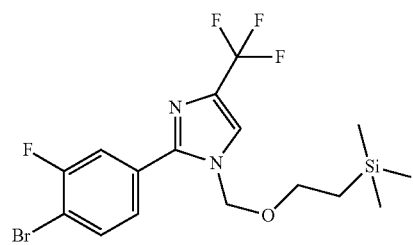 |

TABLE 8-continued
| 80 | 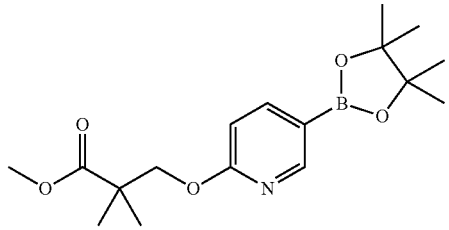 | 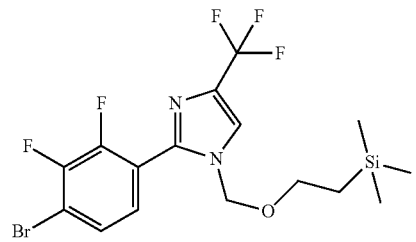 [SMILES: C[Si](C)(C)CCOCn1cc(C(F)(F)F)nc1-c1ccc(Br)c(F)c1F] |
| --- | --- | --- |
| 81 | 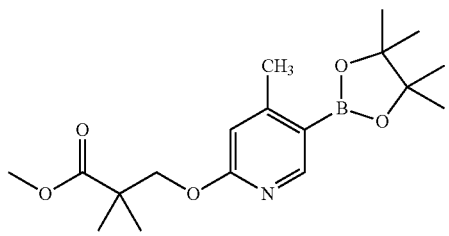 | 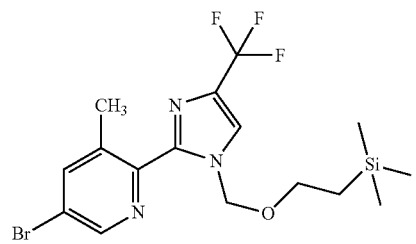 |
| 82 | 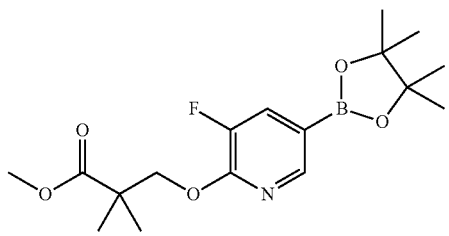 | 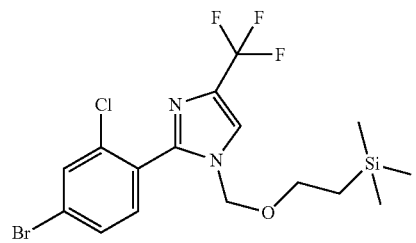 |
| 83 | 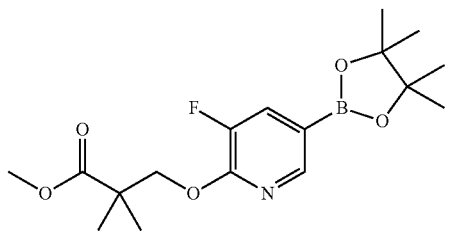 | 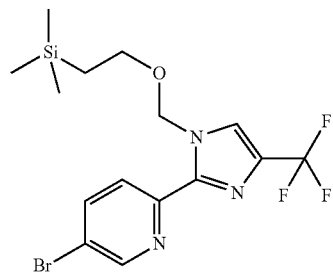 [SMILES: C[Si](C)(C)CCOCn1cc(C(F)(F)F)nc1-c1ccc(Br)cn1] |
| 84 | 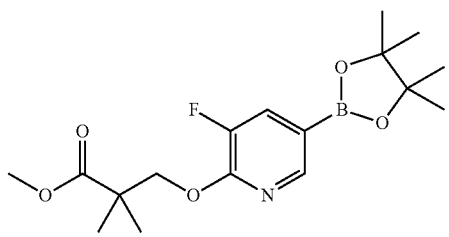 | 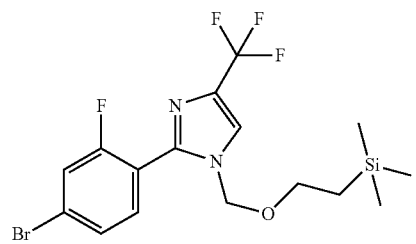 |

TABLE 8-continued

| Example | Product | MS (m/z) |
|---|---|---|
| 64 | | 424 [M + H]+ |
| 65 | | 420 [M + H]+ |
| 66 | | 407 [M + H]+ |
| 67 | | 407 [M + H]+ |

TABLE 8-continued
| 68 | 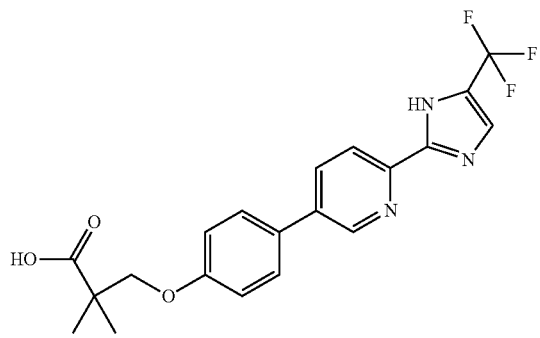 [SMILES: CC(C)(COc1ccc(-c2ccc(-c3ncc(C(F)(F)F)[nH]3)nc2)cc1)C(=O)O] | 406 [M + H]+ |
| 69 | 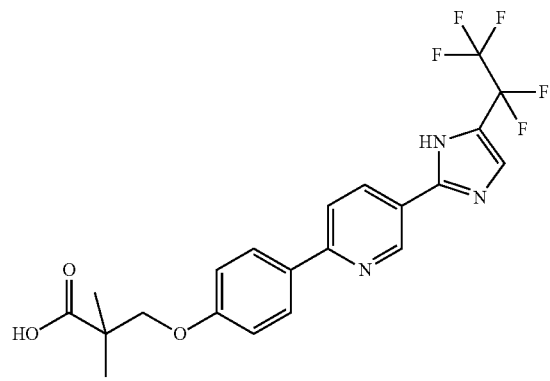 [SMILES: CC(C)(COc1ccc(-c2ccc(-c3ncc(C(F)(F)C(F)(F)F)[nH]3)cn2)cc1)C(=O)O] | 456 [M + H]+ |
| 70 | 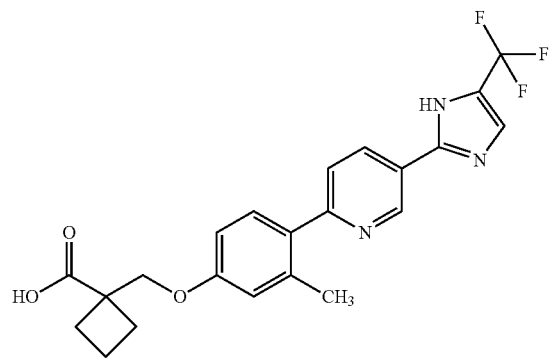 [SMILES: Cc1cc(OCC2(C(=O)O)CCC2)ccc1-c1ccc(-c2ncc(C(F)(F)F)[nH]2)cn1] | 432 [M + H]+ |
| 71 | 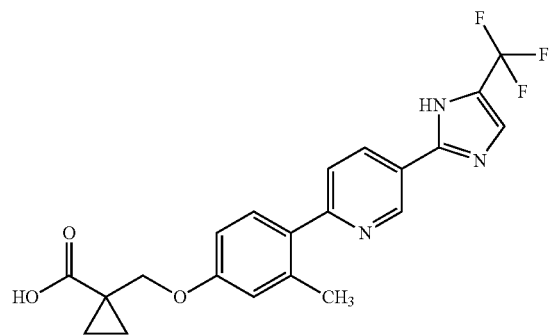 [SMILES: Cc1cc(OCC2(C(=O)O)CC2)ccc1-c1ccc(-c2ncc(C(F)(F)F)[nH]2)cn1] | 418 [M + H]+ |

TABLE 8-continued
| | | |
|---|---|---|
| 72 | 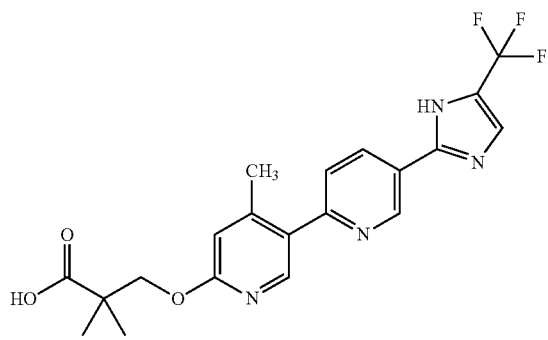 [SMILES: Cc1cc(OCC(C)(C)C(=O)O)ncc1-c1ccc(-c2ncc(C(F)(F)F)[nH]2)cn1] | 421 [M + H]+ |
| 73 | 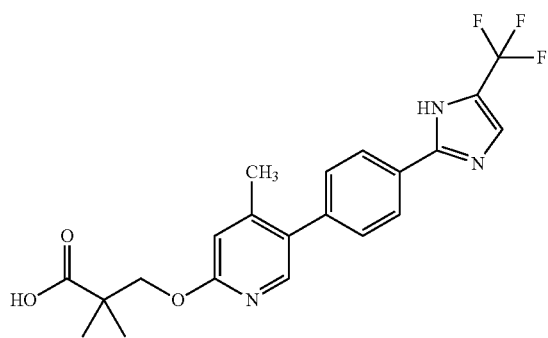 [SMILES: Cc1cc(OCC(C)(C)C(=O)O)ncc1-c1ccc(-c2ncc(C(F)(F)F)[nH]2)cc1] | 420 [M + H]+ |
| 74 | 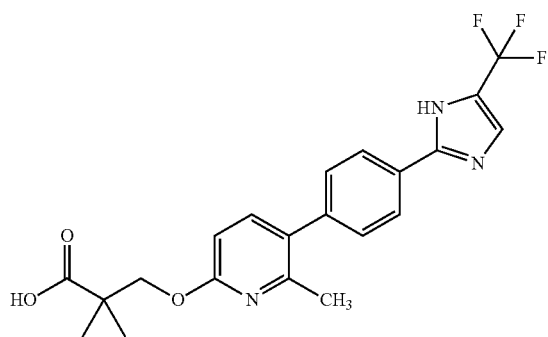 [SMILES: Cc1nc(OCC(C)(C)C(=O)O)ccc1-c1ccc(-c2ncc(C(F)(F)F)[nH]2)cc1] | 420 [M + H]+ |
| 75 | 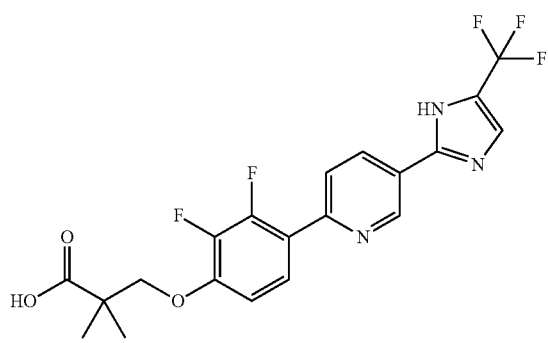 [SMILES: CC(C)(COc1ccc(-c2ccc(-c3ncc(C(F)(F)F)[nH]3)cn2)c(F)c1F)C(=O)O] | 442 [M + H]+ |

TABLE 8-continued
| 76 | 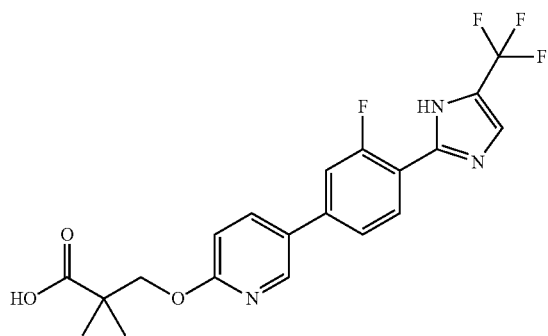 [SMILES: CC(C)(COc1ccc(-c2ccc(-c3ncc(C(F)(F)F)[nH]3)c(F)c2)cn1)C(=O)O] | 424 [M + H]+ |
| 77 | 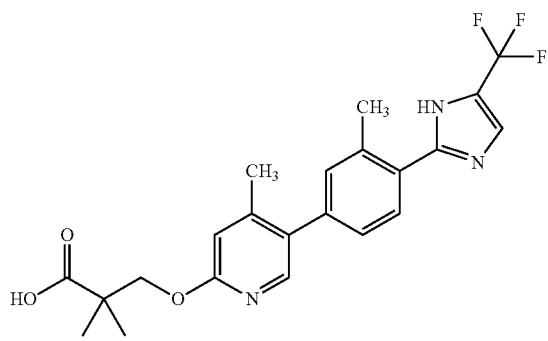 [SMILES: Cc1cc(OCC(C)(C)C(=O)O)ncc1-c1ccc(-c2ncc(C(F)(F)F)[nH]2)c(C)c1] | 434 [M + H]+ |
| 78 | 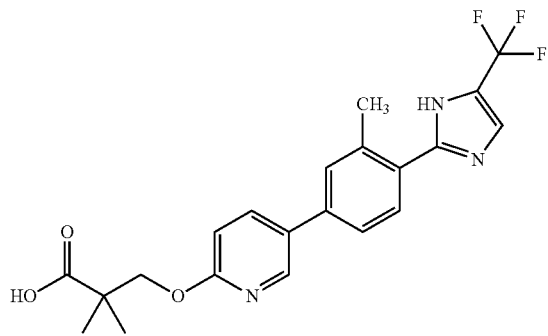 [SMILES: Cc1cc(-c2ccc(OCC(C)(C)C(=O)O)nc2)ccc1-c1ncc(C(F)(F)F)[nH]1] | 420 [M + H]+ |
| 79 | 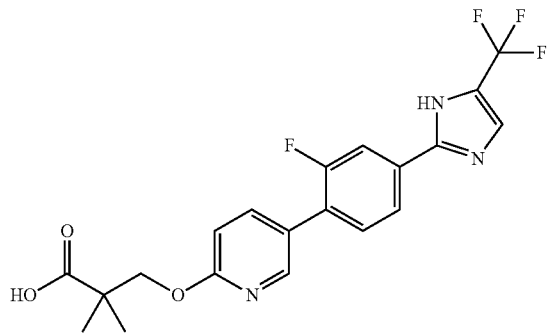 [SMILES: CC(C)(COc1ccc(-c2ccc(-c3ncc(C(F)(F)F)[nH]3)cc2F)cn1)C(=O)O] | 424 [M + H]+ |

TABLE 8-continued
| | | |
|---|---|---|
| 80 | 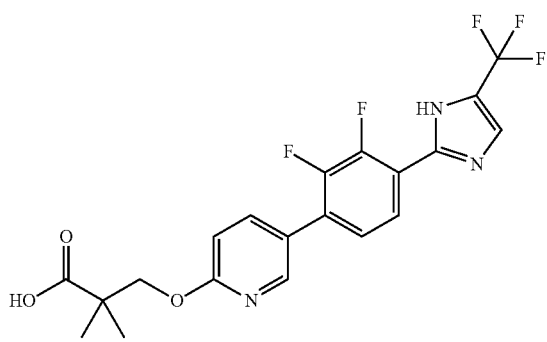 [SMILES: CC(C)(COc1ccc(-c2ccc(-c3ncc(C(F)(F)F)[nH]3)c(F)c2F)cn1)C(=O)O] | 442<br>[M + H]+ |
| 81 | 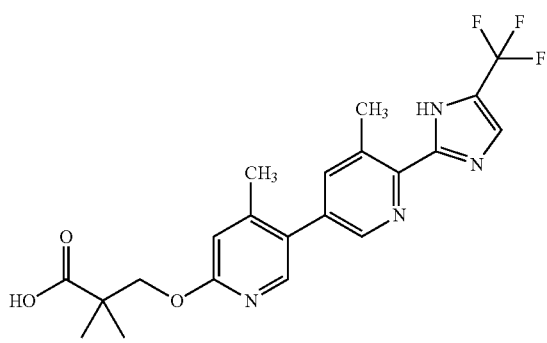 [SMILES: Cc1cc(OCC(C)(C)C(=O)O)ncc1-c1cnc(-c2ncc(C(F)(F)F)[nH]2)c(C)c1] | 435<br>[M + H]+ |
| 82 | 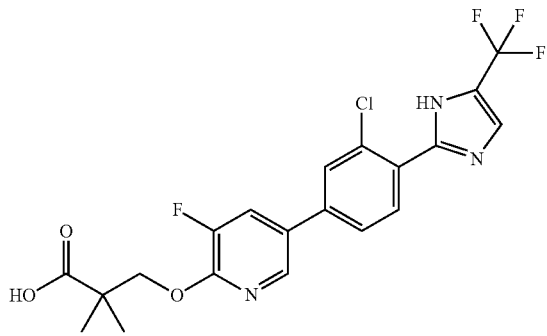 [SMILES: CC(C)(COc1ncc(-c2ccc(-c3ncc(C(F)(F)F)[nH]3)c(Cl)c2)cc1F)C(=O)O] | 458/460<br>[M + H]+ |
| 83 | 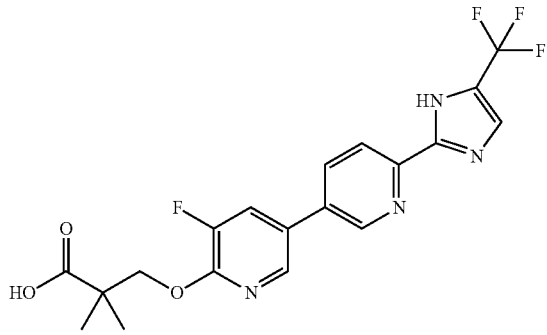 [SMILES: CC(C)(COc1ncc(-c2ccc(-c3ncc(C(F)(F)F)[nH]3)nc2)cc1F)C(=O)O] | 425<br>[M + H]+ |

TABLE 8-continued

| 84 | 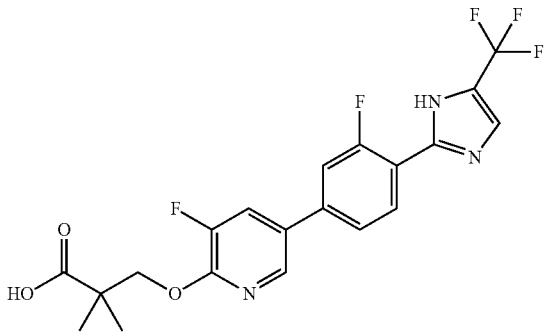 [SMILES: CC(C)(COc1ncc(-c2ccc(-c3ncc(C(F)(F)F)[nH]3)c(F)c2)cc1F)C(=O)O] | 442 [M + H]⁺ |

Example 85

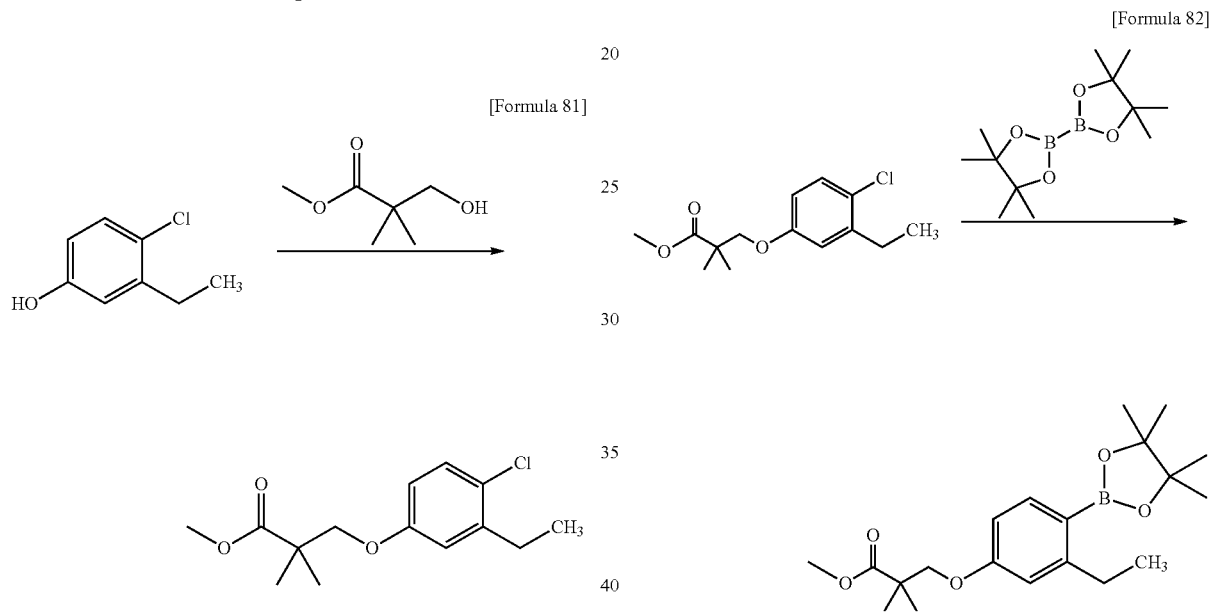

[Formula 81]

[Formula 82]

1) By using 4-chloro-3-ethylphenol (2000 mg) and methyl hydroxypivalate (2025 mg), the procedure was carried out in the same manner as in Example 1-1) to obtain methyl 3-(4-chloro-3-ethylphenoxy)-2,2-dimethylpropanoate (2951 mg).

MS (m/z): 288/290 [M+NH$_4$]⁺

2) By using methyl 3-(4-chloro-3-ethylphenoxy)-2,2-dimethylpropanoate (2000 mg), the procedure was carried out in the same manner as in Reference example 6-2) to obtain methyl 3-[3-ethyl-4-(4,4,5,5-tetramethyl-1,3,2-dioxaboloran-2-yl)phenoxy]-2,2-diethylpropanoate (2311 mg).

MS (m/z): 380 [M+NH$_4$]⁺

[Formula 83]

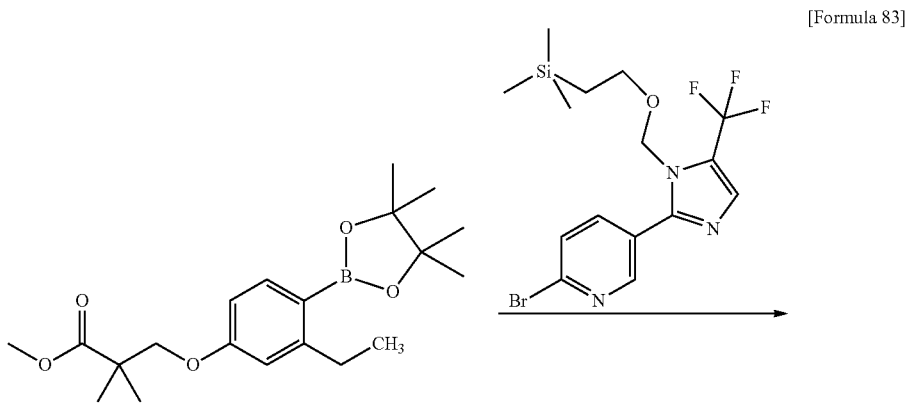

-continued

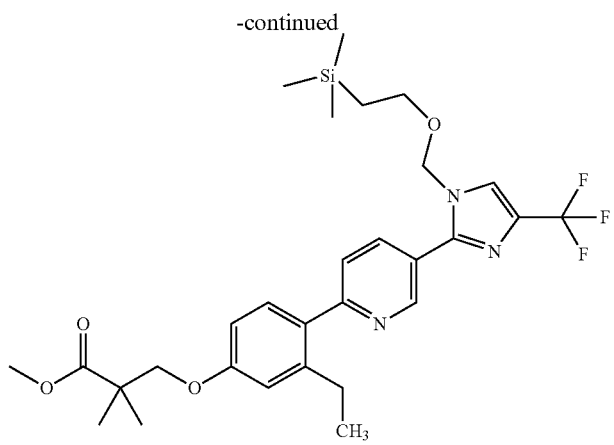

3) By using methyl 3-[3-ethyl-4-(4,4,5,5-tetramethyl-1,3,2-dioxaboloran-2-yl)phenoxy]-2,2-diethylpropanoate (200 mg) and 2-bromo-5-[4-(trifluoromethyl)-1-{[2-(trimethylsilyl)ethoxy]methyl}-1H-imidazol-2-yl]pyridine (233.2 mg), the procedure was carried out in the same manner as in Reference example 1-3) to obtain methyl 3-(3-ethyl-4-{5-[4-(trifluoromethyl)-1-{[2-(trimethylsilyl)ethoxy]methyl}-1H-imidazol-2-yl]pyridin-2-yl}phenoxy)-2,2-dimethylpropanoate (94 mg).

MS (m/z): 578 [M+H]+

[Formula 84]

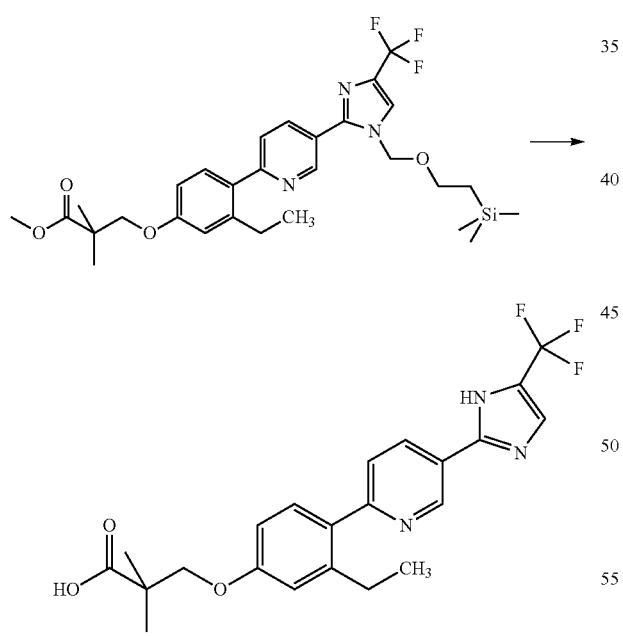

4) By using methyl 3-(3-ethyl-4-{5-[4-(trifluoromethyl)-1-{[2-(trimethylsilyl)ethoxy]-methyl}-1H-imidazol-2-yl]pyridin-2-yl}phenoxy)-2,2-dimethylpropanoate (80 mg), the procedures were carried out in the same manner as in Example 4-1) and 4-2) to obtain 3-(3-ethyl-4-{5-[5-(trifluoromethyl)-1H-imidazol-2-yl]pyridin-2-yl}phenoxy)-2,2-dimethylpropanoic acid (434 mg).

MS (m/z): 434 [M+H]+

Example 86

[Formula 85]

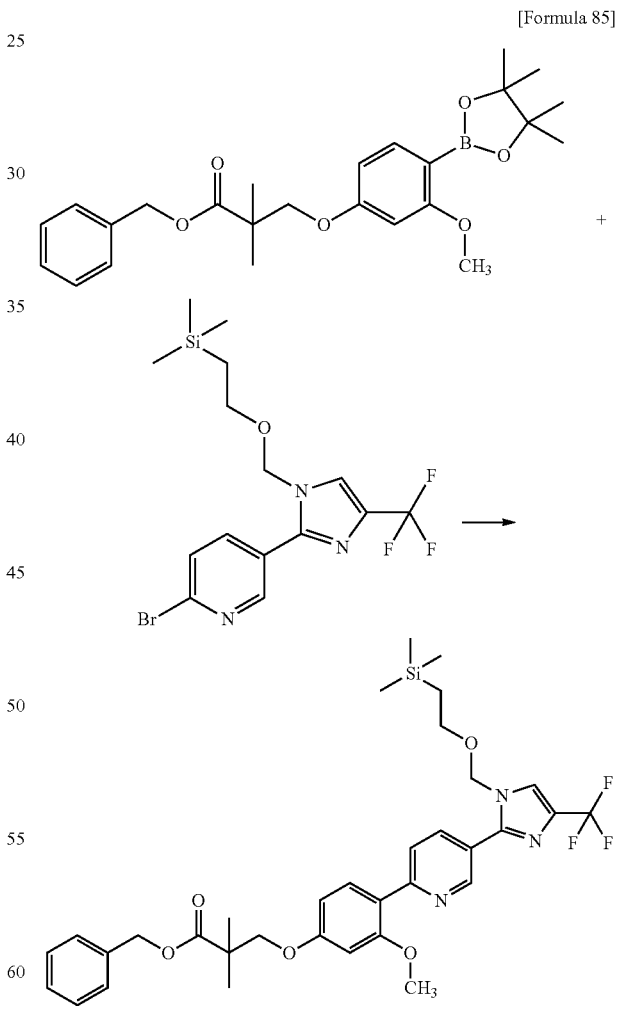

1) By using benzyl 3-[3-methoxy-4-(4,4,5,5-tetramethyl-1,3,2-dioxaborolan-2-yl)phenoxy]-2,2-dimethylpropanoate (1.03 g) and 2-bromo-5-[4-(trifluoromethyl)-1-{[2-(trimethylsilyl)ethoxy]methyl}-1H-imidazol-2-yl]pyridine (494 mg), the procedure was carried out in the same manner as in Reference example 1-3) to obtain benzyl 3-[3-methoxy-4-[5-[4-(trifluoromethyl)-1-(2-trimethylsilylethoxymethyl) imidazol-2-yl]-2-pyridyl]phenoxy]-2,2-dimethylpropanoate (639 mg).

MS (m/z): 656 [M+H]⁺

[Formula 86]

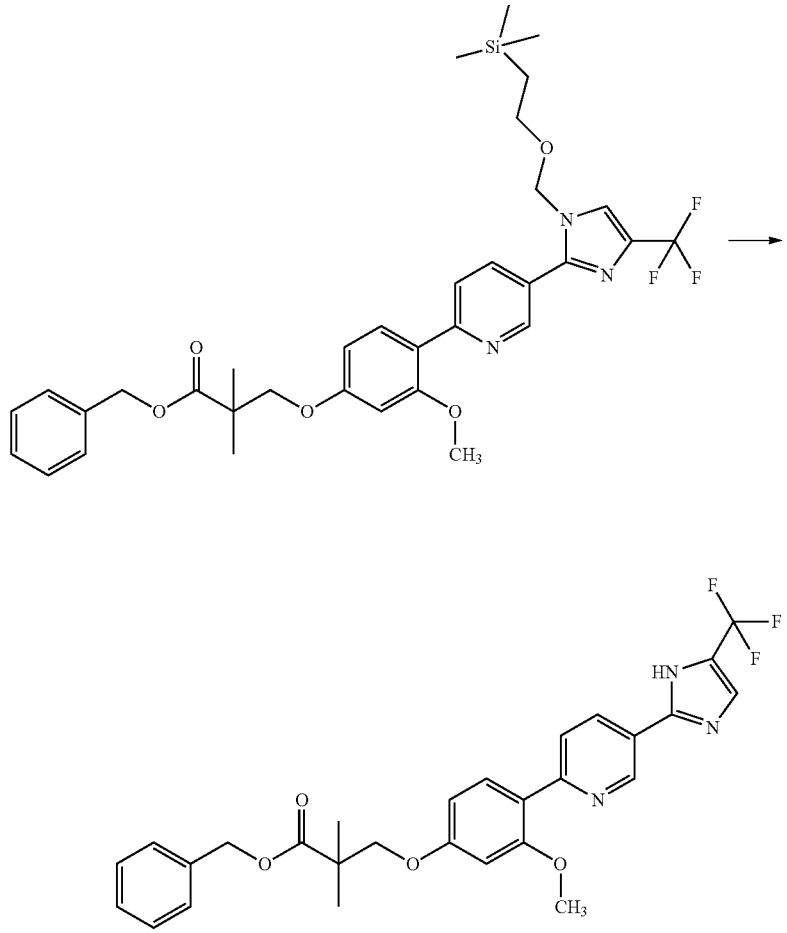

2) By using benzyl 3-[3-methoxy-4-[5-[4-(trifluoromethyl)-1-(2-trimethylsilylethoxymethyl)imidazol-2-yl]-2-pyridyl]phenoxy]-2,2-dimethylpropanoate (638 mg), the procedure was carried out in the same manner as in Example 1-2) to obtain benzyl 3-[3-methoxy-4-[5-[5-(trifluoromethyl)-1H-imidazol-2-yl]-2-pyridyl]phenoxy]-2,2-dimethylpropanoate.

MS (m/z): 526 [M+H]⁺

[Formula 87]

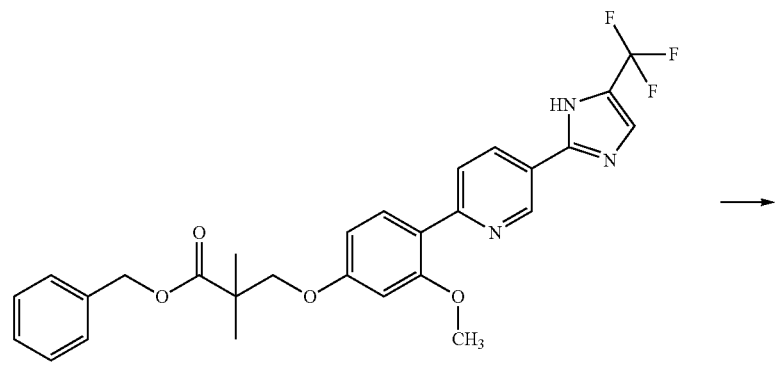

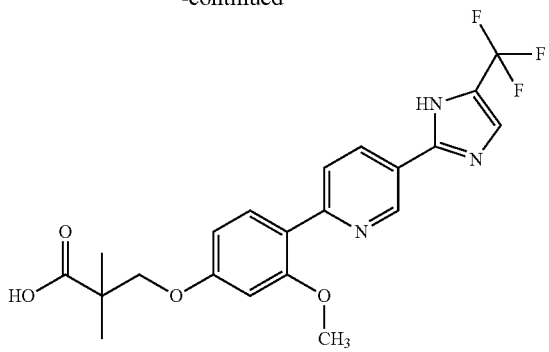

3) By using benzyl 3-[3-methoxy-4-[5-[5-(trifluoromethyl)-1H-imidazol-2-yl]-2-pyridyl]phenoxy]-2,2-dimethylpropanoate obtained in the above-mentioned 2), the procedure was carried out in the same manner as in Example 18-2) to obtain 3-[3-methoxy-4-[5-[5-(trifluoromethyl)-1H-imidazol-2-yl]-2-pyridyl]phenoxy]-2,2-dimethylpropanoic acid (246 mg).

MS (m/z): 436 [M+H]$^+$

Example 87

[Formula 88]

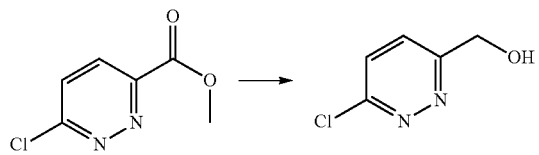

1) In tetrahydrofuran (100 mL) was dissolved methyl 6-chloropyridazin-3-carboxylate (1.726 g), the solution was cooled to 0° C., 1M diisobutylaluminum hydride-tetrahydrofuran solution (20 mL) was added dropwise to the solution, and the mixture was stirred at the same temperature for 20 minutes. To the reaction mixture were successively added water (10 mL) and 1N hydrochloric acid (20 mL) at 0° C. After adding a saturated aqueous sodium bicarbonate solution to the mixture at room temperature, the mixture was extracted with chloroform. The extract was dried over anhydrous sodium sulfate, and the residue obtained by concentrating the extract under reduced pressure was purified by silica gel column chromatography (n-hexane:ethyl acetate=90:10 to 25:75) to obtain (6-chloropyridazin-3-yl)methanol (177 mg).

MS (m/z): 147/145 [M+H]$^+$

[Formula 89]

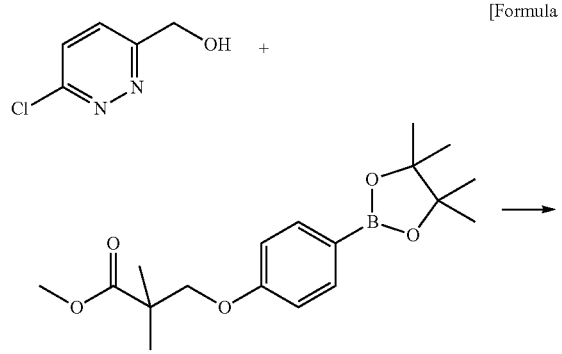

2) By using (6-chloropyridazin-3-yl)methanol (170 mg), and methyl 3-[3-fluoro-4-(4,4,5,5-tetramethyl-1,3,2-dioxaboloran-2-yl)phenoxy]-2,2-dimethylpropanoate (606 mg), the procedure was carried out in the same manner as in Reference example 1-3) to obtain methyl 3-{4-[6-(hydroxymethyl)pyridazin-3-yl]phenoxy}-2,2'-dimethylpropanoate (188 mg).

MS (m/z): 317 [M+H]$^+$

[Formula 90]

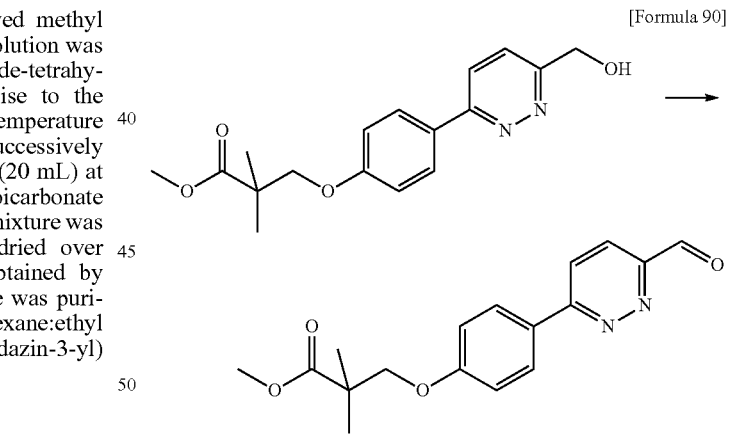

3) To a methylene chloride (8 mL) solution containing oxalyl chloride (278 µL) was added dropwise a methylene chloride solution (2 mL) containing dimethylsulfoxide (350 µL) at −78° C., and the mixture was stirred at the same temperature for 10 minutes. A methylene chloride (5 mL) containing methyl 3-{4-[6-(hydroxymethyl)pyridazin-3-yl]phenoxy}-2,2'-dimethylpropanoate (519 mg) was added dropwise to the mixture over 10 minutes, and the mixture was stirred at the same temperature for 1 hour. Triethylamine (1.6 mL) was added dropwise to the mixture at 0° C., and the mixture was stirred for 30 minutes. To the reaction mixture were added a saturated aqueous ammonium chloride solution and ethyl acetate, and the liquids were separated. The aqueous layer was extracted twice with ethyl acetate. The organic layers were combined, washed successively with water (twice), and saturated brine, dried over anhydrous sodium sulfate, and concentrated under reduced pressure. The obtained residue was purified by silica gel column chromatography (n-hexane:ethyl acetate=90:10 to 50:50) to obtain methyl 3-[4-(6-formylpyridazin-3-yl)phenoxy]-2,2'-dimethylpropanoate (443 mg).

MS (m/z): 315 [M+H]$^+$

5) By using methyl 2,2-dimethyl-3-(4-{6-[5-(trifluoromethyl)-1H-imidazol-2-yl]-pyridazin-3-yl}phenoxy)propanoate (359 mg), the procedure was carried out in the same manner as in Reference example 1-2) to obtain methyl 2,2-dimethyl-3-(4-{6-[4-(trifluoromethyl)-1-{[2-(trimethylsilyl)ethoxy]methyl}-1H-imidazol-2-yl]pyridazin-3-yl}phenoxy)propanoate (309 mg).

MS (m/z): 551 [M+H]$^+$

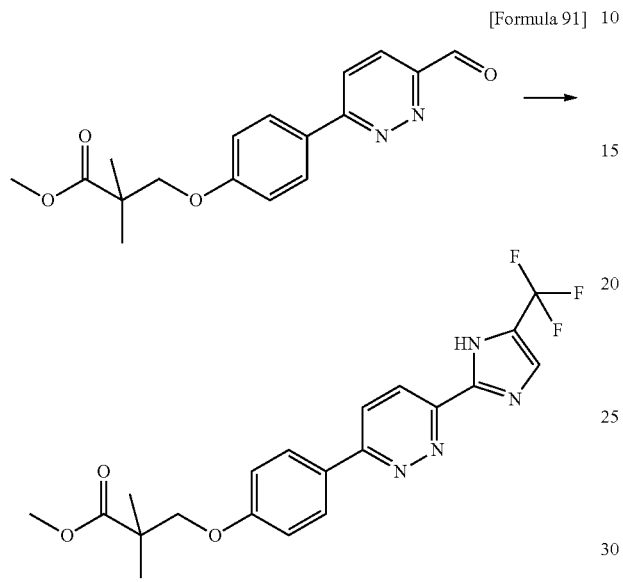

[Formula 91]

4) By using methyl 3-[4-(6-formylpyridazin-3-yl)phenoxy]-2,2'-dimethylpropanoate (443 mg), the procedure was carried out in the same manner as in Reference example 1-1) to obtain methyl 2,2-dimethyl-3-(4-{6-[5-(trifluoromethyl)-1H-imidazol-2-yl]-pyridazin-3-yl}phenoxy)propanoate (360 mg).

MS (m/z): 421 [M+H]$^+$

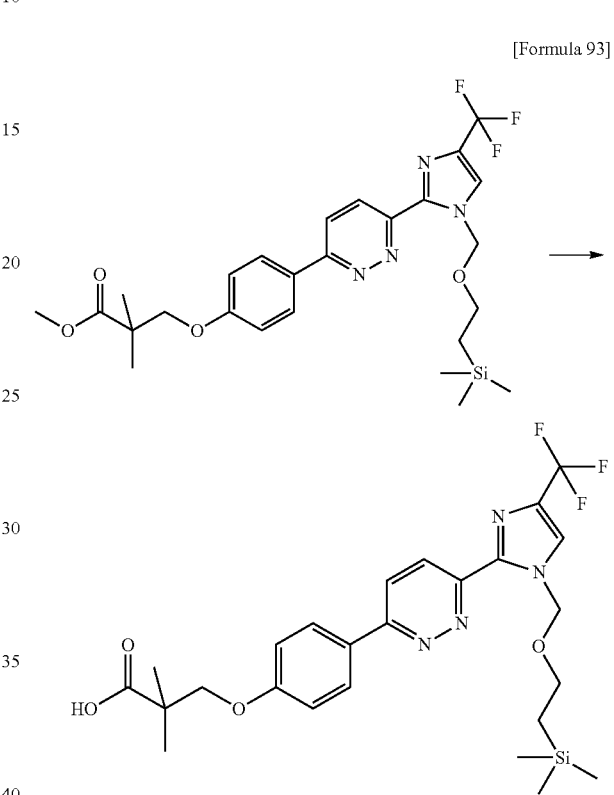

[Formula 93]

6) By using methyl 2,2-dimethyl-3-(4-{6-[4-(trifluoromethyl)-1-{[2-(trimethylsilyl)ethoxy]methyl}-1H-imidazol-2-yl]pyridazin-3-yl}phenoxy)propanoate (309 mg), the procedure was carried out in the same manner as in Example 3-2) to obtain 2,2-dimethyl-3-(4-{6-[4-(trifluoromethyl)-1-{[2-(trimethylsilyl)ethoxy]methyl}-1H-imidazol-2-yl]pyridazin-3-yl}phenoxy)propanoic acid (259 mg).

MS (m/z): 537 [M+H]$^+$

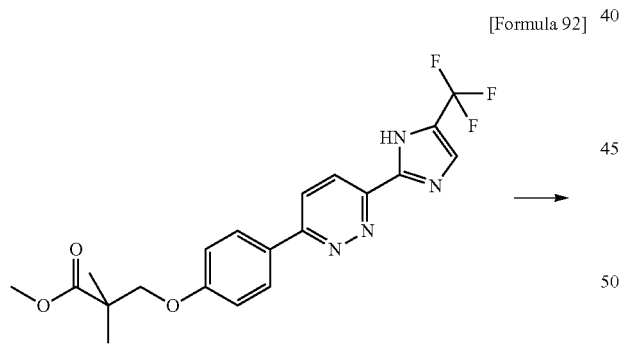

[Formula 92]

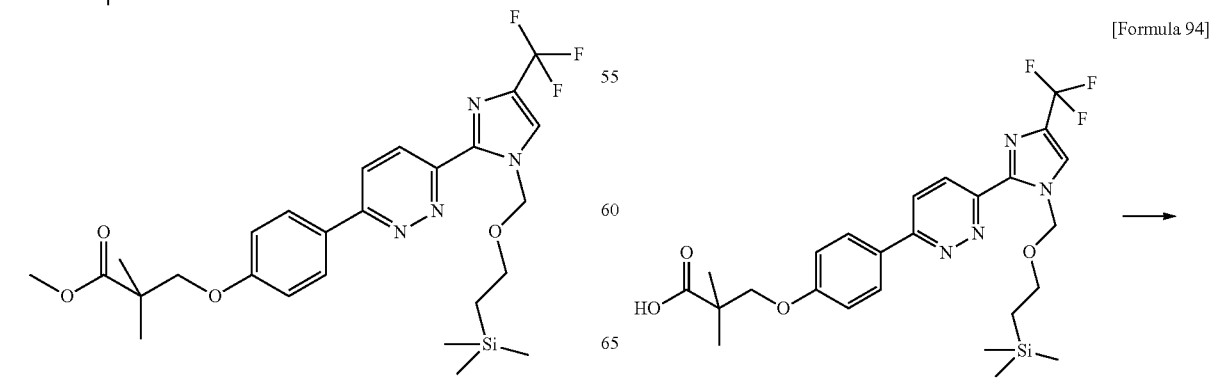

[Formula 94]

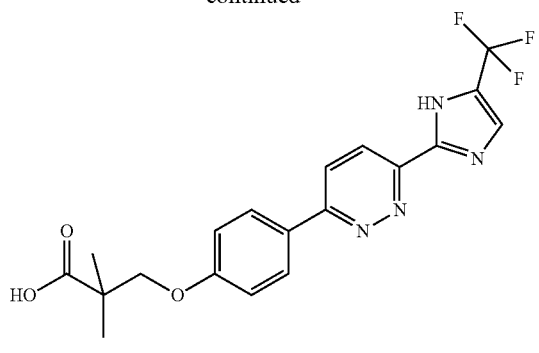

7) By using 2,2-dimethyl-3-(4-{6-[4-(trifluoromethyl)-1-{[2-(trimethylsilyl)ethoxy]-methyl}-1H-imidazol-2-yl]pyridazin-3-yl}phenoxy)propanoic acid (257 mg), the procedure was carried out in the same manner as in Example 3-3) to obtain 2,2-dimethyl-3-(4-{6-[4-(trifluoromethyl)-1H-imidazol-2-yl]pyridazin-3-yl}phenoxy)propanoic acid (194 mg).

MS (m/z): 407 [M+H]$^+$

Example 88

[Formula 95]

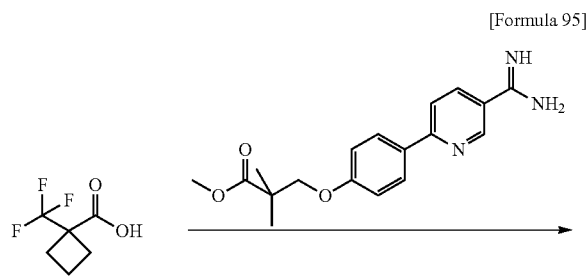

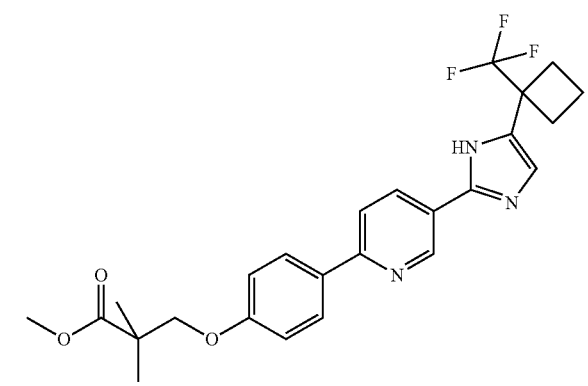

1) By using 1-(trifluoromethyl)-1-cyclobutane carboxylic acid (300 mg), and methyl 3-(4-{5-[amino(imino)methyl]pyridin-2-yl}phenoxy)-2,2-dimethylpropanoate acetate (415 mg), the procedure was carried out in the same manner as in Example 2-1) to obtain methyl 2,2-dimethyl-3-[4-(5-{5-[1-(trifluoromethyl)cyclobutyl]-1H-imidazol-2-yl}pyridin-2-yl)phenoxy)propanoate (369 mg).

MS (m/z): 474 [M+H]$^+$

[Formula 96]

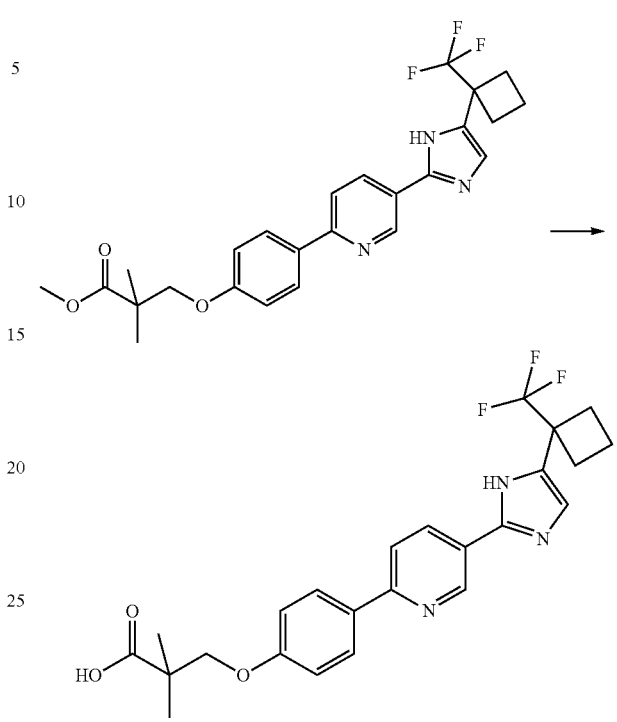

2) By using methyl 2,2-dimethyl-3-[4-(5-{5-[1-(trifluoromethyl)cyclobutyl]-1H-imidazol-2-yl}pyridin-2-yl)phenoxy)propanoate (367 mg), the procedure was carried out in the same manner as in Example 2-2) to obtain 2,2-dimethyl-3-[4-(5-{5-[1-(trifluoromethyl)cyclobutyl]-1H-imidazol-2-yl}pyridin-2-yl)phenoxy)propanoic acid (350 mg).

MS (m/z): 460 [M+H]$^+$

[Formula 97]

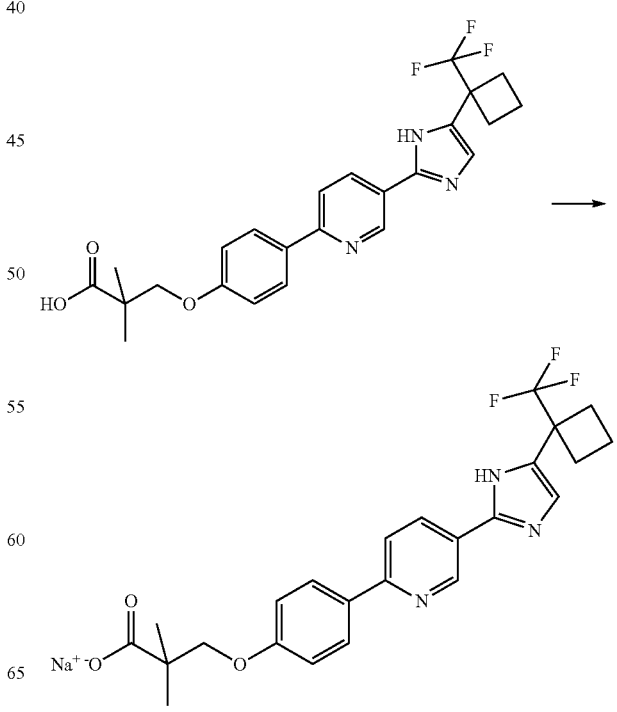

3) By using 2,2-dimethyl-3-[4-(5-{5-[1-(trifluoromethyl)cyclobutyl]-1H-imidazol-2-yl}pyridin-2-yl)phenoxy)propanoic acid (350 mg), the procedure was carried out in the same manner as in Example 2-3) to obtain sodium 2,2-dimethyl-3-[4-(5-{5-[1-(trifluoromethyl)cyclobutyl]-1H-imidazol-2-yl}pyridin-2-yl)phenoxy)propanoate (296 mg).

MS (m/z): 458 [M−Na]⁻

Example 89

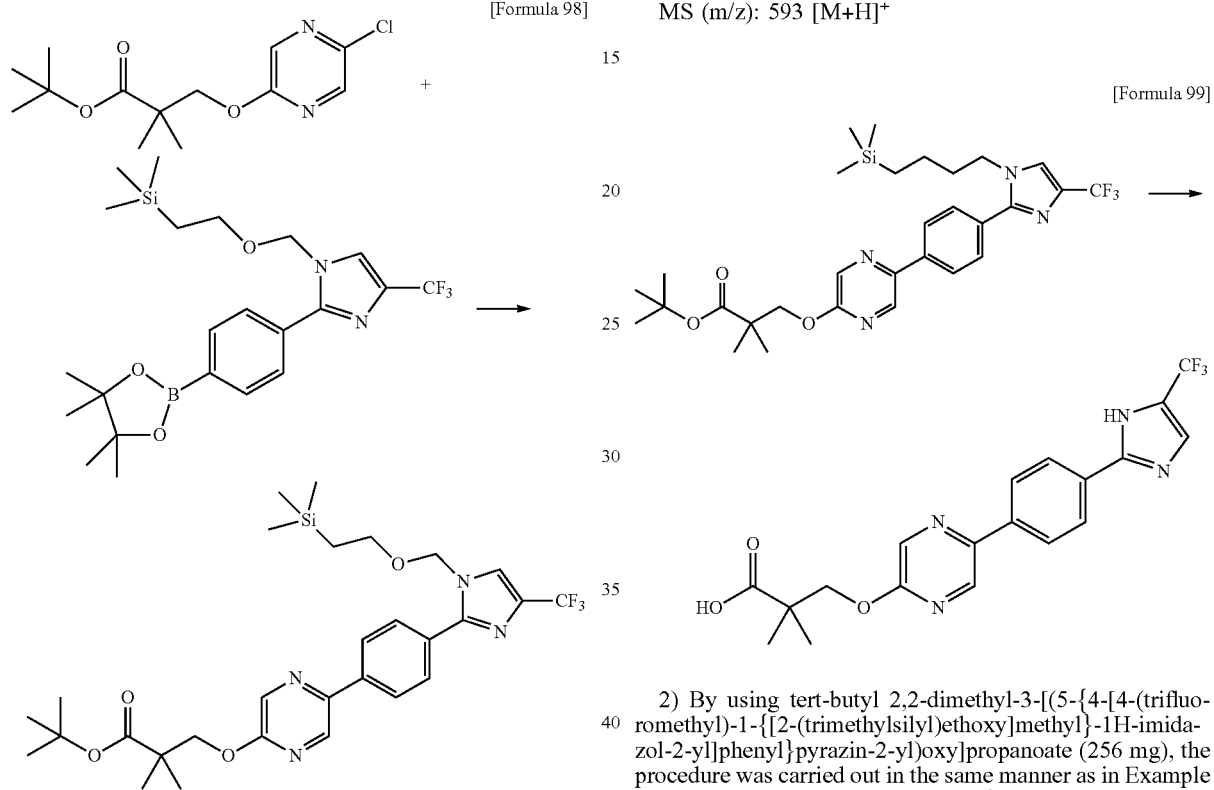

[Formula 98]

1) Dimethoxyethane (10 mL) and 2M aqueous sodium carbonate solution (1290 μL) were added to tert-butyl 3-[(5-chloropyrazin-2-yl)oxy]-2,2-dimethylpropanoate (185 mg), tetrakistriphenylphosphine palladium (75 mg) and 2-[4-(4,4,5,5-tetramethyl-1,3,2-dioxaboloran-2-yl)phenyl]-4-(trifluoromethyl)-1-{[2-(trimethylsilyl)ethoxy]methyl}-1H-imidazole (363 mg), and the mixture was stirred at 80° C. for 4 hours. The reaction mixture was cooled to room temperature, and filtered by using Celite. To the filtrate were added ethyl acetate and water, and the liquids were separated. The organic layer was separated, washed with saturated brine, dried over anhydrous sodium sulfate, and concentrated under reduced pressure. The obtained residue was purified by silica gel column chromatography (n-hexane:ethyl acetate=99:1 to 90:10) to obtain tert-butyl 2,2-dimethyl-3-[(5-{4-[4-(trifluoromethyl)-1-{[2-(trimethylsilyl)ethoxy]methyl}-1H-imidazol-2-yl]phenyl}pyrazin-2-yl)oxy]propanoate (256.2 mg).

MS (m/z): 593 [M+H]⁺

[Formula 99]

2) By using tert-butyl 2,2-dimethyl-3-[(5-{4-[4-(trifluoromethyl)-1-{[2-(trimethylsilyl)ethoxy]methyl}-1H-imidazol-2-yl]phenyl}pyrazin-2-yl)oxy]propanoate (256 mg), the procedure was carried out in the same manner as in Example 8-2) to obtain 2,2-dimethyl-3-[(5-{4-[4-(trifluoromethyl)-1H-imidazol-2-yl]phenyl}pyrazin-2-yl)oxy]-propanoic acid (122.7 mg).

MS (m/z): 407 [M+H]⁺

By using the corresponding starting materials, the following compounds were synthesized in the same manner as in Example 89.

TABLE 9

| Example | Starting substance 1 | Starting substance 2 |
|---|---|---|
| 90 | | |

TABLE 9-continued
| 91 | 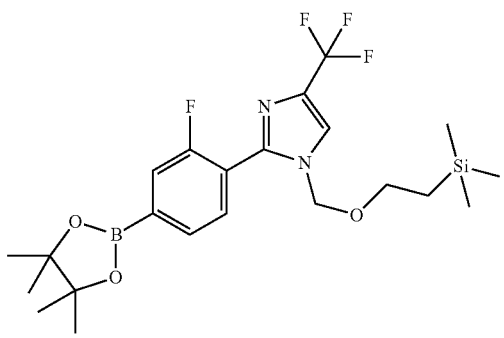 | 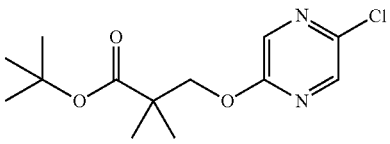 [SMILES: CC(C)(C)OC(=O)C(C)(C)COc1cnc(Cl)cn1] |
| 92 | 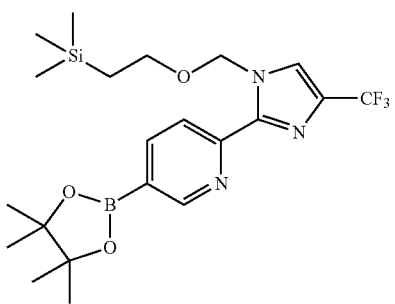 [SMILES: CC1(C)OB(c2ccc(-c3nc(C(F)(F)F)cn3COCC[Si](C)(C)C)nc2)OC1(C)C] | 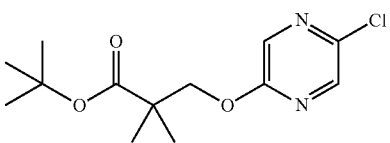 [SMILES: CC(C)(C)OC(=O)C(C)(C)COc1cnc(Cl)cn1] |
| Example | Product | MS (m/z) |
|---|---|---|
| 90 | 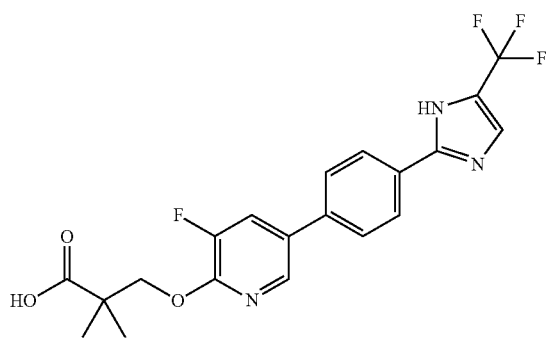 [SMILES: CC(C)(COc1ncc(-c2ccc(-c3ncc(C(F)(F)F)[nH]3)cc2)cc1F)C(=O)O] | 424 [M + H]+ |
| 91 | 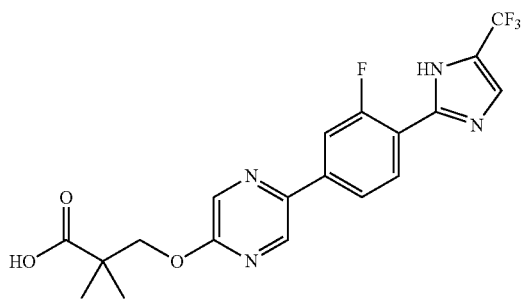 [SMILES: CC(C)(COc1cnc(-c2ccc(-c3ncc(C(F)(F)F)[nH]3)c(F)c2)cn1)C(=O)O] | 425 [M + H]+ |

TABLE 9-continued

| 92 | 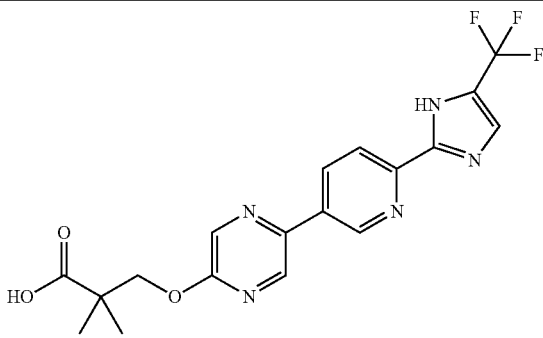 | 408 [M + H]+ |

Example 93

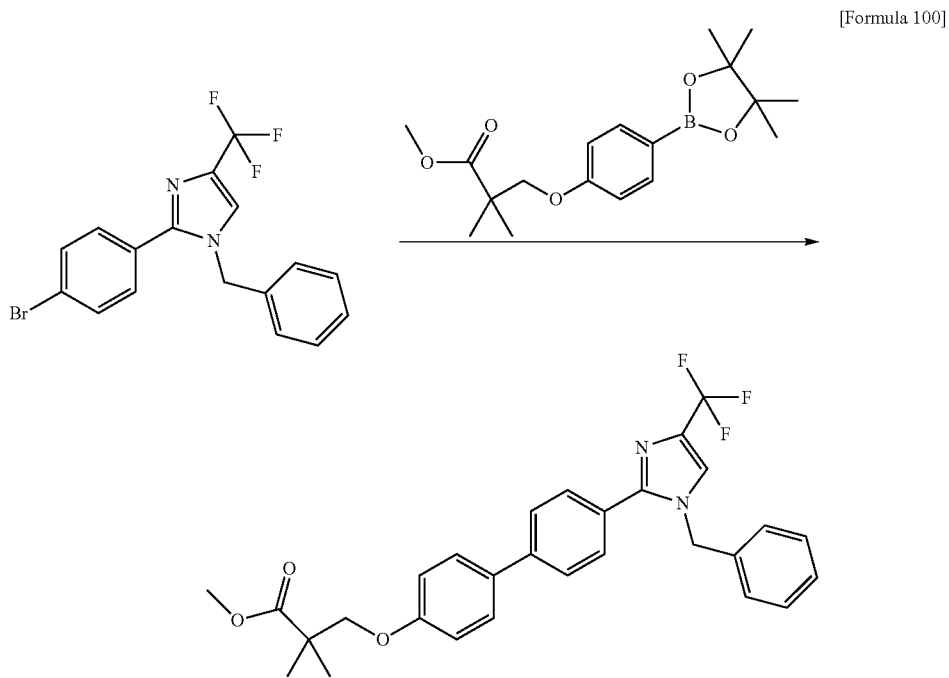

[Formula 100]

1) By using 1-benzyl-2-(4-bromophenyl)-4-(trifluoromethyl)-1H-imidazole (815 mg) and methyl 2,2-dimethyl-3-[4-(4,4,5,5-tetramethyl-1,3,2-dioxaboloran-2-yl)phenoxy]-propanoate (1.43 g), the procedure was carried out in the same manner as in Reference example 1-3) to obtain methyl 3-({4'-[1-benzyl-4-(trifluoromethyl)-1H-imidazol-2-yl]-biphenyl-4-yl}oxy)-2,2-dimethylpropanoate (901 mg).

MS (m/z): 509 [M+H]+

[Formula 101]

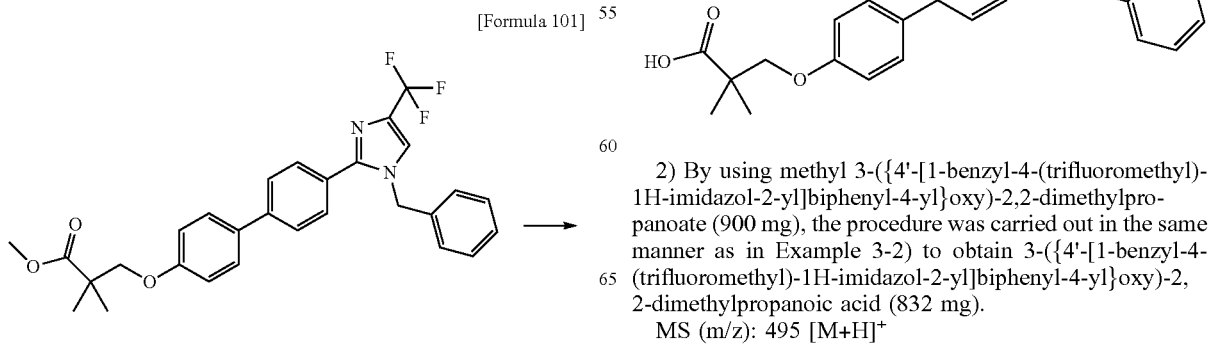

2) By using methyl 3-({4'-[1-benzyl-4-(trifluoromethyl)-1H-imidazol-2-yl]biphenyl-4-yl}oxy)-2,2-dimethylpropanoate (900 mg), the procedure was carried out in the same manner as in Example 3-2) to obtain 3-({4'-[1-benzyl-4-(trifluoromethyl)-1H-imidazol-2-yl]biphenyl-4-yl}oxy)-2,2-dimethylpropanoic acid (832 mg).

MS (m/z): 495 [M+H]+

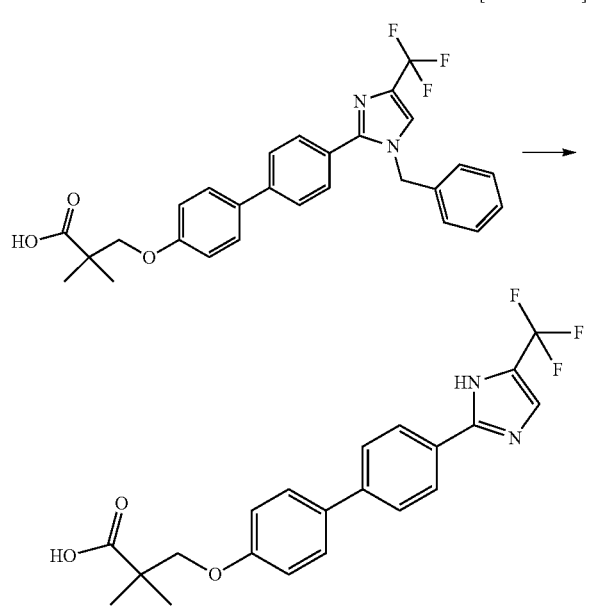

[Formula 102]

3) The mixture of 3-({4'-[1-benzyl-4-(trifluoromethyl)-1H-imidazol-2-yl]biphenyl-4-yl}oxy)-2,2-dimethylpropanoic acid (830 mg), 20% palladium hydroxide-carbon (850 mg) and tetrahydrofuran (20 mL) was stirred at 60° C. under hydrogen atmosphere for 6 hours. Nitrogen gas was passed through the reaction mixture, and the mixture was diluted with chloroform. The mixture was filtered by using a membrane filter, and the filtrate was washed with tetrahydrofuran, methanol and chloroform. The filtrates were combined, and n-hexane and propanol were added to the residue obtained by concentrating the same under the reduced pressure. The precipitated solid was collected by filtration to obtain 3-({4'-[5-(trifluoromethyl)-1H-imidazol-2-yl]biphenyl-4-yl}oxy)-2,2-dimethylpropanoic acid (635 mg).

MS (m/z): 405 [M+H]$^+$

Example 94

[Formula 104]

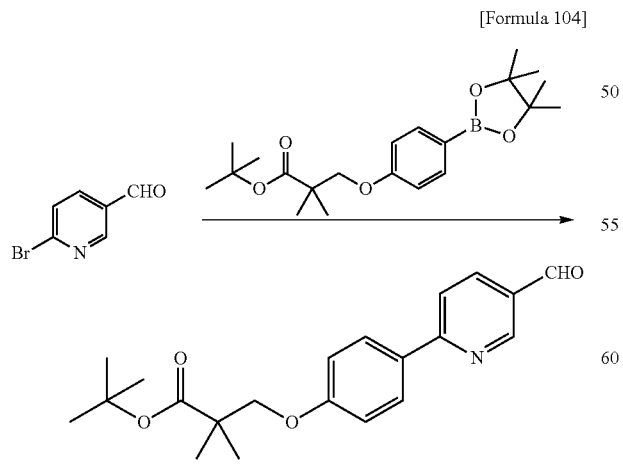

1) N,N-dimethylformamide (7.4 mL) was added to 6-bromo-nicotinaldehyde (273 mg), tert-butyl 2,2-dimethyl-3-[4-(4,4,5,5-tetramethyl-1,3,2-dioxaboloran-2-yl)phenoxy]-propanoate (552 mg) and 2N aqueous sodium carbonate solution (2.2 mL), and after replacing the atmosphere with nitrogen, palladium chloride (dppf) methylene chloride complex (60 mg) was added to the mixture and the resulting mixture was stirred at 60° C. overnight. To the reaction mixture were added ethyl acetate and water, and the liquids were separated. After filtration with Celite, the organic layer was separated, washed with water and then with a saturated brine, dried over anhydrous sodium sulfate, and concentrated under reduced pressure. The obtained residue was purified by silica gel column chromatography (n-hexane: ethyl acetate=90:10 to 70:30) to obtain tert-butyl 3-[4-(5-formylpyridin-2-yl)-phenoxy]-2,2-dimethylpropanoate (459 mg).

MS (m/z): 356 [M+H]$^+$

[Formula 104]

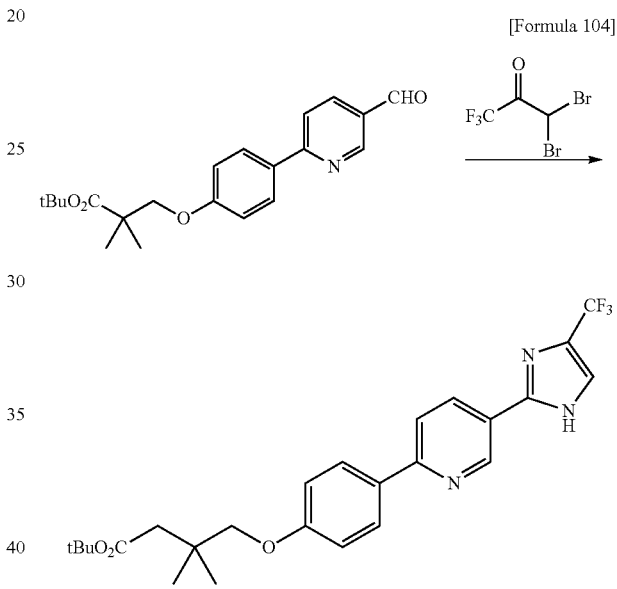

2) By using 3,3-dibromo-1,1,1-trifluoropropan-2-one (2.02 g), and tert-butyl 3-[4-(5-formylpyridin-2-yl)-phenoxy]-2,2-dimethylpropanoate (889 mg), the procedure was carried out in the same manner as in Reference example 1-1) to obtain tert-butyl 2,2-dimethyl-3-{4-[5-(4-trifluoromethyl-1H-imidazol-2-yl)-pyridin-2-yl]-phenoxy}propanoate as pale yellow solid (806 mg).

MS (m/z): 462 [M+H]$^+$

[Formula 5]

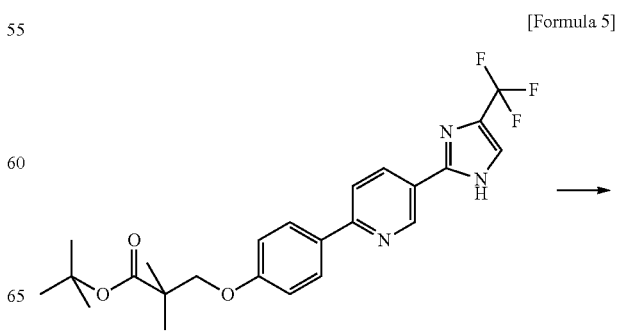

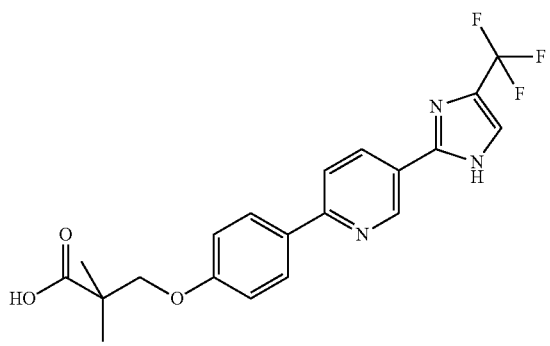

3) By using tert-butyl 2,2-dimethyl-3-{4-[5-(4-trifluoromethyl-1H-imidazol-2-yl)pyridin-2-yl]-phenoxy}-propanoate (325 mg), the procedure was carried out in the same manner as in Example 8-2) to obtain 2,2-dimethyl-3-[4-[5-[4-(trifluoromethyl)-1H-imidazol-2-yl]-2-pyridyl]phenoxy]propanoic acid (167 mg).

MS (m/z):420 [M+H]$^+$

[Formula 106]

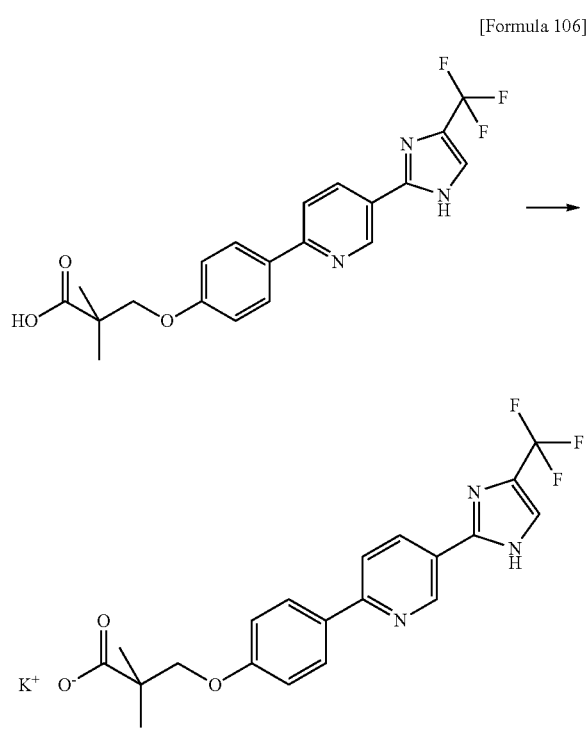

4) In tetrahydrofuran (10 mL) was suspended 2,2-dimethyl-3-[4-[5-[4-(trifluoromethyl)-1H-imidazol-2-yl]-2-pyridyl]phenoxy]propanoic acid (1001 mg), and the mixture was stirred at room temperature for 30 minutes. 10M aqueous potassium hydroxide solution (0.25 mL) was added dropwise to the mixture, and the mixture was stirred at room temperature for 2 hours. The precipitated solid was collected by filtration, washed with tetrahydrofuran, and dried under reduced pressure to obtain potassium 2,2-dimethyl-3-[4-[5-[4-(trifluoromethyl)-1H-imidazol-2-yl]-2-pyridyl]phenoxy]propanoate (995 mg).

MS (m/z): 406 [M-K+2H]$^+$

Example 95

[Formula 107]

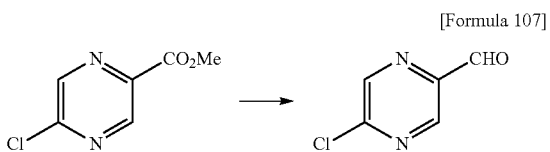 [SMILES: COC(=O)c1cnc(Cl)cn1 ; O=Cc1cnc(Cl)cn1]

1) In tetrahydrofuran (66 mL) was dissolved methyl 5-chloropyrazine-2-carboxylate (3.3 g), and 1M diisobutylaluminum hydride/hexane solution (38.3 mL) was added dropwise to the solution under nitrogen atmosphere at −70° C. or lower over 10 minutes, and the resulting mixture was further stirred for 10 minutes. At −60° C. or lower, 1M diisobutylaluminum hydride/hexane solution (31.3 mL) was added dropwise to the mixture over 20 minutes, and the mixture was further stirred at −70° C. or lower for 1 hour. The reaction mixture was poured into a saturated aqueous ammonium chloride solution, and after stirring at room temperature, filtered with Celite. The filtrate was extracted with ethyl acetate, washed with a saturated brine, dried over anhydrous magnesium sulfate, and concentrated under reduced pressure. The obtained residue was purified by silica gel column chromatography (n-hexane:ethyl acetate=100:0 to 80:20) to obtain 5-chloropyrazine-2-carbaldehyde (970 mg).

MS (m/z): 142/144 [M+H]$^+$

[Formula 108]

2) N,N-dimethylformamide (10 mL) was added to 5-chloropyrazine-2-carbaldehyde (500 mg), methyl 2,2-dimethyl-3-{[4-methyl-5-(4,4,5,5-tetramethyl-1,3,2-dioxaborolan-2-yl)pyridin-2-yl]oxy}propanoate (1410 mg) and 2N aqueous sodium carbonate solution (5.26 mL), and after replacing the atmosphere with nitrogen, palladium chloride (dppf) methylene chloride complex (143 mg) was added to the mixture and the resulting mixture was stirred at 65° C. for 2 hours. To the reaction mixture were added ethyl acetate and water, and the liquids were separated. After filtration with Celite, the organic layer was separated, washed with water and then with a saturated brine, dried over anhydrous magnesium sulfate, and concentrated under reduced pressure. The obtained residue was purified by silica gel column chromatography (n-hexane:ethyl acetate=100:0 to 70:30) to obtain methyl 3-{[5-(5-formylpyrazin-2-yl)-4-methylpyridin-2-yl]oxy}-2,2-dimethylpropanoate (855 mg).

MS (m/z): 330 [M+H]$^+$

[Formula 109]

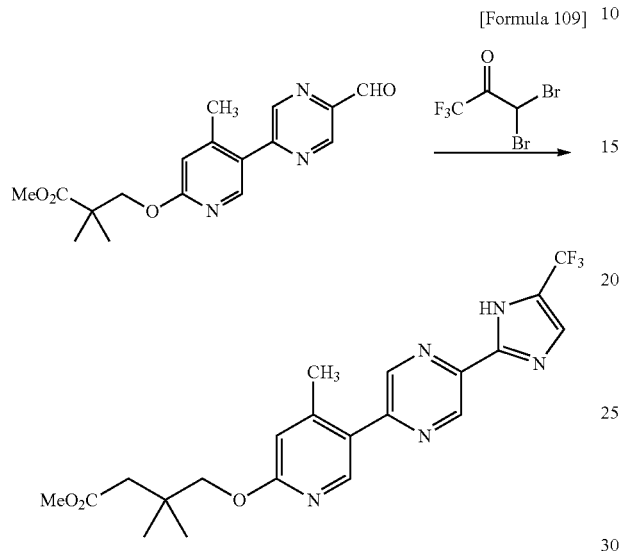

3) A mixture in which 3,3-dibromo-1,1,1-trifluoropropan-2-one (1311 mg) and sodium acetate (797 mg) were added to water (2 mL) was stirred at 90° C. for 1 hour and then ice-cooled. After dissolving methyl 3-{[5-(5-formylpyrazin-2-yl)-4-methylpyridin-2-yl]oxy}-2,2-dimethylpropanoate (400 mg) and 28% aqueous ammonia (8 mL) in methanol (4 mL) and tetrahydrofuran (4 mL), to the solution was added to the above-mentioned reaction solution, and the mixture was stirred at room temperature for 3 hours. The reaction mixture was concentrated under reduced pressure, ethyl acetate was added to the residue and the liquids were separated. The organic layer was separated, washed with a saturated brine, dried over anhydrous magnesium sulfate, and concentrated under reduced pressure. The obtained residue was purified by silica gel column chromatography (n-hexane:ethyl acetate=90:10 to 66:34) to obtain methyl 2,2-dimethyl-3-[(4-methyl-5-{5-[5-(trifluoromethyl)-1H-imidazol-2-yl]pyrazin-2-yl}-pyridin-2-yl)oxy]propanoate (325 mg).

MS (m/z): 436 [M+H]$^+$

[Formula 110]

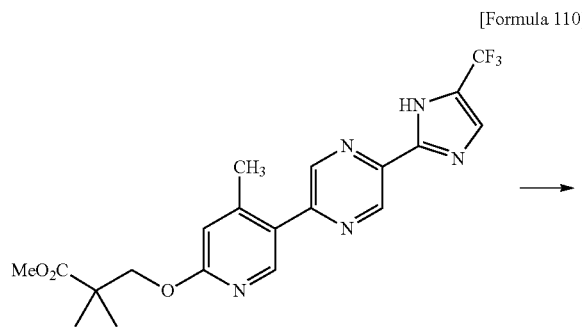

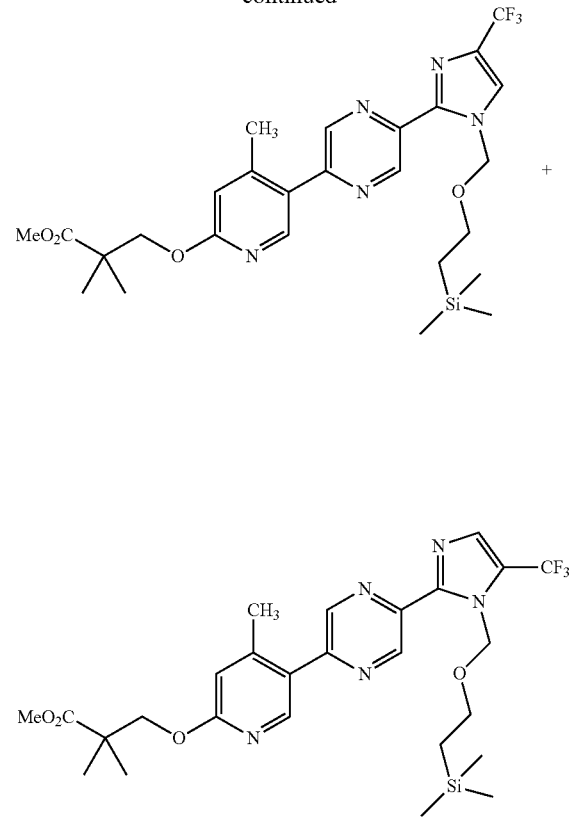

4) Sodium hydride (60%, 35 mg) was added to an N,N-dimethylformamide (3 mL) solution containing methyl 2,2-dimethyl-3-[(4-methyl-5-{5-[5-(trifluoromethyl)-1H-imidazol-2-yl]pyrazin-2-yl}pyridin-2-yl)oxy]propanoate (320 mg) at 0° C., and the resulting mixture was stirred at the same temperature for 1 hour. To the mixture was added 2-(trimethylsilyl)ethoxymethyl chloride (195 μL), a temperature of the mixture was raised to room temperature and the mixture was stirred for 1 hour. Water was added to the reaction mixture, and the mixture was extracted with ethyl acetate. The organic layer was separated, washed with water and then with a saturated brine, dried over anhydrous magnesium sulfate, and concentrated under reduced pressure. The obtained residue was purified by silica gel column chromatography (n-hexane:ethyl acetate=90:10 to 80:20) to obtain a mixture (324 mg) of methyl 2,2-dimethyl-3-[(4-methyl-5-{5-[4-(trifluoromethyl)-1-{[2-(trimethylsilyl)ethoxy]methyl}-1H-imidazol-2-yl]pyrazin-2-yl}pyridin-2-yl)oxy]propanoate and methyl 2,2-dimethyl-3-[(4-methyl-5-{5-[5-(trifluoromethyl)-1-{[2-(trimethylsilyl)ethoxy]methyl}-1H-imidazol-2-yl]-pyrazin-2-yl}pyridin-2-yl)oxy]propanoate.

MS (m/z): 566 [M+H]$^+$

[Formula 111]

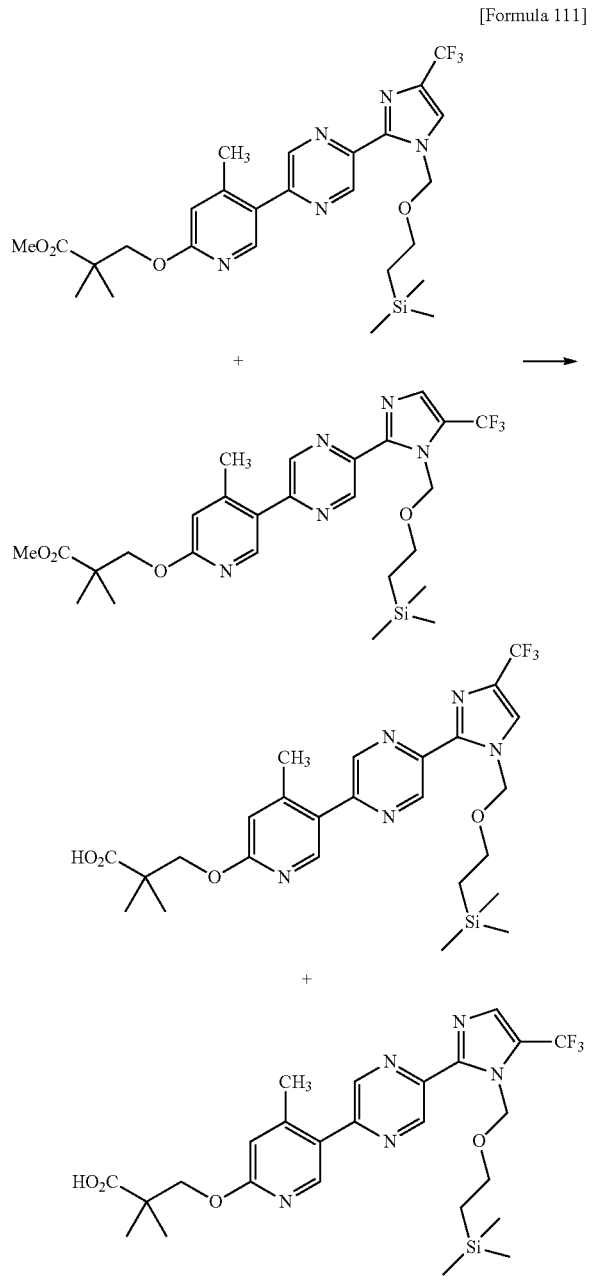

5) In methanol (6.4 mL) were dissolved a mixture (320 mg) of methyl 2,2-dimethyl-3-[(4-methyl-5-{5-[4-(trifluoromethyl)-1-{[2-(trimethylsilyl)ethoxy]methyl}-1H-imidazol-2-yl]pyrazin-2-yl}pyridin-2-yl)oxy]propanoate and methyl 2,2-dimethyl-3-[(4-methyl-5-{5-[5-(trifluoromethyl)-1-{[2-(trimethylsilyl)ethoxy]methyl}-1H-imidazol-2-yl]pyrazin-2-yl}pyridin-2-yl)oxy]propanoate, and 1N aqueous sodium hydroxide solution (2.83 mL), and the resulting mixture was refluxed for 1 hour. After concentrating the mixture under reduced pressure, the residue was made acidic (pH=4) by adding 1N hydrochloric acid, and the mixture was extracted with ethyl acetate. The extract was washed with a saturated brine, dried over anhydrous magnesium sulfate, and concentrated under reduced pressure to obtain a mixture of 2,2-dimethyl-3-[(4-methyl-5-{5-[4-(trifluoromethyl)-1-{[2-(trimethylsilyl)ethoxy]methyl}-1H-imidazol-2-yl]-pyrazin-2-yl}pyridin-2-yl)oxy]propanoic acid and 2,2-dimethyl-3-[(4-methyl-5-{5-[5-(trifluoromethyl)-1-{[2-(trimethylsilyl)ethoxy]methyl}-1H-imidazol-2-yl]pyrazin-2-yl}pyridin-2-yl)oxy]propanoic acid.

MS (m/z): 552 [M+H]$^+$

[Formula 112]

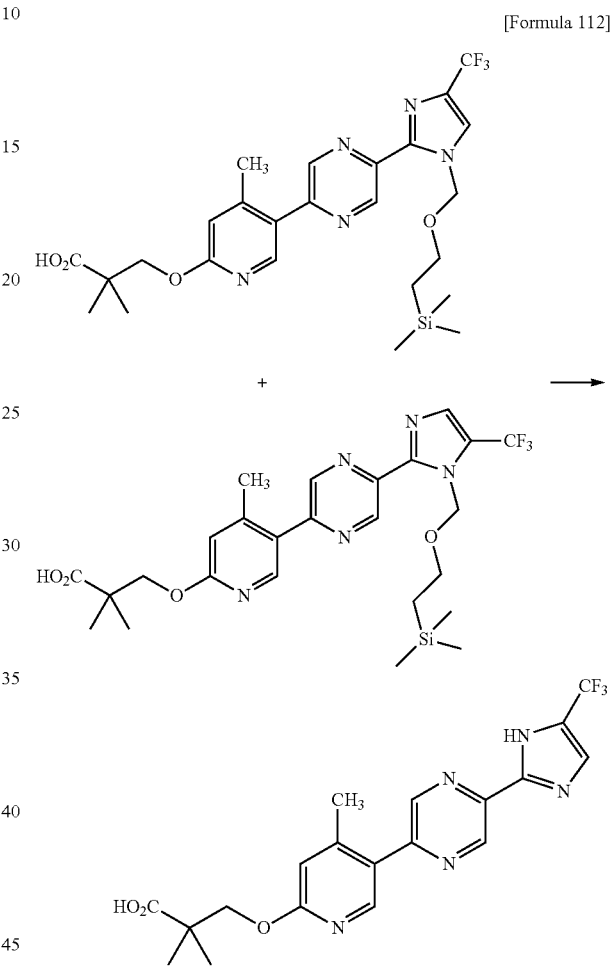

6) In trifluoroacetic acid (3.1 mL) and water (0.31 mL) was dissolved the mixture of 2,2-dimethyl-3-[(4-methyl-5-{5-[4-(trifluoromethyl)-1-{[2-(trimethylsilyl)ethoxy]-methyl}-1H-imidazol-2-yl]pyrazin-2-yl}pyridin-2-yl)oxy]propanoic acid and 2,2-dimethyl-3-[(4-methyl-5-{5-[5-(trifluoromethyl)-1-{[2-(trimethylsilyl)ethoxy]methyl}-1H-imidazol-2-yl]pyrazin-2-yl}pyridin-2-yl)oxy]-propanoic acid obtained in the above-mentioned 5), and the solution was stirred at room temperature. Acetic acid was added to the residue obtained by concentrating the solution under reduced pressure, and the resulting mixture was concentrated under reduced pressure. Isopropyl ether was added to the solid residue to pulverize the same, and the pulverized material was dried to obtain 2,2-dimethyl-3-[(4-methyl-5-{5-[5-(trifluoromethyl)-1H-imidazol-2-yl]pyrazin-2-yl}pyridin-2-yl)oxy]propanoic acid (197 mg).

MS (m/z): 422 [M+H]$^+$

Example 96

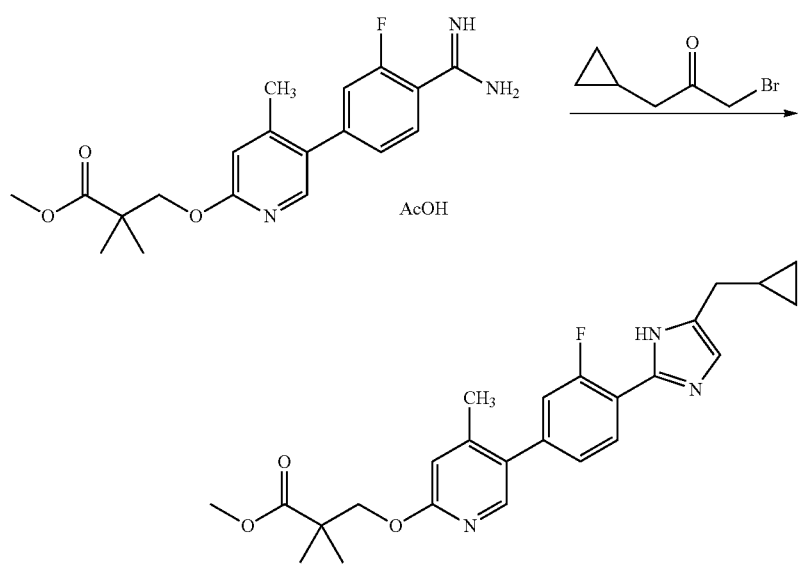

1) A mixture in which methylene chloride (10 mL) and a saturated brine (10 mL) were added to methyl 3-{[5-(4-carbamimidoyl-3-fluorophenyl)-4-methylpyridin-2-yl]oxy}-2,2-dimethylpropanoate acetic acid salt (300 mg), 1-bromo-3-cyclopropylpropan-2-one (190 mg) and potassium carbonate (346 mg) was stirred at 40° C. for 5 hours. The organic layer was separated, dried over anhydrous sodium sulfate, and concentrated under reduced pressure. The obtained residue was purified by silica gel column chromatography (chloroform:methanol=100:0 to 97:3) to obtain methyl 3-[(5-{4-[5-(cyclopropylmethyl)-1H-imidazol-2-yl]-3-fluorophenyl}-4-methylpyridin-2-yl)oxy]-2,2-dimethylpropanoate (248 mg).
MS (m/z): 438 [M+H]$^+$

[Formula 114]

2) In tetrahydrofuran (10 mL) and methanol (10 mL) was dissolved methyl 3-[(5-{4-[5-(cyclopropylmethyl)-1H-imidazol-2-yl]-3-fluorophenyl}-4-methylpyridin-2-yl)oxy]-2,2-dimethylpropanoate (247 mg), and after adding 2N aqueous sodium hydroxide solution (2.8 mL) to the solution, the resulting mixture was stirred at 50° C. for 7 hours. Water and acetic acid were added to the residue obtained by concentrating the reaction mixture under reduced pressure. The precipitated solid was collected by filtration, washed with water and dried to obtain 3-[(5-{4-[5-(cyclopropylmethyl)-1H-imidazol-2-yl]-3-fluorophenyl}-4-methylpyridin-2-yl)oxy]-2,2-dimethylpropanoic acid (339 mg).
MS (m/z): 424 [M+H]$^+$

Example 97

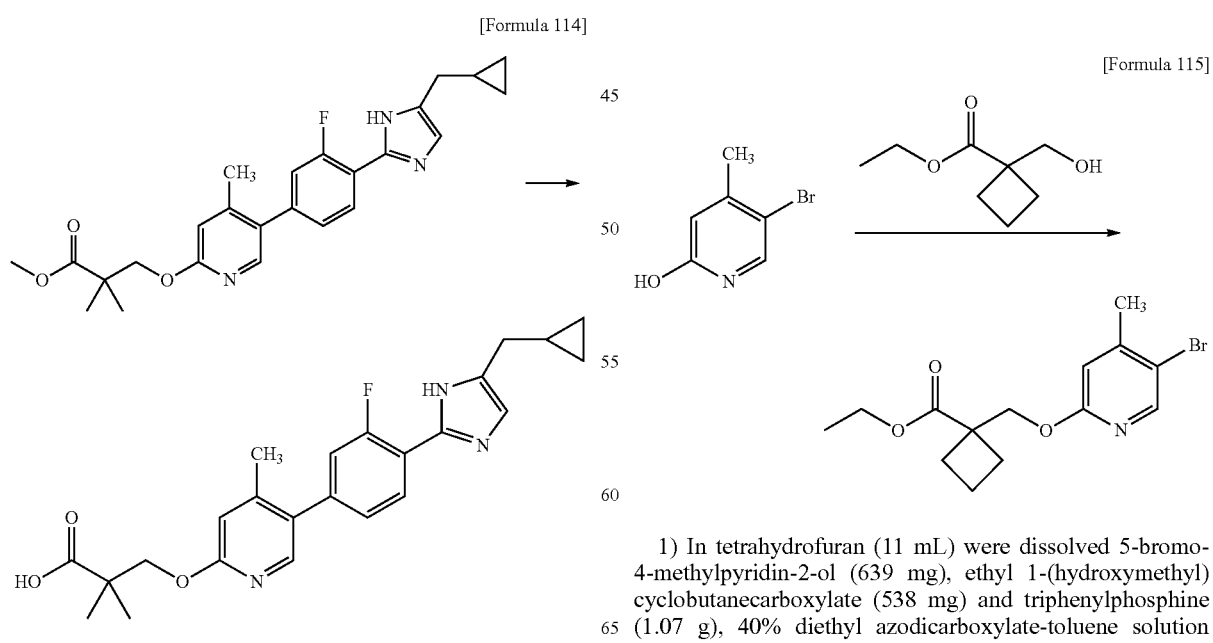

[Formula 115]

1) In tetrahydrofuran (11 mL) were dissolved 5-bromo-4-methylpyridin-2-ol (639 mg), ethyl 1-(hydroxymethyl)cyclobutanecarboxylate (538 mg) and triphenylphosphine (1.07 g), 40% diethyl azodicarboxylate-toluene solution (1.86 mL) was added dropwise to the solution at room temperature, and then, the resulting mixture was stirred at 60° C. for 3 hours. The reaction mixture was cooled to room temperature, concentrated under reduced pressure, and the precipitated solid was removed by filtration. The filtrate was concentrated under reduced pressure, and the obtained residue was purified by silica gel column chromatography (n-hexane:ethyl acetate=100:0 to 90:10) to obtain ethyl 1-{[(5-bromo-4-methylpyridin-2-yl)oxy]methyl}cyclobutanecarboxylate (638 mg).

MS (m/z): 328/330 [M+H]+

[Formula 116]

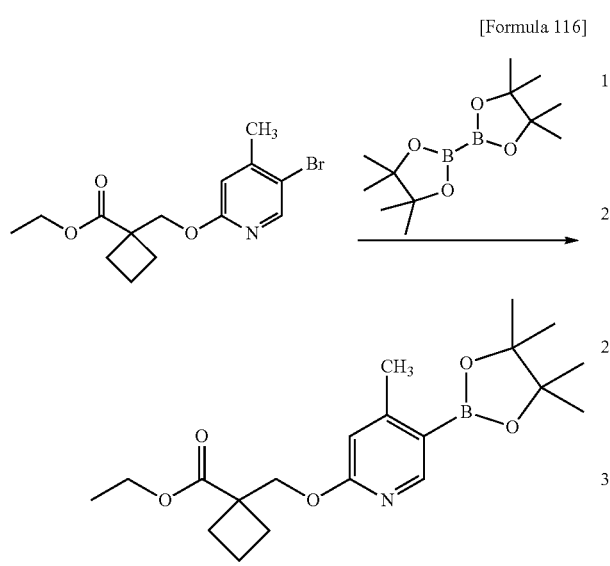

2) 1,4-Dioxane (32 mL) was added to ethyl 1-{[(5-bromo-4-methylpyridin-2-yl)oxy]-methyl}cyclobutanecarboxylate (1.6 g), 4,4,4',4',5,5,5',5'-octamethyl-2,2'-bi-1,3,2-dioxaborolane (1.24 g), palladium chloride (dppf) methylene chloride complex (170 mg) and potassium acetate (1.44 g), and the mixture was stirred under nitrogen atmosphere at 100° C. for 4 hours. To the reaction mixture were added ethyl acetate and water to extract the objective compound. The organic layer was washed with a saturated brine, and dried over anhydrous magnesium sulfate. After concentrating the mixture under reduced pressure, the obtained residue was purified by silica gel column chromatography (n-hexane:ethyl acetate=100:0 to 80:20) to obtain ethyl 1-({[4-methyl-5-(4,4,5,5-tetramethyl-1,3,2-dioxaborolan-2-yl)pyridin-2-yl]oxy}methyl)cyclobutanecarboxylate (1.30 g).

MS (m/z): 376 [M+H]+

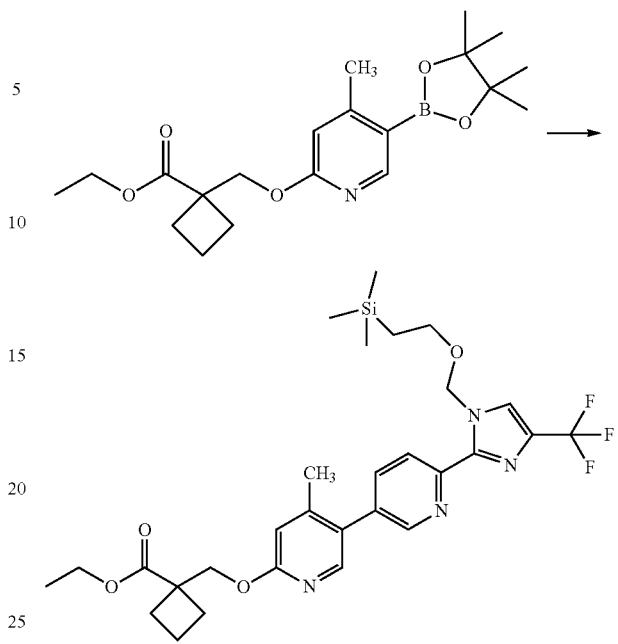

3) N,N-dimethylformamide (3 mL) was added to 5-bromo-2-[4-(trifluoromethyl)-1-{[2-(trimethylsilyl)ethoxy]methyl}-1H-imidazol-2-yl]pyridine (338 mg), ethyl 1-({[4-methyl-5-(4,4,5,5-tetramethyl-1,3,2-dioxaborolan-2-yl)pyridin-2-yl]oxy}methyl)cyclobutanecarboxylate (300 mg) and palladium chloride (dppf) methylene chloride complex (33 mg), and after adding 2N aqueous sodium carbonate solution (1.2 mL) to the mixture, the atmosphere was replaced with nitrogen and the mixture was stirred at 65° C. for 2 hours. The reaction mixture was filtered by using Celite, and ethyl acetate and water were added to the filtrate to extract the objective compound. The organic layer was separated, washed with a saturated brine, and dried over anhydrous magnesium sulfate. After concentrating the mixture under reduced pressure, the obtained residue was purified by silica gel column chromatography (n-hexane:ethyl acetate=100:0 to 90:10) to obtain ethyl 1-[({4-methyl-6'-[4-(trifluoromethyl)-1-{[2-(trimethylsilyl)ethoxy]methyl}-1H-imidazol-2-yl]-3,3'-bipyridin-6-yl}oxy)methyl]-cyclobutanecarboxylate (344 mg).

MS (m/z): 591 [M+H]+

[Formula 117]

[Formula 118]

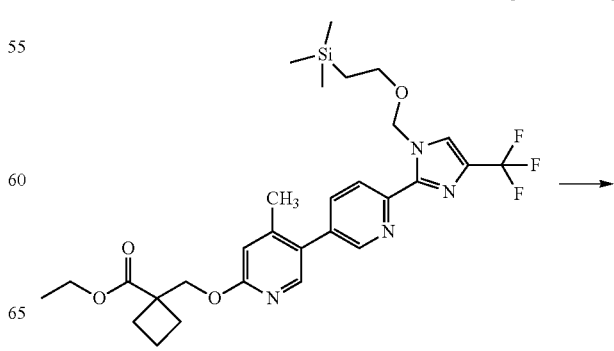

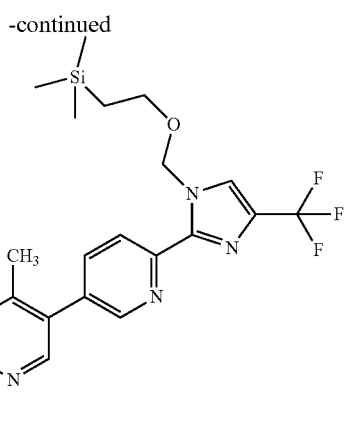

4) Methanol (7 mL) was added to ethyl 1-[({4-methyl-6'-[4-(trifluoromethyl)-1-{[2-(trimethylsilyl)ethoxy]methyl}-1H-imidazol-2-yl]-3,3'-bipyridin-6-yl}oxy)methyl]cyclobutanecarboxylate (343 mg), 1N aqueous sodium hydroxide solution (2.9 mL) was further added to the mixture and the resulting mixture was refluxed for 1 hour. Methanol was distilled off under reduced pressure, and the residue was neutralized by 1N hydrochloric acid. The mixture was extracted with ethyl acetate, the organic layer was washed with a saturated brine, dried over anhydrous magnesium sulfate, and concentrated under reduced pressure to obtain 1-[({4-methyl-6'-[4-(trifluoromethyl)-1-{[2-(trimethylsilyl)ethoxy]methyl}-1H-imidazol-2-yl]-3,3'-bipyridin-6-yl}oxy)methyl]-cyclobutanecarboxylic acid.

MS (m/z): 563[M+H]$^+$

[Formula 119]

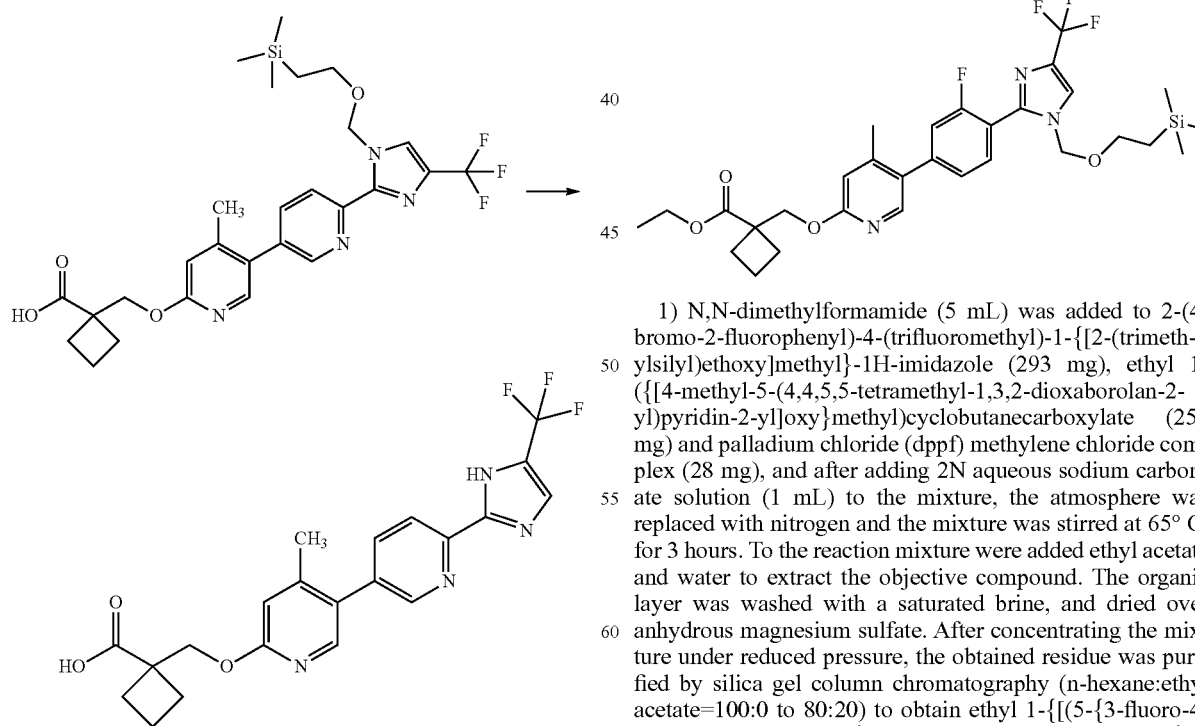

5) In trifluoroacetic acid (3.3 mL) and water (0.33 mL) was dissolved 1-[({4-methyl-6'-[4-(trifluoromethyl)-1-{[2-(trimethylsilyl)ethoxy]methyl}-1H-imidazol-2-yl]-3,3'-bi-pyridin-6-yl}oxy)methyl]cyclobutanecarboxylic acid (327 mg), and the solution was stirred at room temperature for 60 hours. The reaction mixture was concentrated under reduced pressure, subjected to azeotropic distillation with acetic acid, and isopropyl ether was added to the obtained residue. The precipitated solid was collected by filtration and dried under reduced pressure to obtain 1-[({4-methyl-6'-[5-(trifluoromethyl)-1H-imidazol-2-yl]-3,3'-bipyridin-6-yl}oxy)methyl]cyclobutanecarboxylic acid (217 mg).

MS (m/z): 433 [M+H]$^+$

Example 98

[Formula 120]

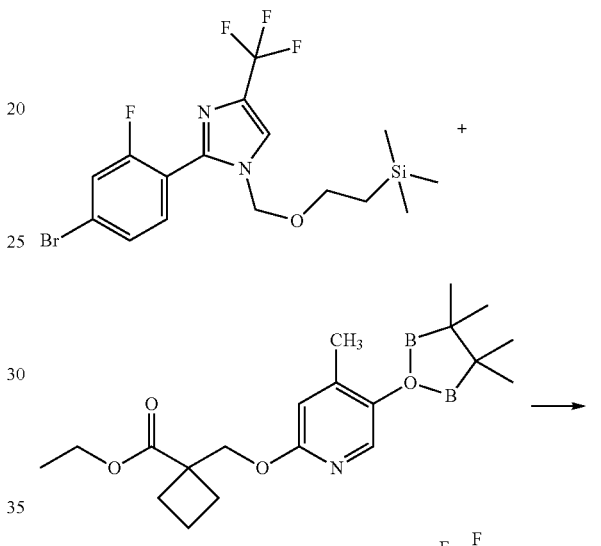

1) N,N-dimethylformamide (5 mL) was added to 2-(4-bromo-2-fluorophenyl)-4-(trifluoromethyl)-1-{[2-(trimethylsilyl)ethoxy]methyl}-1H-imidazole (293 mg), ethyl 1-({[4-methyl-5-(4,4,5,5-tetramethyl-1,3,2-dioxaborolan-2-yl)pyridin-2-yl]oxy}methyl)cyclobutanecarboxylate (250 mg) and palladium chloride (dppf) methylene chloride complex (28 mg), and after adding 2N aqueous sodium carbonate solution (1 mL) to the mixture, the atmosphere was replaced with nitrogen and the mixture was stirred at 65° C. for 3 hours. To the reaction mixture were added ethyl acetate and water to extract the objective compound. The organic layer was washed with a saturated brine, and dried over anhydrous magnesium sulfate. After concentrating the mixture under reduced pressure, the obtained residue was purified by silica gel column chromatography (n-hexane:ethyl acetate=100:0 to 80:20) to obtain ethyl 1-{[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylate (316 mg).

MS (m/z): 608 [M+H]$^+$

[Formula 121]

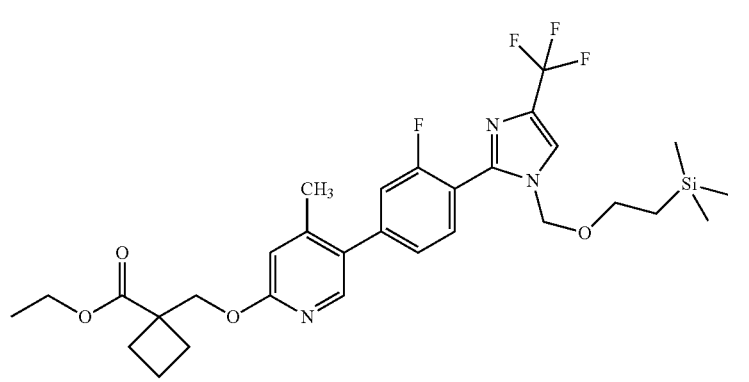

2) Methanol (6.3 mL) and 1N aqueous sodium hydroxide solution (2.6 mL) were added to ethyl 1-{[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylate (315 mg) and the mixture was refluxed for 1 hour. Methanol was distilled off under reduced pressure, and the residue was neutralized by 1N hydrochloric acid. The mixture was extracted with ethyl acetate, the organic layer was washed with a saturated brine, and dried over anhydrous magnesium sulfate. After concentrating the mixture under reduced pressure, the obtained residue was purified by silica gel column chromatography (chloroform:methanol=100:0 to 95:5) to obtain 1-{[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylic acid (308 mg).

MS (m/z): 580 [M+H]$^+$

[Formula 122]

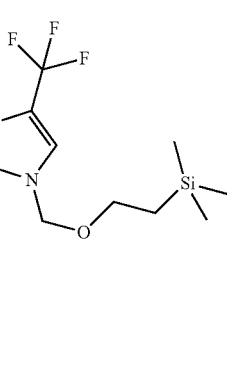

-continued

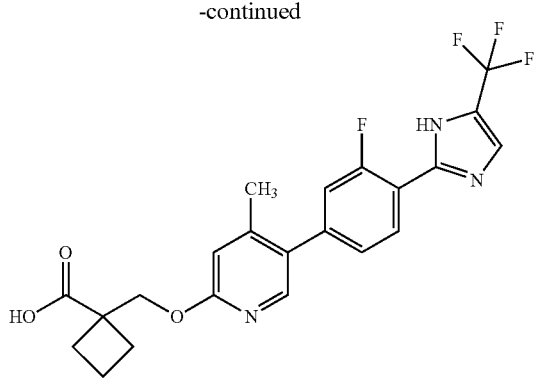

3) In trifluoroacetic acid (3.0 mL) and water (0.3 mL) was dissolved 1-{[(5-{3-fluoro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylic acid (299 mg), and the solution was stirred at 50° C. for 3 hours. The reaction mixture was concentrated under reduced pressure, the residue was made a pH=4 with a saturated aqueous sodium hydrogen carbonate solution and 1N hydrochloric acid, extracted with ethyl acetate, and the organic layer was washed with a saturated brine. The organic layer was dried over anhydrous magnesium sulfate, concentrated under reduced pressure, and isopropyl ether was added to the obtained residue. The precipitated solid was collected by filtration and dried under reduced pressure to obtain 1-{[(5-{3-fluoro-4-[5-(trifluoromethyl)-1H-imidazol-2-yl]phenyl}-4-methylpyridin-2-yl)oxy]methyl}cyclobutanecarboxylic acid (200 mg).

MS (m/z): 450 [M+H]$^+$

Example 99

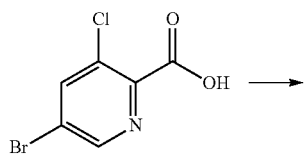

[Formula 123]

1) In N,N-dimethylformamide (24 mL) was dissolved 5-bromo-3-chloropyridine-2-carboxylic acid (2.36 g), 1-hydroxybenzotriazole (2.2 g) and 3-ethyl-3-(3-dimethylaminopropyl)carbodiimide hydrochloride (2.87 g), N,O-dimethylhydroxylamine hydrochloride (1.27 g) and triethylamine (1.95 mL) was added to the solution, and the resulting mixture was stirred at room temperature for 20 hours. Water was added to the obtained residue, extracted with ethyl acetate, and the organic layer was washed with water and then with a saturated brine. After drying the mixture over anhydrous magnesium sulfate, the mixture was concentrated under reduced pressure to obtain 5-bromo-3-chloro-N-methoxy-N-methylpyridine-2-carboxamide (2.67 g).

MS (m/z): 279/281/283 [M+H]$^+$

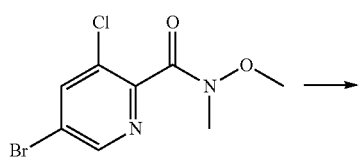

[Formula 124]

2) In tetrahydrofuran (27 mL) was dissolved 5-bromo-3-chloro-N-methoxy-N-methylpyridine-2-carboxamide (2.66 g), the mixture was cooled under nitrogen atmosphere at −70° C. or lower, and a tetrahydrofuran (5 mL) suspension of lithium aluminum hydride (180 mg) was added dropwise to the mixture. The mixture was stirred at −70° C. or lower for 2 hours, then, water (10 mL) and a saturated brine (10 mL) were added dropwise to the mixture. A temperature of the mixture was raised to room temperature, the mixture was extracted with ethyl acetate, and the organic layer was washed with water and a saturated brine. The organic layer was dried over anhydrous magnesium sulfate, concentrated under reduced pressure, and the residue was purified by silica gel column chromatography (n-hexane:ethyl acetate=100:0 to 90:10) to obtain a mixture of an aldehyde compound and an aldehyde equivalent (2.1 g). To water (36 mL) were added 3,3-dibromo-1,1,1-trifluoropropan-2-one (6.61 g) and sodium acetate (4.02 g) and the mixture was stirred at 95° C. for 30 minutes. An aqueous solution obtained by ice-cooling the mixture was added to a mixture comprising the previously obtained mixture of the aldehyde/aldehyde equivalent (1.8 g), 28% aqueous ammonia (18 mL) and methanol (36 mL) at room temperature, and the resulting mixture was stirred at room temperature for 17 hours. The reaction mixture was concentrated, the residue was extracted with ethyl acetate, and the organic layer was washed with a saturated brine, and then, dried over anhydrous magnesium sulfate. After concentrating the mixture under reduced pressure, the residue was purified by silica gel column chromatography (n-hexane:ethyl acetate=80:20), and the obtained solid was collected by filtration, washed with isopropyl ether and dried to obtain 5-bromo-3-chloro-2-[5-(trifluoromethyl)-1H-imidazol-2-yl]pyridine (935 mg).

MS (m/z): 326/328/330 [M+H]$^+$

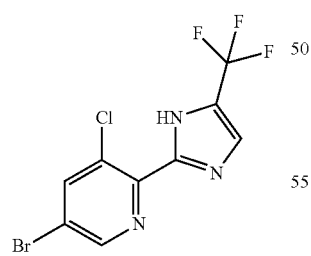

[Formula 125]

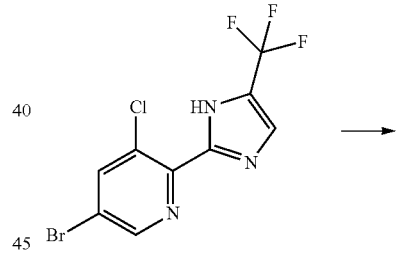

3) In N,N-dimethylformamide (13 mL) was dissolved 5-bromo-3-chloro-2-[5-(trifluoromethyl)-1H-imidazol-2-yl]pyridine (1.27 g), 60% sodium hydride (187 mg) was added to the solution under ice-cooling, and after raising the mixture to room temperature, the mixture was stirred for 1 hour. The reaction mixture was ice-cooled, 2-(trimethylsilyl)ethoxymethyl chloride (1.03 mL) was added to the mixture, and after raising the mixture to room temperature, the mixture was stirred for 1 hour. Water was added to the reaction mixture, the mixture was extracted with ethyl acetate, and the organic layer was washed with water and a saturated brine, and dried over anhydrous magnesium sulfate. After concentrating the mixture under reduced pressure, the obtained residue was purified by silica gel column chromatography (n-hexane:ethyl acetate=100:0 to 95:5) to obtain 5-bromo-3-chloro-2-[4-(trifluoromethyl)-1-{[2-(trimethylsilyl)ethoxy]methyl}-1H-imidazol-2-yl]pyridine (1.56 g).

MS (m/z): 458/460/462 [M+H]+

[Formula 126]

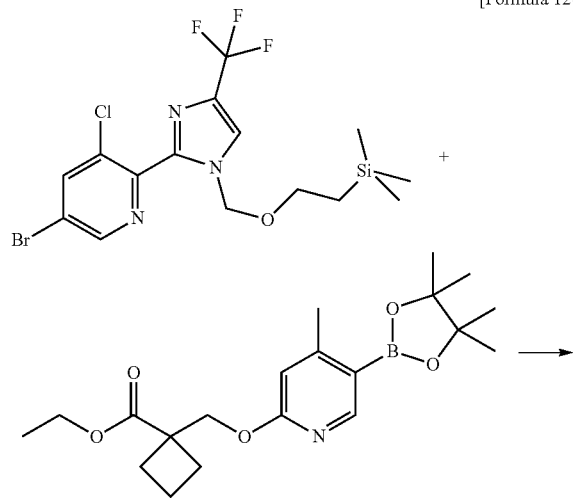

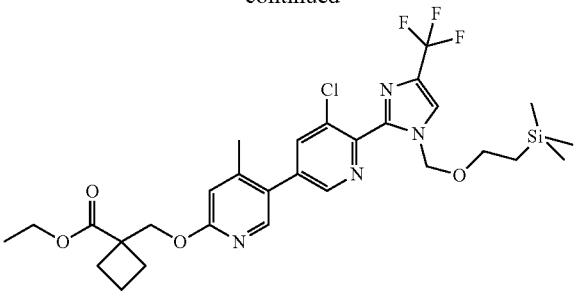

4) N,N-dimethylformamide (3 mL) was added to 5-bromo-3-chloro-2-[4-(trifluoromethyl)-1-{[2-(trimethylsilyl)ethoxy]methyl}-1H-imidazol-2-yl]pyridine (365 mg), ethyl 1-({[4-methyl-5-(4,4,5,5-tetramethyl-1,3,2-dioxaborolan-2-yl)pyridin-2-yl]-oxy}methyl)cyclobutanecarboxylate (300 mg) and palladium chloride (dppf) methylene chloride complex (33 mg), and after adding 2N aqueous sodium carbonate solution (1.2 mL) to the mixture, the atmosphere was replaced with nitrogen and the mixture was stirred at 65° C. for 2 hours. Water was added to the reaction mixture, and the mixture was extracted with ethyl acetate. The organic layer was washed with a saturated brine, concentrated under reduced pressure and the obtained residue was purified by silica gel column chromatography (n-hexane:ethyl acetate=100:0 to 90:10) to obtain ethyl 1-[({5'-chloro-4-methyl-6'-[4-(trifluoromethyl)-1-{[2-(trimethylsilyl)ethoxy]methyl}-1H-imidazol-2-yl]-3,3'-bipyridin-6-yl}oxy)methyl]cyclobutanecarboxylate (318 mg).

MS (m/z): 625/627 [M+H]+

[Formula 127]

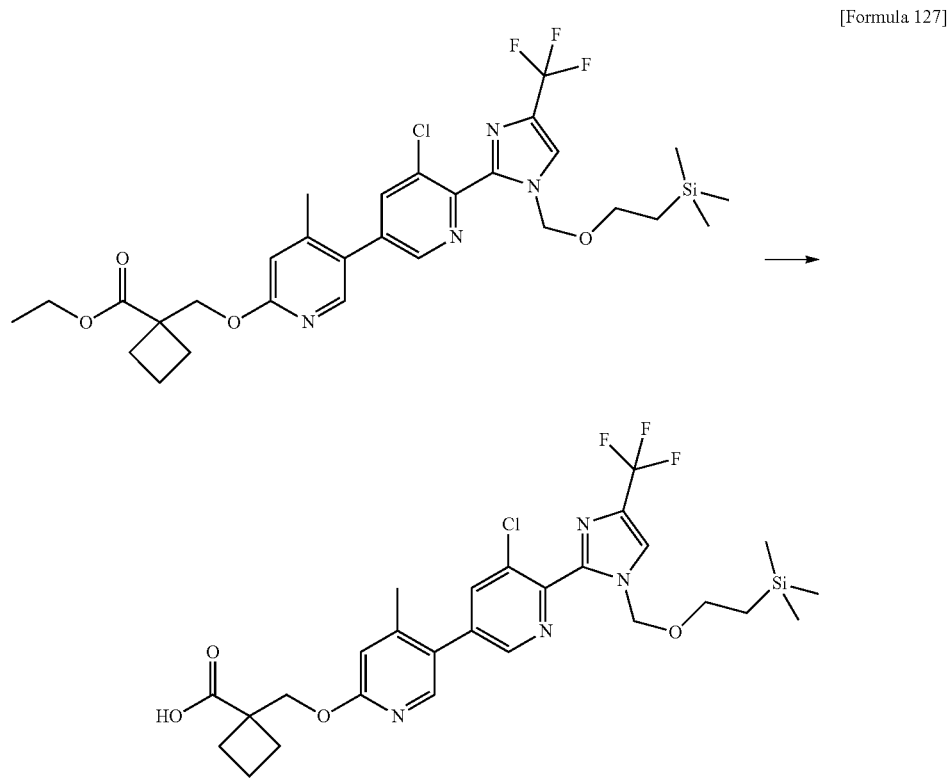 [SMILES: CCOC(=O)C1(COc2cc(C)c(-c3cnc(-c4nc(C(F)(F)F)cn4COCC[Si](C)(C)C)c(Cl)c3)cn2)CCC1 ; Cc1cc(OCC2(C(=O)O)CCC2)ncc1-c1cnc(-c2nc(C(F)(F)F)cn2COCC[Si](C)(C)C)c(Cl)c1]

5) Methanol (7 mL) and 1N aqueous sodium hydroxide solution (2.6 mL) were added to ethyl 1-[({5'-chloro-4-methyl-6'-[4-(trifluoromethyl)-1-{[2-(trimethylsilyl)ethoxy]-methyl}-1H-imidazol-2-yl]-3,3'-bipyridin-6-yl}oxy)methyl]cyclobutanecarboxylate (327 mg), and the mixture was refluxed for 1 hour. Methanol was distilled off under reduced pressure, and the residue was neutralized by 1N hydrochloric acid. The mixture was extracted with ethyl acetate, the organic layer was washed with a saturated brine, and dried over anhydrous magnesium sulfate. The mixture was concentrated under reduced pressure to obtain 1-[({5'-chloro-4-methyl-6'-[4-(trifluoromethyl)-1-{[2-(trimethylsilyl)ethoxy]methyl}-1H-imidazol-2-yl]-3,3'-bipyridin-6-yl}oxy)methyl]-cyclobutanecarboxylic acid.

MS (m/z): 597/599 [M+H]+

[Formula 128]

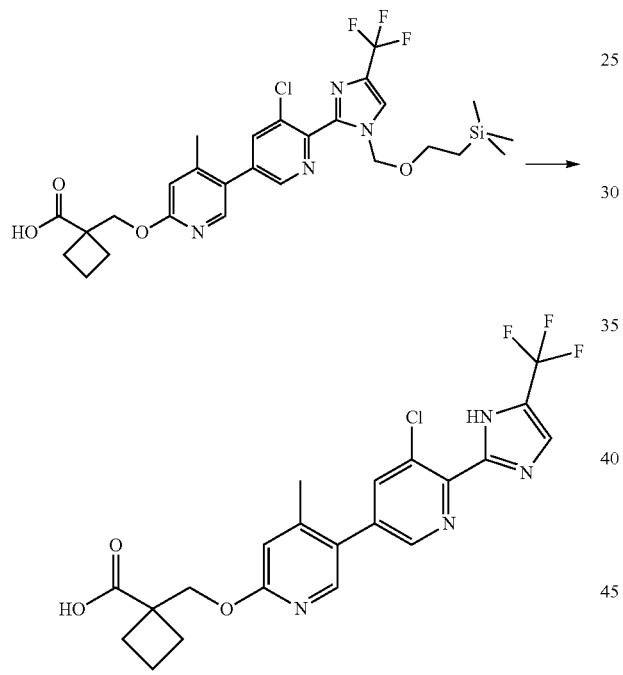

6) In trifluoroacetic acid (3.1 mL) and water (0.3 mL) was dissolved 1-[({5'-chloro-4-methyl-6'-[4-(trifluoromethyl)-1-{[2-(trimethylsilyl)ethoxy]methyl}-1H-imidazol-2-yl]-3,3'-bipyridin-6-yl}oxy)methyl]cyclobutanecarboxylic acid (312 mg), and the mixture was allowed to stand at room temperature for 60 hours. The reaction mixture was concentrated under reduced pressure, subjected to azeotropic distillation with acetic acid, isopropyl ether was added to the obtained residue, and the precipitated solid was collected by filtration and dried under reduced pressure to obtain 1-[({5'-chloro-4-methyl-6'-[5-(trifluoromethyl)-1H-imidazol-2-yl]-3,3'-bipyridin-6-yl}oxy)methyl]cyclobutanecarboxylic acid (151 mg).

MS (m/z): 467/469 [M+H]+

Example 100

[Formula 129]

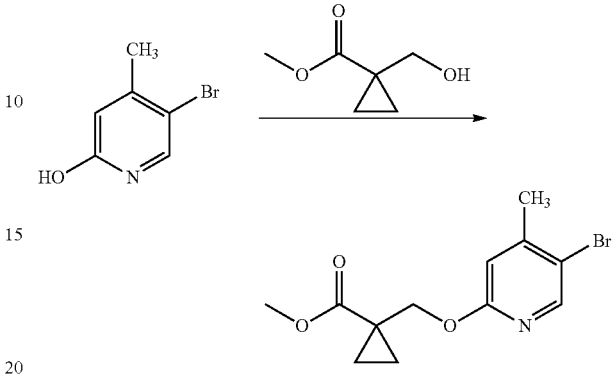

1) In tetrahydrofuran (26 mL) was dissolved 5-bromo-4-methylpyridin-2-ol (1.3 g), methyl 1-(hydroxymethyl)cyclopropanecarboxylate (1.08 g) and triphenylphosphine (2.72 g), and 40% diethyl azodicarboxylate-toluene solution (4.72 mL) was added dropwise to the solution at 0° C. The mixture was stirred at 70° C. for 4 hours. The reaction mixture was cooled to room temperature, water and ethyl acetate were added to the mixture, and the organic layer was washed with a saturated brine and dried over anhydrous sodium sulfate. After concentrating the mixture under reduced pressure, the obtained residue was purified by silica gel column chromatography (n-hexane:ethyl acetate=99:1 to 99:5) to obtain methyl 1-{[(5-bromo-4-methylpyridin-2-yl)oxy]-methyl}cyclopropanecarboxylate (2.08 g).

MS (m/z): 300/302 [M+H]+

[Formula 130]

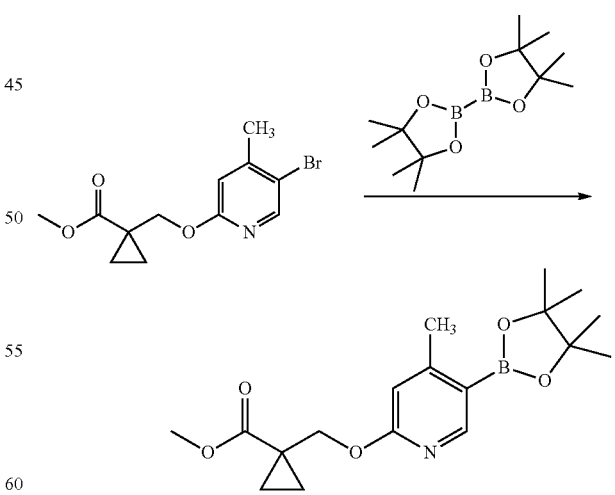

2) 1,4-Dioxane (20 mL) was added to methyl 1-{[(5-bromo-4-methylpyridin-2-yl)oxy]methyl}cyclopropanecarboxylate (1.01 g), 4,4,4',4',5,5,5',5'-octamethyl-2,2'-bi-1,3,2-dioxaborolane (1.03 g), palladium chloride (dppf) methylene chloride complex (71 mg) and potassium acetate (994 mg), and the mixture was stirred under nitrogen atmosphere at 100° C. for 3 hours. To the reaction mixture were added ethyl acetate and water to extract the objective compound. The organic layer was washed with a saturated brine, and dried over anhydrous magnesium sulfate. After concentrating the mixture under reduced pressure, the obtained residue was purified by silica gel column chromatography (n-hexane:ethyl acetate=95:5 to 80:20) to obtain methyl 1-({[4-methyl-5-(4,4,5,5-tetramethyl-1,3,2-dioxaborolan-2-yl)pyridin-2-yl]oxy}methyl)cyclopropanecarboxylate (1.08 g).

MS (m/z): 348 [M+H]$^+$

[Formula 131]

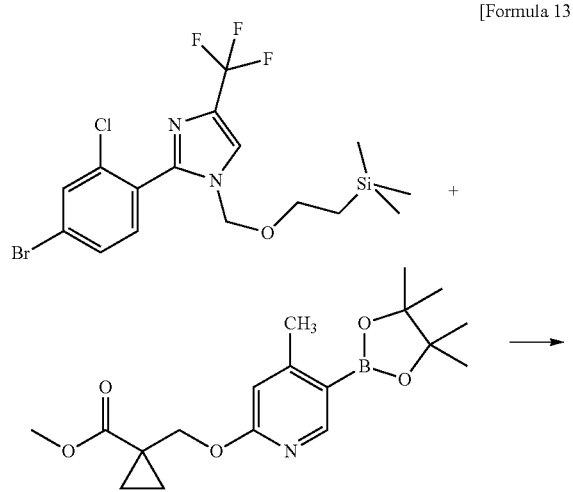

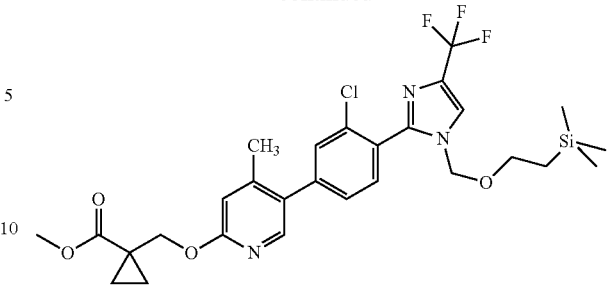

3) N,N-dimethylformamide (11 mL) was added to 2-(4-bromo-2-chlorophenyl)-4-(trifluoromethyl)-1-{[2-(trimethylsilyl)ethoxy]methyl}-1H-imidazole (220 mg), methyl 1-({[4-methyl-5-(4,4,5,5-tetramethyl-1,3,2-dioxaborolan-2-yl)pyridin-2-yl]oxy}-methyl)cyclopropanecarboxylate (201 mg), and palladium chloride (dppf) methylene chloride complex (39 mg), and after adding 2N aqueous sodium carbonate solution (0.72 mL) to the mixture, the atmosphere was replaced with nitrogen and the mixture was stirred at 65° C. for 2 hours. To the reaction mixture were added ethyl acetate and water to extract the objective compound, and the organic layer was washed with a saturated brine, and dried over anhydrous sodium sulfate. After concentrating the mixture under reduced pressure, the obtained residue was purified by silica gel column chromatography (n-hexane:ethyl acetate=95:5 to 80:20) to obtain methyl 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclopropanecarboxylate (237 mg).

MS (m/z): 596/598 [M+H]$^+$

[Formula 132]

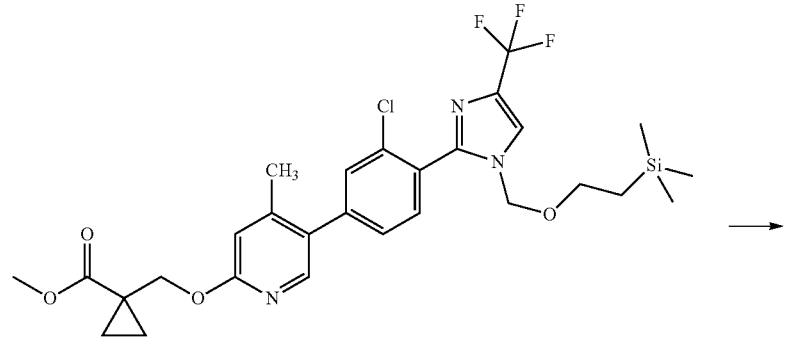

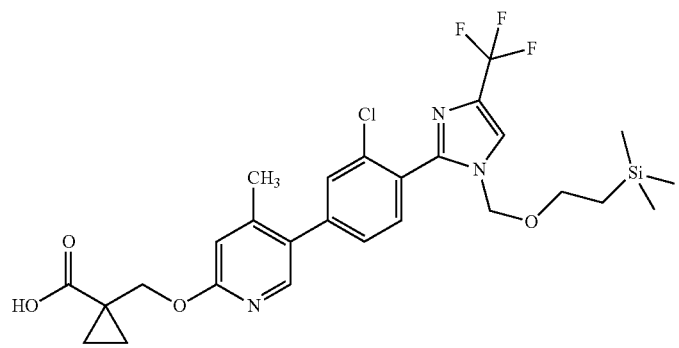

4) In methanol (7 mL) and tetrahydrofuran (7 mL) was dissolved methyl 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclopropanecarboxylate (236 mg), 2N aqueous sodium hydroxide solution (1.98 mL) was added to the solution and the resulting mixture was stirred at 50° C. for 4 hours. The reaction mixture was concentrated under reduced pressure, and acetic acid and ethyl acetate were added to the residue. The organic layer was separated, washed with a saturated brine, dried over anhydrous sodium sulfate, and concentrated under reduced pressure to obtain 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclopropanecarboxylic acid (221 mg).

MS (m/z): 582/584 [M+H]+

5) In trifluoroacetic acid (5.0 mL) and water (0.5 mL) was dissolved 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclopropanecarboxylic acid (219 mg), and the solution was stirred at room temperature for 5 hours. The reaction mixture was concentrated under reduced pressure, a small amount of tetrahydrofuran was added to the residue, and the mixture was neutralized by 1N aqueous sodium hydroxide solution. Several drops of acetic acid was added to the mixture, the mixture was extracted with ethyl acetate, washed with a saturated brine, and the organic layer was separated and concentrated under reduced pressure. Isopropyl ether was added to the obtained residue, and the precipitated solid was collected by filtration and dried under reduced pressure to obtain 1-{[(5-{3-chloro-4-[5-(trifluoromethyl)-1H-imidazol-2-yl]phenyl}-4-methyl-pyridin-2-yl)oxy]methyl}cyclopropanecarboxylic acid (95 mg).

MS (m/z): 452/454 [M+H]+

Example 101

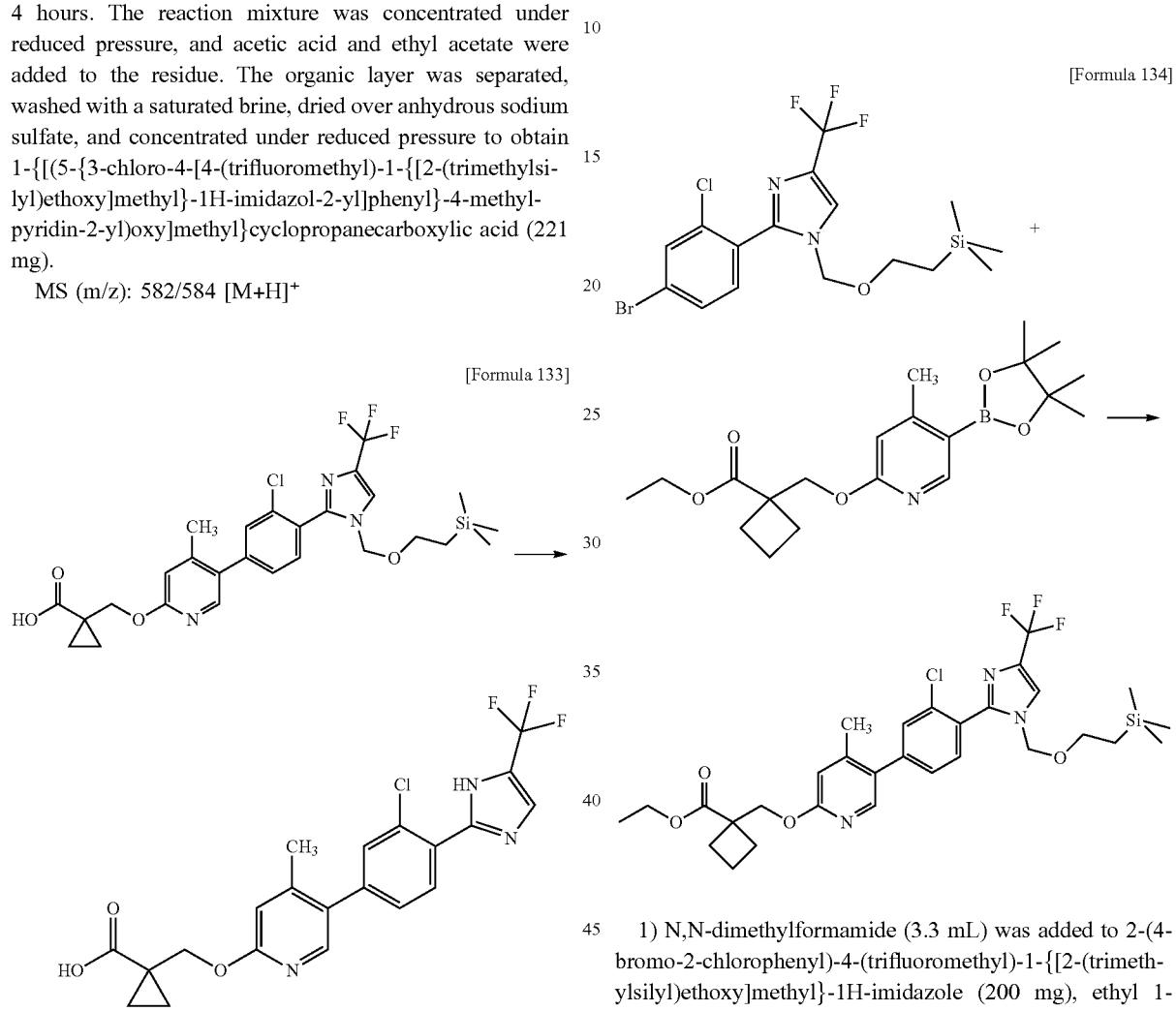

1) N,N-dimethylformamide (3.3 mL) was added to 2-(4-bromo-2-chlorophenyl)-4-(trifluoromethyl)-1-{[2-(trimethylsilyl)ethoxy]methyl}-1H-imidazole (200 mg), ethyl 1-({[4-methyl-5-(4,4,5,5-tetramethyl-1,3,2-dioxaborolan-2-yl)pyridin-2-yl]oxy}-methyl)cyclobutanecarboxylate (164 mg) and palladium chloride (dppf) methylene chloride complex (18 mg), and after adding 2N aqueous sodium carbonate solution (0.66 mL) to the mixture, the atmosphere was replaced with nitrogen and the mixture was stirred at 65° C. for 3 hours. To the reaction mixture were added ethyl acetate and water, and the liquids were separated. The organic layer was separated, washed with a saturated brine, and the residue obtained by concentrating the mixture under reduced pressure was purified by silica gel column chromatography (n-hexane:ethyl acetate=100:0 to 80:20) to obtain ethyl 1-{[(5-{3-chloro-4-[4-(trifluoromethyl)-1-{[2-(trimethylsilyl)ethoxy]methyl}-1H-imidazol-2-yl]phenyl}-4-methyl-pyridin-2-yl)oxy]methyl}cyclobutanecarboxylate (214 mg).

MS (m/z): 624/626 [M+H]+

[Formula 135]

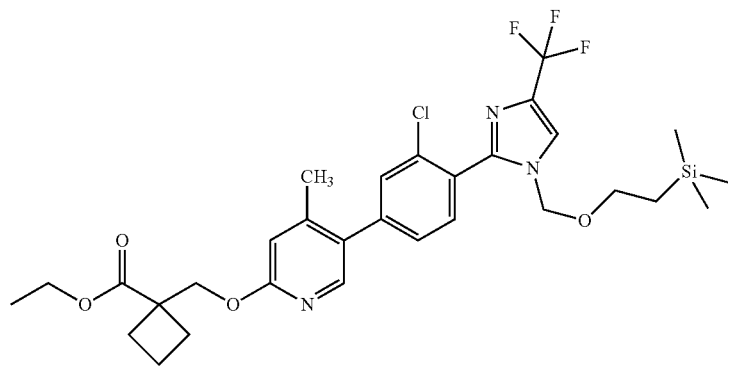

2) Methanol (4.3 mL) and 1N aqueous sodium hydroxide solution (1.7 mL) were added to ethyl 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylate (213 mg), and the mixture was refluxed for 1 hour. Methanol was distilled off under reduced pressure, and the residue was neutralized by 1N hydrochloric acid. The mixture was extracted with ethyl acetate, the organic layer was washed with a saturated brine, and dried over anhydrous magnesium sulfate. After concentrating the mixture under reduced pressure, the obtained residue was purified by silica gel column chromatography (chloroform:methanol=100:0 to 95:5) to obtain 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylic acid (205 mg).

MS (m/z): 596/598 [M+H]+

[Formula 136]

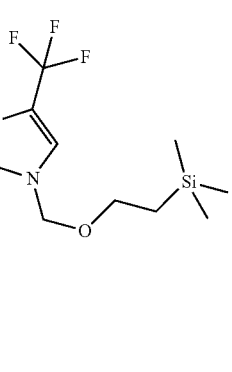

-continued

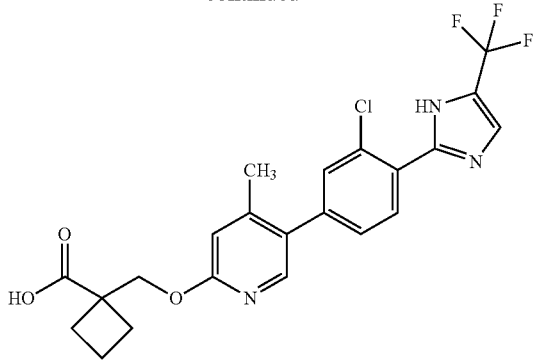

3) In trifluoroacetic acid (2.0 mL) and water (0.2 mL) was dissolved 1-{[(5-{3-chloro-4-[4-(trifluoromethyl)-1-{[2-(trimethylsilyl)ethoxy]methyl}-1H-imidazol-2-yl]phenyl}-4-methylpyridin-2-yl)oxy]methyl}cyclobutanecarboxylic acid (202 mg), and the solution was stirred at 50° C. for 3 hours. The reaction mixture was concentrated under reduced pressure, the pH of the residue was made 4 with a saturated aqueous sodium hydrogen carbonate solution and 1N hydrochloric acid, and the mixture was extracted with ethyl acetate. The extract was washed with a saturated brine, the organic layer was separated and concentrated under reduced pressure. Isopropyl ether was added to the obtained residue, and the precipitated solid was collected by filtration and dried under reduced pressure to obtain 1-{[(5-{3-chloro-4-[5-(trifluoromethyl)-1H-imidazol-2-yl]phenyl}-4-methyl-pyridin-2-yl)oxy]methyl}cyclobutanecarboxylic acid (137 mg).

MS (m/z): 466/468 [M+H]+

By using the corresponding starting materials, the following compounds were synthesized in the same manner as in Examples 1 to 101.

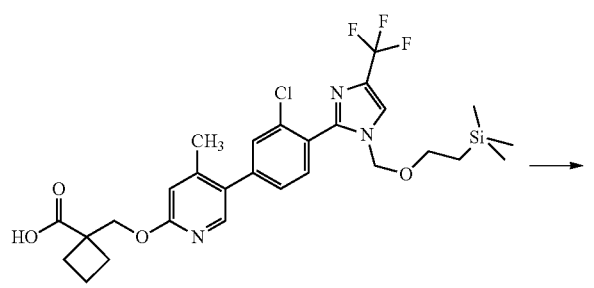

TABLE 10
| Example | Starting substance 1 | Starting substance 2 |
|---|---|---|
| 102 | 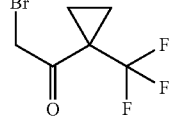 | 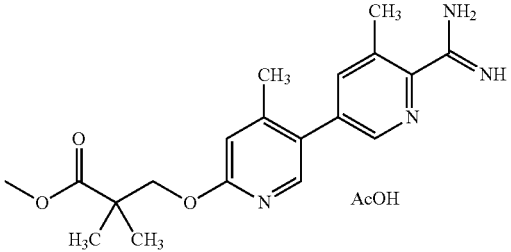 [SMILES: "AcOH" ; COC(=O)C(C)(C)COc1cc(C)c(-c2cnc(C(=N)N)c(C)c2)cn1] |
| 103 | 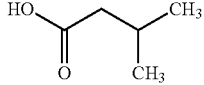 | 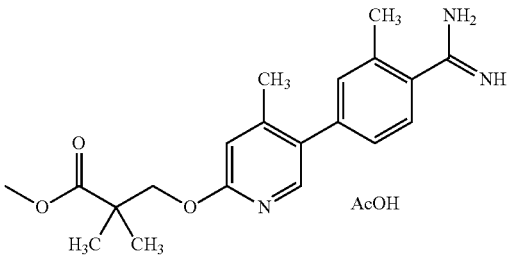 [SMILES: "AcOH" ; COC(=O)C(C)(C)COc1cc(C)c(-c2ccc(C(=N)N)c(C)c2)cn1] |
| 104 | 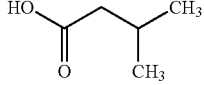 | 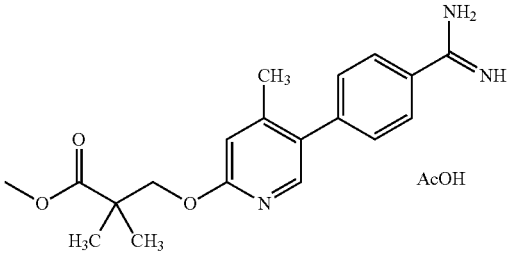 [SMILES: "AcOH" ; COC(=O)C(C)(C)COc1cc(C)c(-c2ccc(C(=N)N)cc2)cn1] |
| 105 | 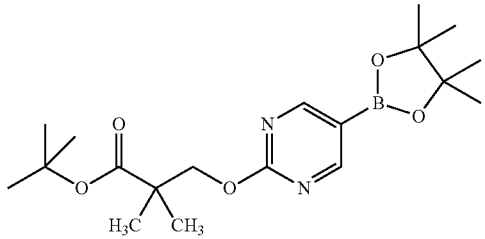 [SMILES: CC(C)(C)OC(=O)C(C)(C)COc1ncc(B2OC(C)(C)C(C)(C)O2)cn1] | 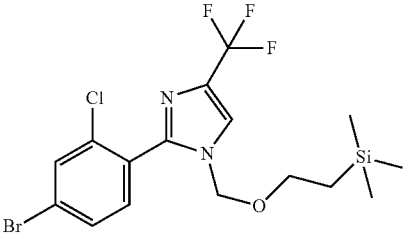 |
| 106 | 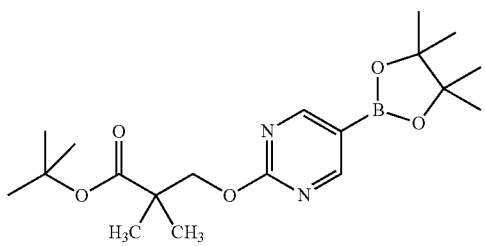 [SMILES: CC(C)(C)OC(=O)C(C)(C)COc1ncc(B2OC(C)(C)C(C)(C)O2)cn1] | 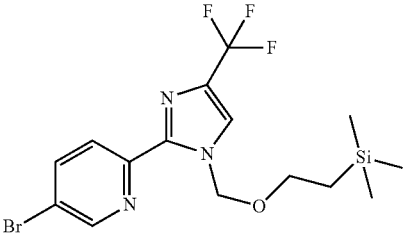 [SMILES: C[Si](C)(C)CCOCn1cc(C(F)(F)F)nc1-c1ccc(Br)cn1] |
| 107 | 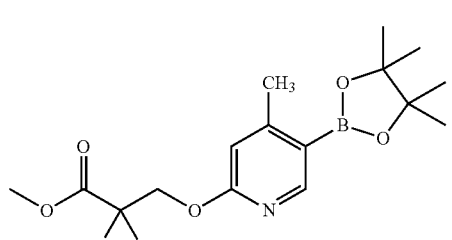 | 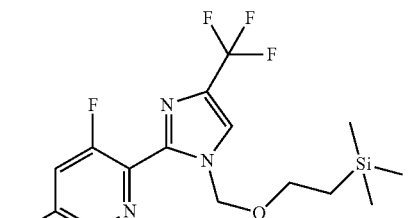 |

TABLE 10-continued
| 108 | 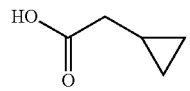 | 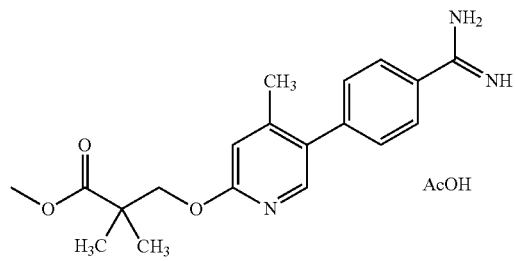 |
| --- | --- | --- |
| 109 | 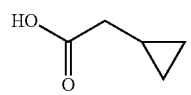 | |
| 110 | 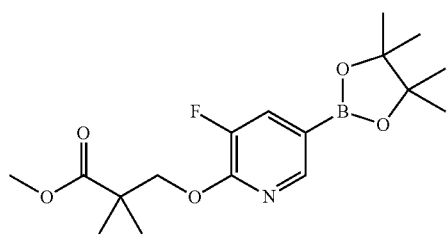 | 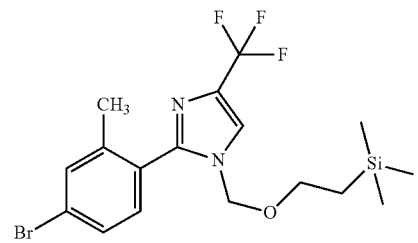 |
| 111 | 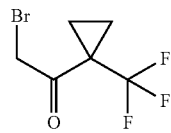 [SMILES: O=C(CBr)C1(C(F)(F)F)CC1] | 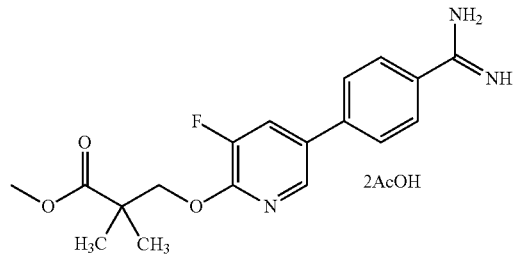 |
| 112 | 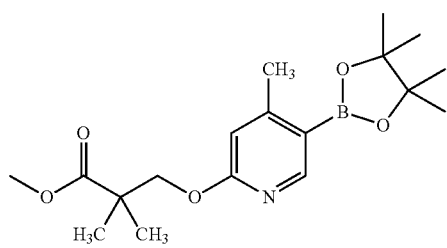 | 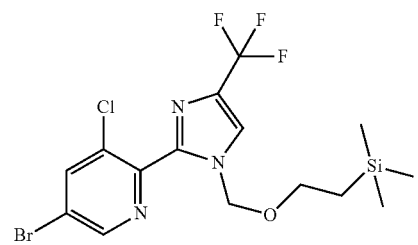 [SMILES: C[Si](C)(C)CCOCn1cc(C(F)(F)F)nc1-c1ncc(Br)cc1Cl] |

TABLE 10-continued
| | | |
|---|---|---|
| 113 | 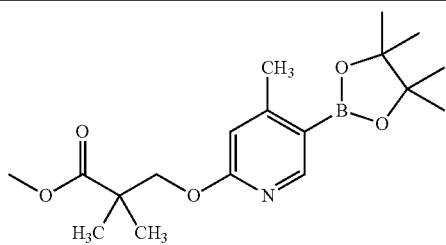 | 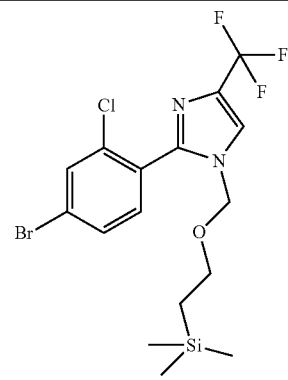 |
| 114 | 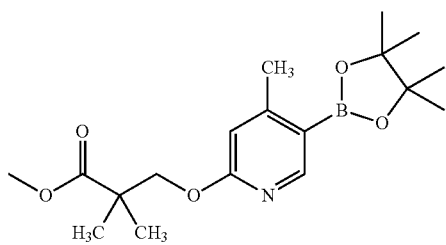 | 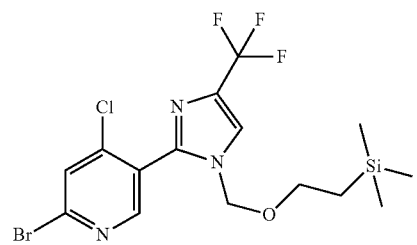 [SMILES: C[Si](C)(C)CCOCn1cc(C(F)(F)F)nc1-c1cnc(Br)cc1Cl] |
| 115 | 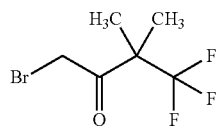 | 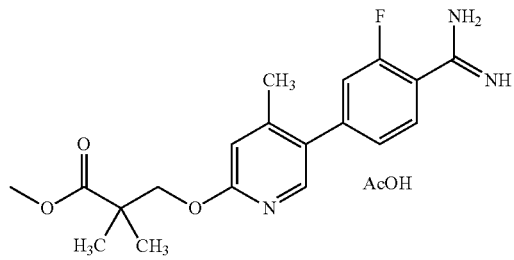 [SMILES: "AcOH" ; COC(=O)C(C)(C)COc1cc(C)c(-c2ccc(C(=N)N)c(F)c2)cn1] |
| 116 | 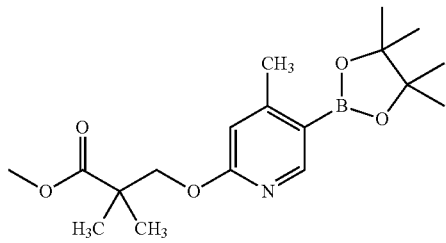 | 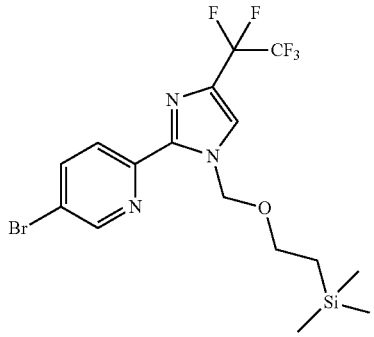 [SMILES: C[Si](C)(C)CCOCn1cc(C(F)(F)C(F)(F)F)nc1-c1ccc(Br)cn1] |
| 117 | 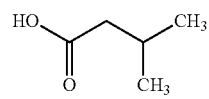 | 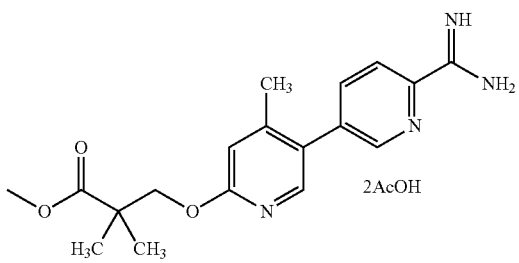 |

TABLE 10-continued
| 118 | 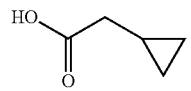 | 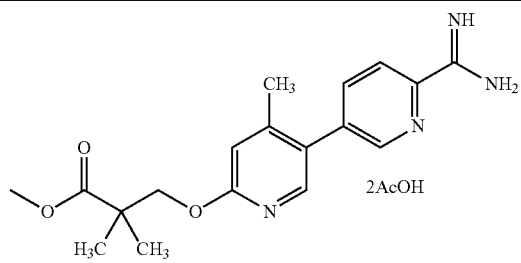 |
| --- | --- | --- |
| 119 | 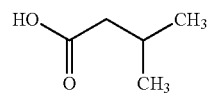 | 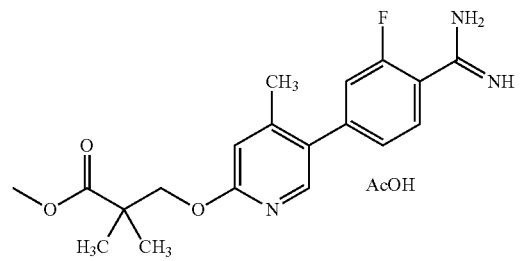 [SMILES: "AcOH" ; COC(=O)C(C)(C)COc1cc(C)c(-c2ccc(C(=N)N)c(F)c2)cn1] |
| 120 | 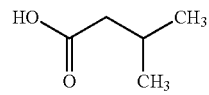 | 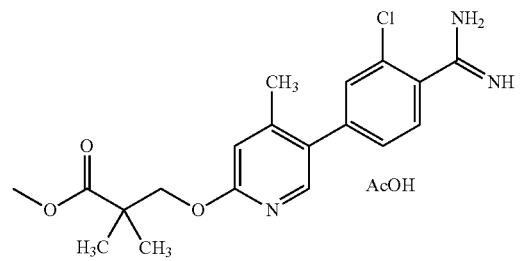 [SMILES: "AcOH" ; COC(=O)C(C)(C)COc1cc(C)c(-c2ccc(C(=N)N)c(Cl)c2)cn1] |
| 121 | 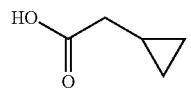 | 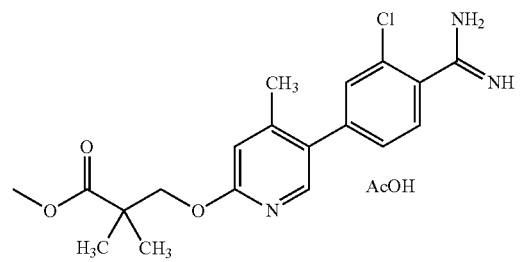 [SMILES: "AcOH" ; COC(=O)C(C)(C)COc1cc(C)c(-c2ccc(C(=N)N)c(Cl)c2)cn1] |
| 122 | 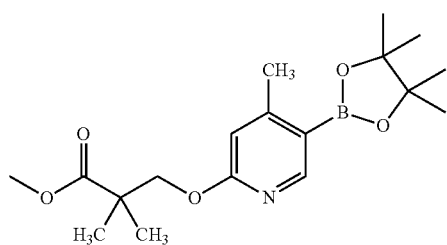 | 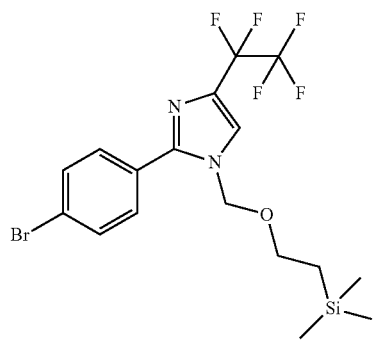 [SMILES: C[Si](C)(C)CCOCn1cc(C(F)(F)C(F)(F)F)nc1-c1ccc(Br)cc1] |

TABLE 10-continued
| 123 | 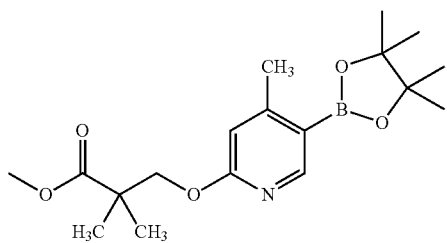 | 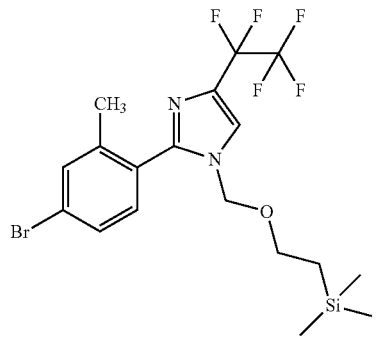 [SMILES: Cc1cc(Br)ccc1-c1nc(C(F)(F)C(F)(F)F)cn1COCC[Si](C)(C)C] |
| 124 | 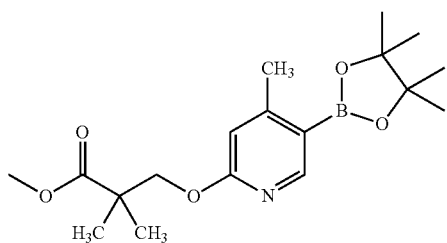 | 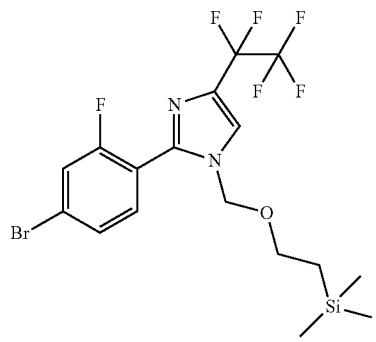 [SMILES: C[Si](C)(C)CCOCn1cc(C(F)(F)C(F)(F)F)nc1-c1ccc(Br)cc1F] |
| 125 | 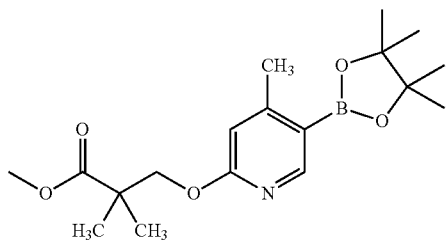 | 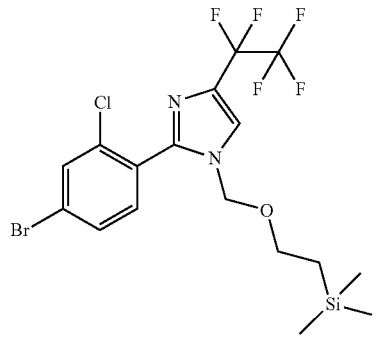 [SMILES: C[Si](C)(C)CCOCn1cc(C(F)(F)C(F)(F)F)nc1-c1ccc(Br)cc1Cl] |
| 126 | 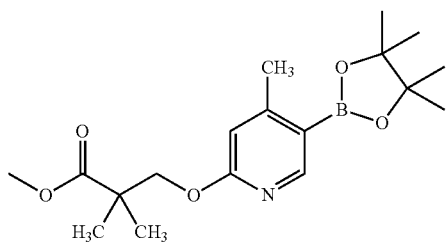 | 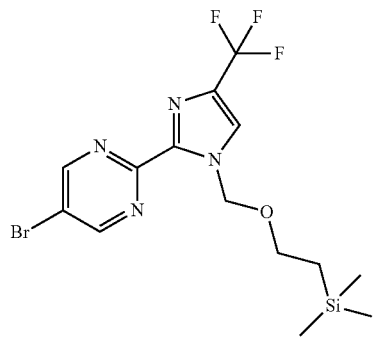 [SMILES: C[Si](C)(C)CCOCn1cc(C(F)(F)F)nc1-c1ncc(Br)cn1] |

TABLE 10-continued
| | | |
|---|---|---|
| 127 | 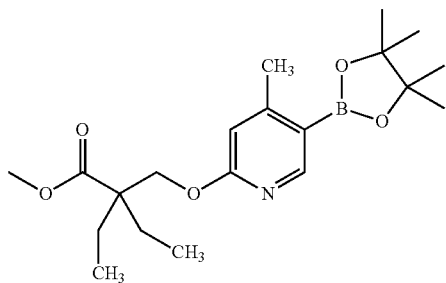 | 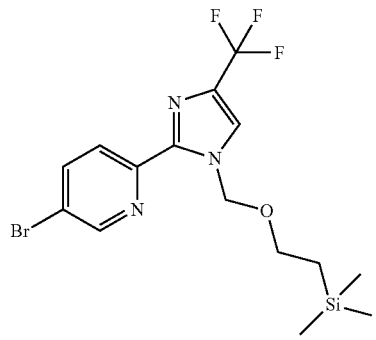 [SMILES: C[Si](C)(C)CCOCn1cc(C(F)(F)F)nc1-c1ccc(Br)cn1] |
| 128 | 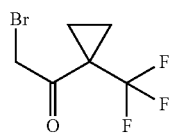 [SMILES: O=C(CBr)C1(C(F)(F)F)CC1] | 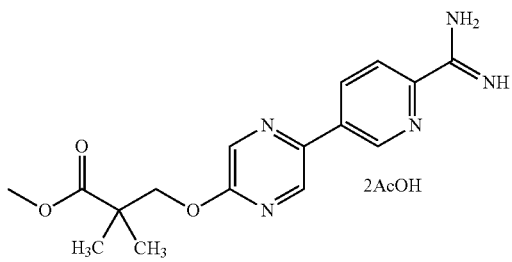 |
| 129 | 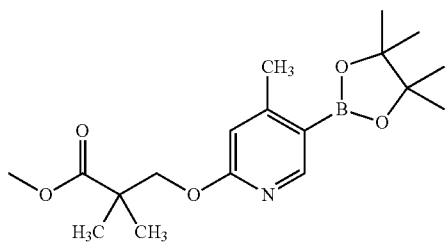 | 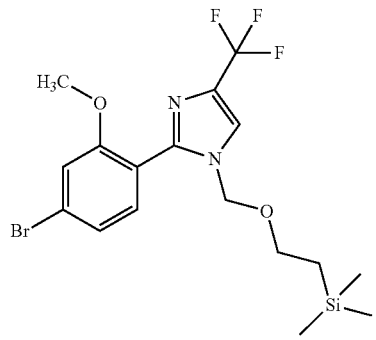 [SMILES: COc1cc(Br)ccc1-c1nc(C(F)(F)F)cn1COCC[Si](C)(C)C] |
| 130 | 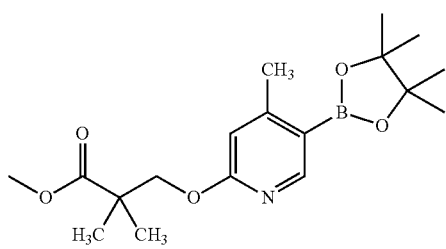 | 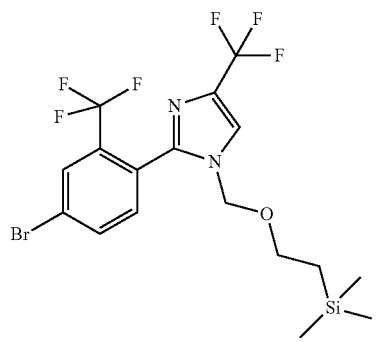 [SMILES: C[Si](C)(C)CCOCn1cc(C(F)(F)F)nc1-c1ccc(Br)cc1C(F)(F)F] |
| 131 | 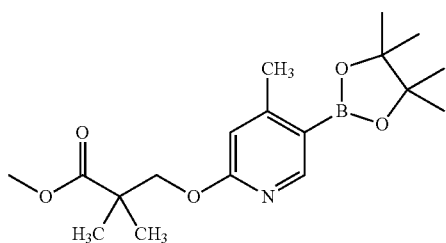 | 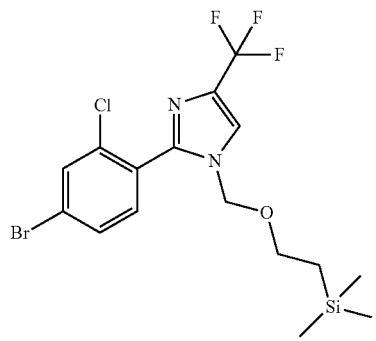 [SMILES: C[Si](C)(C)CCOCn1cc(C(F)(F)F)nc1-c1ccc(Br)cc1Cl] |

TABLE 10-continued
| | | |
|---|---|---|
| 132 | 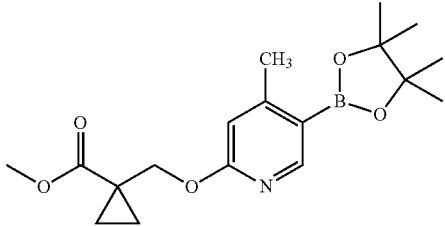 | 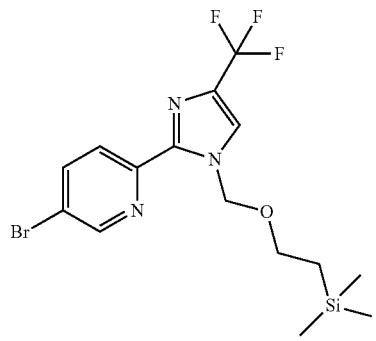 [SMILES: C[Si](C)(C)CCOCn1cc(C(F)(F)F)nc1-c1ccc(Br)cn1] |
| 133 | 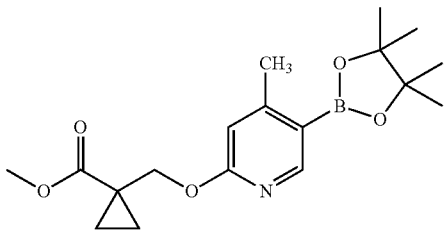 | 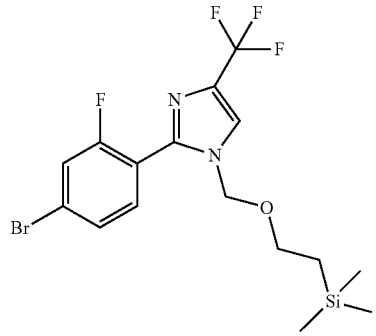 [SMILES: C[Si](C)(C)CCOCn1cc(C(F)(F)F)nc1-c1ccc(Br)cc1F] |
| 134 | 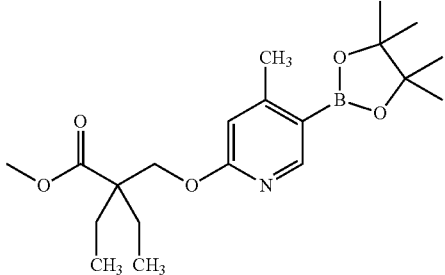 | 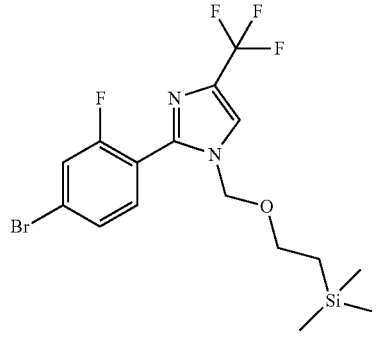 [SMILES: C[Si](C)(C)CCOCn1cc(C(F)(F)F)nc1-c1ccc(Br)cc1F] |
| 135 | 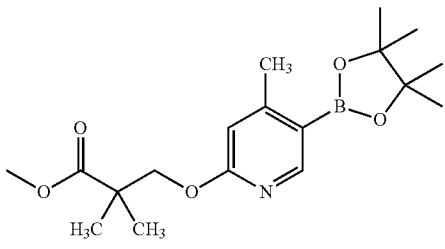 | 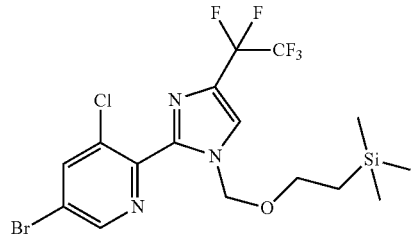 [SMILES: C[Si](C)(C)CCOCn1cc(C(F)(F)C(F)(F)F)nc1-c1ncc(Br)cc1Cl] |
| 136 | 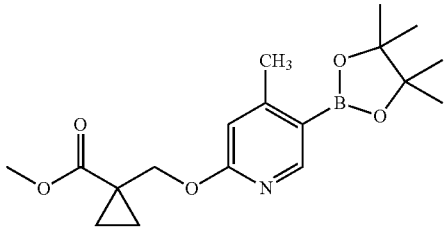 | 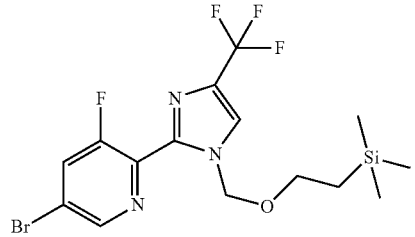 |

TABLE 10-continued
| | | |
|---|---|---|
| 137 | 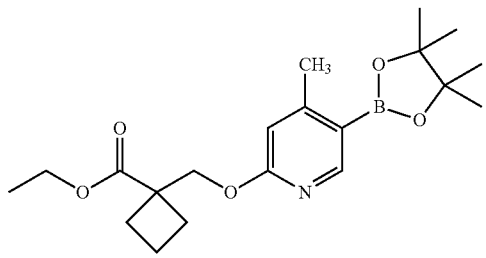 [SMILES: CCOC(=O)C1(COc2cc(C)c(B3OC(C)(C)C(C)(C)O3)cn2)CCC1] | 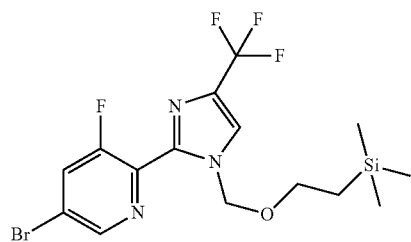 [SMILES: C[Si](C)(C)CCOCn1cc(C(F)(F)F)nc1-c1ncc(Br)cc1F] |
| 138 | 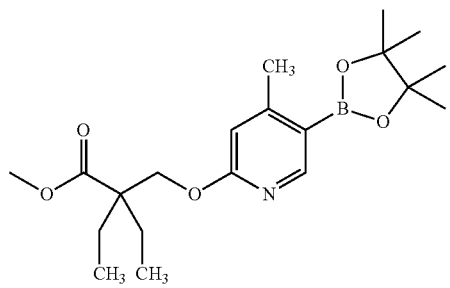 | 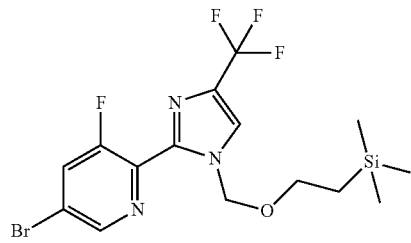 [SMILES: C[Si](C)(C)CCOCn1cc(C(F)(F)F)nc1-c1ncc(Br)cc1F] |
| 139 | 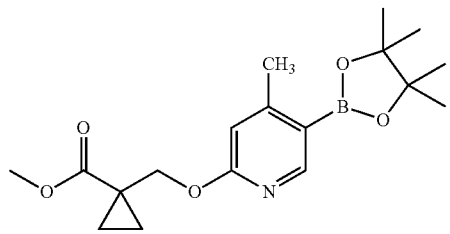 | 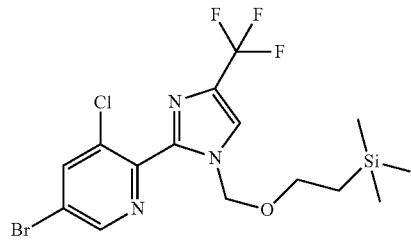 |
| 140 | 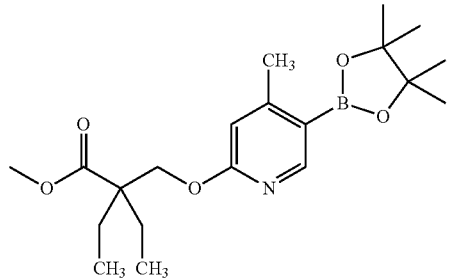 | 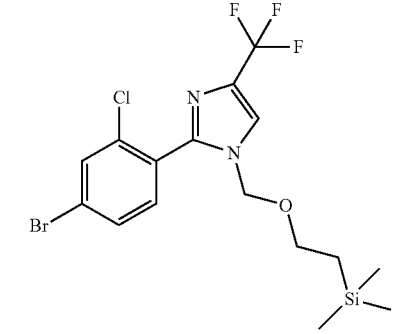 |
| 141 | 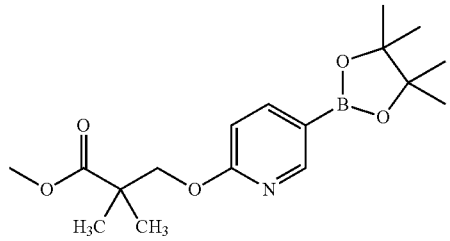 | 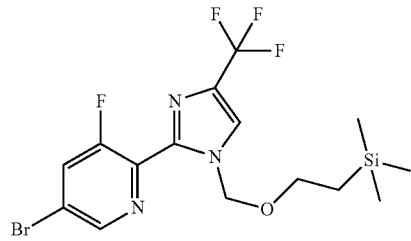 [SMILES: C[Si](C)(C)CCOCn1cc(C(F)(F)F)nc1-c1ncc(Br)cc1F] |
| 142 | 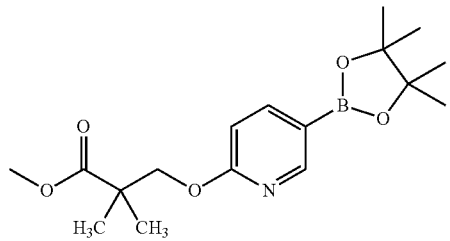 | 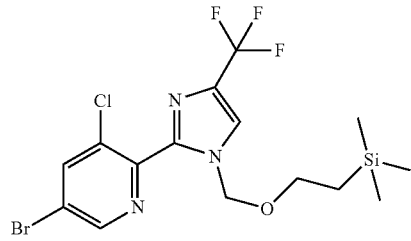 |

TABLE 10-continued
| 143 | 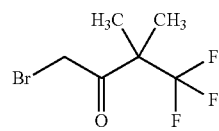 | 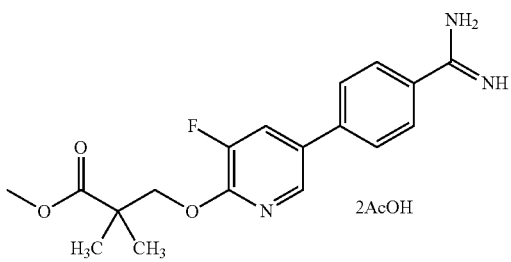 |
| --- | --- | --- |
| 144 | 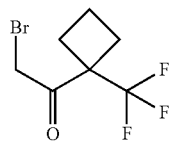 | |
| 145 | 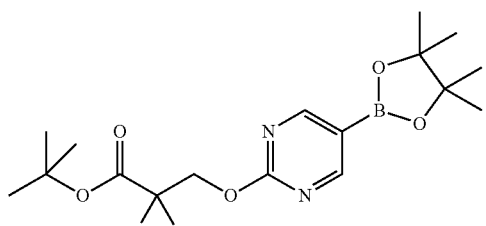 | |
| 146 | 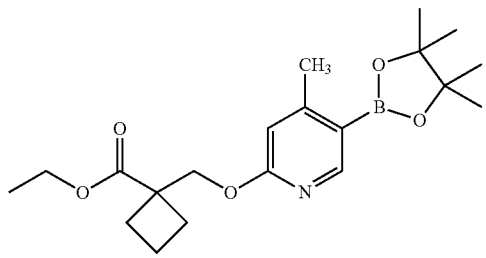 [SMILES: CCOC(=O)C1(COc2cc(C)c(B3OC(C)(C)C(C)(C)O3)cn2)CCC1] | 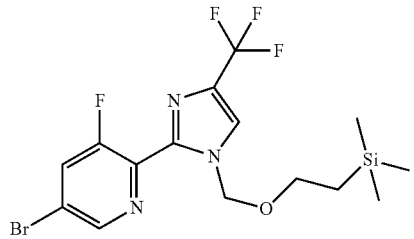 [SMILES: C[Si](C)(C)CCOCn1cc(C(F)(F)F)nc1-c1ncc(Br)cc1F] |
| 147 | 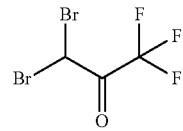 | 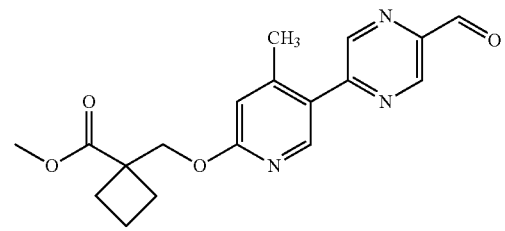 [SMILES: COC(=O)C1(COc2cc(C)c(-c3cnc(C=O)cn3)cn2)CCC1] |
| 148 | 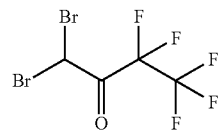 | 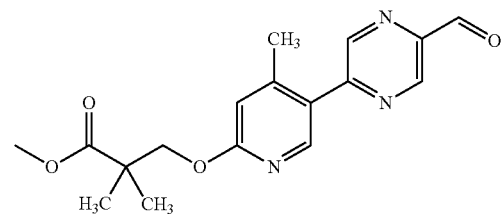 [SMILES: COC(=O)C(C)(C)COc1cc(C)c(-c2cnc(C=O)cn2)cn1] |

TABLE 10-continued
| Example | Product | MS (m/z) |
|---|---|---|
| 102 | 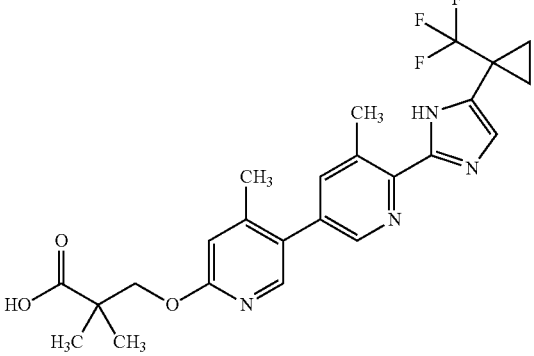 | 475 [M + H]+ |
| 103 | 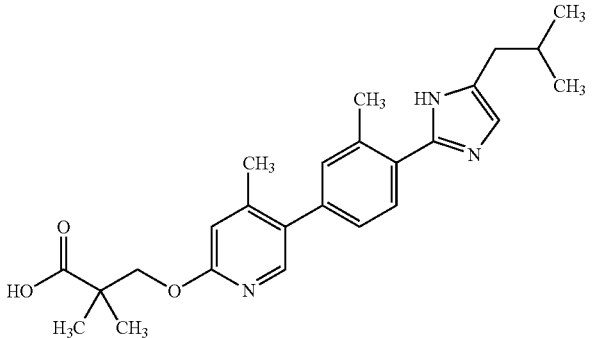 [SMILES: Cc1cc(OCC(C)(C)C(=O)O)ncc1-c1ccc(-c2ncc(CC(C)C)[nH]2)c(C)c1] | 422 [M + H]+ |
| 104 | 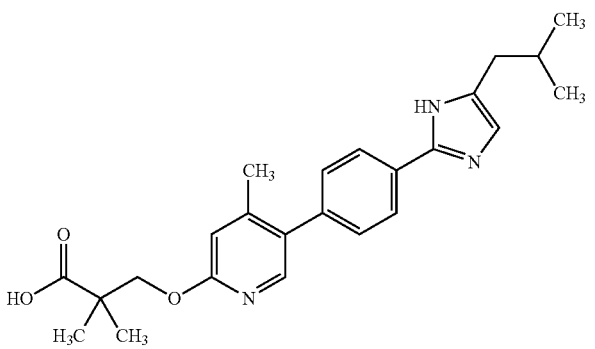 [SMILES: Cc1cc(OCC(C)(C)C(=O)O)ncc1-c1ccc(-c2ncc(CC(C)C)[nH]2)cc1] | 408 [M + H]+ |
| 105 | 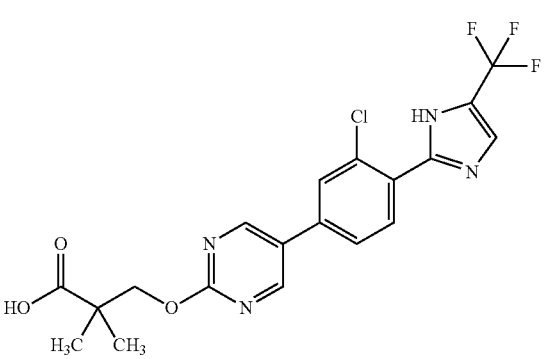 [SMILES: CC(C)(COc1ncc(-c2ccc(-c3ncc(C(F)(F)F)[nH]3)c(Cl)c2)cn1)C(=O)O] | 441/443 [M + H]+ |

TABLE 10-continued
| 106 | 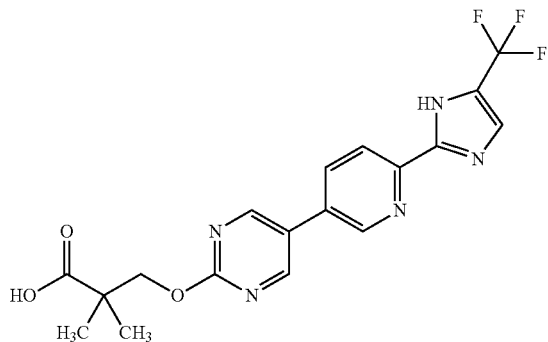 [SMILES: CC(C)(COc1ncc(-c2ccc(-c3ncc(C(F)(F)F)[nH]3)nc2)cn1)C(=O)O] | 408 [M + H]+ |
| 107 | 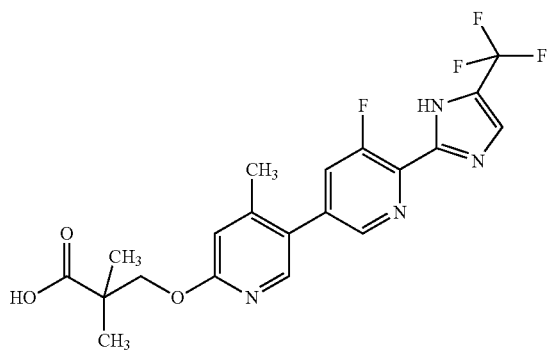 [SMILES: Cc1cc(OCC(C)(C)C(=O)O)ncc1-c1cnc(-c2ncc(C(F)(F)F)[nH]2)c(F)c1] | 439 [M + H]+ |
| 108 | 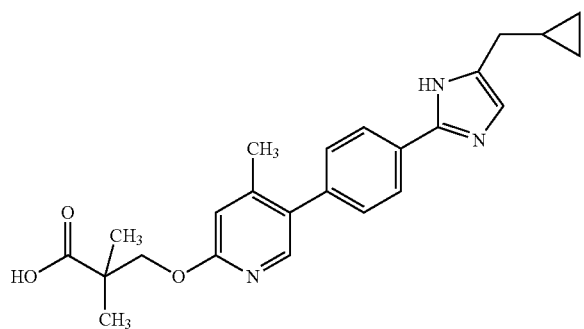 [SMILES: Cc1cc(OCC(C)(C)C(=O)O)ncc1-c1ccc(-c2ncc(CC3CC3)[nH]2)cc1] | 406 [M + H]+ |
| 109 | 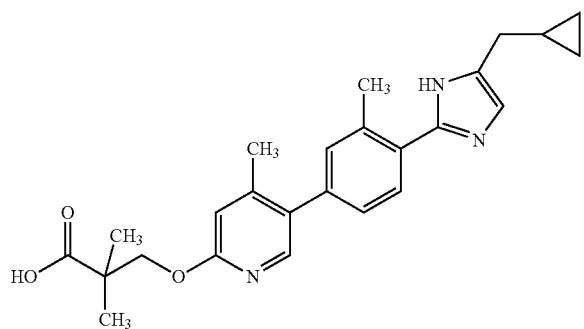 [SMILES: Cc1cc(OCC(C)(C)C(=O)O)ncc1-c1ccc(-c2ncc(CC3CC3)[nH]2)c(C)c1] | 420 [M + H]+ |

TABLE 10-continued
| | | |
|---|---|---|
| 110 | 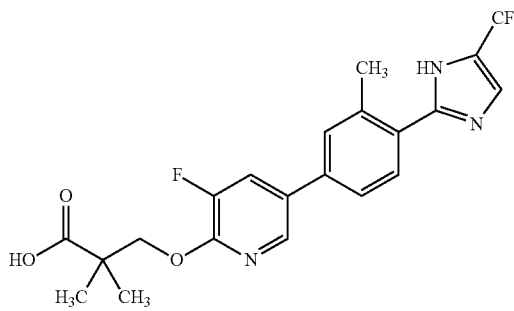 | 438 [M + H]+ |
| 111 | 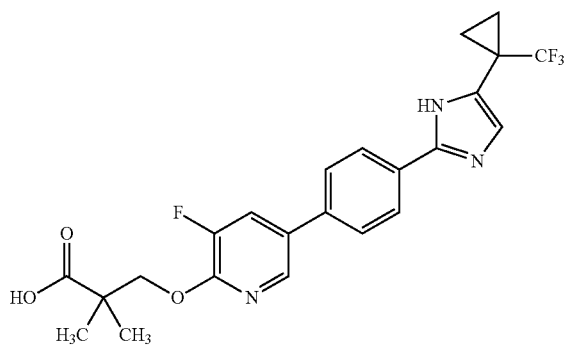 [SMILES: CC(C)(COc1ncc(-c2ccc(-c3ncc(C4(C(F)(F)F)CC4)[nH]3)cc2)cc1F)C(=O)O] | 464 [M + H]+ |
| 112 | 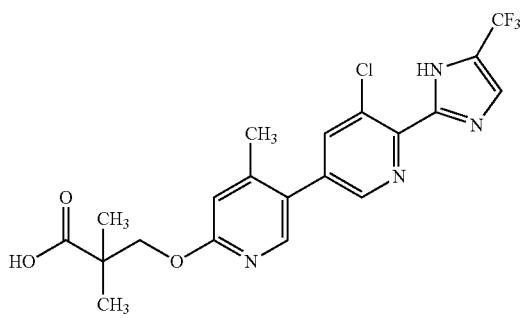 [SMILES: Cc1cc(OCC(C)(C)C(=O)O)ncc1-c1cnc(-c2ncc(C(F)(F)F)[nH]2)c(Cl)c1] | 455/457 [M + H]+ |
| 113 | 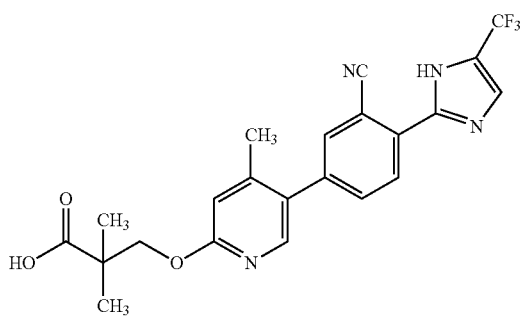 [SMILES: Cc1cc(OCC(C)(C)C(=O)O)ncc1-c1ccc(-c2ncc(C(F)(F)F)[nH]2)c(C#N)c1] | 445 [M + H]+ |
| 114 | 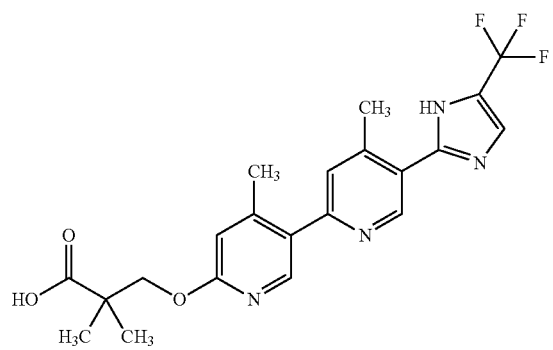 [SMILES: Cc1cc(OCC(C)(C)C(=O)O)ncc1-c1cc(C)c(-c2ncc(C(F)(F)F)[nH]2)cn1] | 435 [M + H]+ |

TABLE 10-continued
| | | |
|---|---|---|
| 115 | 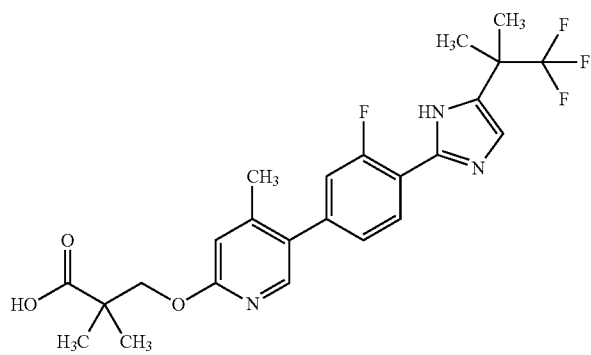 [SMILES: Cc1cc(OCC(C)(C)C(=O)O)ncc1-c1ccc(-c2ncc(C(C)(C)C(F)(F)F)[nH]2)c(F)c1] | 480 [M + H]+ |
| 116 | 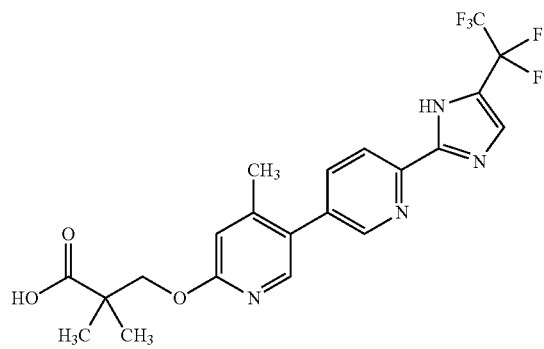 [SMILES: Cc1cc(OCC(C)(C)C(=O)O)ncc1-c1ccc(-c2ncc(C(F)(F)C(F)(F)F)[nH]2)nc1] | 471 [M + H]+ |
| 117 | 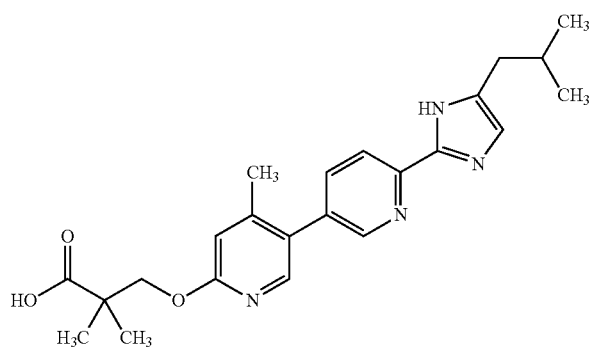 | 409 [M + H]+ |
| 118 | 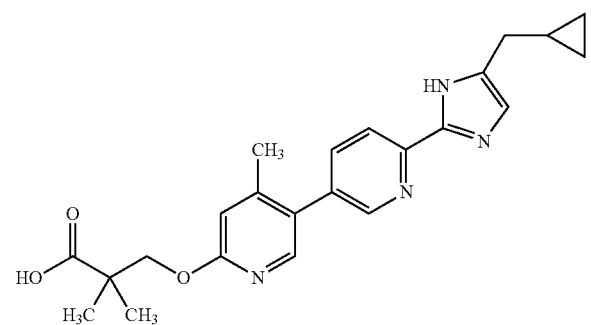 [SMILES: Cc1cc(OCC(C)(C)C(=O)O)ncc1-c1ccc(-c2ncc(CC3CC3)[nH]2)nc1] | 407 [M + H]+ |

TABLE 10-continued
| | | |
|---|---|---|
| 119 | 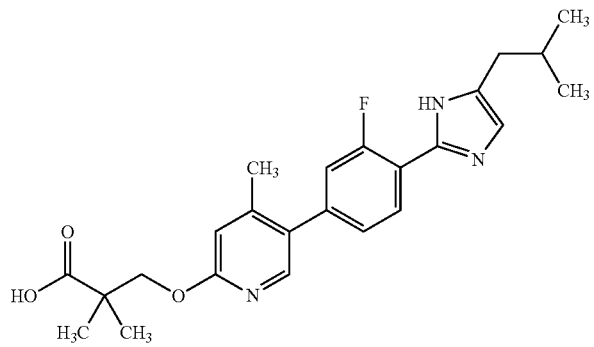 [SMILES: Cc1cc(OCC(C)(C)C(=O)O)ncc1-c1ccc(-c2ncc(CC(C)C)[nH]2)c(F)c1] | 426 [M + H]+ |
| 120 | 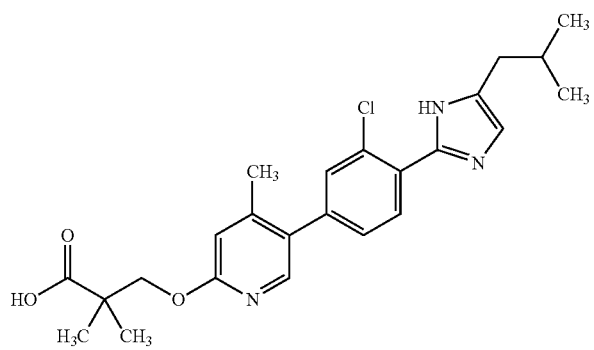 [SMILES: Cc1cc(OCC(C)(C)C(=O)O)ncc1-c1ccc(-c2ncc(CC(C)C)[nH]2)c(Cl)c1] | 442 [M + H]+ |
| 121 | 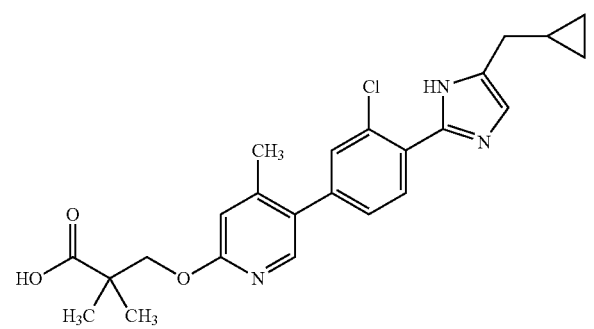 | 440/442 [M + H]+ |
| 122 | 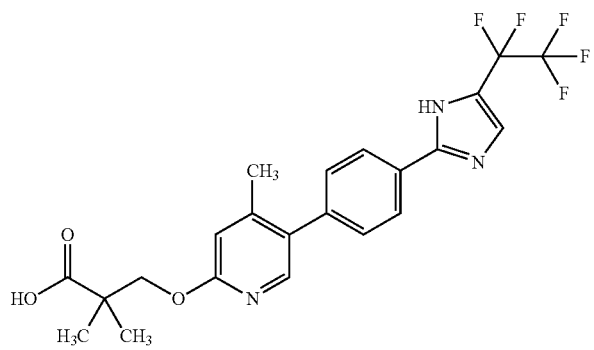 [SMILES: Cc1cc(OCC(C)(C)C(=O)O)ncc1-c1ccc(-c2ncc(C(F)(F)C(F)(F)F)[nH]2)cc1] | 470 [M + H]+ |

TABLE 10-continued
| | | |
|---|---|---|
| 123 | 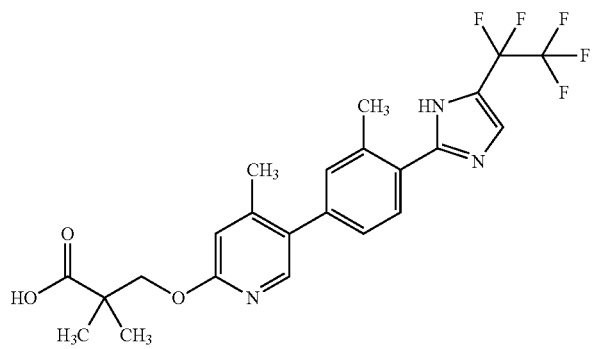 [SMILES: Cc1cc(OCC(C)(C)C(=O)O)ncc1-c1ccc(-c2ncc(C(F)(F)C(F)(F)F)[nH]2)c(C)c1] | 484 [M + H]+ |
| 124 | 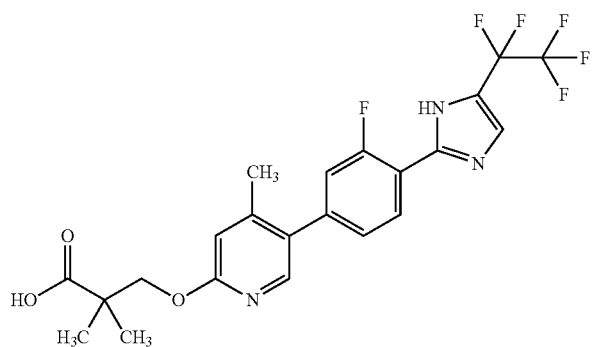 [SMILES: Cc1cc(OCC(C)(C)C(=O)O)ncc1-c1ccc(-c2ncc(C(F)(F)C(F)(F)F)[nH]2)c(F)c1] | 488 [M + H]+ |
| 125 | 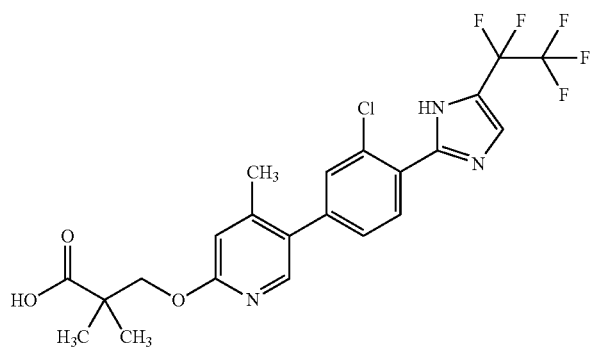 [SMILES: Cc1cc(OCC(C)(C)C(=O)O)ncc1-c1ccc(-c2ncc(C(F)(F)C(F)(F)F)[nH]2)c(Cl)c1] | 504/506 [M + H]+ |
| 126 | 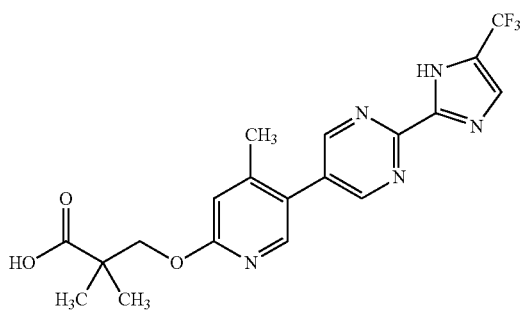 [SMILES: Cc1cc(OCC(C)(C)C(=O)O)ncc1-c1cnc(-c2ncc(C(F)(F)F)[nH]2)nc1] | 422 [M + H]+ |

TABLE 10-continued
| | | |
|---|---|---|
| 127 | 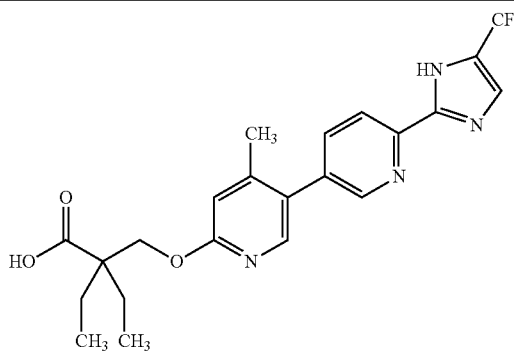 | 449<br>[M + H]+ |
| 128 | 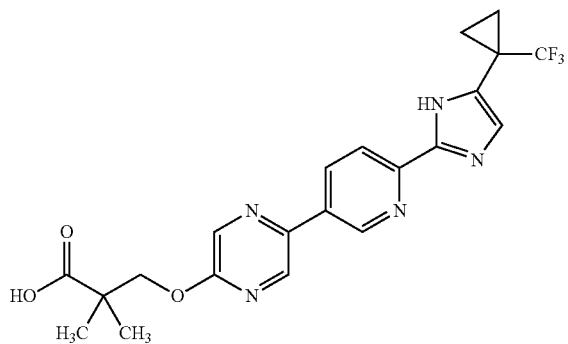 [SMILES: CC(C)(COc1cnc(-c2ccc(-c3ncc(C4(C(F)(F)F)CC4)[nH]3)nc2)cn1)C(=O)O] | 448<br>[M + H]+ |
| 129 | 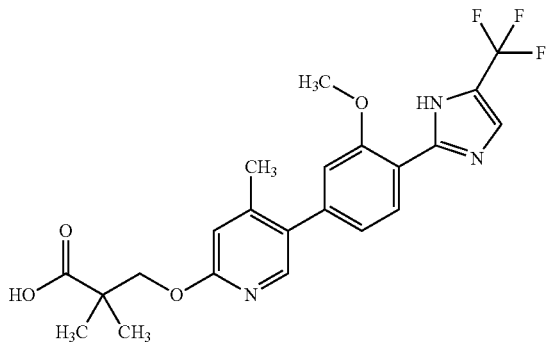 [SMILES: COc1cc(-c2cnc(OCC(C)(C)C(=O)O)cc2C)ccc1-c1ncc(C(F)(F)F)[nH]1] | 450<br>[M + H]+ |
| 130 | 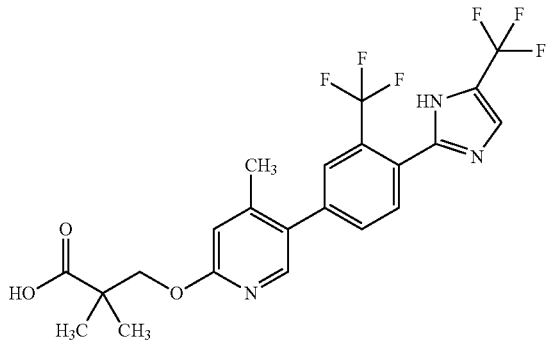 [SMILES: Cc1cc(OCC(C)(C)C(=O)O)ncc1-c1ccc(-c2ncc(C(F)(F)F)[nH]2)c(C(F)(F)F)c1] | 488<br>[M + H]+ |

TABLE 10-continued
| | | |
|---|---|---|
| 131 | 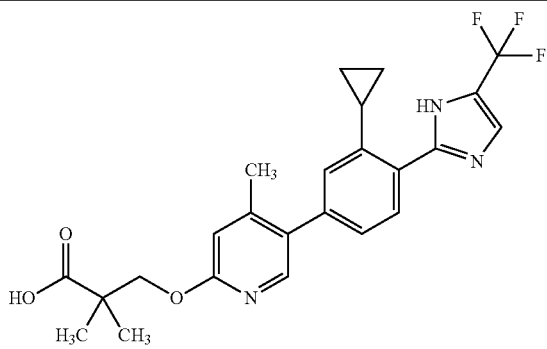 | 460 [M + H]+ |
| 132 | 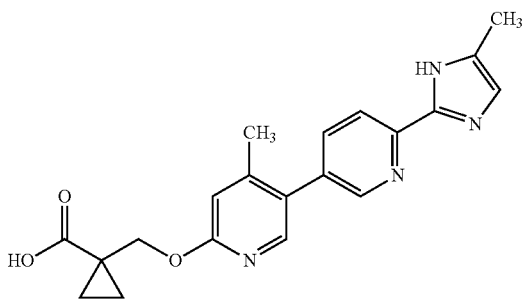 | 419 [M + H]+ |
| 133 | 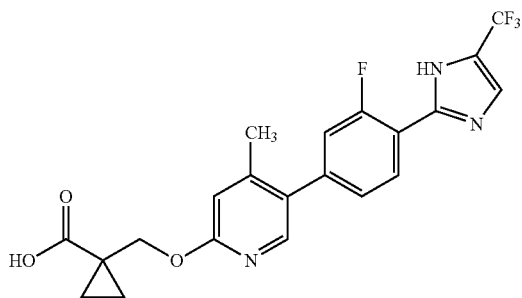 [SMILES: Cc1cc(OCC2(C(=O)O)CC2)ncc1-c1ccc(-c2ncc(C(F)(F)F)[nH]2)c(F)c1] | 436 [M + H]+ |
| 134 | 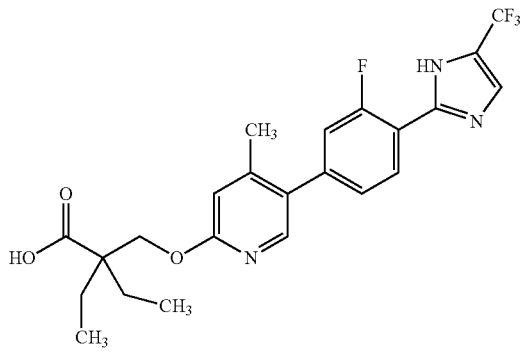 [SMILES: CCC(CC)(COc1cc(C)c(-c2ccc(-c3ncc(C(F)(F)F)[nH]3)c(F)c2)cn1)C(=O)O] | 466 [M + H]+ |
| 135 | 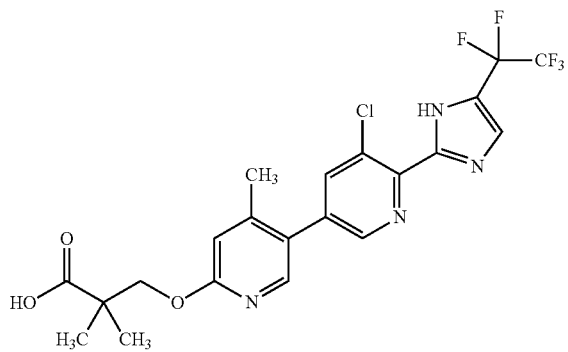 [SMILES: Cc1cc(OCC(C)(C)C(=O)O)ncc1-c1cnc(-c2ncc(C(F)(F)C(F)(F)F)[nH]2)c(Cl)c1] | 505/507 [M + H]+ |

TABLE 10-continued

| | | |
|---|---|---|
| 136 | (structure) | 437 [M + H]+ |
| 137 | (structure) | 451 [M + H]+ |
| 138 | (structure) | 467 [M + H]+ |
| 139 | (structure) | 453/455 [M + H]+ |
| 140 | (structure) | 482/484 [M + H]+ |

TABLE 10-continued
| | | |
|---|---|---|
| 141 | 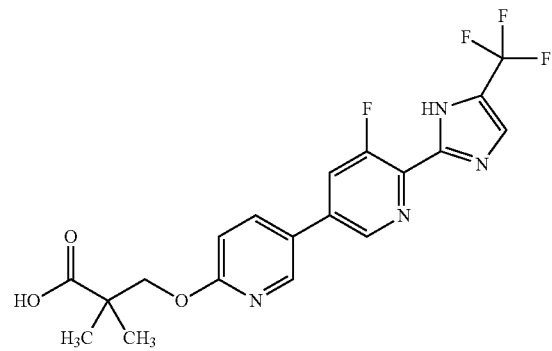 [SMILES: CC(C)(COc1ccc(-c2cnc(-c3ncc(C(F)(F)F)[nH]3)c(F)c2)cn1)C(=O)O] | 425<br>[M + H]+ |
| 142 | 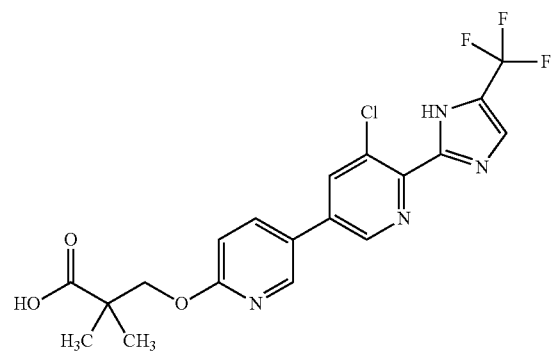 [SMILES: CC(C)(COc1ccc(-c2cnc(-c3ncc(C(F)(F)F)[nH]3)c(Cl)c2)cn1)C(=O)O] | 441/443<br>[M + H]+ |
| 143 | 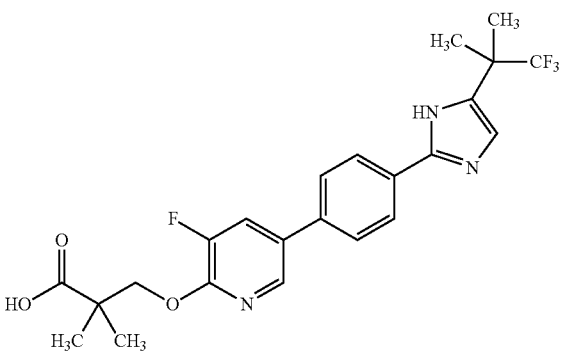 [SMILES: CC(C)(COc1ncc(-c2ccc(-c3ncc(C(C)(C)C(F)(F)F)[nH]3)cc2)cc1F)C(=O)O] | 466<br>[M + H]+ |
| 144 | 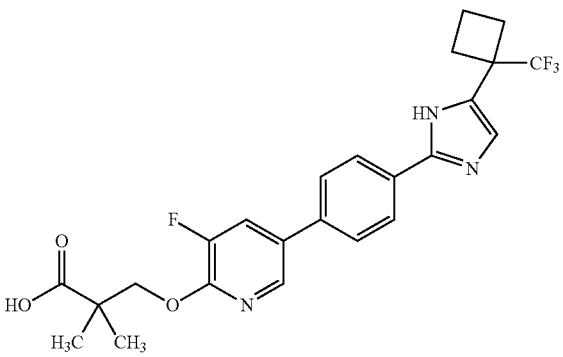 [SMILES: CC(C)(COc1ncc(-c2ccc(-c3ncc(C4(C(F)(F)F)CCC4)[nH]3)cc2)cc1F)C(=O)O] | 478<br>[M + H]+ |

TABLE 10-continued
| | | |
|---|---|---|
| 145 | 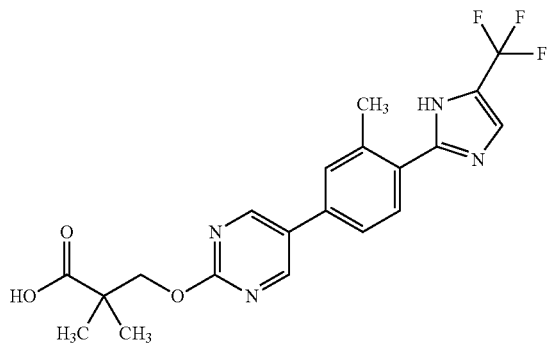 | 421 [M + H]+ |
| 146 | 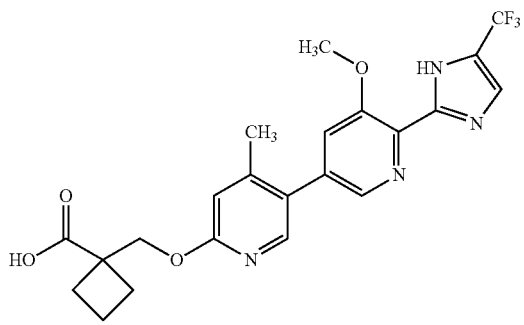 [SMILES: COc1cc(-c2cnc(OCC3(C(=O)O)CCC3)cc2C)cnc1-c1ncc(C(F)(F)F)[nH]1] | 463 [M + H]+ |
| 147 | 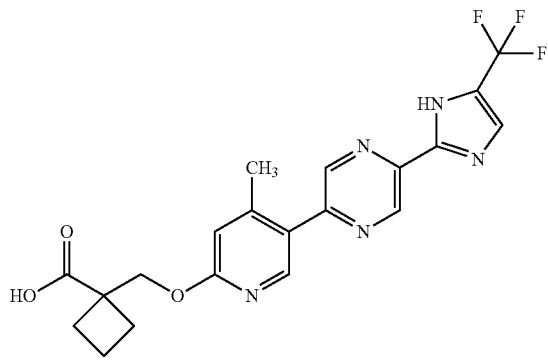 [SMILES: Cc1cc(OCC2(C(=O)O)CCC2)ncc1-c1cnc(-c2ncc(C(F)(F)F)[nH]2)cn1] | 434 [M + H]+ |
| 148 | 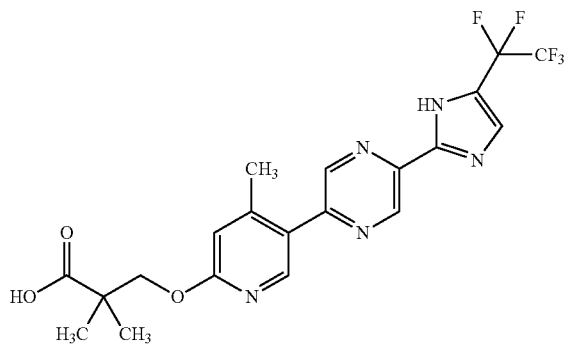 [SMILES: Cc1cc(OCC(C)(C)C(=O)O)ncc1-c1cnc(-c2ncc(C(F)(F)C(F)(F)F)[nH]2)cn1] | 472 [M + H]+ |

Reference Example 1

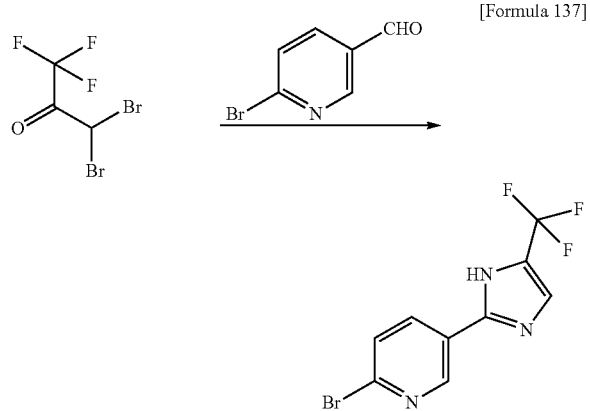

[Formula 137]

1) To water (15 mL) were added 3,3-dibromo-1,1,1-trifluoropropan-2-one (4.05 g) and sodium acetate (2.46 g), and the mixture was stirred at 95° C. for 30 minutes. The solution obtained by ice-cooling was added to a solution in which 6-bromo-nicotinaldehyde (1.86 g) was dissolved in 28% aqueous ammonia (20 mL) and methanol (60 mL) under ice-cooling, and the mixture was stirred overnight while the temperature of the mixture was gradually raised to room temperature. The reaction mixture was concentrated under reduced pressure, then, water and ethyl acetate were added thereto and the liquids were separated, and the organic layer was dried over anhydrous sodium sulfate and concentrated under reduced pressure. To the obtained solid residue was added ether to pulverize the same, and the solid was collected by filtration and dried to obtain 2-bromo-5-[5-(trifluoromethyl)-1H-imidazol-2-yl]pyridine (1.25 g).

MS (m/z): 292/294 [M+H]$^+$

[Formula 138]

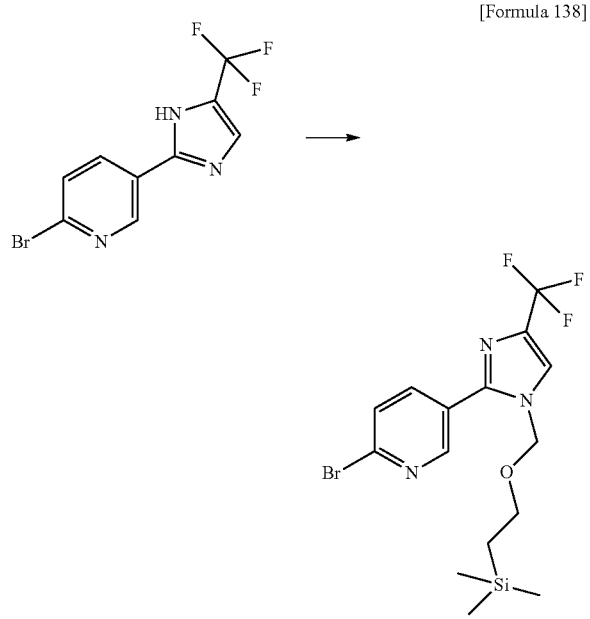

2) 60% Sodium hydride (2.62 g) was added to a solution of 2-bromo-5-[5-(trifluoromethyl)-1H-imidazol-2-yl]pyridine (13.65 g) dissolved in N,N-dimethylformamide (150 mL) under nitrogen atmosphere and under ice-cooling, and the mixture was stirred for 30 minutes. To the mixture was added 2-(trimethylsilyl)ethoxymethyl chloride (12.4 mL) under ice-cooling, and the mixture was stirred overnight while the temperature of the mixture was gradually raised to room temperature. To the reaction mixture was added a saturated aqueous ammonium chloride solution, and the mixture was extracted with ethyl acetate. The organic layer was washed with saturated brine, and the aqueous layer at this time was extracted with ethyl acetate. The organic layers were combined and dried, and the residue obtained by concentrating the reaction mixture under reduced pressure was purified by silica gel column chromatography (n-hexane:ethyl acetate) to obtain 2-bromo-5-[4-(trifluoromethyl)-1-{[2-(trimethylsilyl)ethoxy]methyl}-1H-imidazol-2-yl]pyridine (9.42 g).

MS (m/z): 422/424 [M+H]$^+$

[Formula 139]

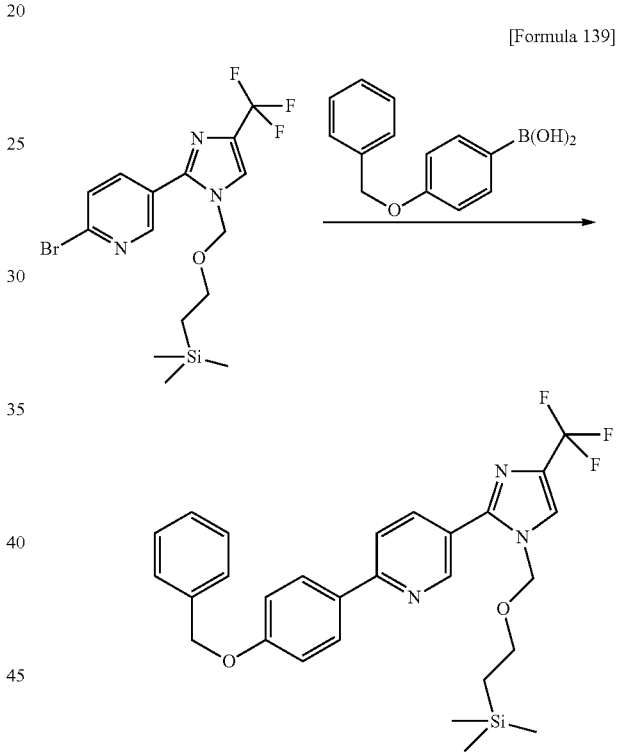

3) Palladium chloride (dppf) methylene chloride complex (0.193 g) was added to a mixture of 2-bromo-5-[4-(trifluoromethyl)-1-{[2-(trimethylsilyl)ethoxy]methyl}-1H-imidazol-2-yl]pyridine (1.0 g), (4-benzyloxyphenyl)boronic acid (1.08 g), 2M aqueous sodium carbonate solution (4.74 mL) and N,N-dimethylformamide (18.9 mL) under nitrogen atmosphere, and the mixture was stirred at 65° C. under nitrogen atmosphere overnight. To the mixture were added water and ethyl acetate, and then, insoluble material was removed by filtration using Celite. The organic layer was separated, washed with saline, dried over anhydrous sodium sulfate, and concentrated under reduced pressure. The residue was purified by silica gel column chromatography (n-hexane:ethyl acetate=88:12 to 80:20) to obtain 2-[4-(benzyloxy)phenyl]-5-[4-(trifluoromethyl)-1-{[2-(trimethylsilyl)ethoxy]methyl}-1H-imidazol-2-yl]pyridine (1.038 g).

MS (m/z): 526 [M+H]$^+$

[Formula 140]

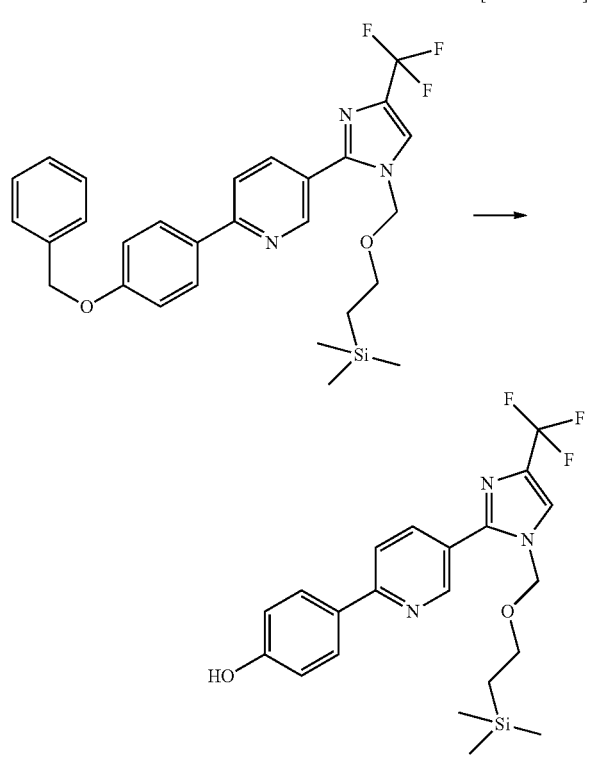

4) In methanol (8 mL) and tetrahydrofuran (6 mL) was dissolved 2-[4-(benzyloxy)phenyl]-5-[4-(trifluoromethyl)-1-{[2-(trimethylsilyl)ethoxy]methyl}-1H-imidazol-2-yl] pyridine (0.77 g), and after adding palladium carbon (0.154 g) under nitrogen atmosphere, the atmosphere was replaced by hydrogen, and the mixture was stirred at room temperature for 5 hours. Insoluble material was filtered off by using a membrane filter, and the filtrate was concentrated under reduced pressure. The concentrate was diluted with methanol, activated charcoal was added thereto, and the mixture was filtered by using Celite. The filtrate was concentrated under reduced pressure and crystallized to obtain 4-{5-[4-(trifluoromethyl)-1-{[2-(trimethylsilyl)ethoxy]methyl}-1H-imidazol-2-yl]pyridin-2-yl}phenol (0.612 g).

MS (m/z): 436 [M+H]$^+$

Reference Example 2

[Formula 141]

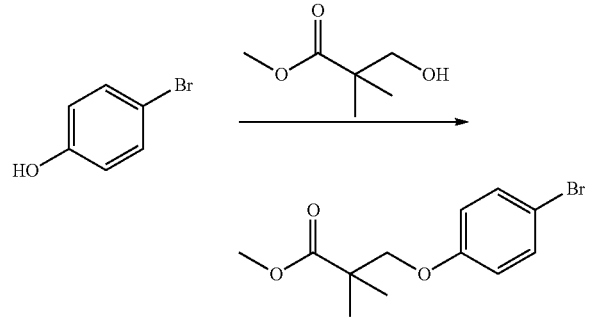

1) 40% Diethyl azodicarboxylate-toluene solution (9.54 mL) was added to a tetrahydrofuran (40 mL) solution containing 4-bromophenol (2.0 g), methyl hydroxypivalate (2.77 g) and triphenylphosphine (5.49 g), and the mixture was stirred at 70° C. for 3 hours. The reaction mixture was concentrated under reduced pressure, and purified by silica gel column chromatography (n-hexane:ethyl acetate=90:10) to obtain methyl 3-(4-bromophenoxy)-2,2-dimethylpropanoate (3.2 g).

MS (m/z): 287/289 [M+H]$^+$

[Formula 142]

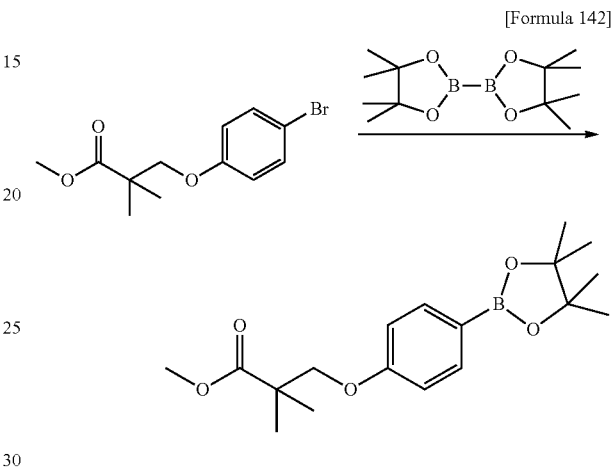

2) To 1,4-dioxane (60 mL) were added methyl 3-(4-bromophenoxy)-2,2-dimethylpropanoate (4.68 g), bis(pinacolato)diboron (5.17 g), palladium chloride (dppf) methylene chloride complex (399 mg) and potassium acetate (4.80 g), and the mixture was stirred at 80° C. under nitrogen atmosphere overnight. The reaction mixture was passed through a short column filled with silica gel and NH-silica gel and washed with ethyl acetate. The residue obtained by concentrating the filtrate under reduced pressure was purified by silica gel column chromatography (n-hexane:ethyl acetate=93:7 to 75:25) to obtain methyl 2,2-dimethyl-3-[4-(4,4,5,5-tetramethyl-1,3,2-dioxaboloran-2-yl)phenoxy]propanoate (4.93 g).

MS (m/z): 335 [M+H]$^+$

[Formula 143]

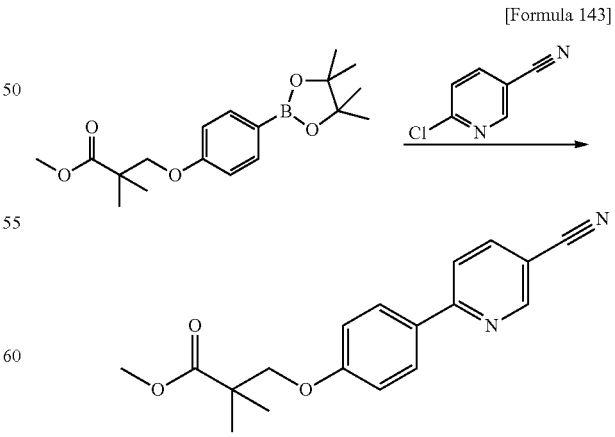

3) To N,N-dimethylformamide (140 mL) were added methyl 2,2-dimethyl-3-[4-(4,4,5,5-tetramethyl-1,3,2-dioxaboloran-2-yl)phenoxy]propanoate (8.6 g), 2-chloropyridin- 5-cyanide (3.0 g), palladium chloride (dppf) complex (788 mg) and 2N aqueous sodium carbonate solution (32 mL), and the mixture was stirred at 65° C. under nitrogen atmosphere overnight. After cooling the reaction mixture to room temperature, water and ethyl acetate were added to the mixture and the mixture was filtered by using Celite. The organic layer was separated, washed with water, dried over anhydrous sodium sulfate, and the residue obtained by concentrating the reaction mixture under reduced pressure was purified by silica gel column chromatography (n-hexane:ethyl acetate=95:5 to 70:30) to obtain methyl 3-[4-(5-cyanopyridin-2-yl)phenoxy]-2,2-dimethylpropanoate (6.0 g).

MS (m/z): 311 [M+H]⁺

[Formula 144]

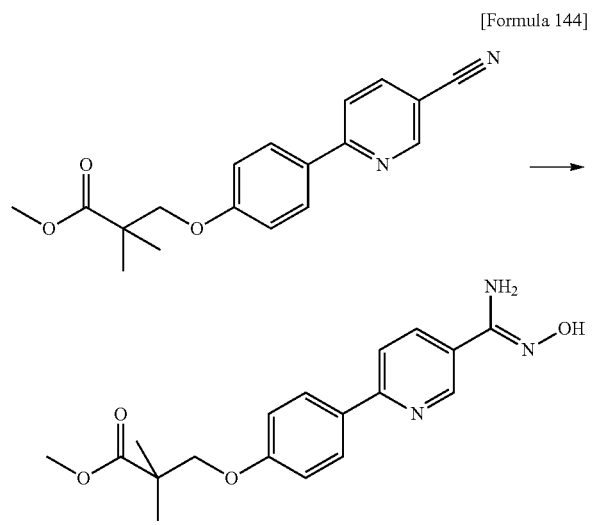

4) 50% Aqueous hydroxylamine solution (40 g) was added to a methanol (100 mL) and tetrahydrofuran (100 mL) solution containing methyl 3-[4-(5-cyanopyridin-2-yl)phenoxy]-2,2-dimethylpropanoate (6.0 g), and the mixture was stirred at 80° C. for 4 hours. After cooling the reaction mixture to room temperature, the mixture was concentrated under reduced pressure. To the obtained residue were added ethyl acetate and water, and the liquids were separated. The organic layer was separated, washed with water, and dried over anhydrous sodium sulfate. Ether was added to the solid residue obtained by concentrating the mixture under reduced pressure to pulverize the same, and the solid was collected by filtration and dried to obtain methyl 3-(4-{5-[amino(hydroxyimino)methyl]pyridin-2-yl}phenoxy)-2,2-dimethylpropanoate (5.8 g).

MS (m/z): 344 [M+H]⁺

[Formula 145]

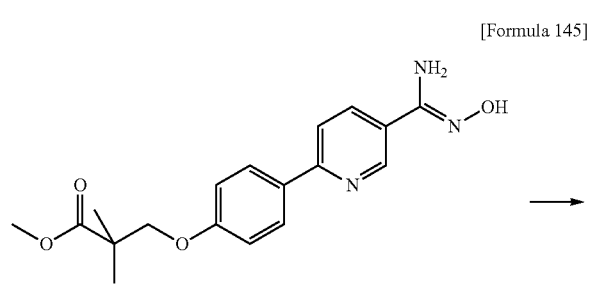

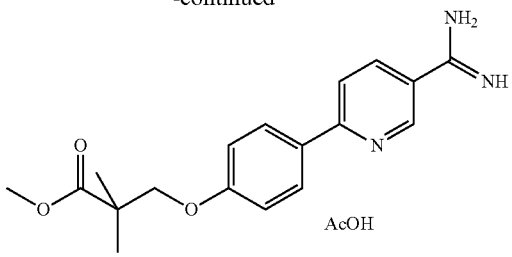

5) In acetic acid (60 mL) was dissolved methyl 3-(4-{5-[amino(hydroxyimino)methyl]-pyridin-2-yl}phenoxy)-2,2-dimethylpropanoate (5.8 g), acetic anhydride (4 mL) was added to the solution and the mixture was stirred at room temperature for 2 hours. To the residue obtained by concentrating the mixture under reduced pressure were added methanol (300 mL) and tetrahydrofuran (70 mL), and 10% palladium carbon (1.2 g) was added to the mixture under nitrogen atmosphere. The atmosphere of the reaction mixture was made hydrogen atmosphere, and the mixture was stirred at room temperature for 2 hours. After replacing the atmosphere with nitrogen, the mixture was filtered using Celite. The filtrate was concentrated under reduced pressure, ether was added to the obtained residue to pulverize the solid, and the solid was collected by filtration and dried to obtain methyl 3-(4-{5-[amino(imino)methyl]pyridin-2-yl}phenoxy)-2,2-dimethylpropanoate acetate (6.11 g).

MS (m/z): 328 [M+H]⁺

Reference Example 3

[Formula 146]

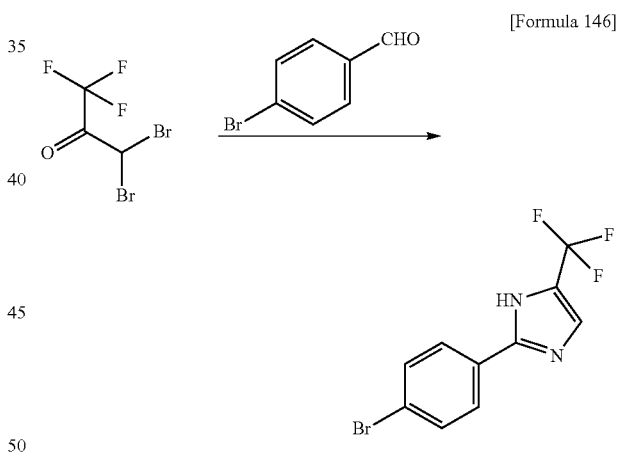

1) By using 4-bromobenzaldehyde (1.0 g), the procedure was carried out in the same manner as in Reference example 1-1) to obtain 2-(4-bromophenyl)-5-(trifluoromethyl)-1H-imidazole (1.22 g).

MS (m/z): 291/293 [M+H]⁺

[Formula 147]

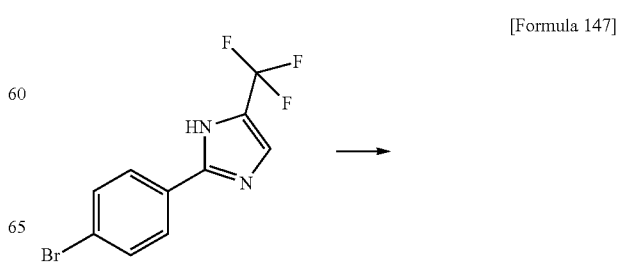

215

-continued

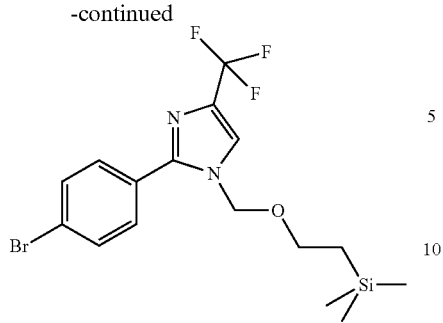

2) By using 2-(4-bromophenyl)-5-(trifluoromethyl)-1H-imidazole (1.22 g), the procedure was carried out in the same manner as in Reference example 1-2) to obtain 2-(4-bromophenyl)-4-(trifluoromethyl)-1-{[2-(trimethylsilyl)ethoxy]methyl}-1H-imidazole (1.63 g).
MS (m/z): 421/423 [M+H]⁺

Reference Example 4

[Formula 148]

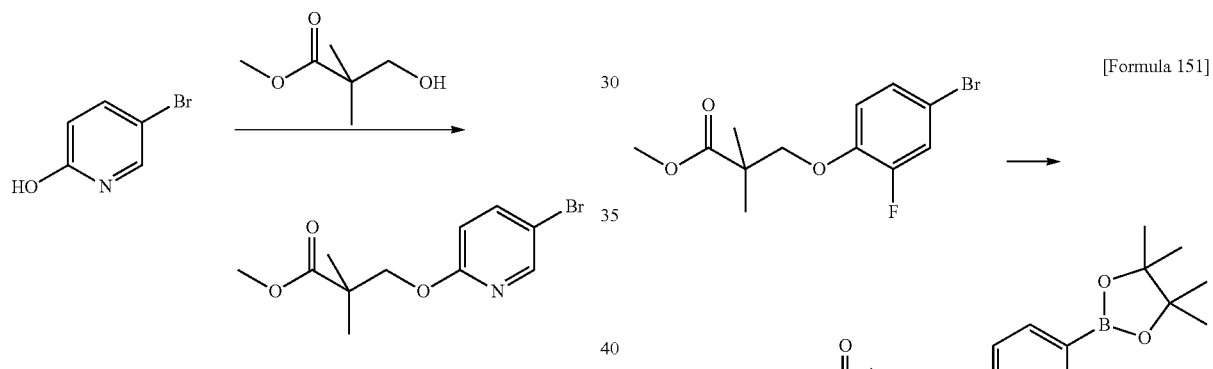

1) By using 3-bromo-6-hydroxypyridine (3.57 g), the procedure was carried out in the same manner as in Reference example 2-1) to obtain methyl 3-[(5-bromopyridin-2-yl)oxy]-2,2-dimethylpropanoate (4.83 g).
MS (m/z): 288/290 [M+H]⁺

[Formula 149]

2) By using methyl 3-[(5-bromopyridin-2-yl)oxy]-2,2-dimethylpropanoate (4.82 g), the procedure was carried out in the same manner as in Reference example 2-2) to obtain

216 methyl 2,2-dimethyl-3-{[5-(4,4,5,5-tetramethyl-1,3,2-dioxaboloran-2-yl)pyridin-2-yl]oxy}propanoate (6.16 g).
MS (m/z): 336 [M+H]⁺

Reference Example 5

[Formula 150]

1) By using 4-bromo-2-fluorophenol (2.0 g), the procedure was carried out in the same manner as in Reference example 2-1) to obtain methyl 3-(4-bromo-2-fluorophenoxy)-2,2-dimethylpropanoate (3.11 g).
MS (m/z): 305/307 [M+H]⁺

[Formula 151]

2) By using methyl 3-(4-bromo-2-fluorophenoxy)-2,2-dimethylpropanoate (3.1 g), the procedure was carried out in the same manner as in Reference example 2-2) to obtain methyl 3-[2-fluoro-4-(4,4,5,5-tetramethyl-1,3,2-dioxaboloran-2-yl)phenoxy]-2,2-dimethylpropanoate (1.912 g).
MS (m/z): 370 [M+H]⁺

Reference Example 6

[Formula 152]

1) In N,N-dimethylformamide (40 mL) was dissolved 4-bromo-2-methyl-phenol (1.87 g), potassium carbonate (4.15 g) and benzyl bromide (1.3 mL) were added to the solution, and the mixture was stirred at room temperature for 2 hours. To the reaction mixture were added water and ethyl acetate, and the liquids were separated. The organic layer was separated, washed with saturated brine, dried over anhydrous magnesium sulfate, and concentrated under reduced pressure. The obtained residue was purified by silica gel column chromatography (n-hexane:ethyl acetate=98:2 to 95:5) to obtain 1-benzyloxy-4-bromo-2-methylbenzene (2.73 g).

NMR (400 MHz, d$_6$-DMSO) σ: 2.19 (s, 3H), 5.11 (s, 2H), 6.97 (d, J=8 Hz, 1H), 7.29-7.46 (m, 7H)

[Formula 153]

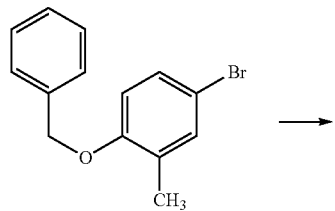

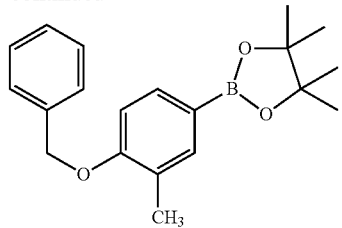

2) To 1,4-dioxane (50 mL) were added 1-benzyloxy-4-bromo-2-methylbenzene (2.73 g), tris(dibenzylideneacetone)dipalladium (0.18 g), 2-dicyclohexylphosphino-2',4',6'-triisopropyl-1,1'-biphenyl (0.19 g), potassium acetate (2.90 g) and bis(pinacolato)diboron (7.52 g), and the mixture was stirred at 110° C. under nitrogen atmosphere overnight. After cooling the reaction mixture to room temperature, insoluble material was removed by filtration using Celite, and washed with ethyl acetate. The filtrate was concentrated under reduced pressure, and the obtained residue was purified by silica gel column chromatography (n-hexane:ethyl acetate=98:2 to 95:5) to obtain 2-(4-benzyloxy-3-methylphenyl)-4,4,5,5-tetramethyl-1,3,2-dioxaborolane (3.22 g).

MS (m/z): 325 [M+H]$^+$

[Formula 154]

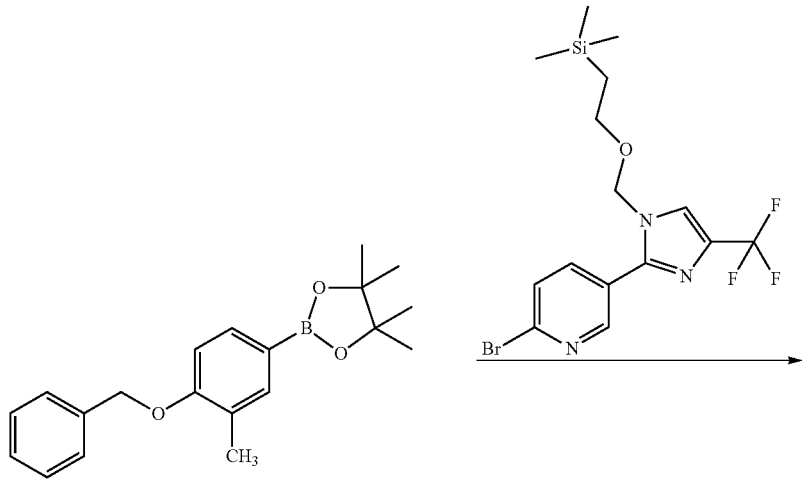

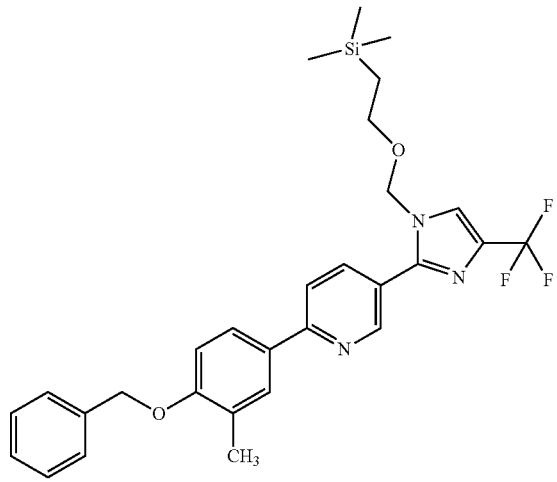

3) By using 2-(4-benzyloxy-3-methylphenyl)-4,4,5,5-tetramethyl-1,3,2-dioxaborolane (1.08 g) and 2-bromo-5-[4-(trifluoromethyl)-1-[[2-(trimethylsilyl)ethoxy]methyl]-1H-imidazol-2-yl]pyridine (0.7 g), the procedure was carried out in the same manner as in Reference example 1-3) to obtain 2-[[2-[6-(4-benzyloxy-3-methylphenyl)-3-pyridyl]-4-(trifluoromethyl)imidazol-1-yl]methoxy]ethyltrimethylsilane (0.892 g).

MS (m/z): 540 [M+H]+

[Formula 155]

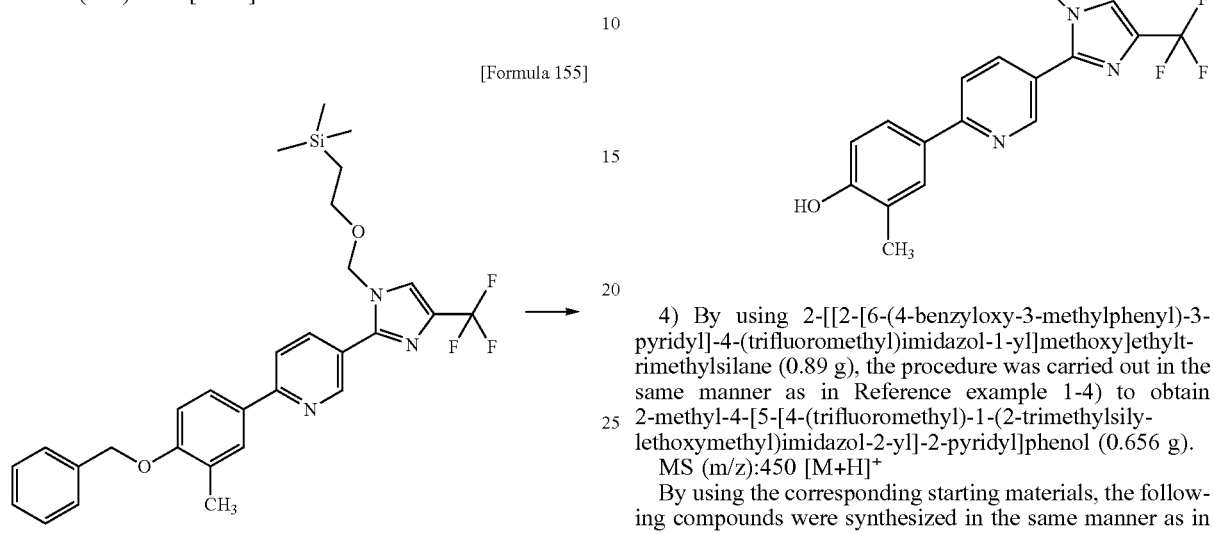

4) By using 2-[[2-[6-(4-benzyloxy-3-methylphenyl)-3-pyridyl]-4-(trifluoromethyl)imidazol-1-yl]methoxy]ethyltrimethylsilane (0.89 g), the procedure was carried out in the same manner as in Reference example 1-4) to obtain 2-methyl-4-[5-[4-(trifluoromethyl)-1-(2-trimethylsilylethoxymethyl)imidazol-2-yl]-2-pyridyl]phenol (0.656 g).

MS (m/z):450 [M+H]+

By using the corresponding starting materials, the following compounds were synthesized in the same manner as in Reference example 6.

TABLE 11

| Reference example | Starting substance | Product | MS (m/z) |
|---|---|---|---|
| 7 | ![structure] | ![structure] | 450 [M + H]+ |
| 8 | ![structure] | ![structure] | 437 [M + H]+ |

TABLE 11-continued

| Reference example | Starting substance | Product | MS (m/z) |
|---|---|---|---|
| 9 | 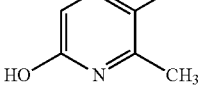 | 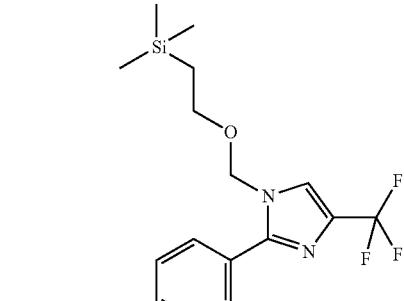 | 451 [M + H]+ |
| 10 | 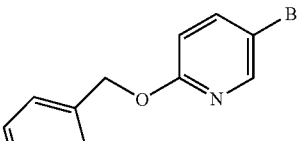 | 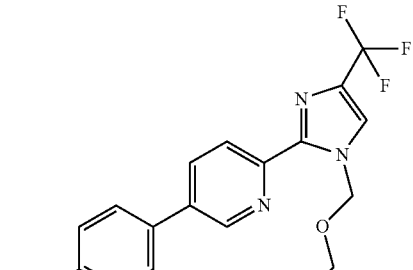 | 437 [M + H]+ |

Reference Example 11

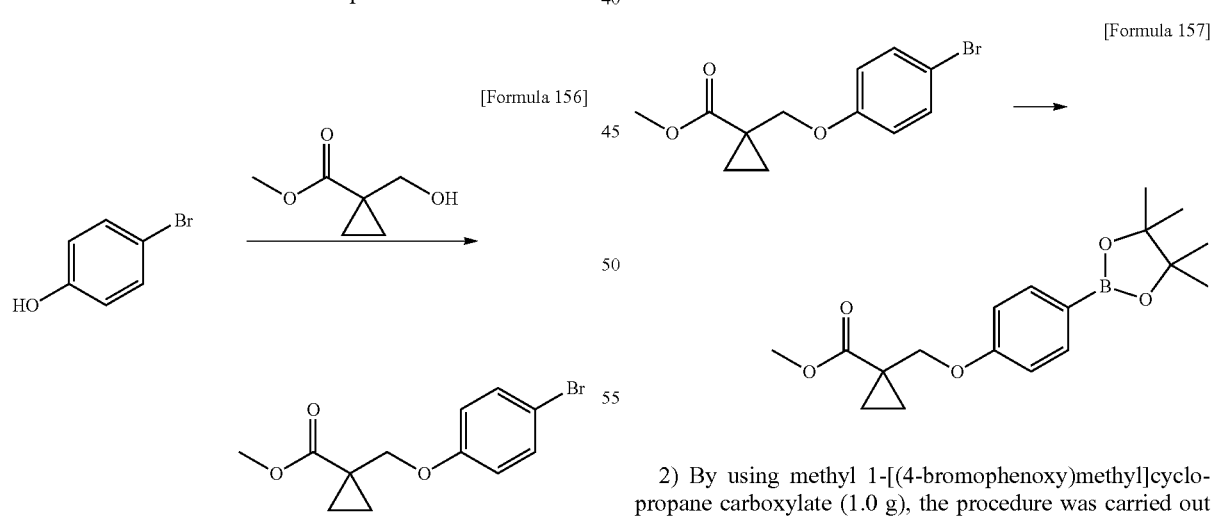

[Formula 156]

[Formula 157]

1) By using 4-bromophenol (1.33 g) and methyl 1-(hydroxymethyl)cyclopropane carboxylate (663 mg), the procedure was carried out in the same manner as in Reference example 2-1) to obtain methyl 1-[(4-bromophenoxy)methyl] cyclopropane carboxylate (1.03 g).

MS (m/z): 302/304 [M+H]+

2) By using methyl 1-[(4-bromophenoxy)methyl]cyclopropane carboxylate (1.0 g), the procedure was carried out in the same manner as in Reference example 2-2) to obtain methyl 1-[[4-(4,4,5,5-tetramethyl-1,3,2-dioxaboloran-2-yl) phenoxy]methyl]cyclopropane carboxylate (930 mg).

MS (m/z): 350 [M+H]+

By using the corresponding starting materials, the following compounds were synthesized in the same manner as in Reference example 11.

TABLE 12

| Reference example | Starting substance 1 | Starting substance 2 | Product | MS (m/z) |
|---|---|---|---|---|
| 12 | | | | 370 [M + H]⁺ |
| 13 | | | | 458 [M + H]⁺ |
| 14 | | | | 375 [M + H]⁺ |
| 15 | | | | 347 [M + H]⁺ |
| 16 | | | | 350 [M + H]⁺ |
| 17 | | | | 350 [M + H]⁺ |

TABLE 12-continued

| Reference example | Starting substance 1 | Starting substance 2 | Product | MS (m/z) |
|---|---|---|---|---|
| 18 | (structure) | (structure) | (structure) | 371 [M + H]⁺ |
| 19 | (structure) | (structure) | (structure) | 354 [M + H]⁺ |

Reference Example 20

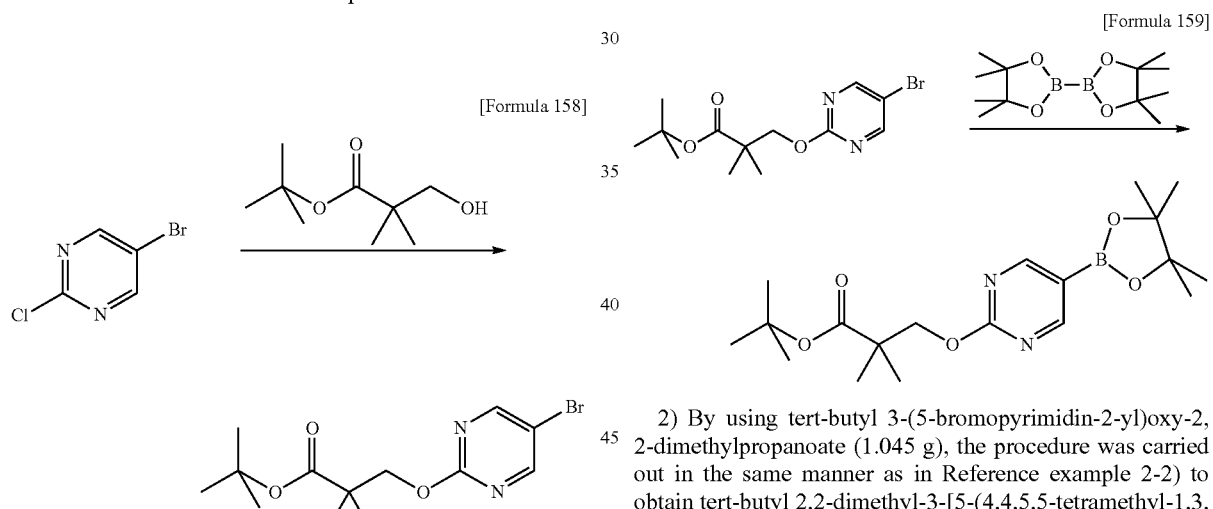

1) In N,N-dimethylformamide (10 mL) were dissolved 5-bromo-2-chloropyridine (1000 mg) and tert-butyl 3-hydroxy-2,2-dimethylpropanoate (991 mg), and 60% sodium hydride (248 mg) was added to the solution under ice-cooling. The reaction mixture was stirred at room temperature for 6 hours, at 50° C. for 1 hour and 45 minutes, and then, at room temperature overnight. Water was added to the reaction mixture under ice-cooling, and the mixture was extracted with ether. The organic layer was separated, washed with saturated brine, dried over anhydrous magnesium sulfate, and concentrated under reduced pressure. The obtained residue was purified by silica gel column chromatography (n-hexane:ethyl acetate=100:0 to 95:5) to obtain tert-butyl 3-(5-bromopyrimidin-2-yl)oxy-2,2-dimethylpropanoate (1.048 g).

MS (m/z): 331/333 [M+H]⁺

2) By using tert-butyl 3-(5-bromopyrimidin-2-yl)oxy-2,2-dimethylpropanoate (1.045 g), the procedure was carried out in the same manner as in Reference example 2-2) to obtain tert-butyl 2,2-dimethyl-3-[5-(4,4,5,5-tetramethyl-1,3,2-dioxaboloran-2-yl)pyrimidin-2-yl]oxopropanoate (795 mg).

MS (m/z): 379 [M+H]⁺

Reference Example 21

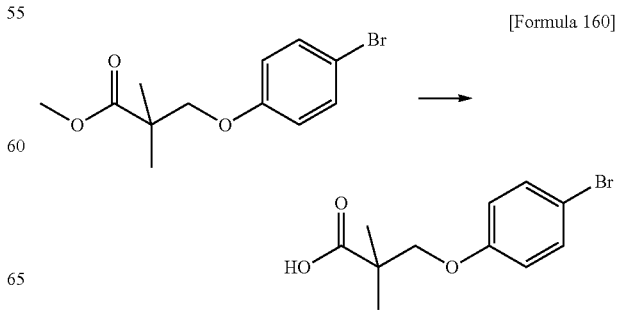

1) In tetrahydrofuran (40 mL) was dissolved methyl 3-(4-bromophenoxy)-2,2-dimethylpropanoate (3.2 g), 2N aqueous sodium hydroxide solution (10 mL) was added to the solution, and the mixture was stirred at room temperature overnight. After adding methanol (10 mL) to the mixture, the resulting mixture was refluxed for 3 hours. To the residue obtained by concentrating the reaction mixture under reduced pressure were added ethyl acetate and 1N hydrochloric acid, and the liquids were separated. The organic layer was separated, washed with saturated brine, dried over anhydrous sodium sulfate, and concentrated under reduced pressure to obtain 3-(4-bromophenoxy)-2,2-dimethylpropanoic acid (2.886 g).

MS (m/z): 273/275 [M+H]$^+$

2) In methylene chloride (10 mL) was dissolved 3-(4-bromophenoxy)-2,2-dimethylpropanoic acid (500 mg), oxalyl chloride (240 μL) and N,N-dimethylformamide (1 drop) were added dropwise to the solution under ice-cooling, and the mixture was stirred at room temperature for 1 hour. The residue obtained by concentrating the reaction mixture under reduced pressure was dissolved in acetonitrile (5 mL), and an n-hexane solution (1.83 mL) containing 2M (trimethylsilyl)diazomethane was added dropwise to the mixture under ice-cooling. Then, the reaction mixture was stirred under ice-cooling for 1 hour and at room temperature overnight. To the residue obtained by concentrating the reaction mixture under reduced pressure were added ethyl acetate and a saturated aqueous sodium bicarbonate solution, and the liquids were separated. The organic layer was separated, washed with saturated brine, dried over anhydrous sodium sulfate, and concentrated under reduced pressure. The obtained residue was dissolved in ethanol (20 mL), triethylamine (2.04 mL) and silver benzoate (168 mg) were added to the solution, and the mixture was refluxed under nitrogen atmosphere for 2 hours. Insoluble material was filtered off using a membrane filter, the filtrate was concentrated under reduced pressure, and the residue was purified by silica gel column chromatography (n-hexane:ethyl acetate=95:5 to 90:10) to obtain ethyl 4-(4-bromophenoxy)-3,3-dimethylbutanoate (397 mg).

MS (m/z): 315/317 [M+H]$^+$

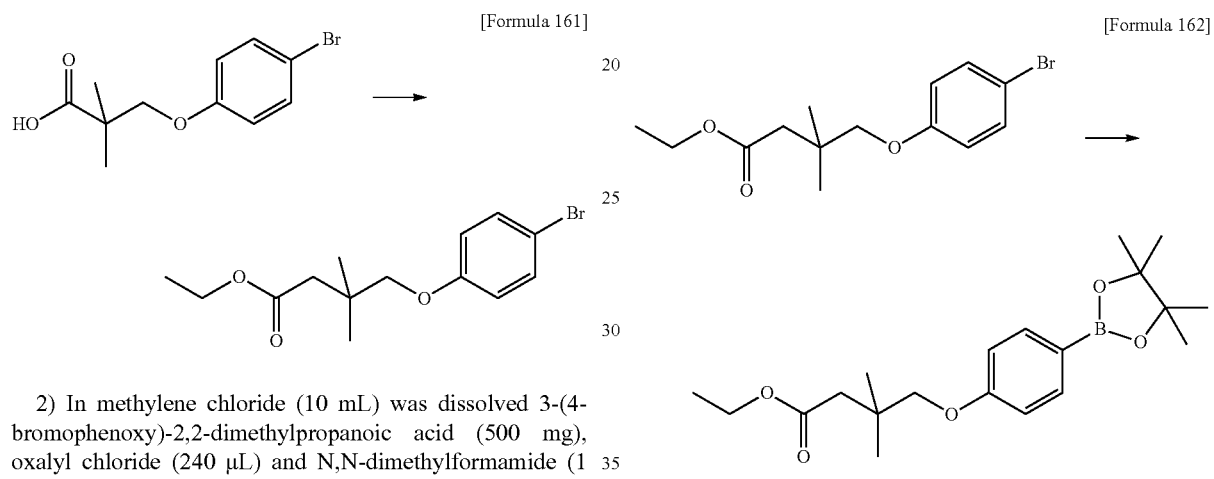

[Formula 161]

[Formula 162]

3) By using ethyl 4-(4-bromophenoxy)-3,3-dimethylbutanoate (396 mg), the procedure was carried out in the same manner as in Reference example 2-2) to obtain ethyl 3,3-dimethyl-4-[4-(4,4,5,5-tetramethyl-1,3,2-dioxaboloran-2-yl)phenoxy]butanoate (190 mg).

MS (m/z): 363 [M+H]$^+$

By using the corresponding starting materials, the following compounds were synthesized in the same manner as in Reference example 1.

TABLE 13

| Reference example | Starting substance 1 | Starting substance 2 | Product | MS (m/z) |
|---|---|---|---|---|
| 22 | (structure with F, Br, Br, O) | (5-bromopyridine-2-CHO) | (imidazole product structure) | 422/424 [M + H]$^+$ |

TABLE 13-continued

| Reference example | Starting substance 1 | Starting substance 2 | Product | MS (m/z) |
|---|---|---|---|---|
| 23 | | | | 472/474 [M + H]+ |
| 24 | | | | 439/441 [M + H]+ |
| 25 | | | | 392/394 [M + H]+ |
| 26 | | | | 435/437 [M + H]+ |

TABLE 13-continued
| Reference example | Starting substance 1 | Starting substance 2 | Product | MS (m/z) |
|---|---|---|---|---|
| 27 | 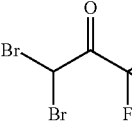 | 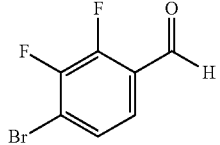 [SMILES: O=Cc1ccc(Br)c(F)c1F] | 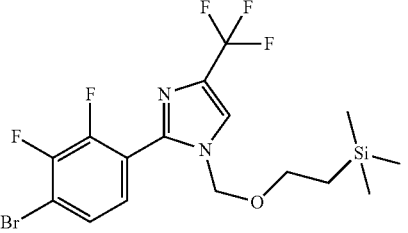 [SMILES: C[Si](C)(C)CCOCn1cc(C(F)(F)F)nc1-c1ccc(Br)c(F)c1F] | 457/459 [M + H]+ |
| 28 | 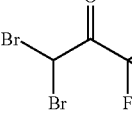 | 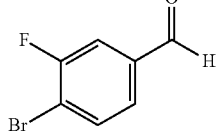 | 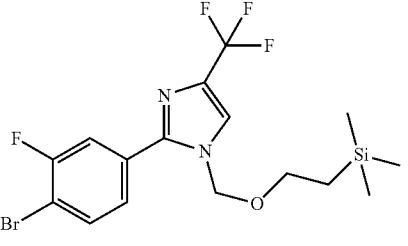 [SMILES: C[Si](C)(C)CCOCn1cc(C(F)(F)F)nc1-c1ccc(Br)c(F)c1] | 439/441 [M + H]+ |
| 29 | 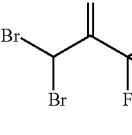 | 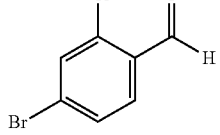 | 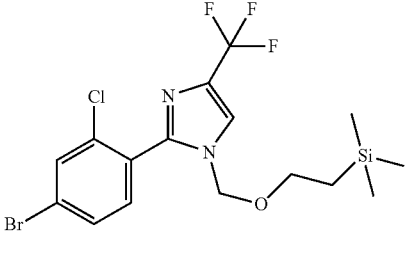 | 455/457/459 [M + H]+ |
| 30 | 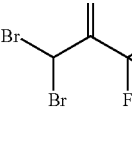 | 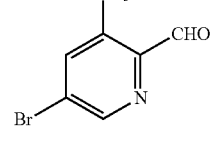 | 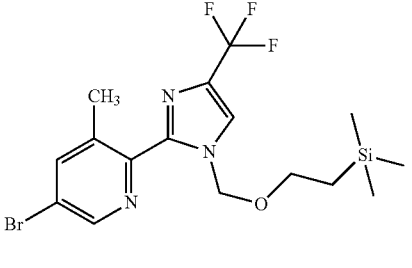 [SMILES: Cc1cc(Br)cnc1-c1nc(C(F)(F)F)cn1COCC[Si](C)(C)C] | 436/438 [M + H]+ |
| 31 | 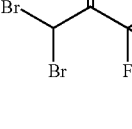 | 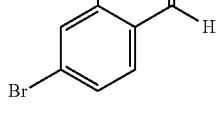 | 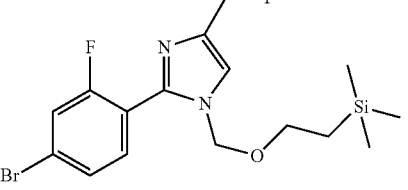 | 439/441 [M + H]+ |

Reference Example 32

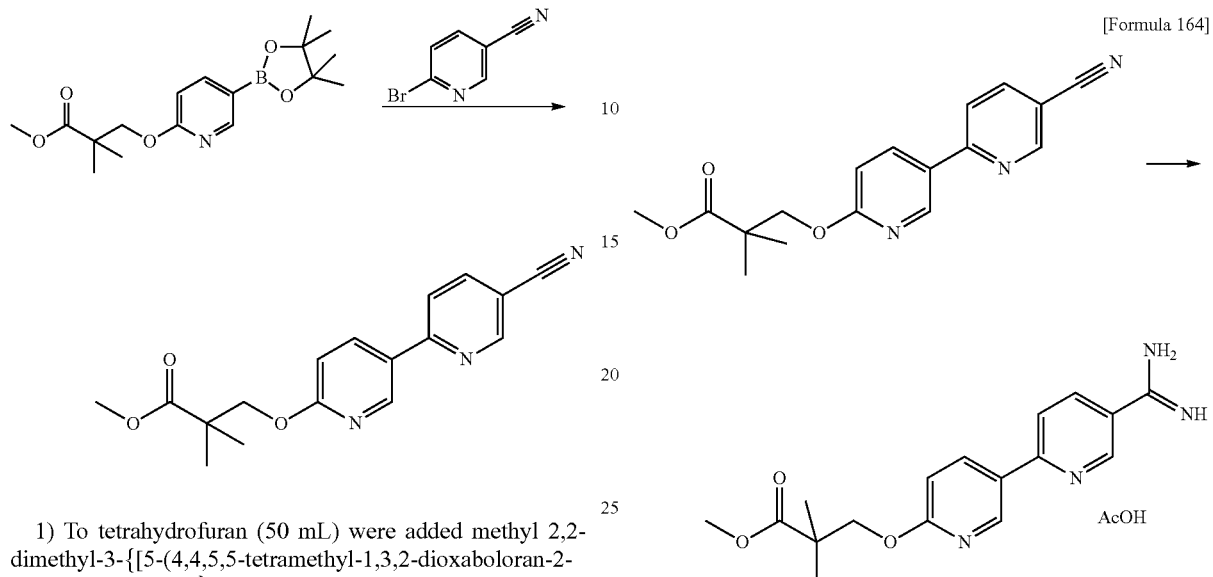

[Formula 163]

[Formula 164]

1) To tetrahydrofuran (50 mL) were added methyl 2,2-dimethyl-3-{[5-(4,4,5,5-tetramethyl-1,3,2-dioxaboloran-2-yl)pyridin-2-yl]oxy}propanoate (3000 mg), 2-bromopyridin-5-cyanide (1965.4 mg), palladium acetate (100.5 mg), 2-dicyclohexylphosphino-2',6'-dimethoxybiphenyl (367 mg) and potassium phosphate (3799.4 mg), and the mixture was stirred at 50° C. under nitrogen atmosphere for 2 days. To the reaction mixture was added saturated brine, and the mixture was extracted with ethyl acetate. The organic layer was separated, washed with water, dried over anhydrous sodium sulfate, and the residue obtained by concentrating the reaction mixture under reduced pressure was purified by silica gel column chromatography (n-hexane:ethyl acetate=85:15 to 65:35) to obtain methyl 3-{[5-(5-cyanopyridin-2-yl)pyridin-2-yl]oxy}-2,2-dimethylpropanoate (720 mg).

MS (m/z): 312 [M+H]$^+$

2) By using methyl 3-{[5-(5-cyanopyridin-2-yl)pyridin-2-yl]oxy}-2,2-dimethylpropanoate (718 mg), the procedure was carried out in the same manner as in Reference example 2-4) and 2-5) to obtain methyl 3-[(5-{5-[amino(imino)methyl]pyridin-2-yl}-pyridin-2-yl)oxy]-2,2-dimethylpropanoate acetate (467 mg).

MS (m/z): 329 [M+H]$^+$

By using the corresponding starting materials, the following compounds were synthesized in the same manner as in Reference example 32.

TABLE 14

| Reference example | Starting substance 1 | Starting substance 2 |
|---|---|---|
| 33 | ![structure] 5-bromo-2-cyanopyridine | ![structure] methyl 3-{[4-methyl-5-(pinacol boronate)pyridin-2-yl]oxy}-2,2-dimethylpropanoate |
| 34 | ![structure] 4-bromo-2-methylbenzonitrile | ![structure] methyl 3-{[4-methyl-5-(pinacol boronate)pyridin-2-yl]oxy}-2,2-dimethylpropanoate |

TABLE 14-continued
| | | |
|---|---|---|
| 35 | 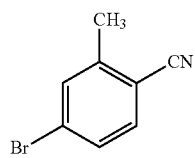 | 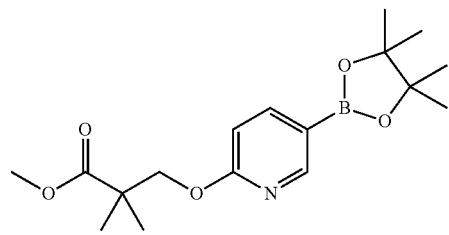 |
| 36 | 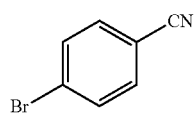 | 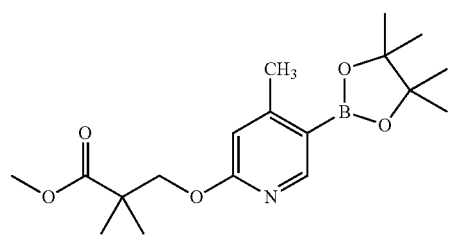 |
| 37 | 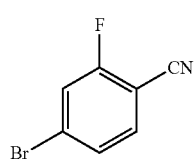 | 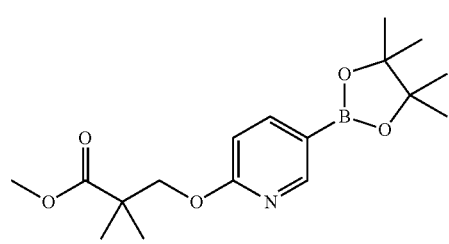 |
| 38 | 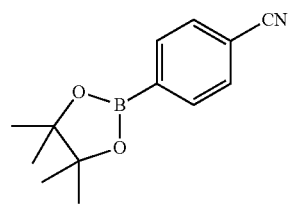 [SMILES: CC1(C)OB(c2ccc(C#N)cc2)OC1(C)C] | 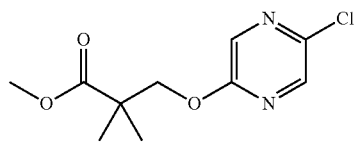 [SMILES: COC(=O)C(C)(C)COc1cnc(Cl)cn1] |
| 39 | 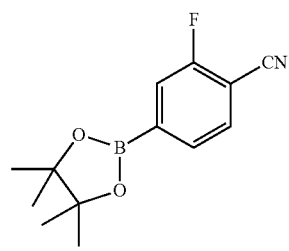 [SMILES: CC1(C)OB(c2ccc(C#N)c(F)c2)OC1(C)C] | 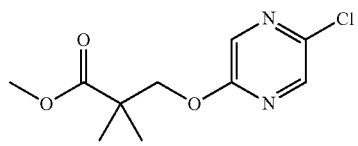 [SMILES: COC(=O)C(C)(C)COc1cnc(Cl)cn1] |
| 40 | 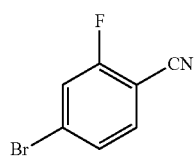 | 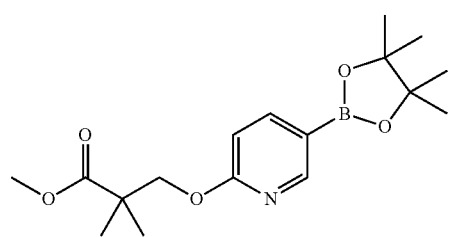 |

TABLE 14-continued

| Reference example | Product | MS (m/z) |
|---|---|---|
| 33 | (structure) 2AcOH | 343 [M + H]+ |
| 34 | (structure) AcOH | 356 [M + H]+ |
| 35 | (structure) | 342 [M + H]+ |
| 36 | (structure) AcOH | 342 [M + H]+ |
| 37 | (structure) 2AcOH | 346 [M + H]+ |
| 38 | (structure) AcOH | 329 [M + H]+ |

| 39 | 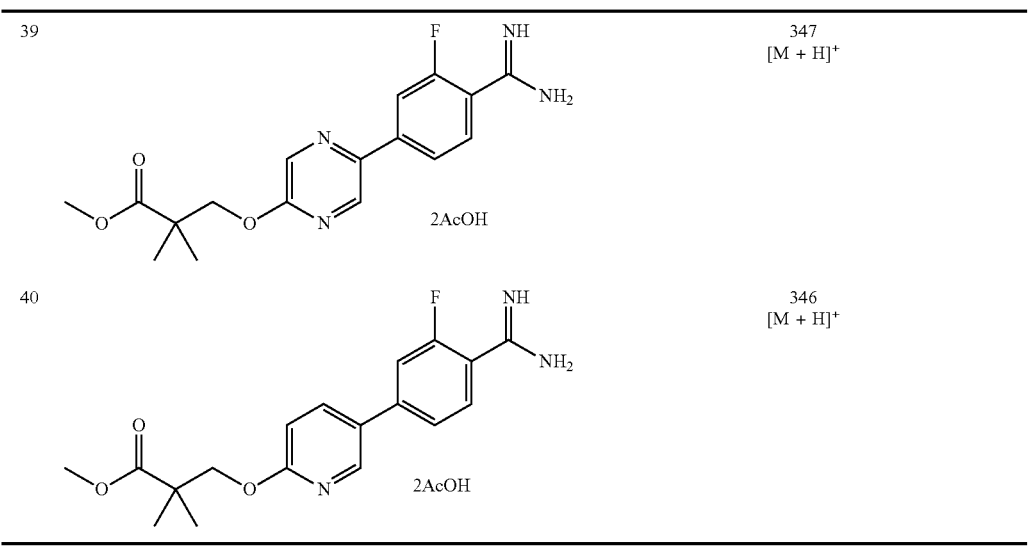 | 347 [M + H]+ |
|---|---|---|
| 40 | | 346 [M + H]+ |

Reference Example 41

[Formula 165]

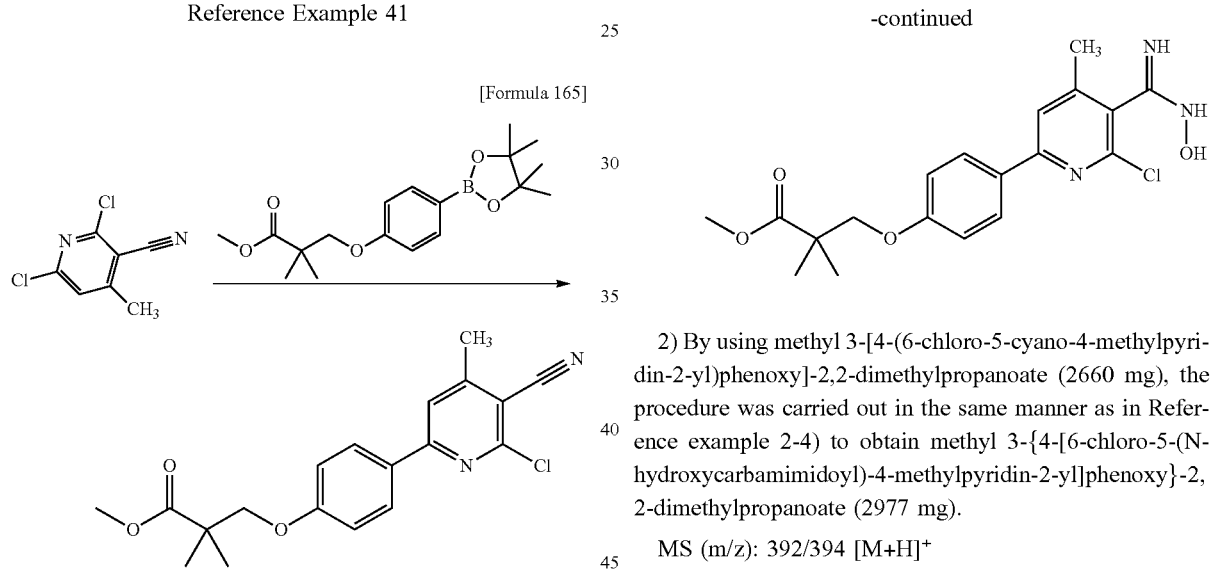

1) By using 2,6-dichloro-4-methylpyridin-3-carbonitrile (2000 mg) and methyl 2,2-dimethyl-3-[4-(4,4,5,5-tetramethyl-1,3,2-dioxaboloran-2-yl)phenoxy]propanoate (3573.9 mg), the procedure was carried out in the same manner as in Reference example 1-3) to obtain methyl 3-[4-(6-chloro-5-cyano-4-methylpyridin-2-yl)phenoxy]-2,2-dimethylpropanoate (2697 mg).

MS (m/z): 359/361 [M+H]+

[Formula 166]

2) By using methyl 3-[4-(6-chloro-5-cyano-4-methylpyridin-2-yl)phenoxy]-2,2-dimethylpropanoate (2660 mg), the procedure was carried out in the same manner as in Reference example 2-4) to obtain methyl 3-{4-[6-chloro-5-(N-hydroxycarbamimidoyl)-4-methylpyridin-2-yl]phenoxy}-2,2-dimethylpropanoate (2977 mg).

MS (m/z): 392/394 [M+H]+

[Formula 167]

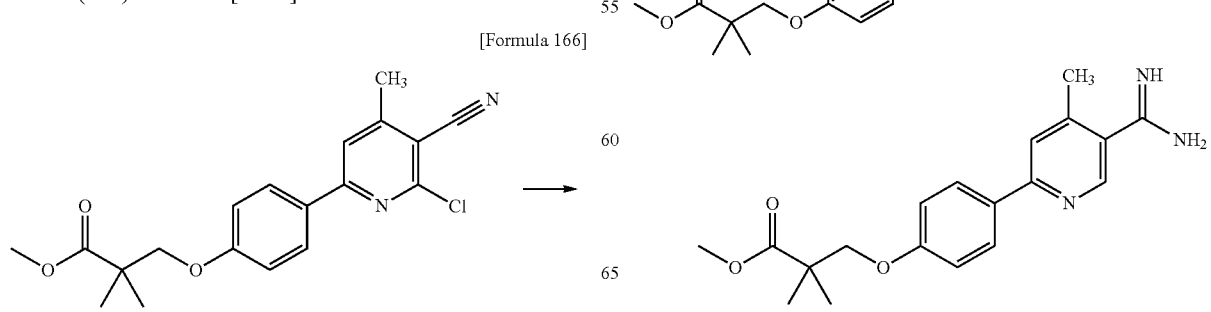

3) By using methyl 3-{4-[6-chloro-5-(N-hydroxycarbamimidoyl)-4-methylpyridin-2-yl]phenoxy}-2,2-dimethylpropanoate (2900 mg), the procedure was carried out in the same manner as in Reference example 2-5) to obtain methyl 3-[4-(5-carbamimidoyl-4-methylpyridin-2-yl)phenoxy]-2,2-dimethylpropanoate (2300 mg).

MS (m/z): 342 [M+H]+

Reference Example 42

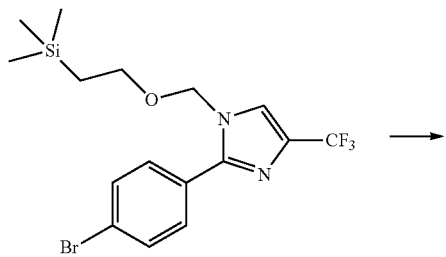

[Formula 168]

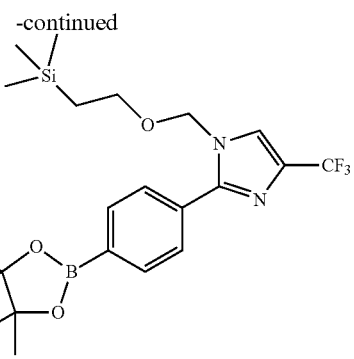

By using 2-(4-bromophenyl)-4-(trifluoromethyl)-1-{[2-(trimethylsilyl)ethoxy]-methyl}-1H-imidazole (869 mg), the procedure was carried out in the same manner as in Reference example 2-2) to obtain 2-[4-(4,4,5,5-tetramethyl-1,3,2-dioxaboloran-2-yl)phenyl]-4-(trifluoromethyl)-1-{[2-(trimethylsilyl)ethoxy]methyl}-1H-imidazole (724.9 mg).

MS (m/z): 469 [M+H]+

By using the corresponding starting materials, the following compounds were synthesized in the same manner as in Reference example 42.

TABLE 15

| Reference example | Starting substance | Product | MS (m/z) |
|---|---|---|---|
| 43 | (structure) | (structure) | 487 [M + H]+ |
| 44 | (structure) | (structure) | 470 [M + H]+ |

Reference Example 45

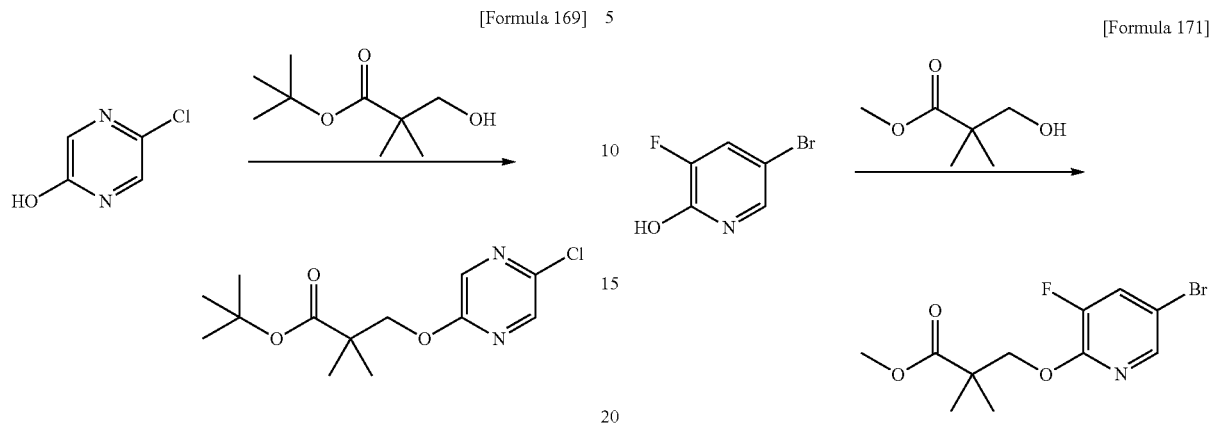

By using 5-chloropyrazin-2-ol (700 mg) and tert-butyl hydroxypivalate (1402 mg), the procedure was carried out in the same manner as in Example 1-1) to obtain tert-butyl 3[(5-chloropyrazin-2-yl)oxy]-2,2-dimethylpropanoate (1294.5 mg).

MS (m/z): 287/289 $[M+H]^+$

Reference Example 46

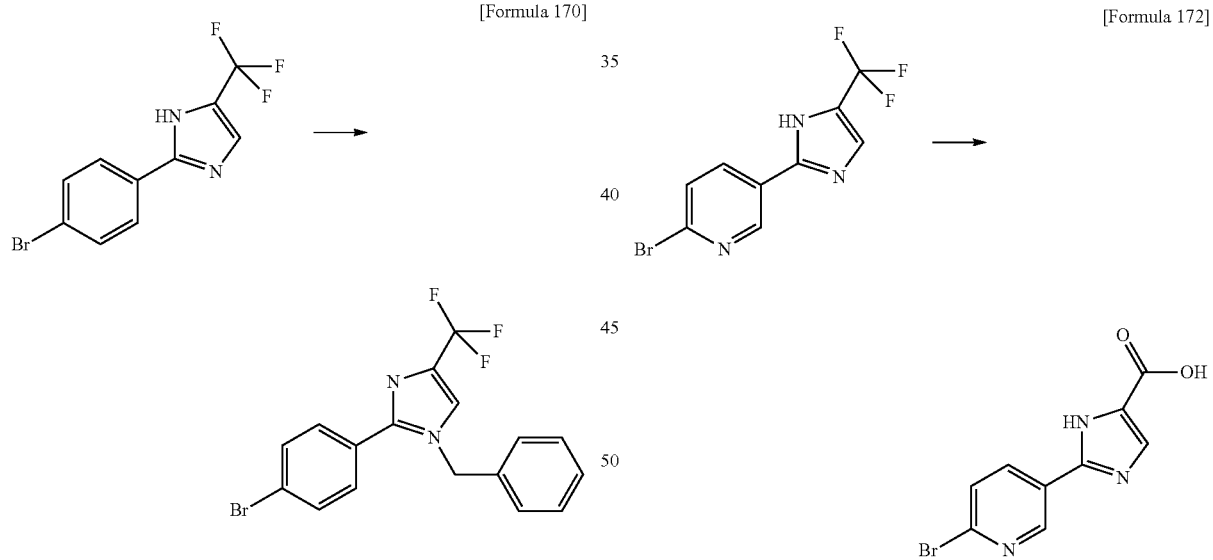

1) A mixture of 2-(4-bromophenyl)-5-(trifluoromethyl)-1H-imidazole (3 g), benzyl bromide (3.52 g), potassium carbonate (2.85 g) and N,N-dimethylformamide (30 mL) was stirred at room temperature overnight. To the reaction mixture were added water and ether, and the liquids were separated. The organic layer was separated, washed with water and then with saturated brine, dried over anhydrous sodium sulfate, and concentrated under reduced pressure. The obtained residue was dissolved in toluene, and purified by silica gel column chromatography (n-hexane:ethyl acetate=100:0 to 70:30) to obtain 1-benzyl-2-(4-bromophenyl)-4-(trifluoromethyl)-1H-imidazole (3.40 g).

MS (m/z): 381/383 $[M+H]^+$

Reference Example 47

By using 5-bromo-3-fluoropyridin-2-ol (0.96 g), the procedure was carried out in the same manner as in Example 1-1) to obtain methyl 3-[(5-bromo-3-fluoropyridin-2-yl)oxy]-2,2-dimethylpropanoate (1.35 g).

MS (m/z): 306/308 $[M+H]^+$

Reference Example 48

1) In ethanol (10 mL) was dissolved 2-bromo-5-[5-(trifluoromethyl)-1H-imidazol-2-yl]-pyridine (500 mg), 2N aqueous sodium hydroxide solution was added to the solution, and the mixture was stirred at 70° C. overnight. The reaction mixture was concentrated under reduced pressure, and 1N aqueous citric acid solution was added thereto. The precipitated solid substance was collected by filtration, washed with water, and then, with ether, and dried to obtain 2-(6-bromopyridin-3-yl)-1H-imidazol-5-carboxylic acid (722 mg).

MS (m/z): 268/270 $[M+H]^+$

[Formula 173]

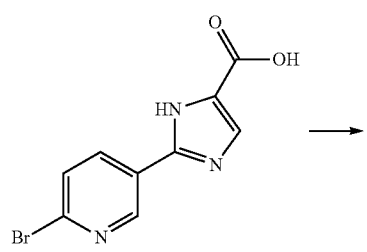

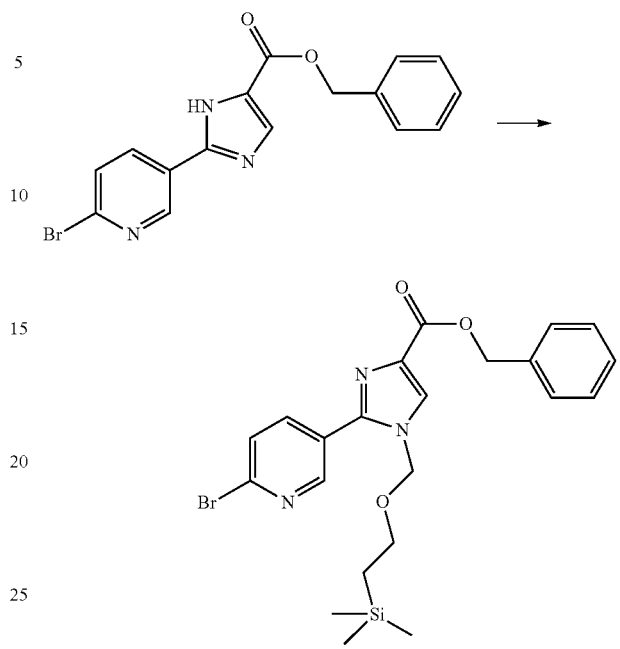

[Formula 174]

2) To an N,N-dimethylacetamide solution containing 2-(6-bromopyridin-3-yl)-1H-imidazol-5-carboxylic acid (4.99 g) and diisopropylethylamine (4.21 mL) was added benzyl bromide (3.81 g) under ice-cooling, after stirring the mixture for 5 minutes, the temperature of the mixture was raised to room temperature and the mixture was stirred overnight. Water was added to the reaction mixture under ice-cooling, and the precipitated solid was collected by filtration, washed with water and n-hexane, and dried to obtain benzyl 2-(6-bromopyridin-3-yl)-1H-imidazol-5-carboxylate (6.01 g).
MS (m/z): 358/360 [M+H]$^+$ 3) By using benzyl 2-(6-bromopyridin-3-yl)-1H-imidazol-5-carboxylate (5.5 g), the procedure was carried out in the same manner as in Reference example 1-2) to obtain benzyl 2-(6-bromopyridin-3-yl)-1-{[2-(trimethylsilyl)ethoxy]-1H-imidazol-4-carboxylate (2.97 g).
MS (m/z): 488/490 [M+H]$^+$

[Formula 175]

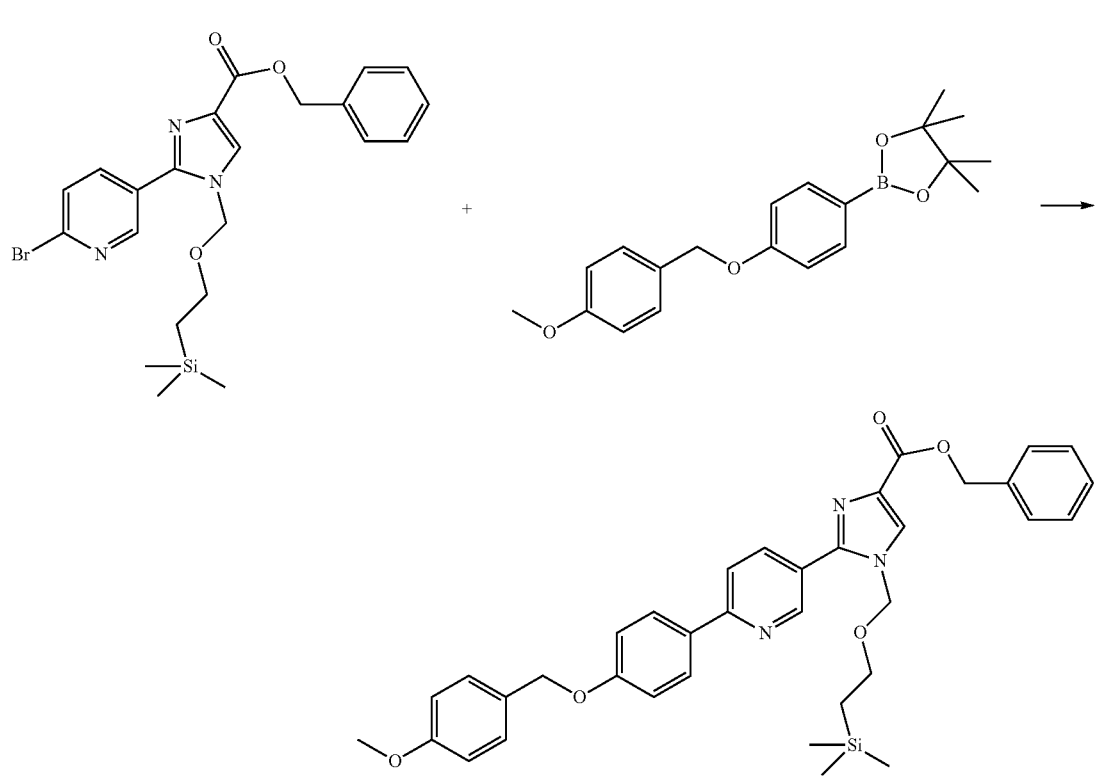

4) By using benzyl 2-(6-bromopyridin-3-yl)-1-{[2-(trimethylsilyl)ethoxy]-1H-imidazol-4-carboxylate (6.69 g) and 2-{4-[(4-methoxybenzyl)oxy]phenyl}-4,4,5,5-tetramethyl-1,3,2-dioxaborolane (6.04 g), the procedure was carried out in the same manner as in Reference example 1-3) to obtain benzyl 2-(6-{4-[(4-methoxybenzyl)oxy]phenyl}-pyridin-3-yl)-1-{[2-(trimethylsilyl)ethoxy]methyl}-1H-imidazol-4-carboxylate (6.54 g).

MS (m/z): 622 [M+H]$^+$

[Formula 177]

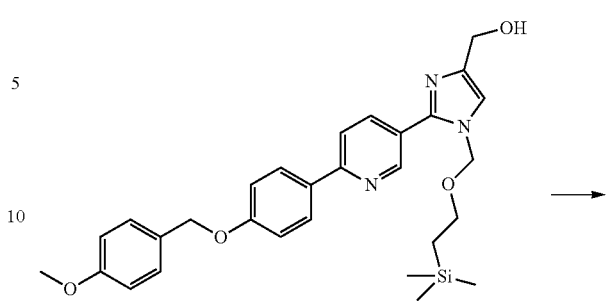

[Formula 176]

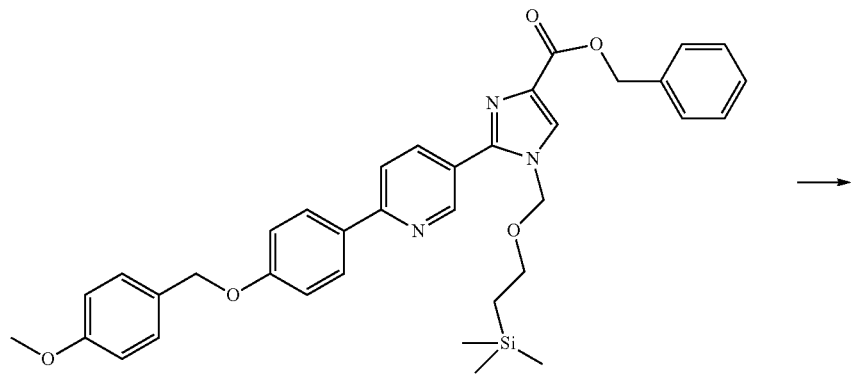

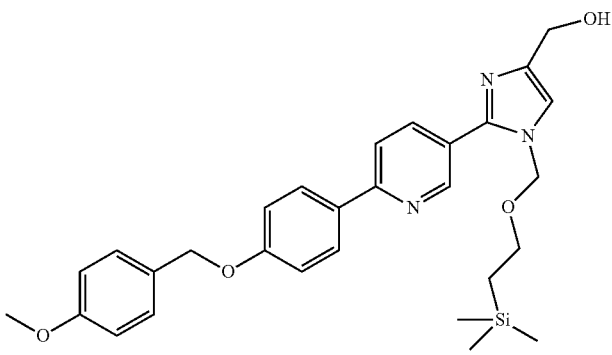

5) To a tetrahydrofuran (40 mL) suspension of lithium aluminum hydride (0.24 g) was added dropwise a tetrahydrofuran (30 mL) solution of benzyl 2-(6-{4-[(4-methoxybenzyl)oxy]phenyl}pyridin-3-yl)-1-{[2-(trimethylsilyl)ethoxy]methyl}-1H-imidazol-4-carboxylate (2 g) under ice-cooling. After stirring for 30 minutes, sodium sulfate (720 mg) and water (0.48 mL) were added to the mixture. The mixture was stirred at room temperature for 1 hour, and filtered. The filtrate was concentrated under reduced pressure, the obtained residue was pulverized by adding ether, and collected by filtration to obtain [2-(6-{4-[(4-methoxybenzyl)oxy]phenyl}pyridin-3-yl)-1-{[2-(trimethylsilyl)ethoxy]methyl}-1H-imidazol-4-yl]methanol.

MS (m/z): 518 [M+H]$^+$

-continued

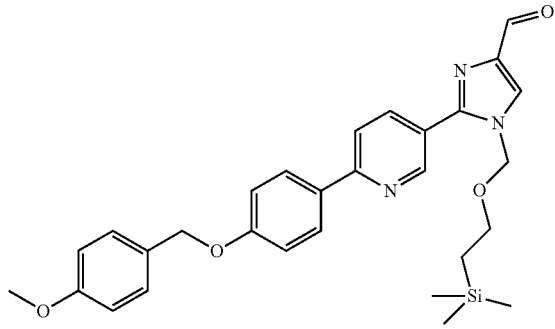

6) In methylene chloride (100 mL) was dissolved [2-(6-{4-[(4-methoxybenzyl)oxy]-phenyl}pyridin-3-yl)-1-{[2-(trimethylsilyl)ethoxy]methyl}-1H-imidazol-4-yl]methanol obtained in the above-mentioned 5), manganese dioxide (5.59 g) was added to the solution, and the mixture was stirred at room temperature for 2 days. The reaction mixture was filtered and then purified by silica gel column chromatography (chloroform to chloroform:methanol=97:3) to obtain 2-(6-{4-[(4-methoxybenzyl)oxy]phenyl}pyridin-3-yl)-1-{[2-(trimethylsilyl)ethoxy]methyl}-1H-imidazol-4-carbaldehyde (1.25 g).

MS (m/z): 516 [M+H]$^+$

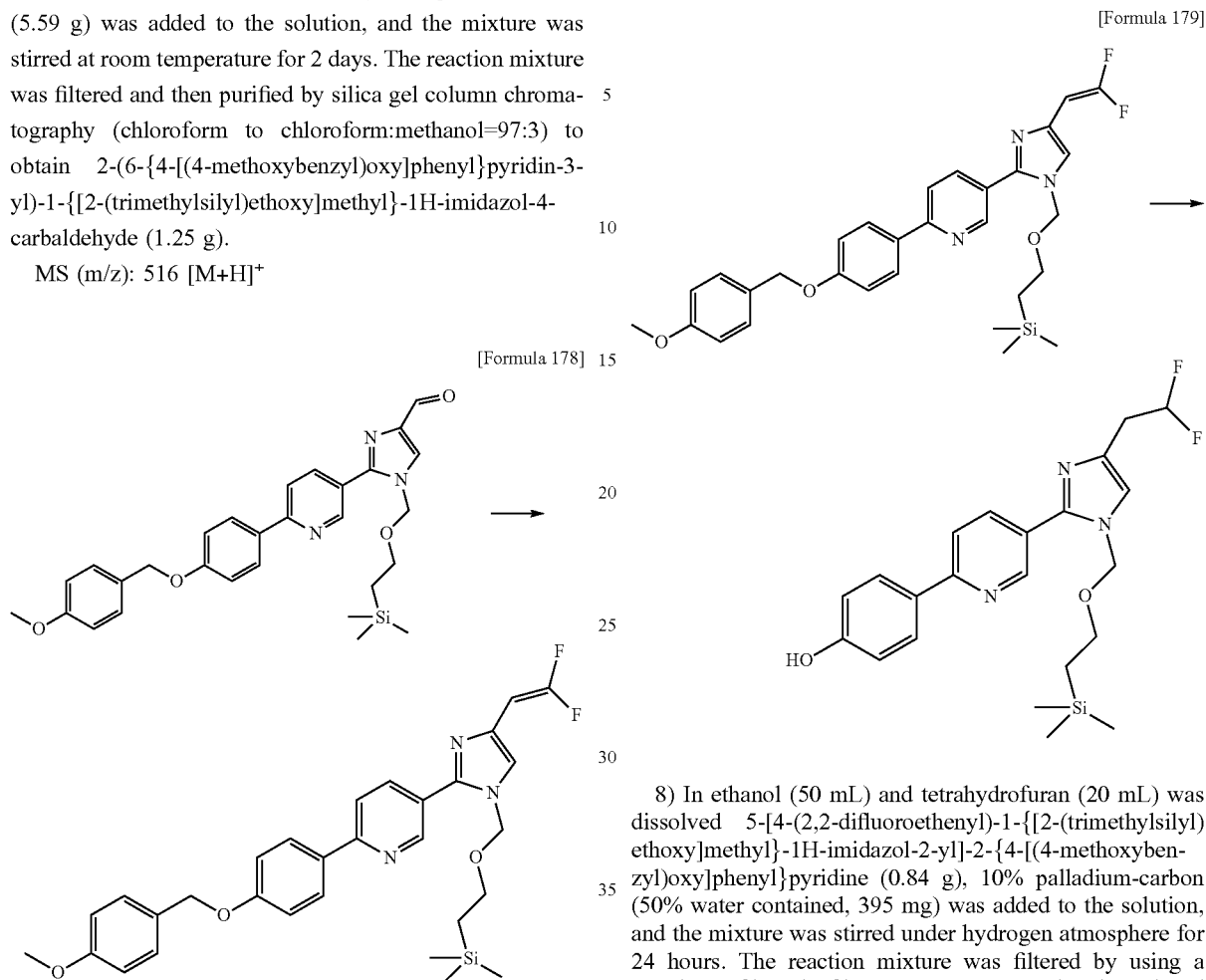

[Formula 178]

[Formula 179]

7) To a tetrahydrofuran (70 mL) solution containing dibromodifluoromethane (5.09 g) was added dropwise hexamethyl phosphoric triamide (8.81 mL) at −78° C. The temperature of the mixture was returned to room temperature, and the mixture was stirred for 30 minutes. The mixture was cooled to −78° C., and a tetrahydrofuran (20 mL) solution of 2-(6-{4-[(4-methoxybenzyl)oxy]phenyl}pyridin-3-yl)-1-{[2-(trimethylsilyl)ethoxy]methyl}-1H-imidazol-4-carbaldehyde (1.25 g) was added dropwise thereto. The temperature of the mixture was returned to room temperature, and the mixture was stirred for 3 hours. To the mixture were added ethyl acetate, water and a saturated aqueous sodium bicarbonate solution, and the liquids were separated. The organic layer was separated, washed with saturated brine, dried over anhydrous sodium sulfate, and concentrated under reduced pressure. The obtained residue was purified by silica gel column chromatography (n-hexane:ethyl acetate=85:15 to 55:45) to obtain 5-[4-(2,2-difluoroethenyl)-1-{[2-(trimethylsilyl)ethoxy]methyl}-1H-imidazol-2-yl]-2-{4-[(4-methoxybenzyl)oxy]phenyl}pyridine (0.84 g).

MS (m/z): 550 [M+H]$^+$

8) In ethanol (50 mL) and tetrahydrofuran (20 mL) was dissolved 5-[4-(2,2-difluoroethenyl)-1-{[2-(trimethylsilyl)ethoxy]methyl}-1H-imidazol-2-yl]-2-{4-[(4-methoxybenzyl)oxy]phenyl}pyridine (0.84 g), 10% palladium-carbon (50% water contained, 395 mg) was added to the solution, and the mixture was stirred under hydrogen atmosphere for 24 hours. The reaction mixture was filtered by using a membrane filter, the filtrate was concentrated under reduced pressure, and the residue was purified by silica gel column chromatography to obtain 4-{5-[4-(2,2-difluoroethyl)-1-{[2-(trimethylsilyl)ethoxy]methyl}-1H-imidazol-2-yl]pyridin-2-yl}phenol (373 mg).

MS (m/z): 432 [M+H]$^+$

Experimental Example 1 (DGAT1 Inhibitory Activity)

<Experimental Method>
(1) Cloning of Human DGAT1 Gene and Preparation of Recombinant Baculovirus Human DGAT1 gene was obtained by using a human cDNA library as a template, and amplifying a base sequence (245-1711 in Genbank Accession No. NM_012079) which encodes DGAT1 by PCR reaction.

The obtained human DGAT1 gene was subjected to ligation to plasmid pVL1392 (BD Biosciences) to prepare expression plasmid pVL1392-DGAT1. Further, by using BD BaculoGold Baculovirus Expression vector system (BD Biosciences), recombinant baculovirus was prepared.
(2) Preparation of Microsome of Human DGAT1 Enzyme Highly Expressed-Insect Cells Preparation of human DGAT1 enzyme was carried out by infecting the recombinant baculovirus obtained in the previous item with expresSF+® insect cells (available from NOSAN Corporation). The recombinant baculovirus was added to the expresSF+® cells and cultured for 72 hours, then, the cells were recovered by centrifugation and preserved under freezing at −80° C. The cells preserved under freezing were melted in ice, then, suspending in a buffer (200 mM Sucrose, 1 mM EDTA, 100 mM Tris-HCl (pH 7.4)) to which Complete Protease Inhibitor (Roche) had been added, and subjected to sonication. Thereafter, microsome fraction was obtained according to the usual method, and preserved as DGAT1 highly expressed-microsome under freezing at −80° C.

(3) Measurement of DGAT1 Inhibitory Activity

As a buffer to be used in the enzymatic reaction of DGAT1, 100 mM Tris-HCl (pH 7.4), 200 mM Sucrose, 20 mM $MgCl_2$, 0.125% Bovine Serum Albumin (BSA) were used. To the buffer were added Test compound with a predetermined concentration as well as 15 μM dioleoylglycerol, 5 μm [$^{14}$C]-palmitoyl-CoA, 100 μg protein/mL DGAT1 highly expressed-expresSF+® microsome, 0.75% acetone, and 1% dimethylsulfoxide, and triglyceride (TG) synthetic reaction was carried out at 30° C. for 20 minutes with a volume of 100 μL. 90 μL of the reaction solution was added to 810 μL of methanol to stop the reaction. The reaction solution was added to Oasis® μElution plate (available from Waters Corporation), and eluted with 150 μL of a mixed solution of acetonitrile:isopropanol (=2:3). To elute was added 150 μL of MicroScinti™-40 (available from PerkinElmer Inc.), and after thoroughly stirring the mixture, a [$^{14}$C]-TG amount formed by the reaction was quantitated by measuring the same using TopCount™-NXT (available from PerkinElmer Inc.).

The inhibition rate was calculated by the following equation.

Inhibition rate (%)=(1−(TG amount at the time of adding Test compound−Blank TG amount)÷(Control TG amount−Blank TG mount))×100

Here, a count of the [$^{14}$C]-TG in the solution in which the reaction had been carried out without adding Test compound is made "Control TG amount" and a count of the [$^{14}$C]-TG in the solution in which Test compound and DGAT1 highly expressed-expresSF+® microsome had not been added is made "Blank TG amount". In addition, a concentration of Test compound necessary to inhibit 50% of [$^{14}$C]-TG synthesis ($IC_{50}$ value) was calculated by Prism 5.01 (available from GrafPad Software Co.).

<Experimental Results>

Experimental results are shown in the following Table 16.

TABLE 16

| Test compound | $IC_{50}$ (nM) | Test compound | $IC_{50}$ (nM) |
| --- | --- | --- | --- |
| Product of Example 1-3) | 4.2 | Product of Example 2-2) | 23 |
| Product of Example 3-3) | 2.9 | Product of Example 4-2) | 2.0 |
| Product of Example 5-3) | 24 | Product of Example 6-3) | 8.9 |
| Product of Example 7-7) | 25 | Product of Example 8-2) | 21 |
| Product of Example 9 | 5.2 | Product of Example 10 | 9.1 |
| Product of Example 11 | 43 | Product of Example 12 | 14 |
| Product of Example 13-3) | 2.3 | Product of Example 14 | 11 |
| Product of Example 15 | 12 | Product of Example 16 | 28 |
| Product of Example 17 | 3.3 | Product of Example 18-2) | 6.7 |
| Product of Example 19-3) | 4 | Product of Example 20 | 8.3 |
| Product of Example 21 | 8.6 | Product of Example 22 | 3.1 |
| Product of Example 23 | 0.76 | Product of Example 24 | 11 |
| Product of Example 25 | 21 | Product of Example 26 | 11 |
| Product of Example 27 | 20 | Product of Example 28 | 19 |
| Product of Example 29 | 20 | Product of Example 30 | 15 |
| Product of Example 31 | 16 | Product of Example 32 | 11 |
| Product of Example 33 | 14 | Product of Example 34 | 16 |
| Product of Example 35-3) | 79.7 | Product of Example 36 | 5.4 |
| Product of Example 37 | 4.4 | Product of Example 38 | 36 |
| Product of Example 39 | 0.63 | Product of Example 40 | 3.7 |
| Product of Example 41 | 2.6 | Product of Example 42 | 5.7 |
| Product of Example 43 | 48 | Product of Example 44 | 26 |
| Product of Example 45 | 2.4 | Product of Example 46 | 11 |
| Product of Example 47 | 11 | Product of Example 48 | 14 |
| Product of Example 49 | 31 | Product of Example 50 | 47 |
| Product of Example 51 | 47 | Product of Example 52 | 1.8 |
| Product of Example 53 | 13 | Product of Example 54-4) | 1.5 |
| Product of Example 55-2) | 3.8 | Product of Example 56 | 11 |
| Product of Example 57 | 16 | Product of Example 58-2) | 17 |
| Product of Example 59 | 2.4 | Product of Example 60-3) | 11 |
| Product of Example 61-3) | 4.2 | Product of Example 62-3) | 0.96 |
| Product of Example 63-3) | 1.2 | Product of Example 64 | 2.7 |
| Product of Example 65 | 2 | Product of Example 66 | 3.8 |
| Product of Example 67 | 11 | Product of Example 68 | 26 |
| Product of Example 69 | 2.7 | Product of Example 70 | 8.1 |
| Product of Example 71 | 13 | Product of Example 72 | 3.1 |
| Product of Example 73 | 2.1 | Product of Example 74 | 21 |
| Product of Example 75 | 2.2 | Product of Example 76 | 1.5 |
| Product of Example 77 | 0.78 | Product of Example 78 | 3.8 |
| Product of Example 79 | 5.8 | Product of Example 80 | 3.1 |
| Product of Example 81 | 12 | Product of Example 82 | 3.0 |
| Product of Example 83 | 4.6 | Product of Example 84 | 2.0 |
| Product of Example 85-4) | 30 | Product of Example 86-3) | 21 |
| Product of Example 87-7) | 32 | Product of Example 88-3) | 5.8 |
| Product of Example 89-2) | 5.3 | Product of Example 90 | 0.87 |
| Product of Example 91 | 10 | Product of Example 92 | 23 |
| Product of Example 93-3) | 11 | Product of Example 94-3) | 1.4 |
| Product of Example 95-6) | 1.7 | Product of Example 96-2) | 3.1 |
| Product of Example 97-5) | 4.7 | Product of Example 98-3) | 0.75 |
| Product of Example 99-6) | 1.6 | Product of Example 100-5) | 2.9 |
| Product of Example 101-3) | 0.82 | Product of Example 102 | 74 |
| Product of Example 103 | 4.8 | Product of Example 104 | 3.6 |
| Product of Example 105 | 19 | Product of Example 106 | 75 |
| Product of Example 107 | 1.4 | Product of Example 108 | 1.2 |
| Product of Example 109 | 2.2 | Product of Example 110 | 19 |
| Product of Example 111 | 5.5 | Product of Example 112 | 1.3 |
| Product of Example 113 | 2.3 | Product of Example 114 | 0.7 |
| Product of Example 115 | 4.5 | Product of Example 116 | 3.5 |
| Product of Example 117 | 3.8 | Product of Example 118 | 8.9 |
| Product of Example 119 | 4.5 | Product of Example 120 | 1.8 |
| Product of Example 121 | 5.4 | Product of Example 122 | 3.4 |
| Product of Example 123 | 3.5 | Product of Example 124 | 2.1 |
| Product of Example 125 | 2.2 | Product of Example 126 | 1.7 |
| Product of Example 127 | 2.6 | Product of Example 128 | 64 |
| Product of Example 129 | 11 | Product of Example 130 | 83 |
| Product of Example 131 | 39 | Product of Example 132 | 3.9 |
| Product of Example 133 | 1.6 | Product of Example 134 | 1.5 |
| Product of Example 135 | 1 | Product of Example 136 | 1.9 |
| Product of Example 137 | 2 | Product of Example 138 | 1.7 |
| Product of Example 139 | 3.5 | Product of Example 140 | 2.1 |
| Product of Example 141 | 3.1 | Product of Example142 | 7.6 |
| Product of Example 143 | 11 | Product of Example 144 | 11 |
| Product of Example 145 | 48 | Product of Example 146 | 8.3 |
| Product of Example 147 | 3.5 | Product of Example 148 | 1.7 |

Experimental Example 2 (Triglyceride (TG) in Blood Plasma Increase-Inhibiting Action Due to Lipid Administration)

<Experimental Method>

6 to 9 weeks-old male ICR mice were fasted overnight, and Test compound suspended in 0.2% carboxymethyl cellulose solution was orally administered to the mice. A lipid (Intralipos 20%, OTSUKA PHARMACEUTICAL CO., LTD., 10 mL/kg) was orally administered after 30 minutes. Blood was collected from tail vein immediately before the lipid administration, and after 2 hours from the same to obtain blood plasma. Measurement of TG in blood plasma was carried out by using a triglyceride E Test Wako (Wako Pure Chemical Industries, Ltd.), and an increased value of TG in blood plasma by administration of the lipid was calculated. An increased value of TG in blood plasma in a solvent control group was used as a control, and an inhibiting rate in increase of TG in blood plasma in the Test compound administered group was calculated.

<Experimental Results>

According to the above-mentioned results, the compounds of Examples showed blood plasma TG increase-inhibiting action at an administration dose of 5 mg/kg shown in the following Table 17.

Experimental Example 3 (Antifeeding Activity)

<Experimental Method>

7 to 10 weeks-old male C57BL/6J mice were fasted overnight, and the test compound suspended in 0.2% carboxymethylcellulose solution was orally administered. Immediately after the administration, high fat diet (Oriental

TABLE 17

| Test compound | Inhibiting rate of TG-increase in blood plasma (5 mg/kg) | Test compound | Inhibiting rate of TG-increase in blood plasma (5 mg/kg) |
|---|---|---|---|
| Product of Example 1-3) | 77% | Product of Example 2-2) | 76% |
| Product of Example 3-3) | 78% | Product of Example 4-2) | 60% |
| Product of Example 5-3) | 71% | Product of Example 6-3) | 78% |
| Product of Example 7-7) | 71% | Product of Example 8-2) | 46% |
| Product of Example 9 | 75% | Product of Example 10 | 62% |
| Product of Example 11 | 31% | Product of Example 12 | 51% |
| Product of Example 13-3) | 51% | Product of Example 14 | 69% |
| Product of Example 15 | 32% | Product of Example 16 | 74% |
| Product of Example 17 | 69% | Product of Example 18-2) | 69% |
| Product of Example 19-3) | 89% | Product of Example 20 | 74% |
| Product of Example 21 | 20% | Product of Example 22 | 76% |
| Product of Example 23 | 85% | Product of Example 24 | 33% |
| Product of Example 25 | 54% | Product of Example 26 | 67% |
| Product of Example 27 | 69% | Product of Example 28 | 59% |
| Product of Example 29 | 52% | Product of Example 30 | 60% |
| Product of Example 31 | 86% | Product of Example 32 | 71% |
| Product of Example 33 | 54% | Product of Example 34 | 19% |
| Product of Example 35-3) | 54% | Product of Example 36 | 69% |
| Product of Example 39 | 54% | Product of Example 45 | 71% |
| Product of Example 46 | 13% | Product of Example 47 | 72% |
| Product of Example 48 | 23% | Product of Example 49 | 48% |
| Product of Example 50 | 21% | Product of Example 52 | 26% |
| Product of Example 53 | 36% | Product of Example 54-4) | 74% |
| Product of Example 55-2) | 60% | Product of Example 56 | 61% |
| Product of Example 57 | 43% | Product of Example 58-2) | 64% |
| Product of Example 59 | 74% | (Blank) | (Blank) |
| Product of Example 60-3) | 48% | Product of Example 61-3) | 68% |
| Product of Example 62-3) | 85% | Product of Example 63-3) | 60% |
| Product of Example 64 | 60% | Product of Example 65 | 75% |
| Product of Example 66 | 83% | Product of Example 67 | 70% |
| Product of Example 68 | 64% | Product of Example 69 | 85% |
| Product of Example 70 | 67% | Product of Example 71 | 50% |
| Product of Example 72 | 85% | Product of Example 73 | 88% |
| Product of Example 74 | 50% | Product of Example 75 | 5% |
| Product of Example 76 | 78% | Product of Example 77 | 75% |
| Product of Example 78 | 61% | Product of Example 79 | 62% |
| Product of Example 80 | 41% | Product of Example 82 | 47% |
| Product of Example 83 | 60% | Product of Example 84 | 75% |
| Product of Example 85-4) | 69% | Product of Example 86-3) | 68% |
| Product of Example 87-7) | 57% | Product of Example 88-3) | 65% |
| Product of Example 89-2) | 52% | Product of Example 90 | 83% |
| Product of Example 91 | 51% | Product of Example 92 | 74% |
| Product of Example 93-3) | 67% | Product of Example 94-3) | 72% |
| Product of Example 95-6) | 70% | Product of Example 96-2) | 48% |
| Product of Example 97-5) | 102% | Product of Example 98-3) | 105% |
| Product of Example 99-6) | 95% | Product of Example 100-5) | 60% |
| Product of Example 101-3) | 71% | Product of Example 103 | 8% |
| Product of Example 104 | 67% | Product of Example 105 | 57% |
| Product of Example 107 | 62% | Product of Example 108 | 52% |
| Product of Example 109 | 50% | Product of Example 111 | 41% |
| Product of Example 112 | 67% | Product of Example 114 | 64% |
| Product of Example 115 | 50% | Product of Example 116 | 82% |
| Product of Example 117 | 57% | Product of Example 118 | 64% |
| Product of Example 119 | 67% | Product of Example 121 | 53% |
| Product of Example 124 | 98% | Product of Example 127 | 44% |
| Product of Example 129 | 16% | Product of Example 131 | 57% |
| Product of Example 132 | 65% | Product of Example 133 | 75% |
| Product of Example 134 | 84% | Product of Example 136 | 64% |
| Product of Example 137 | 81% | Product of Example 139 | 52% |
| Product of Example 140 | 68% | Product of Example 141 | 82% |
| Product of Example 143 | 55% | Product of Example 144 | 7% |
| Product of Example 145 | 43% | (Blank) | (Blank) |

Yeast Co., Ltd, 60 cal % fat) was provided and freely fed. An amount of food ingested up to 4 hours was measured, and a lowering rate (an antifeeding rate) of the amount of food ingested in the Test compound administered group was calculated as compared to that of the solvent control group as a control.

<Experimental Results>

According to the above-mentioned results, the compounds of Examples showed antifeeding rates shown in the following Table 18 with an administration dose of 5 mg/kg.

TABLE 18

| Test compound | Antifeeding rate (5 mg/kg) | Test compound | Antifeeding rate (5 mg/kg) |
|---|---|---|---|
| Product of Example 1-3) | 77% | Product of Example 2-2) | 64% |
| Product of Example 3-3) | 76% | Product of Example 4-2) | 82% |
| Product of Example 5-3) | 37% | Product of Example 6-3) | 71% |
| Product of Example 7-7) | 75% | Product of Example 8-2) | 57% |
| Product of Example 9 | 76% | Product of Example 10 | 62% |
| Product of Example 12 | 40% | Product of Example 13-3) | 60% |
| Product of Example 14 | 66% | Product of Example 16 | 75% |
| Product of Example 17 | 82% | Product of Example 18-2) | 83% |
| Product of Example 19-3) | 78% | Product of Example 20 | 70% |
| Product of Example 22 | 69% | Product of Example 23 | 63% |
| Product of Example 25 | 81% | Product of Example 26 | 79% |
| Product of Example 27 | 66% | Product of Example 28 | 54% |
| Product of Example 29 | 28% | Product of Example 30 | 68% |
| Product of Example 31 | 65% | Product of Example 32 | 42% |
| Product of Example 33 | 44% | Product of Example 35-3) | 56% |
| Product of Example 36 | 63% | Product of Example 39 | 76% |
| Product of Example 45 | 72% | Product of Example 47 | 44% |
| Product of Example 49 | 58% | (Blank) | (Blank) |
| Product of Example 54-4) | 46% | Product of Example 55-2) | 39% |
| Product of Example 56 | 76% | Product of Example 58-2) | 65% |
| Product of Example 59 | 50% | Product of Example 60-3) | 59% |
| Product of Example 61-3) | 80% | Product of Example 62-3) | 63% |
| Product of Example 63-3) | 83% | Product of Example 64 | 78% |
| Product of Example 65 | 79% | Product of Example 66 | 76% |
| Product of Example 67 | 58% | Product of Example 68 | 63% |
| Product of Example 69 | 87% | Product of Example 70 | 59% |
| Product of Example 71 | 29% | Product of Example 72 | 65% |
| Product of Example 73 | 82% | Product of Example 74 | 60% |
| Product of Example 76 | 61% | Product of Example 77 | 65% |
| Product of Example 78 | 62% | Product of Example 79 | 74% |
| Product of Example 82 | 42% | Product of Example 83 | 49% |
| Product of Example 84 | 64% | Product of Example 85-4) | 70% |
| Product of Example 86-3) | 21% | Product of Example 87-7) | 59% |
| Product of Example 88-3) | 55% | Product of Example 89-2) | 75% |
| Product of Example 90 | 75% | Product of Example 91 | 51% |
| Product of Example 92 | 66% | Product of Example 93-3) | 68% |
| Product of Example 94-3) | 66% | Product of Example 95-6) | 83% |
| Product of Example 96-2) | 58% | Product of Example 97-5) | 92% |
| Product of Example 98-3) | 89% | Product of Example 99-6) | 85% |
| Product of Example 101-3) | 57% | Product of Example 104 | 62% |
| Product of Example 105 | 58% | Product of Example 107 | 57% |
| Product of Example 108 | 62% | Product of Example 109 | 41% |
| Product of Example 112 | 52% | Product of Example 114 | 59% |
| Product of Example 115 | 62% | Product of Example 116 | 76% |
| Product of Example 117 | 55% | Product of Example 118 | 61% |
| Product of Example 119 | 51% | Product of Example 121 | 57% |
| Product of Example 124 | 75% | Product of Example 132 | 47% |
| Product of Example 133 | 83% | Product of Example 134 | 74% |
| Product of Example 136 | 62% | Product of Example 137 | 83% |
| Product of Example 140 | 78% | Product of Example 141 | 55% |
| Product of Example 143 | 4% | (Blank) | (Blank) | compound suspended in 0.2% carboxymethylcellulose solution was orally administered once a day. Oral administration was continued for 2 weeks, and a weight gain-inhibiting rate of the Test compound was calculated by using a weight gain amount of the solvent control group during the test period as 100%. After final administration, the mice were fasted overnight, and blood was collected from tail vein. Measurement of a blood-sugar level was carried out by using glucose Ca Test Wako (Wako Pure Chemical Industries, Ltd.), and measurement of insulin in blood plasma was carried out by using a mouse insulin measurement kit (Morinaga Institute of Biological Science, Inc.).

<Experimental Results>

According to the above-mentioned results, the compounds of Examples showed a hypoglycemic action, insulin in blood plasma-lowering action and weight gain-inhibiting Experimental Example 4 (Weight Gain-Inhibiting Action, Hypoglycemic Effect, Insulin in Blood Plasma Lowering Action in KK-Ay Mice)

<Experimental Method>

To 8 weeks-old male KK-Ay mice were provided high fat diet (Oriental Yeast Co., Ltd, 60 cal % fat), and Test action shown in the following table with an administration dose of 30 mg/kg/day.

TABLE 19

| Test compound | Hypoglycemic action (30 mg/kg/day) | Insulin in blood plasma-lowering action (30 mg/kg/day) | Weight gain-inhibiting action (30 mg/kg/day) |
|---|---|---|---|
| Product of Example 1-3) | 43% | 58% | 67% |
| Product of Example 2-3) | 64% | 62% | 53% |
| Product of Example 3-3) | 41% | 51% | 52% |
| Product of Example 4-2) | 50% | 52% | 49% |
| Product of Example 5-3) | 55% | 56% | 48% |
| Product of Example 6-3) | 63% | 72% | 72% |
| Product of Example 7-7) | 62% | 58% | 66% |
| Product of Example 14 | 23% | 27% | 17% |
| Product of Example 22 | 40% | 47% | 30% |
| Product of Example 23 | −13% | 14% | 39% |
| Product of Example 26 | 40% | 27% | 44% |
| Product of Example 33 | 42% | 41% | 39% |
| Product of Example 36 | 23% | 19% | 59% |
| Product of Example 39 | 44% | 50% | 38% |
| Product of Example 45 | 59% | 56% | 42% |
| Product of Example 54-4) | 74% | 93% | 113% |
| Product of Example 61-3) | 60% | 77% | 90% |
| Product of Example 62-3) | 80% | 95% | 161% |
| Product of Example 63-3) | 77% | 90% | 115% |
| Product of Example 66 | 10% | 38% | 46% |
| Product of Example 69 | 61%[#] | 37%[#] | 43%[#] |
| Product of Example 70 | 52% | 27% | 45% |
| Product of Example 72 | 38% | 28% | 43% |
| Product of Example 73 | 40% | 69% | 62% |
| Product of Example 74 | 56% | 51% | 47% |
| Product of Example 76 | 65% | 81% | 69% |
| Product of Example 77 | 60% | 65% | 60% |
| Product of Example 78 | 44% | 49% | 54% |
| Product of Example 83 | 44% | 33% | 42% |
| Product of Example 84 | 65% | 76% | 48% |
| Product of Example 87-7) | 35% | 19% | 22% |
| Product of Example 89-2) | 68% | 88% | 63% |
| Product of Example 92 | 63% | 58% | 60% |
| Product of Example 94-3) | 42%* | 29%* | 35%* |
| Product of Example 95-6) | 66% | 58% | 75% |
| Product of Example 96-2) | 66% | 71% | 75% |
| Product of Example 107 | 57% | 58% | 48% |
| Product of Example 112 | 49% | 61% | 47% |
| Product of Example 114 | 48% | 60% | 45% |
| Product of Example 117 | 36% | 35% | 31% |
| Product of Example 119 | 40% | 28% | 36% |

[#]Value of an administration dose of 10 mg/kg/day
*Value of an administration dose of 1 mg/kg/day

INDUSTRIAL APPLICABILITY

The continuous arycyclic compound (I) or a pharmaceutically acceptable salt thereof of the present invention has excellent DGAT1 inhibitory activity, and can be used as a prophylaxis or treatment agent of diabetes.

The invention claimed is:
1. A continuous arycyclic compound represented by the formula:

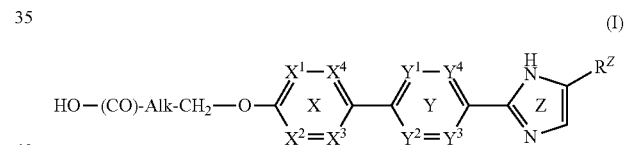

(I)

wherein Alk represents a linear $C_{1-6}$ alkylene group, a branched $C_{1-6}$ alkylene group or a $C_{1-6}$ alkylene group having a ring structure; where a part of the carbon atoms constituting the ring structure may be optionally substituted by an oxygen atom, a nitrogen atom or a sulfur atom, in Ring X,
$X^1$ represents N or $CR^{X1}$,
$X^2$ represents N or $CR^{X2}$,
$X^3$ represents N or $CR^{X3}$,
$X^4$ represents N or $CR^{X4}$,
where $R^{X1}$, $R^{X2}$, $R^{X3}$ and $R^{X4}$ each independently represents a hydrogen atom; a linear or branched $C_{1-6}$ alkyl group which may be substituted by a halogen atom(s); a $C_{3-7}$ alkyl group having a ring structure which may be substituted by a halogen atom(s); a linear or branched $C_{1-6}$ alkoxy group; a halogen atom or a cyano group,
in Ring Y,
$Y^1$ represents N or $CR^{Y1}$,
$Y^2$ represents N or $CR^{Y2}$,
$Y^3$ represents N or $CR^{Y3}$,
$Y^4$ represents N or $CR^{Y4}$,
$R^{Y1}$, $R^{Y2}$, $R^{Y3}$ and $R^{Y4}$ each independently represents a hydrogen atom; a linear or branched $C_{1-6}$ alkyl group which may be substituted by a halogen atom(s); a $C_{3-7}$ alkyl group having a ring structure which may be substituted by a halogen atom(s); a linear or branched $C_{1-6}$ alkoxy group; a halogen atom or a cyano group, in Ring Z, $R^Z$ represents a linear or branched $C_{1-6}$ alkyl group which may be substituted by a halogen atom(s) or $C_{3-7}$ alkyl group having a ring structure which may be substituted by a halogen atom(s), or a pharmaceutically acceptable salt thereof, wherein Ring X and Ring Y have structures represented by any one of the following formulae:

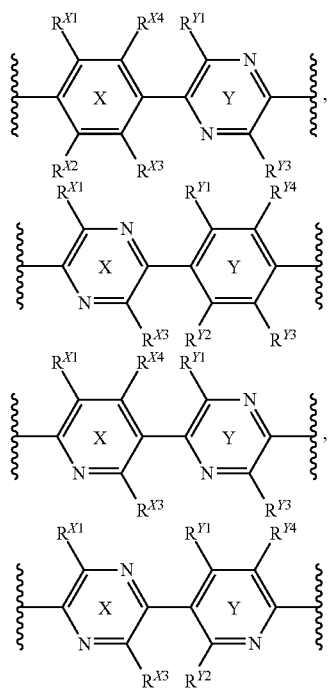

wherein $R^{X1}$ to $R^{X4}$ and $R^{Y1}$ to $R^{Y4}$ have the same meanings as defined above.

2. The continuous arycyclic compound or a pharmaceutically acceptable salt thereof according to claim 1, wherein $R^Z$ is a linear or branched $C_{1-6}$ alkyl group which is substituted by a halogen atom(s) or a $C_{3-7}$ alkyl group having a ring structure which may be substituted by a halogen atom(s).

3. The continuous arycyclic compound or a pharmaceutically acceptable salt thereof according to claim 1, wherein Alk is a branched $C_{2-4}$ alkylene group.

4. A continuous arycyclic compound which is any one of the following compounds:
   2,2-dimethyl-3-(4-{5-[5-(trifluoromethyl)-1H-imidazol-2-yl]pyrazin-2-yl}phenoxy)-propanoic acid;
   2,2-dimethyl-3-[(5-{4-[4-(trifluoromethyl)-1H-imidazol-2-yl]phenyl}pyrazin-2-yl)-oxy]propanoic acid; and
   2,2-dimethyl-3-[(4-methyl-5-{5-[5-(trifluoromethyl)-1H-imidazol-2-yl]pyrazin-2-yl}pyridin-2-yl)oxy]propanoic acid,
   or a pharmaceutically acceptable salt thereof.

5. An acyl coenzyme A: diacylglycerol acyltransferase DGAT1 inhibitor comprising the continuous arycyclic compound or a pharmaceutically acceptable salt thereof according to claim 1 as an effective ingredient.

6. The DGAT1 inhibitor according to claim 5 which is a prophylactic or treatment agent of obesity.

7. The DGAT1 inhibitor according to claim 6 which is a prophylactic or treatment agent of hyperlipidemia or hypertriglyceridemia.

8. The DGAT1 inhibitor according to claim 5 which is a prophylactic or treatment agent of type 2 diabetes or the following obesity-caused diseases: lumbago or knee osteoarthritis.

9. The DGAT1 inhibitor according to claim 8 which is a prophylactic or treatment agent of type 2 diabetes.

10. A prophylaxis or treatment method of hyperlipidemia or obesity, hypertriglyceridemia, type 2 diabetes, or the following obesity-caused diseases; lumbago or knee osteoarthritis which comprises administering therapeutically effective amount of the continuous arycyclic compound or the pharmaceutically acceptable salt thereof according to claim 1 to a patient.

11. The continuous arycyclic compound or a pharmaceutically acceptable salt thereof according to claim 2, wherein $R^Z$ is methyl which is substituted by a halogen atom(s).

12. The continuous arycyclic compound or a pharmaceutically acceptable salt thereof according to claim 3, wherein Alk is —$C(CH_3)_2$—.

* * * * *